(12) United States Patent
Chen et al.

(10) Patent No.: US 8,545,850 B2
(45) Date of Patent: *Oct. 1, 2013

(54) ANTI-CD79B ANTIBODIES AND IMMUNOCONJUGATES AND METHODS OF USE

(75) Inventors: Yvonne Chen, San Mateo, CA (US); Mark Dennis, San Carlos, CA (US); David Dornan, San Mateo, CA (US); Kristi Elkins, San Francisco, CA (US); Jagath Reddy Junutula, Fremont, CA (US); Andrew Polson, San Francisco, CA (US); Bing Zheng, Mountain View, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/940,435

(22) Filed: Nov. 5, 2010

(65) Prior Publication Data

US 2011/0135667 A1 Jun. 9, 2011

Related U.S. Application Data

(63) Continuation of application No. 12/173,465, filed on Jul. 15, 2008, now Pat. No. 8,088,378.

(60) Provisional application No. 60/950,052, filed on Jul. 16, 2007, provisional application No. 61/025,137, filed on Jan. 31, 2008, provisional application No. 61/032,790, filed on Feb. 29, 2008, provisional application No. 61/054,709, filed on May 20, 2008.

(51) Int. Cl.
*A61K 51/10* (2006.01)
*A61K 39/44* (2006.01)
*C07K 19/00* (2006.01)

(52) U.S. Cl.
USPC ............ 424/178.1; 424/179.1; 424/181.1; 424/183.1; 424/1.49; 424/1.53; 530/391.1; 530/391.5; 530/391.7; 530/391.9; 530/391.3

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,975,278 A | 12/1990 | Senter et al. |
| 5,208,020 A | 5/1993 | Chari et al. |
| 5,416,064 A | 5/1995 | Chari et al. |
| 5,644,033 A | 7/1997 | Seon |
| 5,655,033 A | 8/1997 | Inoguchi |
| 5,767,237 A | 6/1998 | Sakakibara et al. |
| 6,075,181 A | 6/2000 | Kucherlapati et al. |
| 6,124,431 A | 9/2000 | Sakakibara et al. |
| 6,150,584 A | 11/2000 | Kucherlapati et al. |
| 6,172,213 B1 | 1/2001 | Lowman et al. |
| 6,248,564 B1 | 6/2001 | Walter et al. |
| 2002/0150573 A1 | 10/2002 | Nussenzweig |
| 2004/0001827 A1 | 1/2004 | Dennis |
| 2004/0018194 A1 | 1/2004 | Francisco et al. |
| 2005/0169933 A1 | 8/2005 | Steeves et al. |
| 2005/0238649 A1 | 10/2005 | Doronina et al. |
| 2005/0238650 A1 | 10/2005 | Crowley et al. |
| 2005/0256030 A1 | 11/2005 | Feng |
| 2005/0276812 A1 | 12/2005 | Ebens et al. |
| 2007/0092940 A1 | 4/2007 | Eigenbrot et al. |
| 2007/0207142 A1 | 9/2007 | Crowley et al. |
| 2009/0028856 A1 | 1/2009 | Chen et al. |
| 2009/0053226 A1 | 2/2009 | Crowley |
| 2009/0068178 A1 | 3/2009 | Crowley |
| 2009/0068202 A1 | 3/2009 | Chen et al. |
| 2010/0215669 A1 | 8/2010 | Chen |
| 2011/0042260 A1 | 2/2011 | Crowley |
| 2011/0045005 A1 | 2/2011 | Crowley |
| 2011/0070243 A1 | 3/2011 | Crowley |

FOREIGN PATENT DOCUMENTS

| | | |
|---|---|---|
| EP | 0 425 235 B1 | 9/1996 |
| EP | 1 391 213 A1 | 2/2004 |
| EP | 1013761 | 8/2007 |
| EP | 1689432 | 12/2009 |
| EP | 2161283 | 3/2010 |
| EP | 2295073 | 3/2011 |
| EP | 2301568 | 3/2011 |
| WO | WO 00/12130 | 3/2000 |
| WO | 01/31065 | 3/2001 |
| WO | 01/45746 | 6/2001 |
| WO | 01/71005 | 9/2001 |
| WO | 01/74388 | 10/2001 |
| WO | 02/088172 A2 | 11/2002 |

(Continued)

OTHER PUBLICATIONS

Coleman, P.M., "Effects of amino acid sequence changes on antibody-antigen interactions" *Research in Immunology* 145:33-36 (1994).

Dennis et al., "Albumin binding as a general strategy for improving the pharmacokinetics of proteins" *Journal of Biological Chemistry* 277 (38):35035-35043 (Sep. 20, 2002).

Fisher et al., "Current therapeutic paradigm for the treatmentn of non-Hodgkin's lymphoma" *Semin Oncol.* 27(6 Suppl 12):2-8 (2000).

Ghetie V, et al., "Immunotoxins in the therapy of cancer: From Bench to Clinic" *Pharmacology and Therapeutics*, Elsevier, GB 63(3):221-227 (Jan. 1, 1994).

Harris et al., "The World Health Organization classification of neoplasms of the hematopoietic and lymphoid tissues: report of the Clinical Advisory Committee meeting—Airlie House, Virginia, Nov. 1997" *Hematol J.* 1:53-66 (2000).

(Continued)

*Primary Examiner* — Ronald Schwadron
(74) *Attorney, Agent, or Firm* — Bonny G. Yeung

(57) ABSTRACT

The present invention is directed to compositions of matter comprising immunoconjugates comprising an anti-CD79b antibody comprising: (i) an HVR-L1 sequence of KASQS-VDYEGDSFLN (SEQ ID NO: 194), (ii) an HVR-L2 sequence of AASNLES (SEQ ID NO: 195), (iii) an HVR-L3 sequence of QQSNEDPLT (SEQ ID NO: 196), (iv) an HVR-H1 sequence of GYTFSSYWIE (SEQ ID NO: 202), (v) an HVR-H2 sequence of GEILPGGGDTNYNEIFKG (SEQ ID NO: 203), and (vi) an HVR-H3 sequence of TRRVPIRLDY (SEQ ID NO: 204) and to methods of using those compositions of matter for the treatment of hematopoietic tumor in mammals.

8 Claims, 44 Drawing Sheets

(56) References Cited

FOREIGN PATENT DOCUMENTS

| | | |
|---|---|---|
| WO | 02/098883 | 12/2002 |
| WO | 03/072036 A2 | 4/2003 |
| WO | 03/043583 A2 | 5/2003 |
| WO | 03/062401 | 7/2003 |
| WO | 03/074567 | 9/2003 |
| WO | 2004/032828 A2 | 4/2004 |
| WO | 2005/037992 | 4/2005 |
| WO | 2005/049075 A2 | 6/2005 |
| WO | 2005/081711 A2 | 9/2005 |
| WO | 2005/117986 | 12/2005 |
| WO | 2005/117986 A2 | 12/2005 |
| WO | 2006/017173 A1 | 2/2006 |
| WO | 2006/034488 A2 | 3/2006 |
| WO | 2007/008603 A1 | 1/2007 |
| WO | 2007/008848 A2 | 1/2007 |
| WO | 2009/012256 | 1/2009 |
| WO | 2009/012268 | 1/2009 |
| WO | 2009/099719 | 8/2009 |
| WO | 2009/099728 | 8/2009 |

OTHER PUBLICATIONS

Herrera et al., "Treatment of SCID/human B cell precursor ALL with anti-CD19 and anti-CD22 immunotoxins" *Leukemia* 17(2):334-338 (Feb. 2003).

Jemal et al., "Cancer Statistics, 2002" *CA-A Cancer Journal for Physicians* 52:23-47 (2002).

Miura et al., "Molecular cloning of a human RP105 homologue and chromosomal localization of the mouse and human RP105 genes (Ly64 and LY64)" *Genomics* 38(3):299-304 (Dec. 15, 1996).

Miyake et al., "RP105, a novel B cell surface molecule implicated in B cell activation, is a member of the leucine-rich repeat protein family" *J Immunol.* 154(7):3333-3340 (Apr. 1, 1995).

Szatrowski et al., "Lineage specific treatment of adult patients with acute lymphoblastic leukemia in first remission with anti-B4-blocked ricin or high-dose cytarabine: Cancer and Leukemia Group B Study 93" *Cancer* 97(6):1471-1480 (Mar. 15, 2003).

Tobinai kensei, "Rituximab and other emerging antibodies as molecular target-based therapy of lymphoma" *Int J Clin Oncol.* 8(4):212-223 (Aug. 2003).

Yamashita et al., "Activation mediated by RP105 but not CD40 makes normal B cells susceptible to anti-IgM-induced apoptosis: a role for Fc receptor coligation" *J Exp Med.* 184(1):113-120 (Jul. 1, 1996).

Alfarano et al., "An alternatively spliced form of CD79b gene may account for altered B-cell receptor expression in B-chronic lymphocytic leukemia" *Blood* 93(7):2327-2335 (Apr. 1, 1999).

Andrew G. Polson, et al., "Antibody-drug conjugates targeted to CD79 for the treatment of non-Hodgkin lymphoma" *Blood* 110:616-623 (Jul. 15, 2007).

Barbas et al., "In Vitro Evolution of a Neutralizing Human Antibody to Human Immunodeficiency Virus Type 1 to Enhance Affinity and Broaden Strain Cross-Reactivity" *Proc Natl Acad Sci U S A.* 91(9):3809-3813 (Apr. 1994).

Bernhard et al, "Cysteine analogs of recombinant barley ribosome inactivating protein form antibody conjugates with enhanced stability and potency in vitro" *Bioconjug Chem.* 5(2):126-32 (1994).

Better et al., "Gelonin analogs with engineered cysteine residues form antibody immunoconjugates with unique properties" *J Biol Chem.* 269(13):9644-50 (Apr. 1, 1994).

Bhaskar et al., "E-Selectin Up-Regulation Allows for Targeted Drug Delivery in Prostate Cancer" *Cancer Research* 63:6387-6394 (2003).

Boerner et al., "Production of Antigen-Specific Human Monoclonal Antibodies From In Vitro-Primed Human Splenocytes" *J Immunol.* 147(1):86-95 (Jul. 1991).

Boring et al., "Cancer Statistics, 1993" *CA Cancer J. Clin.* 43(1):7-26 (Jan.-Feb. 1993).

Cabezudo et al., "Quantitative analysis of CD79b, CD5 and CD19 in mature B-cell lymphoproliferative disorders" *Haematologica* 84(5):413-418 (May 1999).

Carter et al., "Humanization of an Anti-p185$^{HER2}$ Antibody for Human Cancer Therapy" *Proc Natl Acad Sci U S A.* 89(10):4285-4289 (May 1992).

Chari et al., "Immunoconjugates Containing Novel Maytansinoids: Promising Anticancer Drugs" *Cancer Research* 52:127-131 (Jan. 1992).

Chen et al., "Selection and analysis of an optimized anti-VEGF antibody: crystal structure of an affinity-matured Fab in complex with antigen" *J Mol Biol.* 293(4):865-881 (Nov. 5, 1999).

Chmura et al., "Antibodies with infinite affinity" *Proc Natl Acad Sci U S A.* 98(15):8480-8484. (Jul. 17, 2001).

Chothia and Lesk, "Canonical Structures for the Hypervariable Regions of Immunoglobulins" *J Mol Biol.* 196(4):901-917 (Aug. 20, 1987).

Cole et al., "The EBV-Hybridoma Technique and Its Application to Human Lung Cancer" *Monoclonal Antibodies and Cancer Therapy*, New York:Alan R. Liss, Inc. pp. 77-96 (1985).

Cragg, "The alternative transcript of CD79b is overexpressed in B-CLL and inhibits signaling for apoptosis" *Blood* 100(9):3068-3076 (Nov. 1, 2002).

D'Arena et al., "Quantitative flow cytometry for the differential diagnosis of leukemic B-cell chronic lymphoproliferative disorders" *Am J Hematol.* 64(4):275-281 (Aug. 2000).

De Pascalis et al., "Grafting of "abbreviated"complementarity-determining regions containing specificity-determining residues essential for ligand contact to engineer a less immunogenic humanized monoclonal antibody" *J. Immunol.* 169:3076-3084 (2002).

Doronina et al., "Development of potent monoclonal antibody auristatin conjugates for cancer therapy" *Nature Biotechnology* 21:778-784 (2003).

Doronina et al., "Enhanced activity of monomethylauristatin F through monoclonal antibody delivery: effects of linker technology on efficacy and toxicity" *Bioconjug Chem.* 17(1):114-124 (Jan. 2006).

Erickson et al., "Antibody-maytansinoid conjugates are activated in targeted cancer cells by lysosomal degradation and linker-dependent intracellular processing" *Cancer Research* 66(8):4426-4433 (Apr. 15, 2006).

Francisco et al., "cAC10-vcMMAE, an anti-CD30 monomethyl auristatin E conjugate with potent and selective antitumor activity" *Blood* 102:1458-1465 (2003).

Garman, *Non-Radioactive Labelling: A Practical Approach*, London:Academic Press pp. 55 (1997).

Greenwood et al., "Engineering multiple-domain forms of the therapeutic antibody CAMPATH-1H: effects on complement lysis" *Therapeutic Immunology* 1(5):247-255 (Oct. 1994).

Hashimoto et al., "Alternative splicing of CD79a (Ig-alpha/mb-1) and CD79b (Ig-beta/B29) RNA transcripts in human B cells" *Mol Immunol.* 32(9):651-659 (Jun. 1995).

Hawkins et al., "Selection of Phage Antibodies by Binding Affinity Mimicking Affinity Maturation" *J Mol Biol.* 226:889-896 (1992).

Hinman et al., "Preparation and Characterization of Monoclonal Antibody conjugates of the Calicheamicins: A Novel and Potent Family of Antitumor Antibiotics" *Cancer Research* 53:3336-3342 (Jul. 15, 1993).

Hoogenboom and Winter, "By-passing immunisation. Human antibodies from synthetic repertoires of germline $V_H$ gene segments rearranged in vitro" *J Mol Biol.* 227(2):381-388 (Sep. 20, 1992).

Jackson et al., "In vitro antibody maturation. Improvement of a high affinity, neutralizing antibody against IL-1$_\beta$" *J Immunol.* 154(7):3310-3319 (1995).

Jones et al., "Replacing the Complementarity-Determining Regions in a Human Antibody with Those From a Mouse" *Nature* 321(6069):522-525 (May 29, 1986).

Junutula et al., "Rapid identification of reactive cysteine residues for site-specific labeling of antibody-Fabs" *J Immunol Methods* 332:41-52 (2008).

Kabat et al., "Sequences of Proteins of Immunological Interest" *U.S. Dept. of Health and Human Services* (Publication No. 91-3242), Fifth edition (1991).

Kanno et al., "Assembling of engineered IgG-binding protein on gold surface for highly oriented antibody immobilization" *J Biotechnol.* 76(2-3):207-214 (Jan. 21, 2000).

Klussman et al., "Secondary mAb-vcMMAE Conjugates Are Highly Sensitive Reporters of Antibody Internalization via the Lysosome Pathway" *Bioconjugate Chemistry* 15(4):765-773 (2004).

Kunkel et al., "Rapid and Efficient Site-specific Mutagenesis Without Phenotypic Selection" *Methods in Enzymology* 154:367-382 (1987).

Lambert, J, "Drug-conjugated monoclonal antibodies for the treatment of cancer" *Curr Opin Pharmacol.* 5(5):543-549 (Oct. 2005).

Li et al., "Human antibodies for immunotherapy development generated via a human B cell hybridoma technology" *Proc Natl Acad Sci U S A.* 103(10):3557-62 (Mar. 2006).

Liu et al., "Eradication of large colon tumor xenografts by targeted delivery of maytansinoids" *Proc Natl Acad Sci U S A.* 93(16):8618-8623 (Aug. 6, 1996).

Lode et al., "Targeted Therapy with a Novel Enediyene Antibiotic Calicheamicin θ I1 Effectively Suppresses Growth and Dissemination of Liver Metastases in a Syngeneic Model of Murine Neuroblastoma" *Cancer Research* 58:2925-2928 (Jul. 15, 1998).

MacCallum, et al., "Antibody-antigen interactions: contact analysis and binding site topography" *J. Mol. Biol.* 262:732-745 (1996).

Mandler et al., "Immunoconjugates of Geldanamycin and Anti-HER2 Monoclonal Antibodies: Antiproliferative Activity on Human Breast Carcinoma Cell Lines" *Journal of the National Cancer Institute* 92(19):1573-1581 (Oct. 4, 2000).

Mandler et al., "Modifications in synthesis strategy improve the yield and efficacy of geldanamycin—herceptin immunoconjugates" *Bioconjugate Chem.* 13:786-791 (2002).

Mandler et al., "Synthesis and Evaluation of Antiproliferative Activity of a Geldanamycin-Herceptin(tm) Immunoconjugate" *Bioorganic & Medicinal Chemistry Letters* 10:1025-1028 (2000).

Mao et al., "EphB2 as a Therapeutic Antibody Drug Target for the Treatment of Colorectal Cancer" *Cancer Research* 64:781-788 (2004).

Marks et al., "By-Passing Immunization: Building High Affinity Human Antibodies by Chain Shuffling" *Bio/Technology* 10:779-783 (Jul. 1992).

Marks et al., "By-Passing Immunization: Human Antibodies From V-gene Libraries Displayed on Phage" *J Mol Biol.* 222(3):581-597 (Dec. 5, 1991).

Matsuuchi et al., "New views of BCR structure and organization" *Curr Opin Immunol.* 13(3):270-277 (Jun. 2001).

Niculescu-Duvaz and Springer, "Antibody-Directed Enzyme Prodrug Therapy (ADEPT): A Review" *Adv. Drg. Del. Rev.* 26:151-172 (1997).

Okazaki et al., "Three new monoclonal antibodies that define a unique antigen associated with prolymphocytic leukemia/non-Hodgkin's lymphoma and are effectively internalized after binding to the cell surface antigen" *Blood* 81(1):84-94 (Jan. 1, 1993).

Olejniczak et al., "A quantitative exploration of surface antigen expression in common B-cell malignancies using flow cytometry" *Immunol Invest.* 35(1):93-114 (2006).

Payne, Gillian, "Progress in Immunoconjugate Cancer Therapeutics" *Cancer Cell* 3:207-212 (2003).

Riechmann et al., "Reshaping Human Antibodies for Therapy" *Nature* 332:323-327 (Mar. 24, 1988).

Rowland et al., "Drug Localisation and Growth Inhibition Studies of Vindesine-Monoclonal anti-CEA Conjugates in a Human Tumour Xenograft" *Cancer Immunol. Immunother.* 21:183-187 (1986).

Rudikoff et al., "Single amino acid substitution altering antigen-binding specificity" *Proc. Natl. Acad. Sci. USA* 79:1979-1983 (Mar. 1982).

Schier et al., "Identification of functional and structural amino-acid residues by parsimonious mutagenesis" *Gene* 169(2):147-155 (Mar. 9, 1996).

Senter et al., "Immunoconjugates comprised of drugs with impaired cellular permeability: a new approach to targeted therapy, Abstract No. 623, presented on Mar. 28, 2004, Proceedings of the American Association for Cancer Research" 45:36 (2004).

Syrigos et al., "Antibody Directed Enzyme Prodrug Therapy (ADEPT: A Review of the Experimental and Clinical Considerations" *Anticancer Research* 19:605-613 (1999).

Thorpe, "Antibody Carriers of Cytotoxic Agents in Cancer Therapy: A Review" *Monoclonal Antibodies 84: Biological and Clinical Applications*, A. Pinchera, G. Doria, F. Dammacco & Bargellesi, Editrice Kurtis s.r.l. pp. 475-506 (1985).

Tu et al., "Protein footprinting at cysteines: probing ATP-modulated contacts in cysteine-substitution mutants of yeast DNA topoisomerase II" *Proc Natl Acad Sci U S A.* 96(9):4862-4867 (Apr. 27, 1999).

van Dijk and van de Winkel, "Human antibodies as next generation therapeutics" *Curr Opin Chem Biol.* 5(4):368-74 (Aug. 2001).

Verhoeyen et al., "Reshaping Human Antibodies: Grafting an Antilysozyme Activity" *Science* 239:1534-1536 (Mar. 1988).

Winter et al., "Making antibodies by phage display technology" *Annu Rev Immunol.* 12:433-455 (1994).

Wu et al., "Arming antibodies: prospects and challenges for immunoconjugates" *Nat Biotechnol.* 23(9):1137-1146 (Sep. 23, 2005).

Yelton et al., "Affinity Maturation of the BR96 Anti-Carcinoma Antibody by Codon-Based Mutagenesis" *The Journal of Immunology* 155:1994-2004 (1995).

Zhang et al., "Complete disulfide bond assignment of a recombinant immunoglobulin G4 monoclonal antibody" *Analytical Biochemistry* 311(1):1-9 (Dec. 1, 2002).

Baldwin et al. et al., "Monoclonal Antibodies in Cancer Treatment" LANCET 327(8481):603-605 (Mar. 15, 1986).

Winter et al., "Antibody-based Therapy" *TiPS* 14:139-143 (May 1993).

Vasile et al., "Isolation and Chemical Characterization of the Human B29 and mb-1 Proteins of the B Cell Antigen Receptor Complex" *Molecular Immunology* 31(6):419-427 (1994).

Maynard et al., "Antibody Engineering" *Annu. Rev. Biomed. Eng.* (2):339-376 (2000).

Pini et al., "Design and Use of a Phage Display Library" The Journal of Biological Chemistry 273:21769-21776 (1998).

Carayannopoulos et al. Fundamental Immunology "Chapter 9, Immunoglobulins Structure and Function, Fv Structure and Diversity in Three Dimensions" William E. Paul, Third Edition, New York:Raven Press,:292-295 (1993).

Holt et al., "Domain antibodies: proteins for therapy" *Trends Biotechnol.* 21(11):484-490 (Nov. 2003).

Davies and Reichmann, "Affinity improvement of single antibody VH domains: residues in all three hypervariable regions affect antigen binding" IMMUNOTECHNOLOGY 2(3):169-179 (Sep. 1996).

Noguchi, "Rationale and Clinical Application of Chimeric and Humanized Antibodies (abstract translated)" Journal of Clinical and Experimental Medicine 167(5):457-462 (Oct. 30, 1993).

Foote, J., et al., "Antibody Framework Residues Affecting the Conformation of the Hypervariable Loops", J.Mol.Biol., 224:487-499 (1992).

Roitt et al. Immunology "Immunologiya" Fifth Edition edition, Moscow:Mosby International,:110 (2000) (English translation provided by McElroy Translation Company).

Cruse et al., Illustrated Dictionary of Immunology "Hybridomas, T cell", Boca Raton: CRC Press, Inc., Vol. Second Edition:294 (1995).

Hermanson, Bioconjugate Techniques "Chapter 10 Antibody Modifications and Conjugation", San Diego: Academic Press, Inc.,:456 (1995).

Zomas et al., "Expression of the immunoglobulin-associated protein B29 in B cell disorders with the monoclonal antibody SN8 (CD79b)" Leukemia 10:1966-1970 (1996).

CAGGGGACAGGCTGCAGCCGGTGCAGTTACACGTTTTCCTCCAAGGAGCCTCGGACGTTG
TCACGGGTTTGGGGTCGGGGACAGAGCAGTGACCATGGCCAGGCTGGCGTTGTCTCCTGT
GCCCAGCCACTGGATGGTGGCGTTGCTGCTGCTGCTCTCAGCTGAGCCAGTACCAGCAGC
CAGATCGGAGGACCGGTACCGGAATCCCAAAGGTAGTGCTTGTTCGCGGATCTGGCAGAG
CCCACGTTTCATAGCCAGGAAACGGGGCTTCACGGTGAAAATGCACTGCTACATGAACAG
CGCCTCCGGCAATGTGAGCTGGCTCTGGAAGCAGGAGATGGACGAGAATCCCCAGCAGCT
GAAGCTGGAAAAGGGCCGCATGGAAGAGTCCCAGAACGAATCTCTCGCCACCCTCACCAT
CCAAGGCATCCGGTTTGAGGACAATGGCATCTACTTCTGTCAGCAGAAGTGCAACAACAC
CTCGGAGGTCTACCAGGGCTGCGGCACAGAGCTGCGAGTCATGGGATTCAGCACCTTGGC
ACAGCTGAAGCAGAGGAACACGCTGAAGGATGGTATCATCATGATCCAGACGCTGCTGAT
CATCCTCTTCATCATCGTGCCTATCTTCCTGCTGCTGGACAAGGATGACAGCAAGGCTGG
CATGGAGGAAGATCACACCTACGAGGGCCTGGACATTGACCAGACAGCCACCTATGAGGA
CATAGTGACGCTGCGGACAGGGGAAGTGAAGTGGTCTGTAGGTGAGCACCCAGGCCAGGA
GTGAGAGCCAGGTCGCCCCATGACCTGGGTGCAGGCTCCCTGGCCTCAGTGACTGCTTCG
GAGCTGCCTGGCTCATGGCCCAACCCCTTTCCTGGACCCCCCAGCTGGCCTCTGAAGCTG
GCCCACCAGAGCTGCCATTTGTCTCCAGCCCCTGGTCCCCAGCTCTTGCCAAAGGGCCTG
GAGTAGAAGGACAACAGGGCAGCAACTTGGAGGGAGTTCTCTGGGGATGGACGGGACCCA
GCCTTCTGGGGGTGCTATGAGGTGATCCGTCCCCACACATGGGATGGGGGAGGCAGAGAC
TGGTCCAGAGCCCGCAAATGGACTCGGAGCCGAGGGCCTCCCAGCAGAGCTTGGGAAGGG
CCATGGACCCAACTGGGCCCCAGAAGAGCCACAGGAACATCATTCCTCTCCCGCAACCAC
TCCCACCCCAGGGAGGCCCTGGCCTCCAGTGCCTTCCCCCGTGGAATAAACGGTGTGTCC
TGAGAAACCA

*FIG. 1*

DNA225786

MARLALSPVPSHWMVALLLLLSAEPVPAARSEDRYRNPKGSACSRIWQSPRFIARKRGFT
VKMHCYMNSASGNVSWLWKQEMDENPQQLKLEKGRMEESQNESLATLTIQGIRFEDNGIY
FCQQKCNNTSEVYQGCGTELRVMGFSTLAQLKQRNTLKDGIIMIQTLLIILFIIVPIFLL
LDKDDSKAGMEEDHTYEGLDIDQTATYEDIVTLRTGEVKWSVGEHPGQE

Signal sequence.
amino acids 1-28.

Transmembrane domain.
amino acids 5-25, 159-179.

Immunoglobulin domain.
amino acids 58-124.

Immunoreceptor tyrosine-based activation motif.
amino acids 193-213.

N-glycosylation site.
amino acids 73-76, 101-104, 127-130, 128-131.

Protein kinase C phosphorylation site.
amino acids 49-51, 60-62, 156-158, 212-214.

Casein kinase II phosphorylation site.
amino acids 99-102, 156-159, 206-209, 221-224.

Tyrosine kinase phosphorylation site.
amino acids 113-120.

N-myristoylation site.
amino acids 40-45, 118-123.

*FIG. 2*

CHIMERIC ANTI-HUMAN CD79b (chMA79b) LIGHT CHAIN

CACTCCCAGCTCCAACTGCACCTCGGTTCTATCGATTGAATTCCACCATGGGATGGTCATGT
ATCATCCTTTTTCTAGTAGCAACTGCAACTGGAGTACATTCAGATATCGTGCTGACCCAATC
TCCAGCTTCTTTGGCTGTGTCTCTGGGGCAGAGGGCCACCATCTCCTGCAAGGCCAGCCAAA
GTGTTGATTATGATGGTGATAGTTTTTTGAACTGGTACCAACAGAAACCAGGACAGCCACCC
AAACTCTTCATCTATGCTGCATCCAATCTAGAATCTGGGATCCCAGCCAGGTTTAGTGGCAG
TGGGTCTGGGACAGACTTCACCCTCAACATCCATCCTGTGGAGGAGGAGGATGCTGCAACCT
ATTACTGTCAGCAAAGTAATGAGGATCCGCTCACGTTCGGGGCAGGCACCGAGCTGGAACTC
AAACGGACCGTGGCTGCACCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACTACGAGAAACA
CAAAGTCTACGCCTGCGAAGTCACCCATCAGGGCCTGAGCTCGCCCGTCACAAAGAGCTTCA
ACAGGGGAGAGTGTTAAGCTTGGCCGCCATGGCCCAACTTGTTTATTGCAGCTTATAATGGT
TACAAATAAAGCAATAGCATCACAAATTTCACAAATAAAGCATTTTTTTCACTGCATTCTAG
TTGTGGTTTGTCCAAACTCATCAATGTATCTTATCATGTCTGGATCGGGAATTAATTCGGC

FIG. 3

CHIMERIC ANTI-HUMAN CD79b (chMA79b) LIGHT CHAIN

DIVLTQSPASLAVSLGQRATISCKASQSVDYDGDSFLNWYQQKPGQPPKLFIYAASNLES
GIPARFSGSGSGTDFTLNIHPVEEEDAATYYCQQSNEDPLTFGAGTELELKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

FIG. 4

CHIMERIC ANTI-HUMAN CD79b (chMA79b) HEAVY CHAIN

TCGGTTCTATCGATTGAATTCCACCATGGGATGGTCATGTATCATCCTTTTTCTAGTAGCAA
CTGCAACTGGAGTACATTCAGAAGTTCAGCTGCAGCAGTCTGGGGCTGAACTGATGAAGCCT
GGGGCCTCAGTGAAGATATCCTGCAAGGCTACTGGCTACACATTCAGTAGTTACTGGATAGA
GTGGGTAAAGCAGAGGCCTGGACATGGCCTTGAGTGGATTGGAGAGATTTTACCTGGAGGTG
GTGATACTAACTACAATGAGATTTTCAAGGGCAAGGCCACATTCACTGCAGATACATCCTCC
AACACAGCCTACATGCAACTCAGCAGCCTGACATCTGAGGACTCTGCCGTCTATTACTGTAC
AAGACGAGTACCGGTTTACTTTGACTACTGGGGCCAAGGAACCTCAGTCACCGTCTCCTCAG
CCTCCACCAAGGGCCCATCGGTCTTCCCCCTGGCACCCTCCTCCAAGAGCACCTCTGGGGGC
ACAGCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGACTCT
ACTCCCTCAGCAGCGTGGTGACTGTGCCCTCTAGCAGCTTGGGCACCCAGACCTACATCTGC
AACGTGAATCACAAGCCCAGCAACACCAAGGTGGACAAGAAAGTTGAGCCCAAATCTTGTGA
CAAAACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGAGA
ACCACAGGTGTACACCCTGCCCCCATCCCGGGAAGAGATGACCAAGAACCAGGTCAGCCTGA
CCTGCCTGGTCAAAGGCTTCTATCCCAGCGACATCGCCGTGGAGTGGGAGAGCAATGGGCAG
CCGGAGAACAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCATGCTCCGTGA
TGCATGAGGCTCTGCACAACCACTACACGCAGAAGAGCCTCTCCCTGTCTCCGGGTAAATGA
GTGCGACGGCCCTAGAGTCGACCTGCAGAAGCTTGGCCGCCAT

*FIG. 5*

CHIMERIC ANTI-HUMAN CD79b (chMA79b) HEAVY CHAIN

EVQLQQSGAELMKPGASVKISCKATGYTFSSYWIEWVKQRPGHGLEWIGEILPGGGDTNY
NEIFKGKATFTADTSSNTAYMQLSSLTSEDSAVYYCTRRVPVYFDYWGQGTSVTVSS<u>AST</u>
<u>KGPSVFPLAPSSKSTSGGTAALGCLVKDYFPEPVTVSWNSGALTSGVHTFPAVLQSSGLY</u>
<u>SLSSVVTVPSSSLGTQTYICNVNHKPSNTKVDKKVEPKSCDKTHTCPPCPAPELLGGPSV</u>
<u>FLFPPKPKDTLMISRTPEVTCVVVDVSHEDPEVKFNWYVDGVEVHNAKTKPREEQYNSTY</u>
<u>RVVSVLTVLHQDWLNGKEYKCKVSNKALPAPIEKTISKAKGQPREPQVYTLPPSREEMTK</u>
<u>NQVSLTCLVKGFYPSDIAVEWESNGQPENNYKTTPPVLDSDGSFFLYSKLTVDKSRWQQG</u>
<u>NVFSCSVMHEALHNHYTQKSLSLSPG</u>

VL Sequences

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | Kabat – CDR L3 | | | | | | | | | | | | | | | | | | | | |
| | | | | | | | | | | | | | | | Chothia – CDR L3 | | | | | | | | | | | | | | | | | | | | |
| | | | | | | | | | | | | | | | Contact – CDR L3 | | | | | | | | | | | | | | | | | | | | |
| huKI | E | D | F | A | T | Y | Y | C | Q | Q | Y | N | S | L | P | | | | | | | W | T | F | G | Q | G | T | K | V | E | I | K | R | SEQ ID NO: 9 |
| MA79b | E | D | A | A | T | Y | Y | C | Q | Q | S | E | D | P | | | | | | | | L | T | F | G | A | G | T | L | L | E | L | K | R | SEQ ID NO: 10 |
| huMA79b graft | E | D | F | A | T | Y | Y | C | Q | Q | S | E | D | P | | | | | | | | L | T | F | G | Q | G | T | K | V | E | I | K | R | SEQ ID NO: 11 |
| huMA79b.v17 | E | D | F | A | T | Y | Y | C | Q | Q | S | N | D | P | | | | | | | | L | T | F | G | Q | G | T | K | V | E | I | K | R | SEQ ID NO: 169 |
| huMA79b.v18 | E | D | F | A | T | Y | Y | C | Q | Q | S | N | D | P | | | | | | | | L | T | F | G | Q | G | T | K | V | E | I | K | R | SEQ ID NO: 188 |
| huMA79b.v28 | E | D | F | A | T | Y | Y | C | Q | Q | S | N | D | P | | | | | | | | L | T | F | G | Q | G | T | K | V | E | I | K | R | SEQ ID NO: 207 |
| huMA79b.v32 | E | D | F | A | T | Y | Y | C | Q | Q | S | N | D | P | | | | | | | | L | T | F | G | Q | G | T | K | V | E | I | K | R | SEQ ID NO: 226 |

VH Sequences

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| humIII | E | V | Q | L | V | E | S | G | G | G | L | V | Q | P | G | G | S | L | R | L | S | C | A | A | S | G | F | T | F | S | S | Y | A | M | S | | | W | V | R | Q | A | P |
| MA79b | E | V | Q | L | V | Q | S | G | A | E | L | M | K | P | G | A | S | V | K | I | S | C | K | A | T | G | Y | T | F | S | S | Y | W | I | E | | | W | V | K | Q | R | K |
| huMA79b graft | E | V | Q | L | V | E | S | G | G | G | L | V | Q | P | G | G | S | L | R | L | S | C | A | A | S | G | Y | T | F | S | S | Y | W | I | E | | | W | V | R | Q | A | P |
| huMA79b.v17 | E | V | Q | L | V | E | S | G | G | G | L | V | Q | P | G | G | S | L | R | L | S | C | A | A | S | G | Y | T | F | S | S | Y | W | I | E | | | W | V | R | Q | A | P |
| huMA79b.v18 | E | V | Q | L | V | E | S | G | G | G | L | V | Q | P | G | G | S | L | R | L | S | C | A | A | S | G | Y | T | F | S | S | Y | W | I | E | | | W | V | R | Q | A | P |
| huMA79b.v28 | E | V | Q | L | V | E | S | G | G | G | L | V | Q | P | G | G | S | L | R | L | S | C | A | A | S | G | Y | T | F | S | S | Y | W | I | E | | | W | V | R | Q | A | P |
| huMA79b.v32 | E | V | Q | L | V | E | S | G | G | G | L | V | Q | P | G | G | S | L | R | L | S | C | A | A | S | G | Y | T | F | S | S | Y | W | I | E | | | W | V | R | Q | A | P |

| Kabat# | 42 | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| humIII | G | K | G | L | E | W | V | S | V | I | S | G | D | G | G | S | T | Y | Y | A | D | S | V | K | G | R | F | T | I | S | R | D | N | S | K | N | T | L | Y | L | Q | M |
| MA79b | G | H | G | L | E | W | I | G | E | I | L | P | G | G | G | D | T | N | Y | N | E | I | F | K | G | K | A | T | F | T | A | D | T | S | S | N | T | A | Y | M | Q | L |
| huMA79b graft | G | K | G | L | E | W | V | G | E | I | L | P | G | G | G | D | T | N | Y | N | E | I | F | K | G | R | F | T | I | S | A | D | T | S | K | N | T | A | Y | L | Q | L |
| huMA79b.v17 | G | K | G | L | E | W | I | G | E | I | L | P | G | G | G | D | T | N | Y | N | E | I | F | K | G | R | A | T | F | T | A | D | T | S | K | N | T | A | Y | L | Q | L |
| huMA79b.v18 | G | K | G | L | E | W | I | G | E | I | L | P | G | G | G | D | T | N | Y | N | E | I | F | K | G | R | A | T | F | T | A | D | T | S | K | N | T | A | Y | L | Q | L |
| huMA79b.v28 | G | K | G | L | E | W | I | G | E | I | L | P | G | G | G | D | T | N | Y | N | E | I | F | K | G | R | A | T | F | T | A | D | T | S | K | N | T | A | Y | L | Q | L |
| huMA79b.v32 | G | K | G | L | E | W | I | G | E | I | L | P | G | G | G | D | T | N | Y | N | E | I | F | K | G | R | A | T | F | T | A | D | T | S | K | N | T | A | Y | L | Q | L |

FIG. 8A

VH Sequences

| Kabat# | 81 | 82 | A | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | |
| | | | | | | | | | | | | | | | Kabat - CDR H3 spans 95–102 | | | | | | | | | | | | | | | | | | | | |
| | | | | | | | | | | | | | | | Chothia - CDR H3 | | | | | | | | | | | | | | | | | | | | |
| | | | | | | | | | | | | | Contact - CDR H3 | | | | | | | | | | | | | | | | | | | | | | |
| humIII | Q | M | N | S | L | R | A | E | D | T | A | V | Y | Y | C | A | R | | | | G | | | | | | | | | | | | | | W | G |
| MA79b | Q | L | S | S | L | T | S | E | D | T | A | V | Y | Y | C | T | R | R | V | P | Y | | | | | | | | | | | | F | D | Y | W | G |
| huMA79b graft | Q | M | N | S | L | R | A | E | D | T | A | V | Y | Y | C | A | R | R | V | P | Y | | | | | | | | | | | | F | D | Y | W | G |
| huMA79b.v17 | Q | M | N | S | L | R | A | E | D | T | A | V | Y | Y | C | A | R | R | V | P | V | Y | | | | | | | | | | | F | D | Y | W | G |
| huMA79b.v18 | Q | M | N | S | L | R | A | E | D | T | A | V | Y | Y | C | A | R | R | V | P | V | Y | | | | | | | | | | | L | D | Y | W | G |
| huMA79b.v28 | Q | M | N | S | L | R | A | E | D | T | A | V | Y | Y | C | A | R | R | V | P | I | R | | | | | | | | | | | L | D | Y | W | G |
| huMA79b.v32 | Q | M | N | S | L | R | A | E | D | T | A | V | Y | Y | C | A | R | R | V | P | I | R | | | | | | | | | | | * | * | * | W | G |
| | | | | | | | | | | | | | | | | F1 | 2 | 3 | 4 | 5 | 6 | 7 | | | | | | | | | | | 8 | 9 | 10 | |

| Kabat# | 105 | 106 | 107 | 108 | 109 | 110 | 111 | 112 | 113 | |
|---|---|---|---|---|---|---|---|---|---|---|
| humIII | Q | G | T | L | V | T | V | S | S | |
| MA79b | Q | G | T | S | L | V | T | V | S | S |
| huMA79b graft | Q | G | T | L | V | T | V | S | S | |
| huMA79b.v17 | Q | G | T | L | V | T | V | S | S | |
| huMA79b.v18 | Q | G | T | L | V | T | V | S | S | |
| huMA79b.v28 | Q | G | T | L | V | T | V | S | S | |
| huMA79b.v32 | Q | G | T | L | V | T | V | S | S | |

| | |
|---|---|
| humIII | |
| MA79b | SEQ ID NO: 13 |
| huMA79b graft | SEQ ID NO: 14 |
| huMA79b.v17 | SEQ ID NO: 15 |
| huMA79b.v18 | SEQ ID NO: 170 |
| huMA79b.v28 | SEQ ID NO: 189 |
| huMA79b.v32 | SEQ ID NO: 208 |
| | SEQ ID NO: 227 |

FIG. 8B

```
   A  1  2  3  4  5  6  7  8  9  10 11 12 13 14 15
L1    K  A  S  Q  S  V  D  Y  D  G  D  S  F  L  N    SEQ ID NO: 131
      K  A  S  K  S  V  D  Y  D  G  D  S  F  L  N    SEQ ID NO: 17; SPL-2

B  1  2  3  4  5  6  7
      A  A  S  N  L  E  S    SEQ ID NO: 132
L2    A  A  S  N  R  E  S    SEQ ID NO: 18
      A  A  S  N  L  K  S    SEQ ID NO: 19

C  1  2  3  4  5  6  7  8  9
      Q  Q  S  N  E  D  P  L  T    SEQ ID NO: 133
L3    Q  Q  S  N  S  D  P  L  T    SEQ ID NO: 20; SPL-5
      Q  Q  S  N  K  D  P  L  T    SEQ ID NO: 21
```

*FIG. 9*

|  | Biacore KD (nM) |  |  |
| --- | --- | --- | --- |
| MA79b Variant IgG | Fab | IgG | Immobilized Antigen |
| MA79b | 200 | 2 | hu CD79b.ecd-Fc |
|  |  | 4.7 | hu CD79b.ecd |
| hu MA79b graft |  | 261 | hu CD79b.ecd |
| hu MA79b L2-2 | 44 |  | hu CD79b.ecd-Fc |
|  | 39 | 43 | hu CD79b.ecd |
| hu MA79b H3-10 |  | 29 | hu CD79b.ecd |
| hu MA79b H1-6 |  | 42 | hu CD79b.ecd |
| hu MA79b L2/H3 |  | 2 | hu CD79b.ecd-Fc |
|  |  | 3 | hu CD79b.ecd |
|  |  | 1 | 16mer peptide |

*FIG. 11*

| huMA79 FW Variant IgG | Murine Framework Residues Present VL | Murine Framework Residues Present VH | | | | | | | | Changes for Stability in VL | | | | CDR-H3 seq | $Kd_{variant}/Kd_{chimera}$ |
|---|---|---|---|---|---|---|---|---|---|---|---|---|---|---|---|
| | 4 47 | 48 | 67 | 69 | 71 | 73 | 75 | 78 | 80 | 28 | 29 | 94 | 95 | | |
| huMA79 graft | | | | | 71 | 73 | | 78 | | | | | | wt | 56 |
| All Framework | 4 47 | 48 | 67 | 69 | 71 | 73 | 75 | 78 | 80 | | | | | wt | 1 |
| 1 | | 48 | | | 71 | 73 | | 78 | | | | | | wt | 9.4 |
| 2 | 47 | | | | 71 | 73 | | 78 | | | | | | wt | 18 |
| 3 | | | 67 | 69 | 71 | 73 | 75 | 78 | 80 | | | | | wt | 5.5 |
| 4 | | | | 69 | 71 | 73 | 75 | 78 | 80 | | | | | wt | 12 |
| 5 | | 48 | 67 | 69 | 71 | 73 | 75 | 78 | 80 | | | | | wt | 3.5 |
| 6 | | 48 | 67 | | 71 | 73 | | 78 | | | | | | wt | 7.6 |
| 7 | | 48 | | 69 | 71 | 73 | | 78 | | | | | | wt | 3.5 |
| 8 | | 48 | 67 | 69 | 71 | 73 | | 78 | | | | | | wt | 1.7 |
| 9 | | 48 | 67 | 69 | 71 | 73 | | 78 | 80 | | | | | wt | 1.8 |
| 10 | | 48 | 67 | 69 | 71 | 73 | 75 | 78 | | | | | | wt | NA |
| 11 | | 48 | 67 | 69 | 71 | 73 | 75 | 78 | 80 | | | | | H3-10 | 0.6 |
| 12 | | 48 | 67 | 69 | 71 | 73 | | 78 | | | | | | H3-10 | 0.5 |
| 13 | 47 | 48 | | 69 | 71 | 73 | | 78 | | | | | | wt | 1.8 |
| 14 | 4 | 48 | | 69 | 71 | 73 | | 78 | | | | | | wt | 1.1 |
| 15 | 4 47 | 48 | | 69 | 71 | 73 | | 78 | | | | | | wt | 0.8 |
| 16 | 4 | 48 | 67 | | 71 | 73 | | 78 | | | | | | wt | 1.6 |
| 17 | 4 | 48 | 67 | 69 | 71 | 73 | | 78 | | | | | | wt | 1.0 |
| 18 | 4 | 48 | 67 | 69 | 71 | 73 | | 78 | | | | | | H3-10 | 0.4 |
| 19 | 4 | 48 | 67 | 69 | 71 | 73 | | 78 | | S | | E | | H3-10 | NDB |
| 20 | 4 | 48 | 67 | 69 | 71 | 73 | | 78 | | S | | N | | H3-10 | NDB |
| 21 | 4 | 48 | 67 | 69 | 71 | 73 | | 78 | | E | | N | | H3-10 | NDB |
| 22 | 4 | 48 | 67 | 69 | 71 | 73 | | 78 | | E | | N | | H3-10 | NDB |
| 23 | 4 47 | 48 | 67 | 69 | 71 | 73 | | 78 | | S | | E | | H3-10 | 25 |
| 24 | 4 47 | 48 | 67 | 69 | 71 | 73 | | 78 | | S | | N | | H3-10 | NDB |
| 25 | 4 47 | 48 | 67 | 69 | 71 | 73 | | 78 | | E | | E | | H3-10 | NDB |
| 26 | 4 47 | 48 | 67 | 69 | 71 | 73 | | 78 | | E | | N | | H3-10 | NDB |
| 27 | 4 47 | 48 | 67 | 69 | 71 | 73 | | 78 | | | | | | H3-10 | |
| 28 | 4 | 48 | 67 | 69 | 71 | 73 | | 78 | | E | | | | H3-10 | 0.8 |
| 29 | | 48 | 67 | 69 | 71 | 73 | | 78 | | | | N | | H3-10 | very weak |
| 30 | 4 47 | 48 | 67 | 69 | 71 | 73 | | 78 | | | A | | S | H3-10 | 1.3 |
| 31 | 4 47 | 48 | 67 | 69 | 71 | 73 | | 78 | | | A | | S | H3-10 | 1.0 |
| 32 | 4 47 | 48 | 67 | 69 | 71 | 73 | | 78 | | S | | | | H3-10 | 1.6 |
| 33 | 4 47 | 48 | 67 | 69 | 71 | 73 | | 78 | | | | | A | H3-10 | very weak |
| 34 | 4 47 | 48 | 67 | 69 | 71 | 73 | | 78 | | | | E | | H3-10 | NDB |

FIG. 12

I
A  QVQLVQSGAEVKKPGASVKVSCKASGYTFT -H1- WVRQAPGQGLEWMG -H2-
B  QVQLVQSGAEVKKPGASVKVSCKAS -H1- WVRQAPGQGLEWM -H2-
C  QVQLVQSGAEVKKPGASVKVSCKAS -H1- WVRQAPGQGLEWM -H2-
D  QVQLVQSGAEVKKPGASVKVSCKAS -H1- WVRQAPGQGLEWM -H2-

II
A  QVQLQESGPGLVKPSQTLSLTCTVSGGSVS -H1- WIRQPPGKGLEWIG -H2-
B  QVQLQESGPGLVKPSQTLSLTCTVS -H1- WIRQPPGKGLEWI -H2-
C  QVQLQESGPGLVKPSQTLSLTCTVS -H1- WIRQPPGKGLEWI -H2-
D  QVQLQESGPGLVKPSQTLSLTCTVS -H1- WIRQPPGKGLEWI -H2-

III
A  EVQLVESGGGLVQPGGSLRLSCAASGFTFS -H1- WVRQAPGKGLEWVS -H2-
B  EVQLVESGGGLVQPGGSLRLSCAAS -H1- WVRQAPGKGLEWV -H2-
C  EVQLVESGGGLVQPGGSLRLSCAAS -H1- WVRQAPGKGLEWV -H2-
D  EVQLVESGGGLVQPGGSLRLSCAAS -H1- WVRQAPGKGLEWV -H2-

Acceptor
A  EVQLVESGGGLVQPGGSLRLSCAASGFNIK -H1- WVRQAPGKGLEWVS -H2-
B  EVQLVESGGGLVQPGGSLRLSCAAS -H1- WVRQAPGKGLEWV -H2-
C  EVQLVESGGGLVQPGGSLRLSCAAS -H1- WVRQAPGKGLEWV -H2-

Second Acceptor
A  EVQLVESGGGLVQPGGSLRLSCAASGFNIK -H1- WVRQAPGKGLEWVS -H2-
B  EVQLVESGGGLVQPGGSLRLSCAAS -H1- WVRQAPGKGLEWV -H2-
C  EVQLVESGGGLVQPGGSLRLSCAAS -H1- WVRQAPGKGLEWV -H2-
D  EVQLVESGGGLVQPGGSLRLSCAAS -H1- WVRQAPGKGLEWV -H2-

*FIG. 13A*

| | | | |
|---|---|---|---|
| I | | | |
| A | RVTITADTSTSTAYMELSSLRSEDTAVYYCAR | -H3- | WGQGTLVTVSS SEQ ID NO.: 108 |
| B | RVTITADTSTSTAYMELSSLRSEDTAVYYCAR | -H3- | WGQGTLVTVSS SEQ ID NO.: 109 |
| C | RVTITADTSTSTAYMELSSLRSEDTAVYYCA | -H3- | WGQGTLVTVSS SEQ ID NO.: 110 |
| D | RVTITADTSTSTAYMELSSLRSEDTAVYYC | -H3- | WGQGTLVTVSS SEQ ID NO.: 111 |
| II | | | |
| A | RVTISVDTSKNQFSLKLSSVTAADTAVYYCAR | -H3- | WGQGTLVTVSS SEQ ID NO.: 112 |
| B | RVTISVDTSKNQFSLKLSSVTAADTAVYYCAR | -H3- | WGQGTLVTVSS SEQ ID NO.: 113 |
| C | RVTISVDTSKNQFSLKLSSVTAADTAVYYCA | -H3- | WGQGTLVTVSS SEQ ID NO.: 114 |
| D | RVTISVDTSKNQFSLKLSSVTAADTAVYYC | -H3- | WGQGTLVTVSS SEQ ID NO.: 115 |
| III | | | |
| A | RFTISRDNSKNTLYLQMNSLRAEDTAVYYCAR | -H3- | WGQGTLVTVSS SEQ ID NO.: 116 |
| B | RFTISRDNSKNTLYLQMNSLRAEDTAVYYCAR | -H3- | WGQGTLVTVSS SEQ ID NO.: 117 |
| C | RFTISRDNSKNTLYLQMNSLRAEDTAVYYCA | -H3- | WGQGTLVTVSS SEQ ID NO.: 118 |
| D | RFTISRDNSKNTLYLQMNSLRAEDTAVYYC | -H3- | WGQGTLVTVSS SEQ ID NO.: 119 |
| Acceptor | | | |
| A | RFTISADTSKNTAYLQMNSLRAEDTAVYYCSR | -H3- | WGQGTLVTVSS SEQ ID NO.: 120 |
| B | RFTISADTSKNTAYLQMNSLRAEDTAVYYCSR | -H3- | WGQGTLVTVSS SEQ ID NO.: 121 |
| C | RFTISADTSKNTAYLQMNSLRAEDTAVYYCS | -H3- | WGQGTLVTVSS SEQ ID NO.: 122 |
| Second Acceptor | | | |
| A | RFTISADTSKNTAYLQMNSLRAEDTAVYYCAR | -H3- | WGQGTLVTVSS SEQ ID NO.: 123 |
| B | RFTISADTSKNTAYLQMNSLRAEDTAVYYCAR | -H3- | WGQGTLVTVSS SEQ ID NO.: 124 |
| C | RFTISADTSKNTAYLQMNSLRAEDTAVYYCA | -H3- | WGQGTLVTVSS SEQ ID NO.: 125 |
| D | RFTISADTSKNTAYLQMNSLRAEDTAVYYC | -H3- | WGQGTLVTVSS SEQ ID NO.: 126 |

*FIG. 13B*

A. huMA79b.v17 Light Chain
```
FR1-LC:    DIQLTQSPSSLSASVGDRVTITC (SEQ ID NO: 152)
FR2-LC:    WYQQKPGKAPKLLIY (SEQ ID NO: 153)
FR3-LC:    GVPSRFSGSGSGTDFTLTISSLQPEDFATYYC (SEQ ID NO: 154)
FR4-LC:    FGQGTKVEIKR (SEQ ID NO: 155)
HVR1-LC:   KASQSVDYDGDSFLN (SEQ ID NO: 156)
HVR2-LC:   AASNLES (SEQ ID NO: 157)
HVR3-LC:   QQSNEDPLT (SEQ ID NO: 158)
CL1:       TVAAPSVFIFPPSDEQLKSGTASVVCLLNNFYPREAKVQWKVDNALQSGNSQESVTEQDSK
           DSTYSLSSTLTLSKADYEKHKVYACEVTHQGLSSPVTKSFNRGEC (SEQ ID NO: 159)
```

Light Chain:
DIQLTQSPSSLSASVGDRVTITCKASQSVDYDGDSFLNWYQQKPGKAPKLLIYAASNLESGVPSRFSGS
GSGTDFTLTISSLQPEDFATYYCQQSNEDPLTFGQGTKVEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGLSS
PVTKSFNRGEC (SEQ ID NO: 303)

LC-Variable Domain:
DIQLTQSPSSLSASVGDRVTITCKASQSVDYDGDSFLNWYQQKPGKAPKLLIYAASNLESGVPSRFSGS
GSGTDFTLTISSLQPEDFATYYCQQSNEDPLTFGQGTKVEIKR (SEQ ID NO: 169)

B. huMA79b.v17 Heavy Chain
```
FR1-HC:    EVQLVESGGGLVQPGGSLRLSCAAS (SEQ ID NO: 160)
FR2-HC:    WVRQAPGKGLEWI (SEQ ID NO: 161)
FR3-HC:    RATFSADTSKNTAYLQMNSLRAEDTAVYYC (SEQ ID NO: 162)
FR4-HC:    WGQGTLVTVSS (SEQ ID NO: 163)
HVR1-HC:   GYTFSSYWIE (SEQ ID NO: 164)
HVR2-HC:   GEILPGGGDTNYNEIFKG (SEQ ID NO: 165)
HVR3-HC:   TRRVPVYFDY (SEQ ID NO: 166)
CH1:       ASTKGPSVFPLAPSSKSTSGGTAALGCLVKDYFPEPVTVSWNSGALTSGVHTFPA
           VLQSSGLYSLSSVVTVPSSSLGTQTYICNVNHKPSNTKVDKKVEPKSCDKTHT
           (SEQ ID NO:167)
Fc:        CPPCPAPELLGGPSVFLFPPKPKDTLMISRTPEVTCVVVDVSHEDPEVKFNWYVDGVEVH
           NAKTKPREEQYNSTYRVVSVLTVLHQDWLNGKEYKCKVSNKALPAPIEKTISKAKGQPREP
           QVYTLPPSREEMTKNQVSLTCLVKGFYPSDIAVEWESNGQPENNYKTTPPVLDSDGSFFL
           YSKLTVDKSRWQQGNVFSCSVMHEALHNHYTQKSLSLSPG (SEQ ID NO: 168)
```

Heavy Chain:
EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPVYFDYWGQGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO: 304)

HC-Variable Domain:
EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPVYFDYWGQGTLVTVSS (SEQ ID NO: 170)

FIG. 15

A. huMA79b.v18 Light Chain
```
FR1-LC:   DIQLTQSPSSLSASVGDRVTITC (SEQ ID NO: 171)
FR2-LC:   WYQQKPGKAPKLLIY (SEQ ID NO: 172)
FR3-LC:   GVPSRFSGSGSGTDFTLTISSLQPEDFATYYC (SEQ ID NO: 173)
FR4-LC:   FGQGTKVEIKR (SEQ ID NO: 174)
HVR1-LC:  KASQSVDYDGDSFLN (SEQ ID NO: 175)
HVR2-LC:  AASNLES (SEQ ID NO: 176)
HVR3-LC:  QQSNEDPLT (SEQ ID NO: 177)
CL1:      TVAAPSVFIFPPSDEQLKSGTASVVCLLNNFYPREAKVQWKVDNALQSGNSQESVTEQDSK
          DSTYSLSSTLTLSKADYEKHKVYACEVTHQGLSSPVTKSFNRGEC (SEQ ID NO: 178)
```

Light Chain:
DIQLTQSPSSLSASVGDRVTITCKASQSVDYDGDSFLNWYQQKPGKAPKLLIYAASNLESGVPSRFSGS
GSGTDFTLTISSLQPEDFATYYCQQSNEDPLTFGQGTKVEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGLSS
PVTKSFNRGEC (SEQ ID NO: 305)

LC-Variable Domain:
DIQLTQSPSSLSASVGDRVTITCKASQSVDYDGDSFLNWYQQKPGKAPKLLIYAASNLESGVPSRFSGS
GSGTDFTLTISSLQPEDFATYYCQQSNEDPLTFGQGTKVEIKR (SEQ ID NO: 188)

B. huMA79b.v18 Heavy Chain
```
FR1-HC:   EVQLVESGGGLVQPGGSLRLSCAAS (SEQ ID NO: 179)
FR2-HC:   WVRQAPGKGLEWI (SEQ ID NO: 180)
FR3-HC:   RATFSADTSKNTAYLQMNSLRAEDTAVYYC (SEQ ID NO: 181)
FR4-HC:   WGQGTLVTVSS (SEQ ID NO: 182)
HVR1-HC:  GYTFSSYWIE (SEQ ID NO: 183)
HVR2-HC:  GEILPGGGDTNYNEIFKG (SEQ ID NO: 184)
HVR3-HC:  TRRVPIRLDY (SEQ ID NO: 185)
CH1:      ASTKGPSVFPLAPSSKSTSGGTAALGCLVKDYFPEPVTVSWNSGALTSGVHTFPA
          VLQSSGLYSLSSVVTVPSSSLGTQTYICNVNHKPSNTKVDKKVEPKSCDKTHT
          (SEQ ID NO: 186)
Fc:       CPPCPAPELLGGPSVFLFPPKPKDTLMISRTPEVTCVVVDVSHEDPEVKFNWYVDGVEVH
          NAKTKPREEQYNSTYRVVSVLTVLHQDWLNGKEYKCKVSNKALPAPIEKTISKAKGQPREP
          QVYTLPPSREEMTKNQVSLTCLVKGFYPSDIAVEWESNGQPENNYKTTPPVLDSDGSFFL
          YSKLTVDKSRWQQGNVFSCSVMHEALHNHYTQKSLSLSPG (SEQ ID NO: 187)
```

Heavy Chain:
EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPIRLDYWGQGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO: 306)

HC-Variable Domain:
EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPIRLDYWGQGTLVTVSS (SEQ ID NO: 189)

*FIG. 16*

A. huMA79b.v28 Light Chain

| | |
|---|---|
| FR1-LC: | DIQLTQSPSSLSASVGDRVTITC (SEQ ID NO: 190) |
| FR2-LC: | WYQQKPGKAPKLLIY (SEQ ID NO: 191) |
| FR3-LC: | GVPSRFSGSGSGTDFTLTISSLQPEDFATYYC (SEQ ID NO: 192) |
| FR4-LC: | FGQGTKVEIKR (SEQ ID NO: 193) |
| HVR1-LC: | KASQSVDYEGDSFLN (SEQ ID NO: 194) |
| HVR2-LC: | AASNLES (SEQ ID NO: 195) |
| HVR3-LC: | QQSNEDPLT (SEQ ID NO: 196) |
| CL1: | TVAAPSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC (SEQ ID NO: 197) |

Light Chain:
DIQLTQSPSSLSASVGDRVTITCKASQSVDYEGDSFLNWYQQKPGKAPKLLIYAASNLESGVPSRFSG
SGSGTDFTLTISSLQPEDFATYYCQQSNEDPLTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQG
LSSPVTKSFNRGEC (SEQ ID NO: 307)

B. huMA79b.v28 Heavy Chain

| | |
|---|---|
| FR1-HC: | EVQLVESGGGLVQPGGSLRLSCAAS (SEQ ID NO: 198) |
| FR2-HC: | WVRQAPGKGLEWI (SEQ ID NO: 199) |
| FR3-HC: | RATFSADTSKNTAYLQMNSLRAEDTAVYYC (SEQ ID NO: 200) |
| FR4-HC: | WGQGTLVTVSS (SEQ ID NO: 201) |
| HVR1-HC: | GYTFSSYWIE (SEQ ID NO: 202) |
| HVR2-HC: | GEILPGGGDTNYNEIFKG (SEQ ID NO: 203) |
| HVR3-HC: | TRRVPIRLDY (SEQ ID NO: 204) |
| CH1: | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHT (SEQ ID NO: 205) |
| Fc: | CPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPG (SEQ ID NO: 206) |

Heavy Chain:
EVQLVESGGGLVQPGGSLRLSCAASGYTFSSYWIEWVRQAPGKGLEWIGEILPGGGDTNYNEIFKGRA
TFSADTSKNTAYLQMNSLRAEDTAVYYCTRRVPIRLDYWGQGTLVTVSSASTKGPSVFPLAPSSKSTS
GGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPG (SEQ ID NO: 308)

*FIG. 17*

A. huMA79b.v32 Light Chain
FR1-LC:   DIQLTQSPSSLSASVGDRVTITC (SEQ ID NO: 209)
FR2-LC:   WYQQKPGKAPKLFIY (SEQ ID NO: 210)
FR3-LC:   GVPSRFSGSGSGTDFTLTISSLQPEDFATYYC (SEQ ID NO: 211)
FR4-LC:   FGQGTKVEIKR (SEQ ID NO: 212)
HVR1-LC:  KASQSVDYSGDSFLN (SEQ ID NO: 213)
HVR2-LC:  AASNLES (SEQ ID NO: 214)
HVR3-LC:  QQSNEDPLT (SEQ ID NO: 215)
CL1:      TVAAPSVFIFPPSDEQLKSGTASVVCLLNNFYPREAKVQWKVDNALQSGNSQESVTEQDSK
          DSTYSLSSTLTLSKADYEKHKVYACEVTHQGLSSPVTKSFNRGEC (SEQ ID NO: 216)

Light Chain:
DIQLTQSPSSLSASVGDRVTITCKASQSVDYSGDSFLNWYQQKPGKAPKLFIYAASNLESGVPSRFSGS
GSGTDFTLTISSLQPEDFATYYCQQSNEDPLTFGQGTKVEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGLSS
PVTKSFNRGEC (SEQ ID NO: 309)

LC-Variable Domain:
DIQLTQSPSSLSASVGDRVTITCKASQSVDYSGDSFLNWYQQKPGKAPKLFIYAASNLESGVPSRFSGS
GSGTDFTLTISSLQPEDFATYYCQQSNEDPLTFGQGTKVEIKR (SEQ ID NO: 226)

B. huMA79b.v32 Heavy Chain
FR1-HC:   EVQLVESGGGLVQPGGSLRLSCAAS (SEQ ID NO: 217)
FR2-HC:   WVRQAPGKGLEWI (SEQ ID NO: 218)
FR3-HC:   RATFSADTSKNTAYLQMNSLRAEDTAVYYC (SEQ ID NO: 219)
FR4-HC:   WGQGTLVTVSS (SEQ ID NO: 220)
HVR1-HC:  GYTFSSYWIE (SEQ ID NO: 221)
HVR2-HC:  GEILPGGGDTNYNEIFKG (SEQ ID NO: 222)
HVR3-HC:  TRRVPIRLDY (SEQ ID NO: 223)
CH1:      ASTKGPSVFPLAPSSKSTSGGTAALGCLVKDYFPEPVTVSWNSGALTSGVHTFPA
          VLQSSGLYSLSSVVTVPSSSLGTQTYICNVNHKPSNTKVDKKVEPKSCDKTHT
          (SEQ ID NO: 224)
Fc:       CPPCPAPELLGGPSVFLFPPKPKDTLMISRTPEVTCVVVDVSHEDPEVKFNWYVDGVEVH
          NAKTKPREEQYNSTYRVVSVLTVLHQDWLNGKEYKCKVSNKALPAPIEKTISKAKGQPREP
          QVYTLPPSREEMTKNQVSLTCLVKGFYPSDIAVEWESNGQPENNYKTTPPVLDSDGSFFL
          YSKLTVDKSRWQQGNVFSCSVMHEALHNHYTQKSLSLSPG (SEQ ID NO: 225)

Heavy Chain:
EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPIRLDYWGQGTLVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO: 310)

HC-Variable Domain:
EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPIRLDYWGQGTLVTVSS (SEQ ID NO: 227)

*FIG. 18*

| | | Signal Sequence | Test Peptide | |
|---|---|---|---|---|
| hCD79b | 1 | MARLALSPVPSHWMVALLLLSAEP-VPAARSEDRYRNPKGSACSRIWQS | | 49 |
| CynCD79b | 1 | MARLALSPVSSHWLVALLLLSAAEPVPAAKSEDLYPNPKGSACSRIWQS | | 50 |
| mCD79b | 1 | MATLVLSSMPCHWLLFLLLFSGEP-VPAMTSSDLPLNFQGSPCSQIWQH | | 49 |

| hCD79b | 50 | PRFIARKRGFTVKMHCYMN-SAASGNVSWLWKQEMDENPQQLKEKGRMEE | 98 |
| CynCD79b | 51 | PRFIARKRGFTVKMHCYVTNSTFSIVSWLRKRETDKEPQQVNLEQGHMHQ | 100 |
| mCD79b | 50 | PRFAAKKRSSMVKFHCYTN---HSGALTWFRKRGSQQPQELVSEEGRIVQ | 96 |

| hCD79b | 99 | SQNESLATLTIQGIRFEDNGIYFCQQKCN-NTSEVYQGCGTELRVMGFST | 147 |
| CynCD79b | 101 | TQNSSVTTLIHQDIRFEDNGIYFCQQECS-KTSEVYRGCGTELRVMGFST | 149 |
| mCD79b | 97 | TQNGSVYTLTIQNHQYEDNGIYFCKQKCDSANHNVTDSCGTELLVLGFST | 146 |

ITAM Domain     TM Domain

| hCD79b | 148 | LAQLKQRNTLKDGIIMIQTLLIILFIIVPIFLLLDKDDSKAGMEEDHTYE | 197 |
| CynCD79b | 150 | LAQLKQRNTLKDGIIMIQTLLIILFIIVPIFLLLDKDDSKAGMEADHTYE | 199 |
| mCD79b | 147 | LDQLKRRNTLKDGIILIQTLLILFIIVPIFLLLDKDDGKAGMEEDHTYE | 196 |

| hCD79b | 198 | GLDIDQTATYEDIVTLRTGEVKWSVGEHPGQE | 229 | SEQ ID NO: 2 |
| CynCD79b | 200 | GLDIDQTATYEDIVTLRTGEVKWSVGEHPGQE | 231 | SEQ ID NO: 7 |
| mCD79b | 197 | GLNIDQTATYEDIVTLRTGEVKWSVGEHPGQE | 228 | SEQ ID NO: 8 |

FIG. 19

Anti-CD79b A118C huMA79b.v17 Cysteine Engineered Heavy Chain ThioMAb

A. Light Chain Sequence
Thio-huMA79b.v17-HC-A118C (LC)

DIQLTQSPSSLSASVGDRVTITCKASQSVDYDGDSFLNWYQQKPGKAPKLLIYAASNLESGVPSRFSGS
GSGTDFTLTISSLQPEDFATYYCQQSNEDPLTFGQGTKVEIKR<u>TVAAPSVFIFPPSDEQLKSGTASVVC
LLNNFYPREAKVQWKVDNALQSGNSQESVTEQDSKDSTYSLSSTLTLSKADYEKHKVYACEVTHQGLSS
PVTKSFNRGEC</u> (SEQ ID NO: 229)

B. Heavy Chain Sequence
Thio-huMA79b.v17-HC-A118C (HC)

EVQLVESGGGLVQPGGSLRLSCAASGYTFSSYWIEWVRQAPGKGLEWIGEILPGGGDTNYNEIFKGRATFSAD
TSKNTAYLQMNSLRAEDTAVYYCTRRVPVYFDYWGQGTLVTVSS<u>C</u>STKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKS
CDKTHT*CPPCPAPELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSVMHEALHNHYTQKSLSLSPG*
(SEQ ID NO: 228)

*FIG. 24*

Anti-CD79b A118C huMA79b.v18 Cysteine Engineered Heavy Chain ThioMAb

A. Light Chain Sequence
Thio-huMA79b.v18-HC-A118C (LC)

DIQLTQSPSSLSASVGDRVTITCKASQSVDYDGDSFLNWYQQKPGKAPKLLIYAASNLESGVPSRFSGS
GSGTDFTLTISSLQPEDFATYYCQQSNEDPLTFGQGTKVEIKR<u>TVAAPSVFIFPPSDEQLKSGTASVVC
LLNNFYPREAKVQWKVDNALQSGNSQESVTEQDSKDSTYSLSSTLTLSKADYEKHKVYACEVTHQGLSS
PVTKSFNRGEC</u> (SEQ ID NO: 231)

B. Heavy Chain Sequence
Thio-huMA79b.v18-HC-A118C (HC)

EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPIRLDYWGQGTLVTVSS<u>C</u>STKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHT*CPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG* (SEQ ID NO: 230)

*FIG. 25*

Anti-CD79b A118C huMA79b.v28 Cysteine Engineered Heavy Chain ThioMAb

A. Light Chain Sequence
Thio-huMA79b.v28-HC-A118C (LC)

DIQLTQSPSSLSASVGDRVTITCKASQSVDYEGDSFLNWYQQKPGKAPKLLIYAASNLESGVPSRFSGS
GSGTDFTLTISSLQPEDFATYYCQQSNEDPLTFGQGTKVEIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGLSS
PVTKSFNRGEC (SEQ ID NO: 233)

B. Heavy Chain Sequence
Thio-huMA79b.v28-HC-A118C (HC)

EVQLVESGGGLVQPGGSLRLSCAASGYTFSSYWIEWVRQAPGKGLEWIGEILPGGGDTNYNEIFKGRAT
FSADTSKNTAYLQMNSLRAEDTAVYYCTRRVPIRLDYWGQGTLVTVSS*C*STKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHT*CPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG* (SEQ ID NO: 232)

*FIG. 26*

Anti-CD79b V205C chMA79b Cysteine Engineered Light Chain ThioMAb

A. Light Chain Sequence
Thio chMA79b-LC-V205C (LC)

DIVLTQSPASLAVSLGQRATISCKASQSVDYDGDSFLNWYQQKPGQPPKLFIYAASNLESGIPARFSGS
GSGTDFTLNIHPVEEEDAATYYCQQSNEDPLTFGAGTELELKRTVAAPSVFIFPPSDEQLKSGTASVVC
LLNNFYPREAKVQWKVDNALQSGNSQESVTEQDSKDSTYSLSSTLTLSKADYEKHKVYACEVTHQGLSS
P*C*TKSFNRGEC (SEQ ID NO: 235)

B. Heavy Chain Sequence
Thio chMA79b-LC-V205C (HC)

EVQLQQSGAELMKPGASVKISCKATGYTFSSYWIEWVKQRPGHGLEWIGEILPGGGDTNYNEIFKGKAT
FTADTSSNTAYMQLSSLTSEDSAVYYCTRRVPVYFDYWGQGTSVTVSSASTKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHT*CPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG* (SEQ ID NO: 234)

*FIG. 27*

Anti-CD79b A118C chMA79b Cysteine Engineered Heavy Chain ThioMAb

A. Light Chain Sequence
Thio chMA79b-HC-A118C (LC)

DIVLTQSPASLAVSLGQRATISCKASQSVDYDGDSFLNWYQQKPGQPPKLFIYAASNLESGIPARFSGS
GSGTDFTLNIHPVEEEDAATYYCQQSNEDPLTFGAGTELELKR<u>TVAAPSVFIFPPSDEQLKSGTASVVC</u>
<u>LLNNFYPREAKVQWKVDNALQSGNSQESVTEQDSKDSTYSLSSTLTLSKADYEKHKVYACEVTHQGLSS</u>
<u>PVTKSFNRGEC</u> (SEQ ID NO: 237)

B. Heavy Chain Sequence
Thio chMA79b-HC-A118C (HC)

EVQLQQSGAELMKPGASVKISCKATGYTFSSYWIEWVKQRPGHGLEWIGEILPGGGDTNYNEIFKGKAT
FTADTSSNTAYMQLSSLTSEDSAVYYCTRRVPVYFDYWGQGTSVTVSS<u>C</u>STKGPSVFPLAPSSKSTSGG
TAALGCLVKDYFPEPVTVSWNSGALTSGVHTFPAVLQSSGLYSLSSVVTVPSSSLGTQTYICNVNHKPS
NTKVDKKVEPKSCDKTHT*CPPCPAPELLGGPSVFLFPPKPKDTLMISRTPEVTCVVVDVSHEDPEVKFN*
*WYVDGVEVHNAKTKPREEQYNSTYRVVSVLTVLHQDWLNGKEYKCKVSNKALPAPIEKTISKAKGQPRE*
*PQVYTLPPSREEMTKNQVSLTCLVKGFYPSDIAVEWESNGQPENNYKTTPPVLDSDGSFFLYSKLTVDK*
*SRWQQGNVFSCSVMHEALHNHYTQKSLSLSPG* (SEQ ID NO: 236)

*FIG. 28*

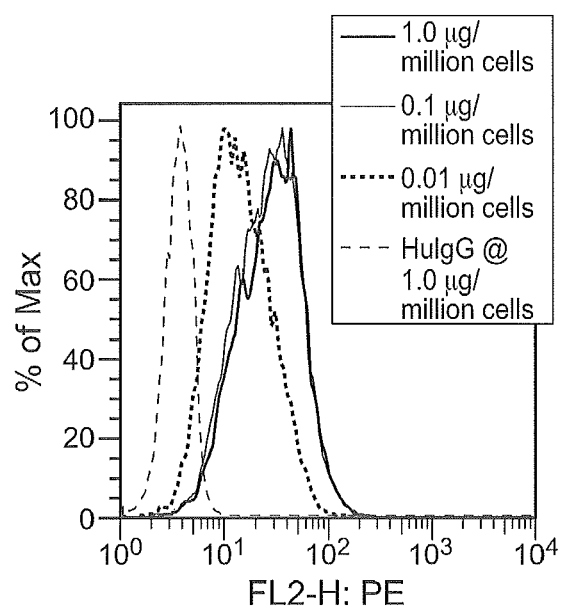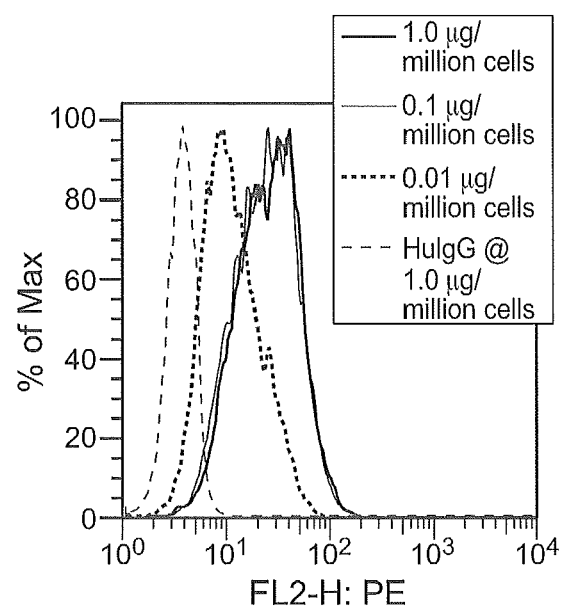
Binding of Thio chMA79b-LC(V205C)-MC-MMAF to BJAB-lucs
FIG. 29A
Binding of Thio chMA79b-HC(A118C)-MC-MMAF to BJAB-lucs
FIG. 29B

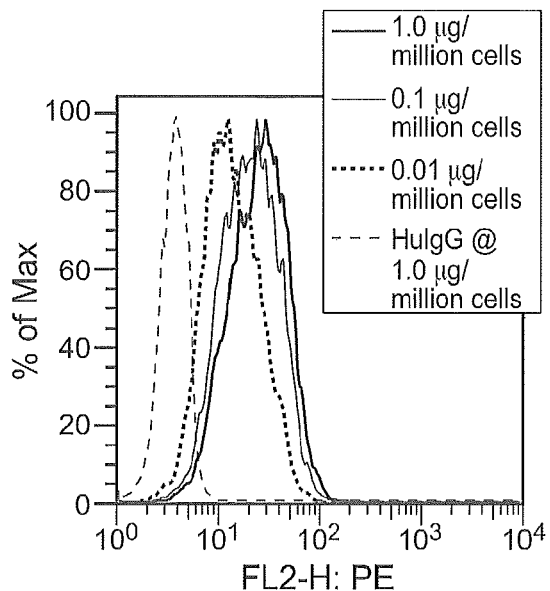
FIG. 30A Binding of Naked Thio MA79b.v18-HC (A118C) to BJAB-lucs
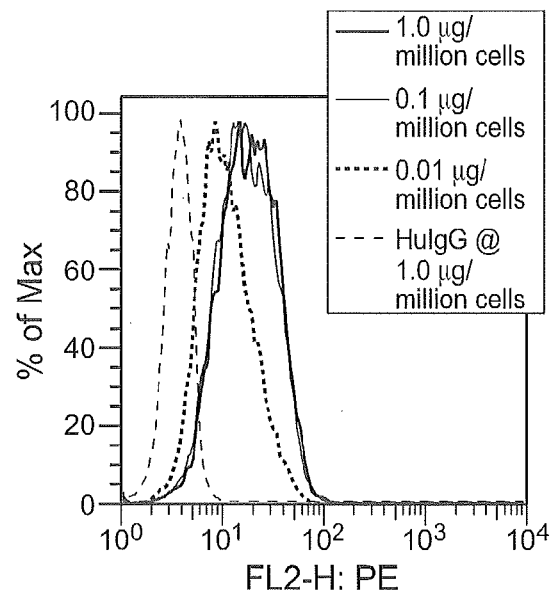
FIG. 30B Binding of Thio MA79b.v18-HC (A118C)-MC-MMAF to BJAB-lucs
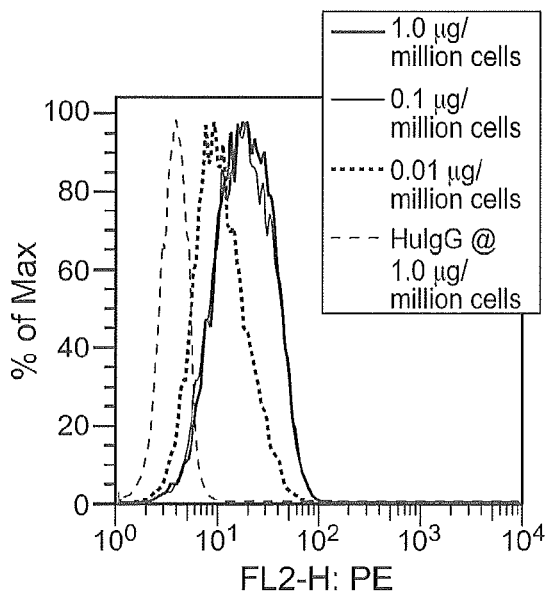
FIG. 30C Binding of Thio MA79b.v18-HC (A118C)-MCvcPAB-MMAE to BJAB-lucs
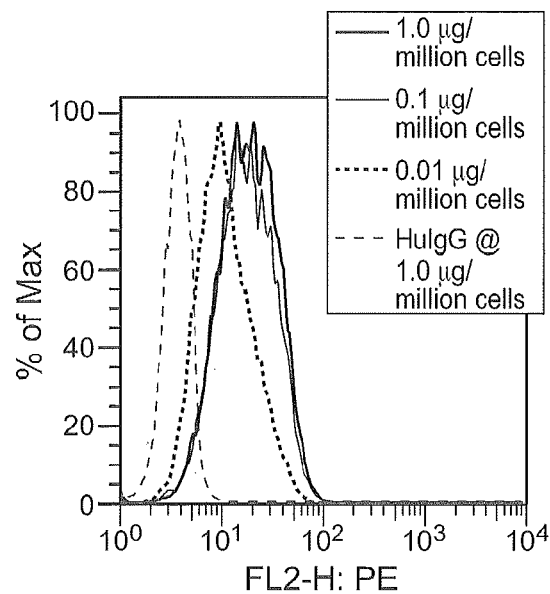
FIG. 30D Binding of Thio MA79b.v18-HC (A118C)-BMPEO-DM1 to BJAB-lucs Binding of Naked Thio Anti-cynoCD79b (ch10D10)-HC(A118C) to BJAB-cynoCD79b Cells Binding of Thio Anti-cynoCD79b (ch10D10)-HC(A118C)-MCvcPAB-MMAE to BJAB-cynoCD79b Cells Binding of Thio Anti-cynoCD79b (ch10D10)-HC(A118C)-BMPEO-DM1 to BJAB-cynoCD79b Cells Binding of Thio Anti-cynoCD79b (ch10D10)-HC(A118C)-MC-MMAF to BJAB-cynoCD79b Cells <p1.cynoCD79b TCATGGTGATGGTGATGATGACCGGTACGCGTAGAATCGAGACCGAGGAGAGGGTTAGGGATAGG
CTTACCTTCGAACCGCGGGCCCTCTAGACTCGAGCGGCCGCCACTGTGCTGGATATCTGCAGAAT
TGCCCTTGGGGACAGAGCAGTGACCATGGCCAGGCTGGCGTTGTCTCCTGTGTCCAGCCACTGGC
TGGTGGCGTTGCTGCTGCTGCTCTCAGCAGCTGAGCCAGTGCCAGCAGCCAAATCAGAGGACCTG
TACCCGAATCCCAAAGGTAGTGCTTGTTCTCGGATCTGGCAGAGCCCACGTTTCATAGCCAGGAA
ACGGGGCTTCACGGTGAAAATGCACTGCTACGTGACCAACAGCACCTTCAGCATCGTGAGCTGGC
TCCGGAAGCGGGAGACGGACAAGGAGCCCCAACAGGTGAACCTGGAGCAGGGCCACATGCATCAG
ACCCAAAACAGCTCTGTCACCACCCTCATCATCCAAGACATCCGGTTTGAGGACAACGGCATCTA
CTTCTGTCAGCAGGAGTGCAGCAAGACCTCGGAGGTCTACCGGGGCTGCGGCACGGAGCTGCGAG
TCATGGGGTTCAGCACCTTGGCACAGCTGAAGCAGAGGAACACGCTGAAGGATGGCATCATCATG
ATCCAGACGCTGCTGATCATCCTCTTCATCATCGTGCCCATCTTCCTGCTGCTGGACAAGGATGA
CAGCAAGGCCGGCATGGAGGAAGATCACACCTACGAGGGCCTGGACATTGACCAGACGGCCACCT
ACGAGGACATAGTGACGCTGCGGACAGGGGAAGTGAAGTGGTCTGTGGGTGAGCACCCAGGTCAG
GAGTGAGAGCCAGGACCTCCCCACGGCCTGGGTGCAGGCTCCCCAGCC

FIG. 42

<p1.cynoCD79b
DNA548455

```
MARLALSPVSSHWLVALLLLLSAAEPVPAAKSEDLYPNPKGSACSRIWQSPRFIARKRGFT
VKMHCYVTNSTFSIVSWLRKRETDKEPQQVNLEQGHMHQTQNSSVTTLIIQDIRFEDNGIY
FCQQECSKTSEVYRGCGTELRVMGFSTLAQLKQRNTLKDGIIMIQTLLIILFIIVPIFLLL
DKDDSKAGMEEDHTYEGLDIDQTATYEDIVTLRTGEVKWSVGEHPGQE
```

Signal sequence.
amino acids 1-26.

Transmembrane domain.
amino acids 161-181.

Immunoglobulin domain.
amino acids 59-126.

Immunoreceptor tyrosine-based activation motif.
amino acids 195-215.

Immunoglobulin V-set domain.
amino acids 44-145.

N-glycosylation site.
amino acids 70-73, 103-106.

cAMP- and cGMP-dependent protein kinase phosphorylation site.
amino acids 81-84.

Protein kinase C phosphorylation site.
amino acids 50-52, 61-63, 84-86, 158-160, 214-216.

Casein kinase II phosphorylation site.
amino acids 22-25, 84-87, 158-161, 208-211, 223-226.

Tyrosine kinase phosphorylation site.
amino acids 115-122.

N-myristoylation site.
amino acids 41-46, 120-125.

FIG. 43

CHIMERIC ANTI-CYNO CD79b (ch10D10) LIGHT CHAIN

ACCTCGGTTC TATCGATTGA ATTCCACCAT GGGATGGTCA TGTATCATCC TTTTTCTAGT
AGCAACTGCA ACTGGAGTAC ATTCAGATAT CGTGCTGACC CAATCTCCAC CCTCTTTGGC
TGTGTCTCTA GGGCAGAGGG CCACCATATC CTGCAGAGCC AGTGAAAGTG TTGATAGTTA
TGGCAAAACT TTTATGCACT GGCACCAGCA GAAACCAGGA CAGCCACCCA AACTCCTCAT
CTATCGTGTA TCCAACCTAG AATCTGGGAT CCCTGCCAGG TTCAGTGGCA GTGGGTCAAG
GACAGACTTC ACCCTCACCA TTAATCCTGT GGAGGCTGAT GATGTTGCAA CCTATTACTG
TCAGCAAAGT AATGAGGATC CGTTCACGTT CGGTGGAGGC ACCAAGCTGG AAATCAAACG
GACCGTGGCT GCACCATCTG TCTTCATCTT CCCGCCATCT GATGAGCAGT TGAAATCTGG
AACTGCCTCT GTTGTGTGCC TGCTGAATAA CTTCTATCCC AGAGAGGCCA AAGTACAGTG
GAAGGTGGAT AACGCCCTCC AATCGGGTAA CTCCCAGGAG AGTGTCACAG AGCAGGACAG
CAAGGACAGC ACCTACAGCC TCAGCAGCAC CCTGACGCTG AGCAAAGCAG ACTACGAGAA
ACACAAAGTC TACGCCTGCG AAGTCACCCA TCAGGGCCTG AGCTCGCCCG TCACAAAGAG
CTTCAACAGG GGAGAGTGTT AAGCTTGGCC GCCATGGCCC AACTTGTTTA TTGCAGCTTA
TAATGGTTAC AAATAAAGCA

FIG. 44

CHIMERIC ANTI-CYNO CD79b (ch10D10) LIGHT CHAIN

DIVLTQSPPSLAVSLGQRATISCRASESVDSYGKTFMHWHQQKPGQPPKLLIYRVSNLESGIPAR
FSGSGSRTDFTLTINPVEADDVATYYCQQSNEDPFTFGGGTKLEIKRTVAAPSVFIFPPSDEQLK
SGTASVVCLLNNFYPREAKVQWKVDNALQSGNSQESVTEQDSKDSTYSLSSTLTLSKADYEKHKV
YACEVTHQGLSSPVTKSFNRGEC

FIG. 45

CHIMERIC ANTI-CYNO CD79b (ch10D10) HEAVY CHAIN

```
CACCTCGGTT CTATCGATTG AATTCCACCA TGGGATGGTC ATGTATCATC CTTTTTCTAG
TAGCAACTGC AACTGGAGTA CATTCAGAAG TTCAGCTGCA GGAGTCGGGA CCTGGCCTGG
TGAAACCTTC TCAGTCTCTG TCCCTCACCT GCACTGTCAC TGGCTACTCA ATCACCAGTG
ATTATGCCTG GAACTGGATC CGGCAGTTTC CAGGAAACAA ACTGGAGTGG ATGGGCAACA
TATGGTACAG TGGTAGCACT ACCTACAACC CATCTCTCAA AAGTCGAATC TCTATCACTC
GAGACACATC CAAGAACCAG TTCTTCCTGC AGTTGAATTC TGTGACTTCT GAGGACACAG
CCACATATTA CTGTTCAAGA ATGGACTTCT GGGGTCAAGG CACCACTCTC ACAGTCTCCT
CAGCCTCCAC CAAGGGCCCA TCGGTCTTCC CCTGGCACC CTCCTCCAAG AGCACCTCTG
GGGGCACAGC GGCCCTGGGC TGCCTGGTCA AGGACTACTT CCCCGAACCG GTGACGGTGT
CGTGGAACTC AGGCGCCCTG ACCAGCGGCG TGCACACCTT CCCGGCTGTC CTACAGTCCT
CAGGACTCTA CTCCCTCAGC AGCGTGGTGA CTGTGCCCTC TAGCAGCTTG GGCACCCAGA
CCTACATCTG CAACGTGAAT CACAAGCCCA GCAACACCAA GGTGGACAAG AAAGTTGAGC
CCAAATCTTG TGACAAAACT CACACATGCC CACCGTGCCC AGCACCTGAA CTCCTGGGGG
GACCGTCAGT CTTCCTCTTC CCCCCAAAAC CCAAGGACAC CCTCATGATC TCCCGGACCC
CTGAGGTCAC ATGCGTGGTG GTGGACGTGA GCCACGAAGA CCCTGAGGTC AAGTTCAACT
GGTACGTGGA CGGCGTGGAG GTGCATAATG CCAAGACAAA GCCGCGGGAG GAGCAGTACA
ACAGCACGTA CCGTGTGGTC AGCGTCCTCA CCGTCCTGCA CCAGGACTGG CTGAATGGCA
AGGAGTACAA GTGCAAGGTC TCCAACAAAG CCCTCCCAGC CCCCATCGAG AAAACCATCT
CCAAAGCCAA AGGGCAGCCC CGAGAACCAC AGGTGTACAC CCTGCCCCCA TCCCGGGAAG
AGATGACCAA GAACCAGGTC AGCCTGACCT GCCTGGTCAA AGGCTTCTAT CCCAGCGACA
TCGCCGTGGA GTGGGAGAGC AATGGGCAGC CGGAGAACAA CTACAAGACC ACGCCTCCCG
TGCTGGACTC CGACGGCTCC TTCTTCCTCT ACAGCAAGCT CACCGTGGAC AAGAGCAGGT
GGCAGCAGGG GAACGTCTTC TCATGCTCCG TGATGCATGA GGCTCTGCAC AACCACTACA
CGCAGAAGAG CCTCTCCCTG TCTCCGGGTA AATGAGTGCG ACGGCCCTAG AGTCGACCTG
CAGAAGCTTG GCCGCCATGG CCCAACTTGT TTATTGCAGC TTATAATGGT TACAAATAAA
```

FIG. 46

CHIMERIC ANTI-CYNO CD79b (ch10D10) HEAVY CHAIN

EVQLQESGPGLVKPSQSLSLTCTVTGYSITSDYAWNWIRQFPGNKLEWMGNIWYSGSTTYNPSLK
SRISITRDTSKNQFFLQLNSVTSEDTATYYCSRMDFWGQGTTLTVSSASTKGPSVFPLAPSSKST
SGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPG

FIG. 47

Anti-cyno CD79b ch10D10 A118C Cysteine Engineered Heavy Chain ThioMAb

A. Light Chain Sequence
Thio-anti-cyno CD79b (ch10D10)-HC-A118C (LC)

DIVLTQSPPSLAVSLGQRATISCRASESVDSYGKTFMHWHQQKPGQPPKLLIYRVSNLESGIPAR
FSGSGSRTDFTLTINPVEADDVATYYCQQSNEDPFTFGGGTKLEIKR<u>TVAAPSVFIFPPSDEQLK</u>
<u>SGTASVVCLLNNFYPREAKVQWKVDNALQSGNSQESVTEQDSKDSTYSLSSTLTLSKADYEKHKV</u>
<u>YACEVTHQGLSSPVTKSFNRGEC</u> (SEQ ID NO: 245)

B. Heavy Chain Sequence
Thio-anti-cyno CD79b (ch10D10)-HC-A118C (HC)

[D]VQLQESGPGLVKPSQSLSLTCTVTGYSITSDYAWNWIRQFPGNKLEWMGNIWYSGSTTYNPSLK
SRISI<u>TRDTSKNQFFLQLNSVTSEDTATYYCSRMDFWGQGTTLTVSS</u>CSTKGPSVFPLAPSSKST
SGGTAALGCLVKDYFPEPVTVSWNSGALTSGVHTFPAVLQSSGLYSLSSVVTVPSSSLGTQTYIC
NVNHKPSNTKVDKKVEPKSCDKTHT*CPPCPAPELLGGPSVFLFPPKPKDTLMISRTPEVTCVVVD*
*VSHEDPEVKFNWYVDGVEVHNAKTKPREEQYNSTYRVVSVLTVLHQDWLNGKEYKCKVSNKALPA*
*PIEKTISKAKGQPREPQVYTLPPSREEMTKNQVSLTCLVKGFYPSDIAVEWESNGQPENNYKTTP*
*PVLDSDGSFFLYSKLTVDKSRWQQGNVFSCSVMHEALHNHYTQKSLSLSPG*
(SEQ ID NO: 244)

FIG. 48

Anti-cyno CD79b ch10D10 V205C Cysteine Engineered Light Chain ThioMAb

A. Light Chain Sequence
Thio-anti-cyno CD79b (ch10D10)-HC-V205C (LC)

DIVLTQSPPSLAVSLGQRATISCRASESVDSYGKTFMHWHQQKPGQPPKLLIYRVSNLESGIPAR
FSGSGSRTDFTLTINPVEADDVATYYCQQSNEDPFTFGGGTKLEIKR<u>TVAAPSVFIFPPSDEQLK</u>
<u>SGTASVVCLLNNFYPREAKVQWKVDNALQSGNSQESVTEQDSKDSTYSLSSTLTLSKADYEKHKV</u>
<u>YACEVTHQGLSSP</u>C<u>TKSFNRGEC</u> (SEQ ID NO: 300)

B. Heavy Chain Sequence
Thio-anti-cyno CD79b (ch10D10)-HC-V205C (HC)

[D]VQLQESGPGLVKPSQSLSLTCTVTGYSITSDYAWNWIRQFPGNKLEWMGNIWYSGSTTYNPSLK
SRISI<u>TRDTSKNQFFLQLNSVTSEDTATYYCSRMDFWGQGTTLTVSS</u>ASTKGPSVFPLAPSSKST
SGGTAALGCLVKDYFPEPVTVSWNSGALTSGVHTFPAVLQSSGLYSLSSVVTVPSSSLGTQTYIC
NVNHKPSNTKVDKKVEPKSCDKTHT*CPPCPAPELLGGPSVFLFPPKPKDTLMISRTPEVTCVVVD*
*VSHEDPEVKFNWYVDGVEVHNAKTKPREEQYNSTYRVVSVLTVLHQDWLNGKEYKCKVSNKALPA*
*PIEKTISKAKGQPREPQVYTLPPSREEMTKNQVSLTCLVKGFYPSDIAVEWESNGQPENNYKTTP*
*PVLDSDGSFFLYSKLTVDKSRWQQGNVFSCSVMHEALHNHYTQKSLSLSPG* (SEQ ID NO: 299)

FIG. 49

ANTI-CD79B ANTIBODIES AND IMMUNOCONJUGATES AND METHODS OF USE

CROSS REFERENCE TO RELATED APPLICATIONS

This non-provisional application filed under 37 CFR 1.53(b) is a continuation of, and claims priority under 35 USC §120 to U.S. patent application Ser. No. 12/173,465, filed on Jul. 15, 2008, now U.S. Pat. No. 8,088,378, granted Jan. 3, 2012, which claims benefit under 35 USC §119 to, U.S. Provisional Patent Application No. 60/950,052, filed Jul. 16, 2007, U.S. Provisional Patent Application No. 61/025,137, filed Jan. 31, 2008, U.S. Provisional Patent Application No. 61/032,790, filed Feb. 29, 2008, and U.S. Provisional Patent Application No. 61/054,709, filed May 20, 2008, each of which are incorporated by reference in entirety.

This application is accompanied by a computer program listing appendix submission on a compact disc (in duplicate copies) which contains the file title "P5111R1C1_Computer_Program_Appendix_Table_1.doc", created on Oct. 23, 2011, that is 112 KB, 115,200 bytes in size, MS-Windows OS, the contents of which are incorporated in their entirety by reference. The computer program listing appendix contains the computer program of originally filed Table 1.

FIELD OF THE INVENTION

The present invention is directed to compositions of matter useful for the treatment of hematopoietic tumor in mammals and to methods of using those compositions of matter for the same.

BACKGROUND OF THE INVENTION

Malignant tumors (cancers) are the second leading cause of death in the United States, after heart disease (Boring et al., *CA Cancel J. Clin.* 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

Cancers which involve cells generated during hematopoiesis, a process by which cellular elements of blood, such as lymphocytes, leukocytes, platelets, erythrocytes and natural killer cells are generated are referred to as hematopoietic cancers. Lymphocytes which can be found in blood and lymphatic tissue and are critical for immune response are categorized into two main classes of lymphocytes: B lymphocytes (B cells) and T lymphocytes (T cells), which mediate humoral and cell mediated immunity, respectively.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

T cells mature within the thymus which provides an environment for the proliferation and differentiation of immature T cells. During T cell maturation, the T cells undergo the gene rearrangements that produce the T-cell receptor and the positive and negative selection which helps determine the cell-surface phenotype of the mature T cell. Characteristic cell surface markers of mature T cells are the CD3:T-cell receptor complex and one of the coreceptors, CD4 or CD8.

In attempts to discover effective cellular targets for cancer therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. In this regard, it is noted that antibody-based therapy has proved very effective in the treatment of certain cancers. For example, HERCEPTIN® and RITUXAN® (both from Genentech Inc., South San Francisco, Calif.) are antibodies that have been used successfully to treat breast cancer and non-Hodgkin's lymphoma, respectively. More specifically, HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are recombinantly produced in CHO cells.

In other attempts to discover effective cellular targets for cancer therapy, researchers have sought to identify (1) non-membrane-associated polypeptides that are specifically produced by one or more particular type(s) of cancer cell(s) as compared to by one or more particular type(s) of non-cancerous normal cell(s), (2) polypeptides that are produced by cancer cells at an expression level that is significantly higher than that of one or more normal non-cancerous cell(s), or (3) polypeptides whose expression is specifically limited to only a single (or very limited number of different) tissue type(s) in both the cancerous and non-cancerous state (e.g., normal prostate and prostate tumor tissue). Such polypeptides may remain intracellularly located or may be secreted by the cancer cell. Moreover, such polypeptides may be expressed not by the cancer cell itself, but rather by cells which produce and/or secrete polypeptides having a potentiating or growth-enhancing effect on cancer cells. Such secreted polypeptides are often proteins that provide cancer cells with a growth advantage over normal cells and include such things as, for example, angiogenic factors, cellular adhesion factors, growth factors, and the like. Identification of antagonists of such non-membrane associated polypeptides would be expected to serve as effective therapeutic agents for the treatment of such cancers. Furthermore, identification of the expression pattern of such polypeptides would be useful for the diagnosis of particular cancers in mammals.

Despite the above identified advances in mammalian cancer therapy, there is a great need for additional therapeutic agents capable of detecting the presence of tumor in a mammal and for effectively inhibiting neoplastic cell growth, respectively. Accordingly, it is an objective of the present invention to identify polypeptides, cell membrane-associated, secreted or intracellular polypeptides whose expression is specifically limited to only a single (or very limited number of different) tissue type(s), hematopoietic tissues, in both a cancerous and non-cancerous state, and to use those polypeptides, and their encoding nucleic acids, to produce compositions of matter useful in the therapeutic treatment and/or detection of hematopoietic cancer in mammals.

CD79 is the signaling component of the B-cell receptor consisting of a covalent heterodimer containing CD79a (Igα, mb-1) and CD79b (Igβ, B29). CD79a and CD79b each contain an extracellular immunoglobulin (Ig) domain, a transmembrane domain, and an intracellular signaling domain, an immunoreceptor tyrosine-based activation motif (ITAM) domain. CD79 is expressed on B cells and in Non-Hodgkin's Lymphoma cells (NHLs) (Cabezudo et al., *Haematologica*, 84:413-418 (1999); D'Arena et al., *Am. J. Hematol.*, 64: 275-281 (2000); Olejniczak et al., *Immunol. Invest.*, 35: 93-114 (2006)). CD79a and CD79b and sIg are all required for surface expression of the CD79 (Matsuuchi et al., *Curr. Opin. Immunol.*, 13(3): 270-7)). The average surface expression of CD79b on NHLs is similar to that on normal B-cells, but with a greater range (Matsuuchi et al., *Curr. Opin. Immunol.*, 13(3): 270-7 (2001)).

Given the expression of CD79b, it is beneficial to produce therapeutic antibodies to the CD79b antigen that create minimal or no antigenicity when administered to patients, especially for chronic treatment. The present invention satisfies this and other needs. The present invention provides anti-CD79b antibodies that overcome the limitations of current therapeutic compositions as well as offer additional advantages that will be apparent from the detailed description below.

The use of antibody-drug conjugates (ADC), i.e. immunoconjugates, for the local delivery of cytotoxic or cytostatic agents, i.e. drugs to kill or inhibit tumor cells in the treatment of cancer (Lambert, J. (2005) Curr. Opinion in Pharmacology 5:543-549; Wu et al (2005) Nature Biotechnology 23(9): 1137-1146; Payne, G. (2003) Cancer Cell 3:207-212; Syrigos and Epenetos (1999) Anticancer Research 19:605-614; Niculescu-Duvaz and Springer (1997) Adv. Drug Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al (ed.s), pp. 475-506). Efforts to improve the therapeutic index, i.e. maximal efficacy and minimal toxicity of ADC have focused on the selectivity of polyclonal (Rowland et al (1986) Cancer Immunol. Immunother., 21:183-87) and monoclonal antibodies (mAbs) as well as drug-linking and drug-releasing properties (Lambert, J. (2005) Curr. Opinion in Pharmacology 5:543-549). Drug moieties used in antibody drug conjugates include bacterial protein toxins such as diphtheria toxin, plant protein toxins such as ricin, small molecules such as auristatins, geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al (1996) Proc. Natl. Acad. Sci. USA 93:8618-8623), calicheamicin (Lode et al (1998) Cancer Res. 58:2928; Hinman et al (1993) Cancer Res. 53:3336-3342), daunomycin, doxorubicin, methotrexate, and vindesine (Rowland et al (1986) supra). The drug moieties may affect cytotoxic and cytostatic mechanisms including tubulin binding, DNA binding, or topoisomerase inhibition. Some cytotoxic drugs tend to be inactive or less active when conjugated to large antibodies or protein receptor ligands.

The auristatin peptides, auristatin E (AE) and monomethylauristatin (MMAE), synthetic analogs of dolastatin (WO 02/088172), have been conjugated as drug moieties to: (i) chimeric monoclonal antibodies cBR96 (specific to Lewis Y on carcinomas); (ii) cAC10 which is specific to CD30 on hematological malignancies (Klussman, et al (2004), Bio-conjugate Chemistry 15(4):765-773; Doronina et al (2003) Nature Biotechnology 21(7):778-784; Francisco et al (2003) Blood 102(4):1458-1465; US 2004/0018194, now abandoned; (iii) anti-CD20 antibodies such as rituxan (WO 04/032828) for the treatment of CD20-expressing cancers and immune disorders; (iv) anti-EphB2R antibody 2H9 for treatment of colorectal cancer (Mao et al (2004) Cancer Research 64(3):781-788); (v) E-selectin antibody (Bhaskar et al (2003) Cancer Res. 63:6387-6394); (vi) trastuzumab (HERCEPTIN®, US 2005/0238649, now U.S. Pat. No. 7,498,298, granted Mar. 3, 2009), and (vi) anti-CD30 antibodies (WO 03/043583). Variants of auristatin E are disclosed in U.S. Pat. No. 5,767,237 and U.S. Pat. No. 6,124,431. Monomethyl auristatin E conjugated to monoclonal antibodies are disclosed in Senter et al, Proceedings of the American Association for Cancer Research, Volume 45, Abstract Number 623, presented Mar. 28, 2004. Auristatin analogs MMAE and MMAF have been conjugated to various antibodies (US 2005/0238649, now U.S. Pat. No. 7,498,298, granted Mar. 3, 2009).

Conventional means of attaching, i.e. linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods may be inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multistep conjugation process may be nonreproducible due to difficulties in controlling the reaction conditions and characterizing reactants and intermediates.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Extracellular proteins generally do not have free thiols (Garman, 1997, Non-Radioactive Labelling: A Practical Approach, Academic Press, London, at page 55). Antibody cysteine thiol groups are generally more reactive, i.e. more nucleophilic, towards electrophilic conjugation reagents than antibody amine or hydroxyl groups. Cysteine residues have been introduced into proteins by genetic engineering techniques to form covalent attachments to ligands or to form new intramolecular disulfide bonds (Better et al (1994) J. Biol. Chem. 13:9644-9650; Bernhard et al (1994) Bioconjugate Chem. 5:126-132; Greenwood et al (1994) Therapeutic Immunology 1:247-255; Tu et al (1999) Proc. Natl. Acad. Sci USA 96:4862-4867; Kanno et al (2000) J. of Biotechnology, 76:207-214; Chmura et al (2001) Proc. Nat. Acad. Sci. USA 98(15):8480-8484; U.S. Pat. No. 6,248,564). However, engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of *E. coli*, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys thiol groups are unavailable for active site participation and interactions. Furthermore, the protein may be rendered inactive or nonspecific, by misfolding or loss of tertiary structure (Zhang et al (2002) Anal. Biochem. 311:1-9).

Cysteine-engineered antibodies have been designed as FAB antibody fragments (thioFab) and expressed as full-length, IgG monoclonal (thioMab) antibodies (Junutula, J. R. et al. (2008) J Immunol Methods 332:41-52; US 2007/0092940, now U.S. Pat. No. 7,521,541, granted on Apr. 21, 2009, the contents of which are incorporated by reference). ThioFab and ThioMab antibodies have been conjugated through linkers at the newly introduced cysteine thiols with thiol-reactive linker reagents and drug-linker reagents to prepare antibody drug conjugates (Thio ADC).

All references cited herein, including patent applications and publications, are incorporated by reference in their entirety.

SUMMARY OF THE INVENTION

The invention provides anti-CD79b antibodies or functional fragments thereof, and their method of use in the treatment of hematopoietic tumors.

In one aspect, the invention provides an antibody which binds, preferably specifically, to any of the above or below described polypeptides. Optionally, the antibody is a monoclonal antibody, antibody fragment, including Fab, Fab', F(ab')$_2$, and Fv fragment, diabody, single domain antibody, chimeric antibody, humanized antibody, single-chain antibody or antibody that competitively inhibits the binding of an anti-CD79b polypeptide antibody to its respective antigenic epitope. Antibodies of the present invention may optionally be conjugated to a growth inhibitory agent or cytotoxic agent such as a toxin, including, for example, an auristatin, a maytansinoid, a dolostatin derivative or a calicheamicin, an antibiotic, a radioactive isotope, a nucleolytic enzyme, or the like. The antibodies of the present invention may optionally be produced in CHO cells or bacterial cells and preferably induce death of a cell to which they bind. For detection purposes, the antibodies of the present invention may be detectably labeled, attached to a solid support, or the like.

In one aspect, the invention provides a humanized anti-CD79b antibody wherein the monovalent affinity (e.g affinity of the antibody as a Fab fragment to CD79b) or affinity in its bivalent form of the antibody to CD79b (e.g. affinity of the antibody as an IgG fragment to CD79b) is substantially the same as, lower than, or greater than, the monovalent affinity or affinity in its bivalent form, respectively, of a murine antibody (e.g. affinity of the murine antibody as a Fab fragment or as an IgG fragment to CD79b) or a chimeric antibody (e.g. affinity of the chimeric antibody as a Fab fragment or as an IgG fragment to CD79b), comprising, consisting or consisting essentially of a light chain and heavy chain variable domain sequence as depicted in FIGS. 7A-B (SEQ ID NO: 10) and FIGS. 8A-B (SEQ ID NO: 14).

In another aspect, the invention provides a humanized anti-CD79b antibody wherein the affinity of the antibody in its bivalent form to CD79b (e.g., affinity of the antibody as an IgG to CD79b) is 0.4 nM, 0.2 nM or 0.5 nM.

In one aspect, an antibody that binds to CD79b is provided, wherein the antibody comprises at least one, two, three, four, five or six HVRs selected from the group consisting of:
  (i) HVR-L1 comprising sequence A1-A15, wherein A1-A15 is KASQSVDYDGDSFLN (SEQ ID NO: 131)
  (ii) HVR-L2 comprising sequence B1-B7, wherein B1-B7 is AASNLES (SEQ ID NO: 132)
  (iii) HVR-L3 comprising sequence C1-C9, wherein C1-C9 is QQSNEDPLT (SEQ ID NO: 133)
  (iv) HVR-H1 comprising sequence D1-D10, wherein D1-D10 is GYTFSSYWIE (SEQ ID NO: 134)
  (v) HVR-H2 comprising sequence E1-E18, wherein E1-E18 is GEILPGGGDTNYNEIFKG (SEQ ID NO: 135) and
  (vi) HVR-H3 comprising sequence F1-F10, wherein F1-F10 IS TRRVPVYFDY (SEQ ID NO: 136).

In one aspect, an antibody that binds to CD79b is provided, wherein the antibody comprises at least one variant HVR wherein the variant HVR sequence comprises modification of at least one residue of the sequence depicted in SEQ ID NOs: 131, 132, 133, 134, 135 or 136.

In one aspect, the invention provides an antibody comprising a heavy chain variable domain comprising the HVR1-HC, HVR2-HC and/or HVR3-HC sequence depicted in FIG. 15 (SEQ ID NO: 164-166).

In one aspect, the invention provides an antibody comprising a light chain variable domain comprising HVR1-LC, HVR2-LC and/or HVR3-LC sequence depicted in FIG. 15 (SEQ ID NO: 156-158).

In one aspect, the invention provides an antibody comprising a heavy chain variable domain comprising the HVR1-HC, HVR2-HC and/or HVR3-HC sequence depicted in FIG. 16 (SEQ ID NO: 183-185).

In one aspect, the invention provides an antibody comprising a light chain variable domain comprising HVR1-LC, HVR2-LC and/or HVR3-LC sequence depicted in FIG. 16 (SEQ ID NO: 175-177).

In one aspect, the invention provides an antibody comprising a heavy chain variable domain comprising the HVR1-HC, HVR2-HC and/or HVR3-HC sequence depicted in FIG. 17 (SEQ ID NO: 202-204).

In one aspect, the invention provides an antibody comprising a light chain variable domain comprising HVR1-LC, HVR2-LC and/or HVR3-LC sequence depicted in FIG. 17 (SEQ ID NO: 194-196).

In one aspect, the invention provides an antibody comprising a heavy chain variable domain comprising the HVR1-HC, HVR2-HC and/or HVR3-HC sequence depicted in FIG. 18 (SEQ ID NO: 221-223).

In one aspect, the invention provides an antibody comprising a light chain variable domain comprising HVR1-LC, HVR2-LC and/or HVR3-LC sequence depicted in FIG. 18 (SEQ ID NO: 213-215).

In one aspect, the invention includes an anti-CD79b antibody comprising a heavy chain variable domain selected from SEQ ID NOs: 170, 189, 208 or 227. In another aspect, the invention includes an anti-CD79b antibody comprising a light chain variable domain selected from SEQ ID NOs: 169, 188, 207 or 226.

In one aspect, the invention includes a cysteine engineered anti-CD79b antibody comprising one or more free cysteine amino acids and a sequence selected from SEQ ID NOs: 251-298. The cysteine engineered anti-CD79b antibody may bind to a CD79b polypeptide. The cysteine engineered anti-CD79b antibody may be prepared by a process comprising replacing one or more amino acid residues of a parent anti-CD79b antibody by cysteine.

In one aspect, the invention includes a cysteine engineered anti-CD79b antibody comprising one or more free cysteine amino acids wherein the cysteine engineered anti-CD79b antibody binds to a CD79b polypeptide and is prepared by a process comprising replacing one or more amino acid residues of a parent anti-CD79b antibody by cysteine wherein the parent antibody comprises at least one HVR sequence selected from:
(a) HVR-L1 comprising sequence A1-A15, wherein A1-A15 is KASQSVDYDGDSFLN (SEQ ID NO: 131) or KASQSVDYEGDSFLN (SEQ ID NO: 137);
(b) HVR-L2 comprising sequence B1-B7, wherein B1-B7 is AASNLES (SEQ ID NO: 132)
(c) HVR-L3 comprising sequence C1-C9, wherein C1-C9 is QQSNEDPLT (SEQ ID NO: 133)
(d) HVR-H1 comprising sequence D1-D10, wherein D1-D10 is GYTFSSYWIE (SEQ ID NO: 134)
(e) HVR-H2 comprising sequence E1-E18, wherein E1-E18 is GEILPGGGDTNYNEIFKG (SEQ ID NO: 135) and
(f) HVR-H3 comprising sequence F1-F10, wherein F1-F10 is TRRVPVYFDY (SEQ ID NO: 136) or TRRVPIRLDY (SEQ ID NO: 138).

The cysteine engineered anti-CD79b antibody may be a monoclonal antibody, antibody fragment, chimeric antibody, humanized antibody, single-chain antibody or antibody that competitively inhibits the binding of an anti-CD79b polypeptide antibody to its respective antigenic epitope. Antibodies of the present invention may optionally be conjugated to a growth inhibitory agent or cytotoxic agent such as a toxin, including, for example, an auristatin or maytansinoid. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In one aspect, the invention provides methods for making an antibody of the invention. For example, the invention provides a method of making a CD79b antibody (which, as defined herein includes full length and fragments thereof), said method comprising expressing in a suitable host cell a recombinant vector of the invention encoding said antibody (or fragment thereof), and recovering said antibody.

In one aspect, the invention is a pharmaceutical formulation comprising an antibody of the invention or an antibody-drug conjugate of the invention, and a pharmaceutically acceptable diluent, carrier or excipient.

In one aspect, the invention provides an article of manufacture comprising a container; and a composition contained within the container, wherein the composition comprises one or more CD79b antibodies of the invention.

In one aspect, the invention provides a kit comprising a first container comprising a composition comprising one or more CD79b antibodies of the invention; and a second container comprising a buffer.

In one aspect, the invention provides use of a CD79b antibody of the invention in the preparation of a medicament for the therapeutic and/or prophylactic treatment of a disease, such as a cancer, a tumor and/or a cell proliferative disorder.

In one aspect, the invention provides use of an article of manufacture of the invention in the preparation of a medicament for the therapeutic and/or prophylactic treatment of a disease, such as a cancer, a tumor and/or a cell proliferative disorder.

In one aspect, the invention provides use of a kit of the invention in the preparation of a medicament for the therapeutic and/or prophylactic treatment of a disease, such as a cancer, a tumor and/or a cell proliferative disorder.

In one aspect, the invention provides a method of inhibiting the growth of a cell that expresses CD79b, said method comprising contacting said cell with an antibody of the invention thereby causing an inhibition of growth of said cell. In one embodiment, the antibody is conjugated to a cytotoxic agent. In one embodiment, the antibody is conjugated to a growth inhibitory agent.

In one aspect, the invention provides a method of therapeutically treating a mammal having a cancerous tumor comprising a cell that expresses CD79b, said method comprising administering to said mammal a therapeutically effective amount of an antibody of the invention, thereby effectively treating said mammal. In one embodiment, the antibody is conjugated to a cytotoxic agent. In one embodiment, the antibody is conjugated to a growth inhibitory agent.

In one aspect, the invention provides a method for treating or preventing a cell proliferative disorder associated with increased expression of CD79b, said method comprising administering to a subject in need of such treatment an effective amount of an antibody of the invention, thereby effectively treating or preventing said cell proliferative disorder. In one embodiment, said proliferative disorder is cancer. In one embodiment, the antibody is conjugated to a cytotoxic agent. In one embodiment, the antibody is conjugated to a growth inhibitory agent.

In one aspect, the invention provides a method for inhibiting the growth of a cell, wherein growth of said cell is at least in part dependent upon a growth potentiating effect of CD79b, said method comprising contacting said cell with an effective amount of an antibody of the invention, thereby inhibiting the growth of said cell. In one embodiment, the antibody is conjugated to a cytotoxic agent. In one embodiment, the antibody is conjugated to a growth inhibitory agent.

In one aspect, the invention provides a method of therapeutically treating a tumor in a mammal, wherein the growth of said tumor is at least in part dependent upon a growth potentiating effect of CD79b, said method comprising contacting said cell with an effective amount of an antibody of the invention, thereby effectively treating said tumor. In one embodiment, the antibody is conjugated to a cytotoxic agent. In one embodiment, the antibody is conjugated to a growth inhibitory agent.

In one aspect, the invention provides a method of treating cancer comprising administering to a patient the pharmaceutical formulation comprising an immunoconjugate described herein, acceptable diluent, carrier or excipient.

In one aspect, the invention provides a method of inhibiting B cell proliferation comprising exposing a cell to an immuno conjugate comprising an antibody of the invention under conditions permissive for binding of the immunoconjugate to CD79b.

In one aspect, the invention provides a method of determining the presence of CD79b in a sample suspected of containing CD79b, said method comprising exposing said sample to an antibody of the invention, and determining binding of said antibody to CD79b in said sample wherein binding of said antibody to CD79b in said sample is indicative of the presence of said protein in said sample.

In one aspect, the invention provides a method of diagnosing a cell proliferative disorder associated with an increase in cells, such as B cells, expressing CD79b is provided, the method comprising contacting a test cells in a biological sample with any of the above antibodies; determining the level of antibody bound to test cells in the sample by detecting binding of the antibody to CD79b; and comparing the level of antibody bound to cells in a control sample, wherein the level of antibody bound is normalized to the number of CD79b-expressing cells in the test and control samples, and wherein a higher level of antibody bound in the test sample as compared to the control sample indicates the presence of a cell proliferative disorder associated with cells expressing CD79b.

In one aspect, the invention provides a method of detecting soluble CD79b in blood or serum, the method comprising contacting a test sample of blood or serum from a mammal suspected of experiencing a B cell proliferative disorder with an anti-CD79b antibody of the invention and detecting a increase in soluble CD79b in the test sample relative to a control sample of blood or serum from a normal mammal.

In one aspect, the invention provides a method of binding an antibody of the invention to a cell that expresses CD79b, said method comprising contacting said cell with an antibody of the invention. In one embodiment, the antibody is conjugated to a cytotoxic agent. In one embodiment, the antibody is conjugated to a growth inhibitory agent.

BRIEF DESCRIPTION OF THE DRAWINGS

FIG. 1 shows a nucleotide sequence (SEQ ID NO: 1) of a PRO36249 cDNA, wherein SEQ ID NO: 1 is a clone designated herein as "DNA225786" (also referred here in as "CD79b"). The nucleotide sequence encodes for CD79b with the start and stop codons shown in bold and underlined.

FIG. 2 shows the amino acid sequence (SEQ ID NO: 2) derived from the coding sequence of SEQ ID NO: 1 shown in FIG. 1.

FIG. 3 shows the nucleotide sequence (SEQ ID NO: 3) of the light chain of chimeric CD79b murine antibody (chMA79b) IgG1 (MA79b is a murine monoclonal anti-CD79b antibody). The nucleotide sequence encodes for the light chain of chMA79b with the start and stop codons shown in bold and underlined.

FIG. 4 shows the amino acid sequence (SEQ ID NO: 4), missing the first 18 amino acid signal sequence, derived from the coding sequence of SEQ ID NO: 3 shown in FIG. 3. Variable regions are regions not underlined.

FIG. 5 shows the nucleotide sequence (SEQ ID NO: 5) of the heavy chain of chimeric murine antibody (chMA79b) IgG1 (MA79b is a murine monoclonal anti-CD79b antibody). The nucleotide sequence encodes for the heavy chain of chMA79b with the start and stop codons shown in bold and underlined.

FIG. 6 shows the amino acid sequence (SEQ ID NO: 6), missing the first 18 amino acid signal sequence and the last lysine (K) prior to the stop codon, derived from the coding sequence of SEQ ID NO: 5 shown in FIG. 5. Variable regions are regions not underlined.

FIGS. 7A-B show the alignment of sequences of the variable light chains for the following: light chain human kappa I consensus sequence (labeled as "huKI"; SEQ ID NO: 9) with VL-FR1, VL-FR2, VL-FR3, VL-FR4 (SEQ ID NOs: 139-142, respectively), murine anti-CD79b antibody (labeled as "MA79b"; SEQ NO: 10), MA79b-grafted "humanized" antibody (labeled as "huMA79b graft"; SEQ ID NO: 11), MA79 b-grated "humanized" antibody variant 17 (labeled as "huMA79b.v17"; SEQ ID NO: 169), MA79b-grafted "humanized" antibody variant 18 (labeled as "huMA79b.v18"; SEQ ID NO: 188), MA79b-grafted "humanized" antibody variant 28 (labeled as "huMA79b.v28"; SEQ ID NO: 207) and MA79b-grafted "humanized" antibody variant 32 (labeled as "huMA79b.v32"; SEQ ID NO: 226). Positions are numbered according to Kabat and hypervariable regions (HVRs) grafted from MA79b to the variable light Kappa I consensus framework are boxed.

FIGS. 8A-B show the alignment of sequences of the variable heavy chains for the following: heavy chain human subgroup III consensus sequence (labeled as "humIII"; SEQ ID NO: 13) with VH-FR1, VH-FR2, VH-FR3, and VH-FR4 (SEQ ID NOs: 143-146), murine anti-CD79b antibody (labeled as "MA79b"; SEQ ID NO: 14), MA79b-grafted "humanized" antibody (labeled as "huMA79b graft"; SEQ ID NO: 15) (containing 71A, 73T and 78A), MA79b-grated "humanized" antibody variant 17 (labeled as "huMA79b.v17"; SEQ ID NO: 170) (containing 71A, 73T and 78A), MA79b-grafted "humanized" antibody variant 18 (labeled as "huMA79b.v18"; SEQ ID NO: 189) (containing 71A, 73T and 78A), MA79b-grafted "humanized" antibody variant 28 (labeled as "huMA79b.v28"; SEQ ID NO: 208) (containing 71A, 73T and 78A) and MA79b-grafted "humanized" antibody variant 32 (labeled as "huMA79b.v32"; SEQ ID NO: 227) (containing 71A, 73T and 78A). Positions are numbered according to Kabat and hypervariable regions (HVRs) grafted from MA79b to the variable heavy subgroup III consensus framework are boxed.

FIG. 9 shows various HVR sequences of selected MA79b-grafted "humanized" antibody variants (SEQ ID NOs: 17-21) wherein each variant has a single amino acid change in a single HVR of the MA79b-grafted "humanized" antibody (HVR-L1 (SEQ ID NO: 131); HVR-L2 (SEQ ID NO: 132); HVR-L3 (SEQ ID NO: 133)). The sequences of the variable light and variable heavy chains outside of the shown single amino acid changes were identical to the huMA79b graft and are not shown. No changes were observed in HVR-H1 (SEQ ID NO: 134), HVR-H2 (SEQ ID NO: 135) or HVR-H3 (SEQ ID NO: 136) of the MA79b-grafted "humanized" antibody.

FIG. 11 shows Biacore analysis of selected anti-CD79b antibodies, including murine CD79b antibody (labeled as "MA79b"), MA79b-grafted "humanized" antibody (labeled as "huMA79b graft"), and MA79b-grafted "humanized" antibody variants, including huMA79b L2-2 (52R, 53K, 55G, 56 R; SEQ ID NO: 22), huMA79b H3-10 (98I, 99R, 100L; SEQ ID NO: 94), huMA79b H1-6 (28P, 30T, 31R, 35N; SEQ ID NO: 57) and huMA79b L2/H3 (L2-2 and H3-10 mutations described below) to designated antigens, including the extracellular domain of human CD79b (huCD79b$_{ecd}$), the extracellular domain of human CD79b fused to Fc (huCD79b$_{ecd}$-Fc) and a 16 amino acid peptide containing the epitope for MA79b and chMA79b (SEQ ID NO: 16).

FIG. 12 shows Biacore analysis of selected anti-CD79b antibodies, including MA79b-grafted "humanized" antibody (labeled as "huMA79b graft") and MA79b-grafted "humanized" antibody variants (labeled as 1-34 in the first column or as "all framework" in the first column) to the extracellular domain of human CD79b (huCD79b-ecd antigen). MA79b-grafted "humanized" antibody variants include an "all framework" variant where potentially important murine framework residues are present and variants (labeled 1-34) with combinations of framework mutations with or without HVR mutations in the variable light chain and variable heavy chain as designated. MA79b-grafted "humanized" antibody variant 17 (herein referred to as "huMA79b.v17") is labeled as 17 in the first column, MA79b-grafted "humanized" antibody variant 18 (herein referred to as "huMA79b.v18") is labeled as 18 in the first column, MA79b-grafted "humanized" antibody variant 28 (herein referred to as "huMA79b.v28") is labeled as 28 in the first column and MA79b-grafted "humanized" antibody variant 32 (herein referred to as "huMA79b.v32") is labeled as 32 in the first column. Bivalent binding fold is represented as the Kd of the particular MA79b-grafted "humanized" antibody variant (labeled as "Kd$_{variant}$")/the Kd of the chimeric MA79b antibody (chMA79b) (labeled as "Kd$_{chimera}$"); values under the column labeled "bivalent binding fold" represents Kd$_{variant}$/Kf$_{chimera}$. No detected binding is designated in the figure as "NDB".

FIGS. 13A-B (variable heavy (VH) consensus frameworks) and FIG. 14 (variable light (VL) consensus frameworks) depict exemplary acceptor human consensus framework sequences for use in practicing the instant invention with sequence identifiers as follows: (FIGS. 13A-B) human VH subgroup I consensus framework minus Kabat CDRs (SEQ ID NO: 108), human VH subgroup I consensus framework minus extended hypervariable regions (SEQ ID NOs: 109-111), human VH subgroup II consensus framework minus Kabat CDRs (SEQ ID NO: 112), human VH subgroup II consensus framework minus extended hypervariable regions (SEQ ID NOs: 113-115), human VH subgroup III consensus framework minus Kabat CDRs (SEQ ID NO: 116), human VH subgroup III consensus framework minus extended hypervariable regions (SEQ ID NOs: 117-119), human VH acceptor framework minus Kabat CDRs (SEQ ID NO: 120), human VH acceptor framework minus extended hypervariable regions (SEQ ID NOs: 121-122), human VH acceptor 2 framework minus Kabat CDRs (SEQ ID NO: 123) and human VH acceptor 2 framework minus extended hypervariable regions (SEQ ID NOs: 124-26) and (FIG. 14) human VL kappa subgroup I consensus framework (SEQ ID NO: 127), human VL kappa subgroup II consensus framework (SEQ ID NO: 128), human kappa subgroup III consensus framework (SEQ ID NO: 129) and human kappa subgroup IV consensus framework (SEQ ID NO: 130).

FIGS. 15A (light chain) and 15B (heavy chain) show amino acid sequences of an antibody of the invention (huMA79b.v17). FIGS. 15A (light chain) and 15B (heavy chain) show amino acid sequences of the framework (FR), hypervariable region (HVR), first constant domain (CL or CH1) and Fc region (Fc) of one embodiment of an antibody of the invention (huMA79b.v17) (SEQ ID NOs: 152-159 (FIG. 15A) and SEQ ID NOs: 160-168 (FIG. 15B)). Full-length amino acid sequences (variable and constant regions) of the light and heavy chains of huMA79b.v17 are shown (SEQ ID NO: 303 (FIG. 15A) and 304 (FIG. 15B), respectively, with the constant domains underlined. Amino acid sequences of the variable domains are shown (SEQ ID NO: 169 (FIG. 15A for light chain) and SEQ ID NO: 170 (FIG. 15B for heavy chain)).

FIGS. 16A (light chain) and 16B (heavy chain) show amino acid sequences of an antibody of the invention (huMA79b.v18). FIGS. 16A (light chain) and 16B (heavy chain) show amino acid sequences of the framework (FR), hypervariable region (HVR), first constant domain (CL or CH1) and Fc region (Fc) of one embodiment of an antibody of the invention (huMA79b.v18) (SEQ ID NOs: 171-178 (FIG. 16A) and SEQ ID NOs: 179-187 (FIG. 16B)). Full-length amino acid sequences (variable and constant regions) of the light and heavy chains of huMA79b.v18 are shown (SEQ ID NO: 305 (FIG. 16A) and 306 (FIG. 16B), respectively, with the constant domains underlined. Amino acid sequences of the variable domains are shown (SEQ ID NO: 188 (FIG. 16A for light chain) and SEQ ID NO: 189 (FIG. 16B for heavy chain)).

FIGS. 17A (light chain) and 17B (heavy chain) show amino acid sequences of an antibody of the invention (huMA79b.v28). FIGS. 17A (light chain) and 17B (heavy chain) show amino acid sequences of the framework (FR), hypervariable region (HVR), first constant domain (CL or CH1) and Fc region (Fc) of one embodiment of an antibody of the invention (huMA79b.v28) (SEQ ID NOs: 190-197 (FIG. 17A) and SEQ ID NOs: 198-206 (FIG. 17B)). Full-length amino acid sequences (variable and constant regions) of the light and heavy chains of huMA79b.v28 are shown (SEQ ID NO: 307 (FIG. 17A) and 308 (FIG. 17B), respectively, with the constant domains underlined. Amino acid sequences of the variable domains are shown (SEQ ID NO: 207 (FIGS. 7A-B for light chain) and SEQ ID NO: 208 (FIGS. 8A-B for heavy chain)).

FIGS. 18A (light chain) and 18B (heavy chain) show amino acid sequences of an antibody of the invention (huMA79b.v32). FIGS. 18A (light chain) and 18B (heavy chain) show amino acid sequences of the framework (FR), hypervariable region (HVR), first constant domain (CL or CH1) and Fc region (Fc) of one embodiment of an antibody of the invention (huMA79b.v32) (SEQ ID NOs: 209-216 (FIG. 18A) and SEQ ID NOs: 217-225 (FIG. 18B)). Full-length amino acid sequences (variable and constant regions) of the light and heavy chains of huMA79b.v32 are shown (SEQ ID NO: 309 (FIG. 18A) and 310 (FIG. 18B), respectively, with the constant domains underlined. Amino acid sequences of the variable domains are shown (SEQ ID NO: 226 (FIG. 18A for light chain) and SEQ ID NO: 227 (FIG. 18B for heavy chain)).

FIG. 19 shows the alignment of the amino acid sequences of CD79b from human (SEQ ID NO: 2), cynomolgus monkey (cyno) (SEQ ID NO: 7) and mouse (SEQ ID NO: 8). Human and cyno-CD79b have 85% amino acid identity. The signal sequence, test peptide (the 11 amino acid epitope for MA79b, chMA79b and anti-cyno CD79b antibody described in Example 1; ARSEDRYRNPK (SEQ ID NO: 12)), transmembrane (TM) domain and immunoreceptor tyrosine-based activation motif (ITAM) domain are indicated. The region boxed is the region of CD79b that is absent in the splice variant of CD79b (described in Example 1).

FIG. 24 shows (A) the light chain sequence (SEQ ID NO: 229) and (B) heavy chain sequence (SEQ ID NO: 228) of humanized cysteine engineered anti-CD79b antibody (thio-huMA79b.v17-HC-A118C), in which an alanine at EU position 118 (sequential position alanine 118; Kabat position 114) of the heavy chain was altered to a cysteine. A drug moiety may be attached to the engineered cysteine group in the heavy chain. In each figure, the altered amino acid is shown in bold text with double underlining. Single underlining indicates constant regions. Variable regions are regions not underlined. Fc region is marked by italic. "Thio" refers to cysteine-engineered antibody while "hu" refers to humanized antibody.

FIG. 25 shows (A) the light chain sequence (SEQ ID NO: 231) and (B) heavy chain sequence (SEQ ID NO: 230) of humanized cysteine engineered anti-CD79b antibody (thio-huMA79b.v18-HC-A118C), in which an alanine at EU position 118 (sequential position alanine 118; Kabat position 114) of the heavy chain was altered to a cysteine. A drug moiety may be attached to the engineered cysteine group in the heavy chain. In each figure, the altered amino acid is shown in bold text with double underlining. Single underlining indicates constant regions. Variable regions are regions not underlined. Fc region is marked by italic. "Thio" refers to cysteine-engineered antibody while "hu" refers to humanized antibody.

FIG. 26 shows (A) the light chain sequence (SEQ ID NO: 233) and (B) heavy chain sequence (SEQ ID NO: 232) of humanized cysteine engineered anti-CD79b antibody (thio-huMA79b.v28-HC-A118C), in which an alanine at EU position 118 (sequential position alanine 118; Kabat position 114) of the heavy chain was altered to a cysteine. A drug moiety may be attached to the engineered cysteine group in the heavy chain. In each figure, the altered amino acid is shown in bold text with double underlining. Single underlining indicates constant regions. Variable regions are regions not underlined. Fc region is marked by italic. "Thio" refers to cysteine-engineered antibody while "hu" refers to humanized antibody.

FIG. 27 shows (A) the light chain sequence (SEQ ID NO: 235) and (B) heavy chain sequence (SEQ ID NO: 234) of cysteine engineered anti-CD79b antibody (thio-MA79b-LC-V205C), a valine at Kabat position 205 (sequential position Valine 209) of the light chain was altered to a cysteine. A drug moiety may be attached the an engineered cysteine group in the light chain. In each figure, the altered amino acid is shown in bold text with double underlining. Single underlining indicates constant regions. Variable regions are regions not underlined. Fc region is marked by italic. "Thio" refers to cysteine-engineered antibody.

FIG. 28 shows (A) the light chain sequence (SEQ ID NO: 237) and (B) heavy chain sequence (SEQ ID NO: 236) of cysteine engineered anti-CD79b antibody (thio-MA79b-HC-A118C), in which an alanine at EU position 118 (sequential position alanine 118; Kabat position 114) of the heavy chain was altered to a cysteine. A drug moiety may be attached to the engineered cysteine group in the heavy chain. In each figure, the altered amino acid is shown in bold text with double underlining. Single underlining indicates constant regions. Variable regions are regions not underlined. Fc region is marked by italic. "Thio" refers to cysteine-engineered antibody.

FIGS. 29A-B are FACS plots indicating that binding of anti-CD79b thioMAb drug conjugates (TDCs) of the invention bind to CD79b expressed on the surface of BJAB-luciferase cells is similar for conjugated (A) LC (V205C) thioMAb variants and (B) HC (A118C) thioMAb variants of chMA79b with MMAF. Detection was with MS anti-human-IgG-PE. "Thio" refers to cysteine-engineered antibody.

FIGS. 30A-D are FACS plots indicating that binding of anti-CD79b thioMAb drug conjugates (TDCs) of the invention bind to CD79b expressed on the surface of BJAB-luciferase cells is similar for (A) naked (unconjugated) HC (A118C) thioMAb variants of huMA79b.v18 and conjugated HC (A118C) thioMAb variants of huMA79b.v18 with the different drug conjugates shown ((B) MMAF, (C) MMAE and (D) DM1)). Detection was with MS anti-humanIgG-PE. "Thio" refers to cysteine-engineered antibody while "hu" refers to humanized antibody.

FIG. 42 shows the nucleotide sequence (SEQ ID NO: 238) of PRO283627 cDNA, wherein SEQ ID NO: 235 is a clone designated as "DNA548455" (also referred herein as "cyno CD79b"). The nucleotide sequence encodes for cynomolgus CD79b with the start and stop codons shown in bold and underlined.

FIG. 43 shows the amino acid sequence (SEQ ID NO: 239) derived from the coding sequence of SEQ ID NO: 235 shown in FIG. 42.

FIG. 44 shows the nucleotide sequence (SEQ ID NO: 240) of the light chain of anti-cyno CD79b antibody (ch10D10). The nucleotide sequence encodes for the light chain of anti-cyno CD79b antibody (ch10D10) with the start and stop codons shown in bold and underlined.

FIG. 45 shows the amino acid sequence (SEQ ID NO: 241), missing the first 18 amino acid signal sequence, derived from the coding sequence of SEQ ID NO: 240 shown in FIG. 44. Variable regions (SEQ ID NO: 302) are regions not underlined.

FIG. 46 shows the nucleotide sequence (SEQ ID NO: 242) of the heavy chain of anti-cyno CD79b antibody (ch10D10). The nucleotide sequence encodes for the heavy chain of anti-cyno CD79b antibody (ch10D10) with the start and stop codons shown in bold and underlined.

FIG. 47 shows the amino acid sequence (SEQ ID NO: 243), missing the first 18 amino acid signal sequence and the last lysine (K) prior to the stop codon, derived from the coding sequence of SEQ ID NO: 242 shown in FIG. 46. Variable regions (SEQ ID NO: 301) are regions not underlined.

FIG. 48 shows (A) the light chain sequence (SEQ ID NO: 245) and (B) heavy chain sequence (SEQ ID NO: 244) of cysteine engineered anti-cyno CD79b antibody (Thio-anti-cynoCD79b-HC-A118C), in which an alanine at EU position 118 (sequential position alanine 118; Kabat position 114) of the heavy chain was altered to a cysteine. Amino acid D at EU position 6 (shaded in Figure) of the heavy chain may alternatively be E. A drug moiety may be attached to the engineered cysteine group in the heavy chain. In each figure, the altered amino acid is shown in bold text with double underlining. Single underlining indicates constant regions. Variable regions are regions not underlined. Fc region is marked by italic. "Thio" refers to cysteine-engineered antibody.

FIG. 49 shows (A) the light chain sequence (SEQ ID NO: 300) and (B) heavy chain sequence (SEQ ID NO: 299) of cysteine engineered anti-cyno CD79b antibody (Thio-anti-cynoCD79b-LC-V205C), in which an a valine at Kabat position 205 (sequential position Valine 209) of the light chain was altered to a cysteine. Amino acid D at EU position 6 (shaded in Figure) of the heavy chain may alternatively be E. A drug moiety may be attached to the engineered cysteine group in the heavy chain. In each figure, the altered amino acid is shown in bold text with double underlining. Single underlining indicates constant regions. Variable regions are regions not underlined. Fc region is marked by italic. "Thio" refers to cysteine-engineered antibody.

DETAILED DESCRIPTION OF THE PREFERRED EMBODIMENTS

Figure 10:
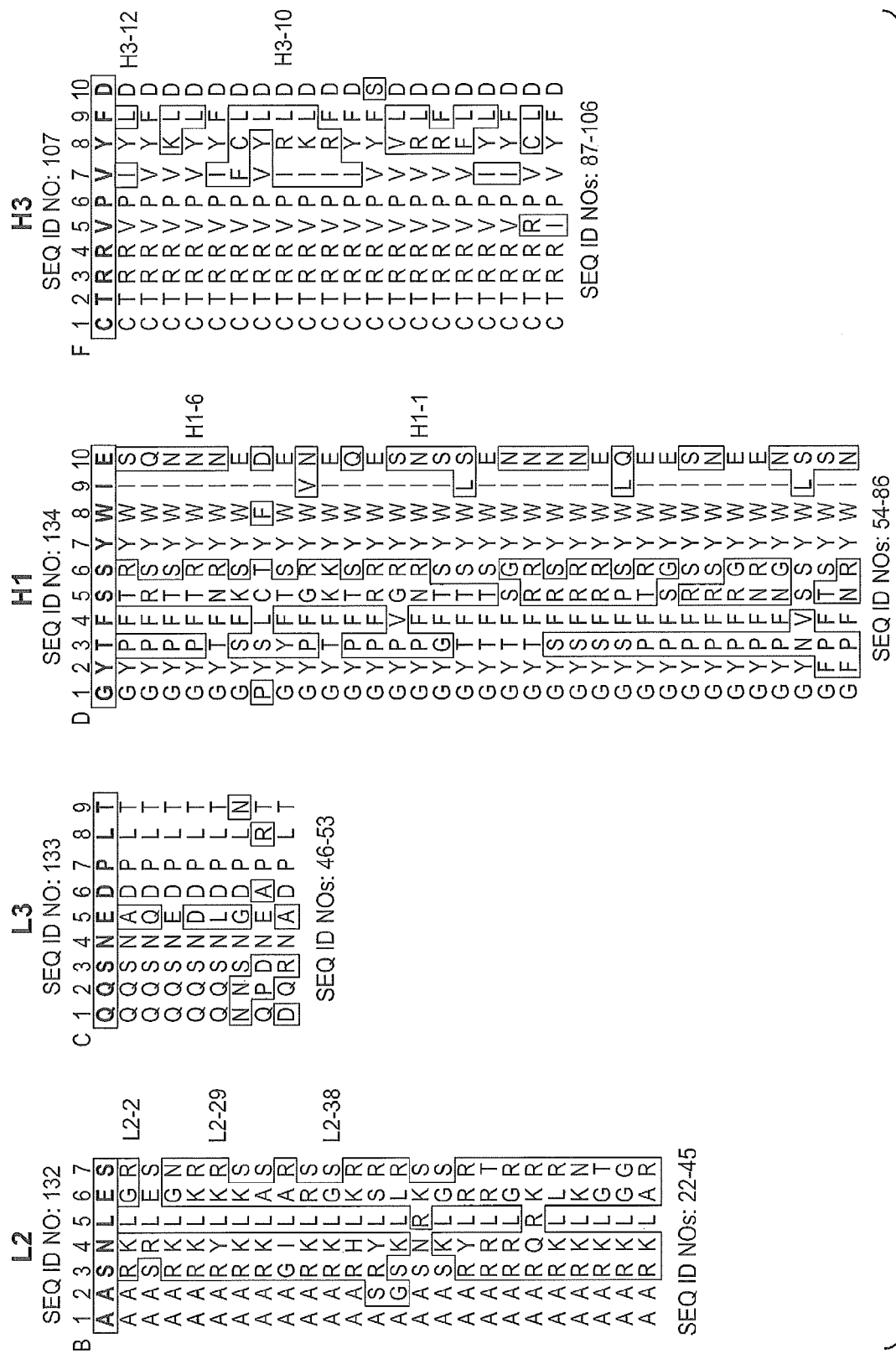
FIG. 10 shows various HVR sequences of selected MA79b-grafted "humanized" antibody variants (SEQ ID NOs: 22-106), including huMA79b L2-2 (also referred to herein as "L2") an huMA79b H3-10 (also referred to herein as "H3") wherein each variant has multiple amino acid changes in a single HVR region of the MA79b-grafted "humanized" antibody (HVR-L2 (SEQ ID NO: 132); HVR-L3 (SEQ ID NO: 133); HVR-H1 (SEQ ID NO: 134); portion of HVR-H3 (SEQ ID NO: 136) is shown in FIG. 10 as SEQ ID NO: 107). The sequences of the variable light and variable heavy chains outside of the shown amino acid changes were identical to the huMA79b graft and are not shown. No changes were observed in HVR-L1 (SEQ ID NO: 131) or HVR-H2 (SEQ ID NO: 135) of the MA79b-grafted "humanized" antibody.
Figure 14:
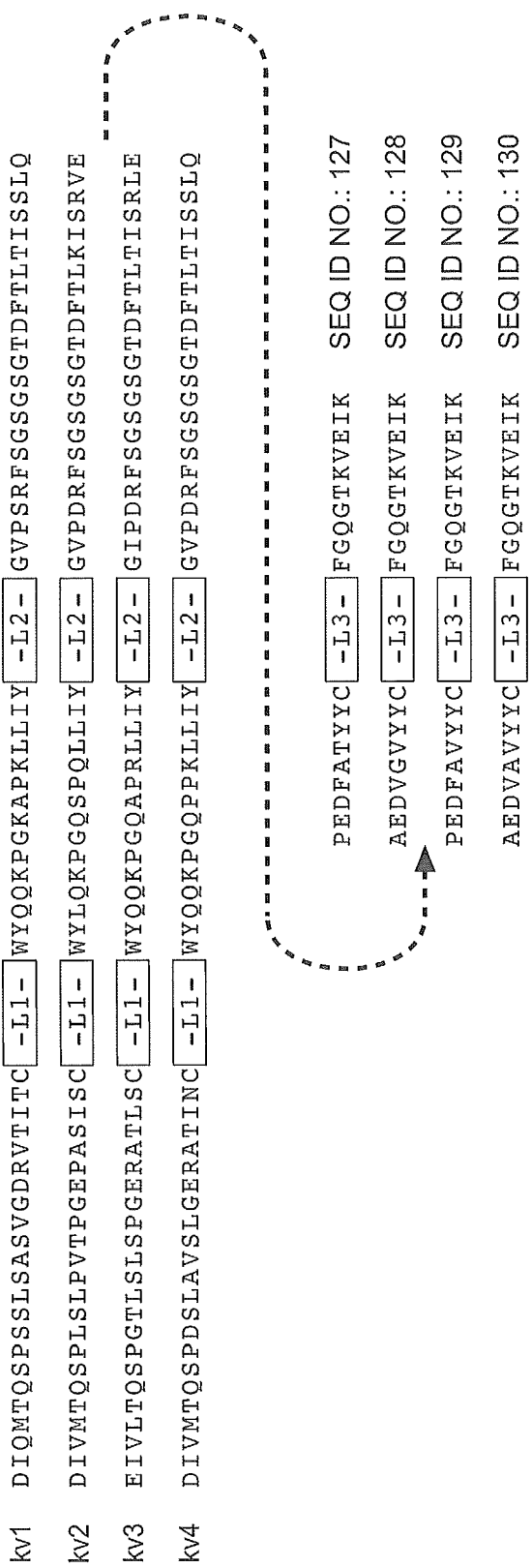

The invention provides methods, compositions, kits and articles of manufacture for identifying compositions useful for the treatment of hematopoietic tumor in mammals and to methods of using those compositions of matter for the same.

Details of these methods, compositions, kits and articles of manufacture are provided herein.

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

II. Definitions

For purposes of interpreting this specification, the following definitions will apply and whenever appropriate, terms used in the singular will also include the plural and vice versa. In the event that any definition set forth conflicts with any document incorporated herein by reference, the definition set forth below shall control.

A "B-cell surface marker" or "B-cell surface antigen" herein is an antigen expressed on the surface of a B cell that can be targeted with an antagonist that binds thereto, including but not limited to, antibodies to a B-cell surface antigen or a soluble form a B-cell surface antigen capable of antagonizing binding of a ligand to the naturally occurring B-cell antigen. Exemplary B-cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see The Leukocyte Antigen Facts Book, 2$^{nd}$ Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, BAFF, BLyS, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a mammal and may be expressed on both precursor B cells and mature B cells.

The term "CD79b", as used herein, refers to any native CD79b from any vertebrate source, including mammals such as primates (e.g. humans, cynomolgus monkey (cyno)) and rodents (.e.g., mice and rats), unless otherwise indicated. Human CD79b is also referred herein to as "PRO36249" (SEQ ID NO: 2) and encoded by the nucleotide sequence (SEQ ID NO: 1) also referred herein to as "DNA225786". Cynomologus CD79b is also referred herein to as "cyno CD79b" or "PRO283627" (SEQ ID NO: 239) and encoded by the nucleotide sequence (SEQ ID NO: 238) also referred herein to as "DNA548455". The term "CD79b" encompasses "full-length," unprocessed CD79b as well as any form of CD79b that results from processing in the cell. The term also encompasses naturally occurring variants of CD79b, e.g., splice variants, allelic variants and isoforms. The CD79b polypeptides described herein may be isolated from a variety of sources, such as from human tissue types or from another source, or prepared by recombinant or synthetic methods. A "native sequence CD79b polypeptide" comprises a polypeptide having the same amino acid sequence as the corresponding CD79b polypeptide derived from nature. Such native sequence CD79b polypeptides can be isolated from nature or can be produced by recombinant or synthetic means. The term "native sequence CD79b polypeptide" specifically encompasses naturally-occurring truncated or secreted forms of the specific CD79b polypeptide (e.g., an extracellular domain sequence), naturally-occurring variant forms (e.g., alternatively spliced forms) and naturally-occurring allelic variants of the polypeptide. In certain embodiments of the invention, the native sequence CD79b polypeptides disclosed herein are mature or full-length native sequence polypeptides comprising the full-length amino acids sequences shown in the accompanying figures. Start and stop codons (if indicated) are shown in bold font and underlined in the figures. Nucleic acid residues indicated as "N" in the accompanying figures are any nucleic acid residue. However, while the CD79b polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the CD79b polypeptides.

Figure 7A:
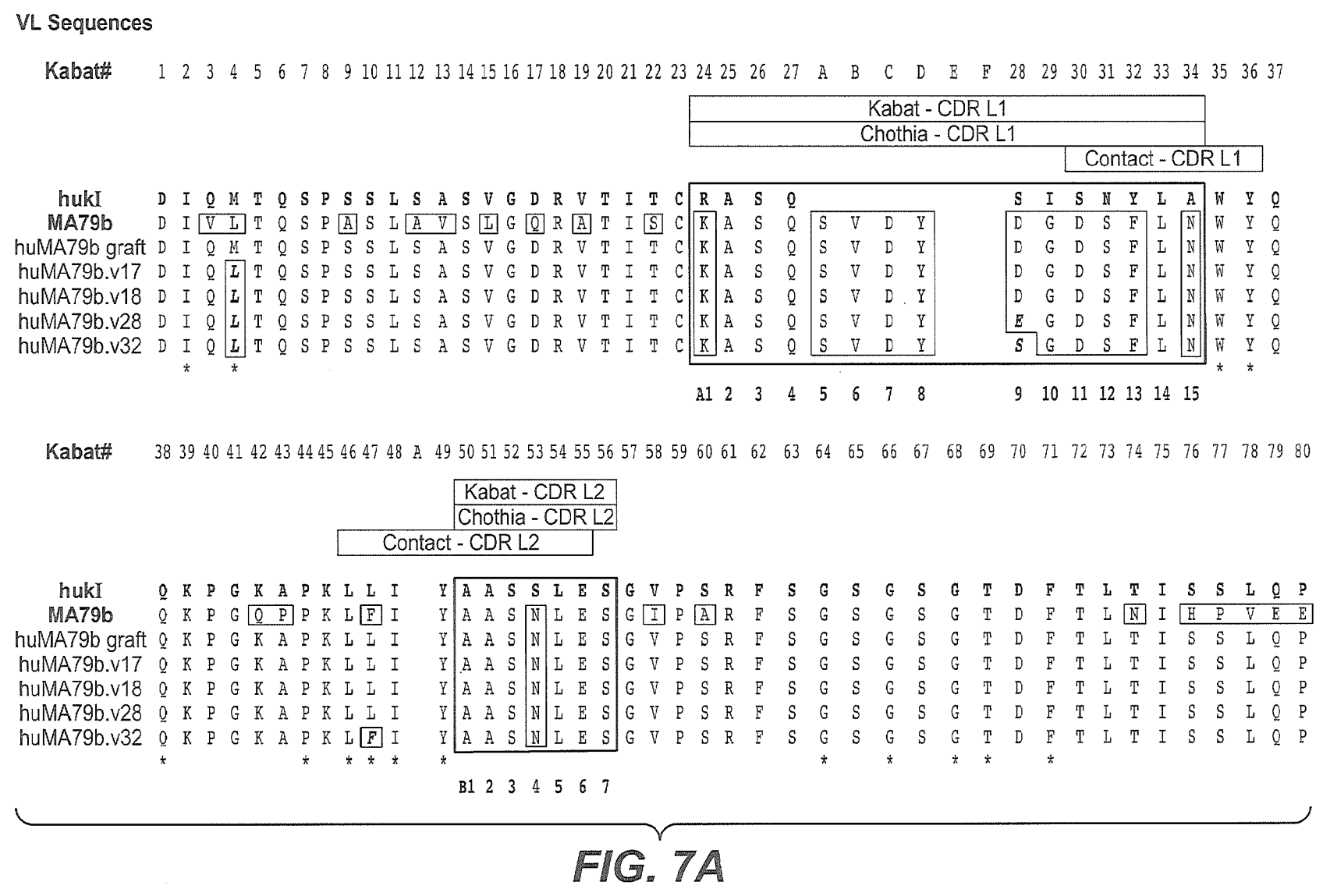

"MA79b" or "murine CD79b antibody" or "murine anti-CD79b antibody" is used herein to specifically refer to murine anti-CD79b monoclonal antibody wherein the murine anti-CD79b monoclonal antibody comprises the light chain variable domain of SEQ ID NO: 10 (FIGS. 7A-B) and the heavy chain variable domain of SEQ ID NO: 14 (FIGS. 8A-B). Murine anti-CD79b monoclonal antibody may be purchased from commercial sources such as Biomeda (anti-human CD79b antibody; Foster City, Calif.), BDbioscience (anti-human CD79b antibody; San Diego, Calif.) or Ancell (anti-human CD79b antibody; Bayport, Minn.) or generated from hybridoma clone 3A2-2E7 American Type Culture Collection (ATCC) deposit designation number HB11413, deposited with the ATCC on Jul. 20, 1993.

"chMA79b" or "chimeric MA79b antibody" is used herein to specifically refer to chimeric anti-human CD79b antibody (as previously described in U.S. application Ser. No. 11/462, 336, filed Aug. 3, 2006,US 2007/0207142, now abandoned) wherein the chimeric anti-CD79b antibody comprises the light chain of SEQ ID NO: 4 (FIG. 4). The light chain of SEQ ID NO: 4 further comprises the variable domain of SEQ ID NO: 10 (FIGS. 7A-B) and the light chain constant domain of human IgG1. The chimeric anti-CD79b antibody further comprises the heavy chain of SEQ ID NO: 6 (FIG. 6). The heavy chain of SEQ ID NO: 6 further comprises the variable domain of SEQ ID NO: 14 (FIGS. 8A-B) and the heavy chain constant domain of human IgG1.

"anti-cynoCD79b" or "anti-cyno CD79b" is used herein to refer to antibodies that binds to cyno CD79b (SEQ ID NO: 239 of FIG. 43) (as previously described in U.S. application Ser. No. 11/462,336, filed Aug. 3, 2006, US 2007/0207142, now abandoned). "anti-cynoCD79b(ch10D10)" or "ch10D10" is used herein to refer to chimeric anti-cynoCD79b (as previously described in U.S. application Ser. No. 11/462,336, filed Aug. 3, 2006, US 2007/0207142, now abandoned) which binds to cynoCD79b (SEQ ID NO: 239 of FIG. 43). Anti-cynoCD79b(ch10D10) or ch10D10 is chimeric anti-cynoCD79b antibody which comprises the light chain of SEQ ID NO: 241 (FIG. 45). Anti-cynoCD79b (ch10D10) or ch10D10 further comprises the heavy chain of SEQ ID NO: 243 (FIG. 47).

"MA79b-graft" or "MA79b-grafted 'humanized' antibody" or "huMA79b graft" is used herein to specifically refer to the graft generated by grafting the hypervariable regions from murine anti-CD79b antibody (MA79b) into the acceptor human consensus VL kappa I (huKI) and human subgroup III consensus VH (huIII) with R71A, N73T and L78A (Carter et al., Proc. Natl. Acad. Sci. USA, 89:4285 (1992)) (See Example 1A and FIGS. 7 (SEQ ID NO: 11) and 8 (SEQ ID NO: 15)).

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution", or variation thereof, refers to the replacement of an existing amino acid residue in a predetermined (starting) amino acid sequence with a different amino acid residue. Generally and preferably, the modification results in alteration in at least one physicobiochemical activity of the variant polypeptide compared to a polypeptide comprising the starting (or "wild type") amino acid sequence. For example, in the case of an antibody, a physicobiochemical activity that is altered can be binding affinity, binding capability and/or binding effect upon a target molecule.

The term "antibody" is used in the broadest sense and specifically covers, for example, single anti-CD79b monoclonal antibodies (including agonist, antagonist, neutralizing antibodies, full length or intact monoclonal antibodies), anti-CD79b antibody compositions with polyepitopic specificity, polyclonal antibodies, multivalent antibodies, multispecific antibodies (e.g., bispecific antibodies so long as they exhibit the desired biological activity), formed from at least two intact antibodies, single chain anti-CD79b antibodies, and fragments of anti-CD79b antibodies (see below), including Fab, Fab', F(ab')$_2$ and Fv fragments, diabodies, single domain antibodies (sdAbs), as long as they exhibit the desired biological or immunological activity. The term "immunoglobulin" (Ig) is used interchangeable with antibody herein. An antibody can be human, humanized and/or affinity matured.

The term "anti-CD79b antibody" or "an antibody that binds to CD79b" refers to an antibody that is capable of binding CD79b with sufficient affinity such that the antibody is useful as a diagnostic and/or therapeutic agent in targeting CD79b. Preferably, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Kd) of ≤1 µM, ≤100 nM, ≤10 nM, ≤1 nM, or ≤0.1 nM. In certain embodiments, anti-CD79b antibody binds to an epitope of CD79b that is conserved among CD79b from different species.

An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for µ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and µ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

A "naked antibody" for the purposes herein is an antibody that is not conjugated to a cytotoxic moiety or radiolabel.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments. In one embodiment, an antibody fragment comprises an antigen binding site of the intact antibody and thus retains the ability to bind antigen.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and—binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Diabodies may be bivalent or bispecific. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; Hudson et al., *Nat. Med.* 9:129-134 (2003); and Hollinger et al., Proc. Natl. Acad. Sci. USA, 90:6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies.

The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992). See also the following review articles and references cited therein: Vaswani and Hamilton, *Ann. Allergy, Asthma and Immunol.*, 1:105-115 (1998); Harris, *Biochem. Soc. Transactions*, 23:1035-1038 (1995); Hurle and Gross, *Curr. Op. Biotech.*, 5:428-433 (1994).

"Thio" when used herein to refer to an antibody refers to a cysteine-engineered antibody while "hu" when used herein to refer to an antibody refers to a humanized antibody.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, A1 an R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H35B | H26-H32..34 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H52-H56 | H47-H58 |
| H3 | H95-H102 | H95-H102 | H95-H102 | H93-H101 |

Hypervariable regions may comprise "extended hypervariable regions" as follows: 24-36 or 24-34 (L1), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "affinity matured" antibody is one with one or more alterations in one or more HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of HVR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293: 865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) *J. Mol Biol* 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) as described above.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

The phrase "substantially reduced," or "substantially different", as used herein, denotes a sufficiently high degree of difference between two numeric values (generally one associated with an antibody of the invention and the other associated with a reference/comparator antibody) such that one of skill in the art would consider the difference between the two values to be of statistical significance within the context of the biological characteristic measured by said values (e.g., Kd values, HAMA response). The difference between said two values is preferably greater than about 10%, preferably greater than about 20%, preferably greater than about 30%, preferably greater than about 40%, preferably greater than about 50% as a function of the value for the reference/comparator antibody.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences:

| | |
|---|---|
| EVQLVESGGGLVQPGGSLRLSCAAS | (SEQ ID NO: 143) |
| -H1-<br>WVRQAPGKGLEWV | (SEQ ID NO: 144) |
| -H2-<br>RFTISRDNSKNTLYLQMNSLRAEDTAVYYC | (SEQ ID NO: 145) |
| -H3-<br>WGQGTLVTVSS. | (SEQ ID NO: 146) |

A "VL subgroup I consensus framework" comprises the consensus sequence obtained from the amino acid sequences in variable light kappa subgroup I of Kabat et al. In one embodiment, the VL subgroup I consensus framework amino acid sequence comprises at least a portion or all of each of the following sequences:

| | |
|---|---|
| DIQMTQSPSSLSASVGDRVTITC | (SEQ ID NO: 139) |
| -L1-<br>WYQQKPGKAPKLLIY | (SEQ ID NO: 140) |
| -L2-<br>GVPSRFSGSGSGTDFTLTISSLQPEDFATYYC | (SEQ ID NO: 141) |
| -L3-<br>FGQGTKVEIKR. | (SEQ ID NO: 142) |

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

An antibody "which binds" an antigen of interest, e.g. a tumor-associated polypeptide antigen target, is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody that "inhibits the growth of tumor cells expressing a CD79b polypeptide" or a "growth inhibitory" antibody is one which results in measurable growth inhibition of cancer cells expressing or overexpressing the appropriate CD79b polypeptide. The CD79b polypeptide may be a transmembrane polypeptide expressed on the surface of a cancer cell or may be a polypeptide that is produced and secreted by a cancer cell. Preferred growth inhibitory anti-CD79b antibodies inhibit growth of CD79b-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody being tested. In one embodiment, growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-CD79b antibody at about 1 µg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a CD79b polypeptide. Preferably the cell is a tumor cell, e.g., a hematopoietic cell, such as a B cell, T cell, basophil, eosinophil, neutrophil, monocyte, platelet or erythrocyte. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay.

An antibody which "induces cell death" is one which causes a viable cell to become nonviable. The cell is one which expresses a CD79b polypeptide and is of a cell type which specifically expresses or overexpresses a CD79b polypeptide. The cell may be cancerous or normal cells of the particular cell type. The CD79b polypeptide may be a transmembrane polypeptide expressed on the surface of a cancer cell or may be a polypeptide that is produced and secreted by a cancer cell. The cell may be a cancer cell, e.g., a B cell or T cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies are those which induce PI uptake in the PI uptake assay in BT474 cells.

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include Clq binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol* 117:587 (1976) and Kim et al., *J. Immunol.* 24:249 (1994)).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g., as described in Gazzano-Santoro et al., *J. Immunol Methods* 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

The CD79b polypeptide "extracellular domain" or "ECD" refers to a form of the CD79b polypeptide which is essentially free of the transmembrane and cytoplasmic domains. Ordinarily, a CD79b polypeptide ECD will have less than 1% of such transmembrane and/or cytoplasmic domains and preferably, will have less than 0.5% of such domains. It will be understood that any transmembrane domains identified for the CD79b polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a CD79b polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the CD79b polypeptide disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"CD79b polypeptide variant" means a CD79b polypeptide, preferably an active CD79b polypeptide, as defined herein having at least about 80% amino acid sequence identity with a full-length native sequence CD79b polypeptide sequence as disclosed herein, a CD79b polypeptide sequence lacking the signal peptide as disclosed herein, an extracellular domain of a CD79b polypeptide, with or without the signal peptide, as disclosed herein or any other fragment of a full-length CD79b polypeptide sequence as disclosed herein (such as those encoded by a nucleic acid that represents only a portion of the complete coding sequence for a full-length CD79b polypeptide). Such CD79b polypeptide variants include, for instance, CD79b polypeptides wherein one or more amino acid residues are added, or deleted, at the N- or C-terminus of the full-length native amino acid sequence. Ordinarily, a CD79b polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence CD79b polypeptide sequence as disclosed herein, a CD79b polypeptide sequence lacking the signal peptide as disclosed herein, an extracellular domain of a CD79b polypeptide, with or without the signal peptide, as disclosed herein or any other specifically defined fragment of a full-length CD79b polypeptide sequence as disclosed herein. Ordinarily, CD79b variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, CD79b variant polypeptides will have no more than one conservative amino acid substitution as compared to the native CD79b polypeptide sequence, alternatively no more than 2, 3, 4, 5, 6, 7, 8, 9, or 10 conservative amino acid substitution as compared to the native CD79b polypeptide sequence.

"Percent (%) amino acid sequence identity" with respect to a peptide or polypeptide sequence, i.e. CD79b polypeptide sequences identified herein, is defined as the percentage of amino acid residues in a candidate sequence that are identical with the amino acid residues in the specific peptide or polypeptide sequence, i.e. CD79b polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"CD79b variant polynucleotide" or "CD79b variant nucleic acid sequence" means a nucleic acid molecule which encodes a CD79b polypeptide, preferably an active CD79b polypeptide, as defined herein and which has at least about 80% nucleic acid sequence identity with a nucleotide acid sequence encoding a full-length native sequence CD79b polypeptide sequence as disclosed herein, a full-length native sequence CD79b polypeptide sequence lacking the signal peptide as disclosed herein, an extracellular domain of a CD79b polypeptide, with or without the signal peptide, as disclosed herein or any other fragment of a full-length CD79b polypeptide sequence as disclosed herein (such as those encoded by a nucleic acid that represents only a portion of the complete coding sequence for a full-length CD79b polypeptide). Ordinarily, a CD79b variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence CD79b polypeptide sequence as disclosed herein, a full-length native sequence CD79b polypeptide sequence lacking the signal peptide as disclosed herein, an extracellular domain of a CD79b polypeptide, with or without the signal sequence, as disclosed herein or any other fragment of a full-length CD79b polypeptide sequence as disclosed herein. Variants do not encompass the native nucleotide sequence.

Ordinarily, CD79b variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to CD79b-encoding nucleic acid sequences identified herein is defined as the percentage of nucleotides in a candidate sequence that are identical with the nucleotides in the CD79b nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. Unless specifically stated otherwise, all % nucleic acid sequence identity values used herein are obtained as described in the immediately preceding paragraph using the ALIGN-2 computer program.

In other embodiments, CD79b variant polynucleotides are nucleic acid molecules that encode a CD79b polypeptide and which are capable of hybridizing, preferably under stringent hybridization and wash conditions, to nucleotide sequences encoding a full-length CD79b polypeptide as disclosed herein. CD79b variant polypeptides may be those that are encoded by a CD79b variant polynucleotide.

The term "full-length coding region" when used in reference to a nucleic acid encoding a CD79b polypeptide refers to the sequence of nucleotides which encode the full-length CD79b polypeptide of the invention (which is often shown between start and stop codons, inclusive thereof, in the accompanying figures). The term "full-length coding region" when used in reference to an ATCC deposited nucleic acid refers to the CD79b polypeptide-encoding portion of the cDNA that is inserted into the vector deposited with the ATCC (which is often shown between start and stop codons, inclusive thereof, in the accompanying figures (start and stop codons are bolded and underlined in the figures)).

"Isolated," when used to describe the various CD79b polypeptides disclosed herein, means polypeptide that has been identified and separated and/or recovered from a component of its natural environment. Contaminant components of its natural environment are materials that would typically interfere with therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the CD79b polypeptide natural environment will not be present. Ordinarily, however, isolated polypeptide will be prepared by at least one purification step.

An "isolated" CD79b polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a CD79b polypeptide or anti-CD79b antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a CD79b polypeptide which retain a biological and/or an immunological activity of native or naturally-occurring CD79b, wherein "biological" activity refers to a biological function (either inhibitory or stimulatory) caused by a native or naturally-occurring CD79b other than the ability to induce the production of an antibody against an antigenic epitope possessed by a native or naturally-occurring CD79b and an "immunological" activity refers to the ability to induce the production of an antibody against an antigenic epitope possessed by a native or naturally-occurring CD79b.

The term "antagonist" is used in the broadest sense, and includes any molecule that partially or fully blocks, inhibits, or neutralizes a biological activity of a native CD79b polypeptide. In a similar manner, the term "agonist" is used in the broadest sense and includes any molecule that mimics a biological activity of a native CD79b polypeptide. Suitable agonist or antagonist molecules specifically include agonist or antagonist antibodies or antibody fragments, fragments or amino acid sequence variants of native CD79b polypeptides, peptides, antisense oligonucleotides, small organic molecules, etc. Methods for identifying agonists or antagonists of a CD79b polypeptide, may comprise contacting a CD79b polypeptide, with a candidate agonist or antagonist molecule and measuring a detectable change in one or more biological activities normally associated with the CD79b polypeptide.

"Purified" means that a molecule is present in a sample at a concentration of at least 95% by weight, or at least 98% by weight of the sample in which it is contained.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromasomally or at a chromosomal location that is different from its natural chromosomal location.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The terms "cancer" and "cancerous" refer to or describe the physiological condition in mammals that is typically characterized by unregulated cell growth. Examples of cancer include, but are not limited to, hematopoietic cancers or blood-related cancers, such as lymphoma, leukemia, myeloma or lymphoid malignancies, but also cancers of the spleen and cancers of the lymph nodes and also carcinoma, blastoma and sarcoma. More particular examples of cancer include B-cell associated cancers, including for example, high, intermediate and low grade lymphomas (including B cell lymphomas such as, for example, mucosa-associated-lymphoid tissue B cell lymphoma and non-Hodgkin's lymphoma (NHL), mantle cell lymphoma, Burkitt' s lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia (CLL), such as B cell leukemia (CD5+ B lymphocytes), myeloid leukemia, such as acute myeloid leukemia, chronic myeloid leukemia, lymphoid leukemia, such as acute lymphoblastic leukemia (ALL) and myelodysplasia), and other hematological and/or B cell- or T-cell-associated cancers. Also included are cancers of additional hematopoietic cells, including polymorphonuclear leukocytes, such as basophils, eosinophils, neutrophils and monocytes, dendritic cells, platelets, erythrocytes and natural killer cells. Also included are cancerous B cell proliferative disorders selected from the following: lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. The origins of B-cell cancers include as follows: marginal zone B-cell lymphoma origins in memory B-cells in marginal zone, follicular lymphoma and diffuse large B-cell lymphoma originates in centrocytes in the light zone of germinal centers, chronic lymphocytic leukemia and small lymphocytic leukemia originates in B1 cells (CD5+), mantle cell lymphoma originates in naive B-cells in the mantle zone and Burkitt' s lymphoma originates in centroblasts in the dark zone of germinal centers. Tissues which include hematopoietic cells referred herein to as "hematopoietic cell tissues" include thymus and bone marrow and peripheral lymphoid tissues, such as spleen, lymph nodes, lymphoid tissues associated with mucosa, such as the gut-associated lymphoid tissues, tonsils, Peyer's patches and appendix and lymphoid tissues associated with other mucosa, for example, the bronchial linings. Further particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

A "B-cell malignancy" herein includes non-Hodgkin's lymphoma (NHL), including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia, non-Hodgkin's lymphoma (NHL), lymphocyte predominant Hodgkin's disease (LPHD), small lymphocytic lymphoma (SLL), chronic lymphocytic leukemia (CLL), indolent NHL including relapsed indolent NHL and rituximab-refractory indolent NHL; leukemia, including acute lymphoblastic leukemia (ALL), chronic lymphocytic leukemia (CLL), Hairy cell leukemia, chronic myeloblastic leukemia; mantle cell lymphoma; and other hematologic malignancies. Such malignancies may be treated with antibodies directed against B-cell surface markers, such as CD79b. Such diseases are contemplated herein to be treated by the administration of an antibody directed against a B cell surface marker, such as CD79b, and includes the administration of an unconjugated ("naked") antibody or an antibody conjugated to a cytotoxic agent as disclosed herein. Such diseases are also contemplated herein to be treated by combination therapy including an anti-CD79b antibody or anti-CD79b antibody drug conjugate of the invention in combination with another antibody or antibody drug conjugate, another cytoxic agent, radiation or other treatment administered simultaneously or in series. In exemplary treatment method of the invention, an anti-CD79b antibody of the invention is administered in combination with an anti-CD20 antibody, immunoglobulin, or CD20 binding fragment thereof, either together or sequentially. The anti-CD20 antibody may be a naked antibody or an antibody drug conjugate. In an embodiment of the combination therapy, the anti-CD79b antibody is an antibody of the present invention and the anti-CD20 antibody is Rituxan® (rituximab).

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology (3rd edition), A. Victor Hoffbrand and John E. Pettit (eds.) (Harcourt Publishers Ltd., 2000). See, in particular, the lists in FIGS. 11.57, 11.58 and 11.59. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include cancerous conditions such as malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders. Disorders further include cancerous conditions such as B cell proliferative disorders and/or B cell tumors, e.g., lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

"Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). Preferred such diseases include autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Specific examples of other autoimmune diseases as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, agranulocytosis, vasculitides (including large-vessel vasculitis such as polymyalgia rheumatica and giant-cell (Takayasu's) arteritis, medium-vessel vasculitis such as Kawasaki's disease and polyarteritis nodosa/periarteritis nodosa, immunovasculitis, CNS vasculitis, cutaneous vasculitis, hypersensitivity vasculitis, necrotizing vasculitis such as fibrinoid necrotizing vasculitis and systemic necrotizing vasculitis, ANCA-negative vasculitis, and ANCA-associated vasculitis such as Churg-Strauss syndrome (CSS), Wegener's granulomatosis, and microscopic polyangiitis), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, antiphospholipid antibody syndrome, motoneuritis, allergic neuritis, Behçet's disease/syndrome, Castleman's syndrome, Goodpasture's syndrome, Reynaud's syndrome, Sjögren's syndrome, Stevens-Johnson syndrome, pemphigoid or pemphigus such as pemphigoid bullous, cicatricial (mucous membrane) pemphigoid, skin pemphigoid, pemphigus vulgaris, paraneoplastic pemphigus, pemphigus foliaceus, pemphigus mucus-membrane pemphigoid, and pemphigus erythematosus, epidermolysis bullosa acquisita, ocular inflammation, preferably allergic ocular inflammation such as allergic conjunctivis, linear IgA bullous disease, autoimmune-induced conjunctival inflammation, autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, Grave's eye disease (ophthalmopathy or thyroid-associated ophthalmopathy), polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, keratitis such as Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica (sympathetic ophthalmitis), neonatal ophthalmitis, optic neuritis, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis. Such diseases are contemplated herein to be treated by the administration of an antibody which binds to a B cell surface marker, such as CD79b, and includes the administration of an unconjugated ("naked") antibody or an antibody conjugated to a cytotoxic agent as disclosed herein. Such diseases are also contemplated herein to be treated by combination therapy including an anti-CD79b antibody or anti-CD79b antibody drug conjugate of the invention in combination with another antibody or antibody drug conjugate, another cytoxic agent, radiation or other treatment administered simultaneously or in series.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a CD79b polypeptide-expressing cancer if, after receiving a therapeutic amount of an anti-CD79b antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-CD79b antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

An "individual" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

"Mammal" for purposes of the treatment of, alleviating the symptoms of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEENO, polyethylene glycol (PEG), and PLURONICS®.

By "solid phase" or "solid support" is meant a non-aqueous matrix to which an antibody of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an CD79b antibody) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "individual," "subject," or "patient" is a vertebrate. In certain embodiments, the vertebrate is a mammal. mammals include, but are not limited to, farm animals (such as cows), sport animals, pets (such as cats, dogs, and horses), primates, mice and rats. In certain embodiments, a mammal is human.

The term "pharmaceutical formulation" refers to a preparation which is in such form as to permit the biological activity of the active ingredient to be effective, and which contains no additional components which are unacceptably toxic to a subject to which the formulation would be administered. Such formulation may be sterile.

A "sterile" formulation is aseptic of free from all living microorganisms and their spores.

An "effective amount" of an antibody as disclosed herein is an amount sufficient to carry out a specifically stated purpose. An "effective amount" may be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

A "growth inhibitory amount" of an anti-CD79b antibody is an amount capable of inhibiting the growth of a cell, especially tumor, e.g., cancer cell, either in vitro or in vivo. A "growth inhibitory amount" of an anti-CD79b antibody for purposes of inhibiting neoplastic cell growth may be determined empirically and in a routine manner.

A "cytotoxic amount" of an anti-CD79b antibody is an amount capable of causing the destruction of a cell, especially tumor, e.g., cancer cell, either in vitro or in vivo. A "cytotoxic amount" of an anti-CD79b antibody for purposes of inhibiting neoplastic cell growth may be determined empirically and in a routine manner.

A "CD79b-expressing cell" is a cell which expresses an endogenous or transfected CD79b polypeptide either on the cell surface or in a secreted form. A "CD79b-expressing cancer" is a cancer comprising cells that have a CD79b polypeptide present on the cell surface or that produce and secrete a CD79b polypeptide. A "CD79b-expressing cancer" optionally produces sufficient levels of CD79b polypeptide on the surface of cells thereof, such that an anti-CD79b antibody can bind thereto and have a therapeutic effect with respect to the cancer. In another embodiment, a "CD79b-expressing cancer" optionally produces and secretes sufficient levels of CD79b polypeptide, such that an anti-CD79b antibody antagonist can bind thereto and have a therapeutic effect with respect to the cancer. With regard to the latter, the antagonist may be an antisense oligonucleotide which reduces, inhibits or prevents production and secretion of the secreted CD79b polypeptide by tumor cells. A cancer which "overexpresses" a CD79b polypeptide is one which has significantly higher levels of CD79b polypeptide at the cell surface thereof, or produces and secretes, compared to a noncancerous cell of the same tissue type. Such overexpression may be caused by gene amplification or by increased transcription or translation. CD79b polypeptide overexpression may be determined in a detection or prognostic assay by evaluating increased levels of the CD79b protein present on the surface of a cell, or secreted by the cell (e.g., via an immunohistochemistry assay using anti-CD79b antibodies prepared against an isolated CD79b polypeptide which may be prepared using recombinant DNA technology from an isolated nucleic acid encoding the CD79b polypeptide; FACS analysis, etc.). Alternatively, or additionally, one may measure levels of CD79b polypeptide-encoding nucleic acid or mRNA in the cell, e.g., via fluorescent in situ hybridization using a nucleic acid based probe corresponding to a CD79b-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One may also study CD79b polypeptide overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin(cis-diamine,dichloroplatinum(II), CAS No. 15663-27-1), carboplatin (CAS No. 41575-94-4), paclitaxel (TAXOL®Bristol-Myers Squibb Oncology, Princeton, N.J.), trastuzumab (HERCEPTIN®, Genentech), temozolomide(4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZAR-NESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaII (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

A "growth inhibitory agent" when used herein refers to a compound or composition which inhibits growth of a cell, especially a CD79b-expressing cancer cell, either in vitro or in vivo. Thus, the growth inhibitory agent may be one which significantly reduces the percentage of CD79b-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

The term "intracellular metabolite" refers to a compound resulting from a metabolic process or reaction inside a cell on an antibody-drug conjugate (ADC). The metabolic process or reaction may be an enzymatic process, such as proteolytic cleavage of a peptide linker of the ADC, or hydrolysis of a functional group such as a hydrazone, ester, or amide. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an antibody-drug conjugate (ADC) whereby the covalent attachment, i e linker, between the drug moiety (D) and the antibody (Ab) is broken, resulting in the free drug dissociated from the antibody inside the cell. The cleaved moieties of the ADC are thus intracellular metabolites.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The term "cytotoxic activity" refers to a cell-killing, cytostatic or growth inhibitory effect of an ADC or an intracellular metabolite of an ADC. Cytotoxic activity may be expressed as the $IC_{50}$ value, which is the concentration (molar or mass) per unit volume at which half the cells survive.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2$ $CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)$ $CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2CH_2CH_2$ $CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heterocycle," "hetercyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco [3.1.0]hexanyl, 3-azabicyclo[4.1.0]heptanyl, azabicyclo [2.2.2]hexanyl, 3H-indolyl quinolizin pyridyl ureas. Spiro moieties are also included within the scope of this definition. Examples of a heterocyclic group wherein 2 ring carbon atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH₂—) 1,2-ethyl (—CH₂CH₂—), 1,3-propyl (—CH₂CH₂CH₂—), 1,4-butyl (—CH₂CH₂CH₂CH₂—), and the like.

A "$C_1$-$C_{10}$ alkylene" is a straight chain, saturated hydrocarbon group of the formula —(CH₂)$_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH₂C≡C—), and 4-pentynyl (—CH₂CH₂CH₂C≡C—).

An "arylene" is an aryl group which has two covalent bonds and can be in the ortho, meta, or para configurations as shown in the following structures:

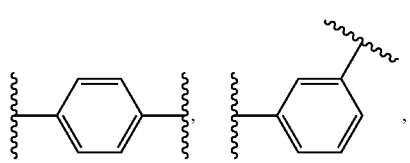

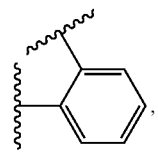

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)NH₂, —C(O)NHR', —C(O)N(R')₂—HC(O)R', —S(O)₂R', —S(O)R', —OH, -halogen, —N₃, —NH₂, —NH(R'), —N(R')₂ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp³ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

The term "prodrug" as used in this application refers to a precursor or derivative form of a compound of the invention that may be less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

Abbreviations

Linker Components:
MC=6-maleimidocaproyl
Val-Cit or "vc"=valine-citrulline (an exemplary dipeptide in a protease cleavable linker)
Citrulline=2-amino-5-ureido pentanoic acid
PAB=p-aminobenzyloxycarbonyl (an example of a "self immolative" linker component)
Me-Val-Cit=N-methyl-valine-citrulline (wherein the linker peptide bond has been modified to prevent its cleavage by cathepsin B)
MC(PEG)6-OH=maleimidocaproyl-polyethylene glycol (can be attached to antibody cysteines).

Cytotoxic Drugs:
MMAE=mono-methyl auristatin E (MW 718)
MMAF=variant of auristatin E (MMAE) with a phenylalanine at the C-terminus of the drug (MW 731.5)
MMAF-DMAEA=MMAF with DMAEA (dimethylaminoethylamine) in an amide linkage to the C-terminal phenylalanine (MW 801.5)
MMAF-TEG=MMAF with tetraethylene glycol esterified to the phenylalanine
MMAF-NtBu=N-t-butyl, attached as an amide to C-terminus of MMAF
DM1=N(2')-deacetyl-N(2')-(3-mercapto-1-oxopropyl)-maytansine
DM3=N(2)-deacetyl-N2-(4-mercapto-1-oxopentyl)-maytansine
DM4=N(2)-deacetyl-N2-(4-mercapto-4-methyl-1-oxopentyl)-maytansine Further abbreviations are as follows: AE is auristatin E, Boc is N-(t-butoxycarbonyl), cit is citrulline, dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleucine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, MeOH is methanol, Mtr is 4-anisyldiphenylmethyl (or 4-methoxytrityl), nor is (1S,2R)-(+)-norephedrine, PBS is phosphate-buffered saline (pH 7.4), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

A "free cysteine amino acid" refers to a cysteine amino acid residue which has been engineered into a parent antibody, has a thiol functional group (—SH), and is not paired as an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 80% yield with a thiol-reactive reagent has a thiol reactivity value of 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

III. Compositions and Methods of the Invention

The invention provides anti-CD79b antibodies or functional fragments thereof, and their method of use in the treatment of hematopoietic tumors.

In one aspect, the invention provides an antibody which binds, preferably specifically, to any of the above or below described polypeptides. Optionally, the antibody is a monoclonal antibody, antibody fragment, including Fab, Fab', F(ab')$_2$, and Fv fragment, diabody, single domain antibody, chimeric antibody, humanized antibody, single-chain antibody or antibody that competitively inhibits the binding of an anti-CD79b polypeptide antibody to its respective antigenic epitope. Antibodies of the present invention may optionally be conjugated to a growth inhibitory agent or cytotoxic agent such as a toxin, including, for example, an auristatin, a maytansinoid, a dolostatin derivative or a calicheamicin, an antibiotic, a radioactive isotope, a nucleolytic enzyme, or the like. The antibodies of the present invention may optionally be produced in CHO cells or bacterial cells and preferably induce death of a cell to which they bind. For detection purposes, the antibodies of the present invention may be detectably labeled, attached to a solid support, or the like.

In one aspect, the invention provides a humanized anti-CD79b antibody wherein the monovalent affinity of the antibody to CD79b (e g affinity of the antibody as a Fab fragment to CD79b) is substantially the same as the monovalent affinity of a murine antibody (e.g. affinity of the murine antibody as a Fab fragment to CD79b) or a chimeric antibody (e.g. affinity of the chimeric antibody as a Fab fragment to CD79b), comprising, consisting or consisting essentially of a light chain and heavy chain variable domain sequence as depicted in FIGS. 7A-B (SEQ ID NO: 10) and FIGS. 8A-B (SEQ ID NO: 14).

In another aspect, the invention provides a humanized anti-CD79b antibody wherein the monovalent affinity of the antibody to CD79b (e.g., affinity of the antibody as a Fab fragment to CD79b) is lower, for example at least 1, 2, 3, 4, 5, 6, 7, 8, 9, 10, 11, 12, 13, 14, 15, 16, 17, 18, 19, 20, 25, 30, 35, 40, 45, 50, 55 or 60-fold lower, than the monovalent affinity of a murine antibody (e.g., affinity of the murine antibody as a Fab fragment to CD79b) or a chimeric antibody (e.g. affinity of the chimeric antibody as a Fab fragment to CD79b), comprising, consisting or consisting essentially of a light chain and heavy chain variable domain sequence as depicted in FIGS. 7A-B (SEQ ID NO: 10) and FIGS. 8A-B (SEQ ID NO: 14).

In another aspect, the invention provides a humanized anti-CD79b antibody wherein the monovalent affinity of the antibody to CD79b (e.g., affinity of the antibody as a Fab fragment to CD79b) is greater, for example at least 1, 2, 3, 4, 5, 6, 7, 8, 9 or 10-fold greater, than the monovalent affinity of a murine antibody (e.g., affinity of the murine antibody as a Fab fragment to CD79b) or a chimeric antibody (e.g. affinity of the chimeric antibody as a Fab fragment to CD79b), comprising, consisting or consisting essentially of a light chain and heavy chain variable domain sequence as depicted in FIGS. 7A-B (SEQ ID NO: 10) and FIGS. 8A-B (SEQ ID NO: 14).

In one aspect, the invention provides a humanized anti-CD79b antibody wherein the affinity of the antibody in its bivalent form to CD79b (e g affinity of the antibody as an IgG to CD79b) is substantially the same as the affinity of a murine antibody (e.g. affinity of the antibody as an IgG to CD79b) or a chimeric antibody (e.g. affinity of the chimeric antibody as a Fab fragment to CD79b) in its bivalent form, comprising, consisting or consisting essentially of a light chain and heavy chain variable domain sequence as depicted in FIGS. 7A-B (SEQ ID NO: 10) and FIGS. 8A-B (SEQ ID NO: 14).

In another aspect, the invention provides a humanized anti-CD79b antibody wherein the affinity of the antibody in its bivalent form to CD79b (e.g. affinity of the antibody as an IgG to CD79b) is lower, for example at least 1, 2, 3, 4, 5, 6, 7, 8, 9, 10, 11, 12, 13, 14, 15, 16, 17, 18, 19, 20, 25, 30, 35, 40, 45, 50, 55 or 60-fold lower, as the affinity of a murine antibody (e.g. affinity of the antibody as an IgG to CD79b) or a chimeric antibody (e.g. affinity of the chimeric antibody as an IgG fragment to CD79b) in its bivalent form, comprising, consisting or consisting essentially of a light chain and heavy chain variable domain sequence as depicted in FIGS. 7A-B (SEQ ID NO: 10) and FIGS. 8A-B (SEQ ID NO: 14).

In another aspect, the invention provides a humanized anti-CD79b antibody wherein the affinity of the antibody in its bivalent form to CD79b (e.g. affinity of the antibody as an IgG to CD79b) is greater, for example at least 1, 2, 3, 4, 5, 6, 7, 8, 9 or 10-fold greater, than the affinity of a murine antibody (e g affinity of the antibody as an IgG to CD79b) or a chimeric antibody (e.g. affinity of the chimeric antibody as an IgG fragment to CD79b) in its bivalent form, comprising, consisting or consisting essentially of a light chain and heavy chain variable domain sequence as depicted in FIGS. 7A-B (SEQ ID NO: 10) and FIGS. 8A-B (SEQ ID NO: 14).

In another aspect, the invention provides a humanized anti-CD79b antibody wherein the affinity of the antibody in its bivalent form to CD79b (e.g., affinity of the antibody as an IgG to CD79b) is 0.4 nM. In a further aspect, the invention provides a humanized anti-CD79b antibody wherein the affinity of the antibody in its bivalent form to CD79b (e.g., affinity of the antibody as an IgG to CD79b) is 0.4 nM +/−0.04.

In another aspect, the invention provides a humanized anti-CD79b antibody wherein the affinity of the antibody in its bivalent form to CD79b (e.g., affinity of the antibody as an IgG to CD79b) is 0.3 nM or better. In another aspect, the invention provides a humanized anti-CD79b antibody wherein the affinity of the antibody in its bivalent form to CD79b (e.g., affinity of the antibody as an IgG to CD79b) is 0.32 nM or better. In another aspect, the invention provides a humanized anti-CD79b antibody wherein the affinity of the antibody in its bivalent form to CD79b (e.g., affinity of the antibody as an IgG to CD79b) is 0.36 nM or better. In another aspect, the invention provides a humanized anti-CD79b antibody wherein the affinity of the antibody in its bivalent form to CD79b (e.g., affinity of the antibody as an IgG to CD79b) is 0.4 nM or better. In another aspect, the invention provides a humanized anti-CD79b antibody wherein the affinity of the antibody in its bivalent form to CD79b (e.g., affinity of the antibody as an IgG to CD79b) is 0.44 nM or better. In another aspect, the invention provides a humanized anti-CD79b antibody wherein the affinity of the antibody in its bivalent form to CD79b (e.g., affinity of the antibody as an IgG to CD79b) is 0.48 nM or better. In another aspect, the invention provides a humanized anti-CD79b antibody wherein the affinity of the antibody in its bivalent form to CD79b (e.g., affinity of the antibody as an IgG to CD79b) is 0.5 nM or better. In another aspect, the invention provides a humanized anti-CD79b antibody wherein the affinity of the antibody in its bivalent form to CD79b (e.g., affinity of the antibody as an IgG to CD79b) is between 0.3 nM and 0.5 nM. In another aspect, the invention provides a humanized anti-CD79b antibody wherein the affinity of the antibody in its bivalent form to CD79b (e.g., affinity of the antibody as an IgG to CD79b) is between 0.32 nM and 0.48 nM. In another aspect, the invention provides a humanized anti-CD79b antibody wherein the affinity of the antibody in its bivalent form to CD79b (e.g., affinity of the antibody as an IgG to CD79b) is between 0.36 nM and 0.44 nM.

In another aspect, the invention provides a humanized anti-CD79b antibody wherein the affinity of the antibody in its bivalent form to CD79b (e.g., affinity of the antibody as an IgG to CD79b) is 0.2 nM. In a further aspect, the invention provides a humanized anti-CD79b antibody wherein the affinity of the antibody in its bivalent form to CD79b (e.g., affinity of the antibody as an IgG to CD79b) is 0.2 nM +/−0.02.

In another aspect, the invention provides a humanized anti-CD79b antibody wherein the affinity of the antibody in its bivalent form to CD79b (e.g., affinity of the antibody as an IgG to CD79b) is 0.1 nM or better. In another aspect, the invention provides a humanized anti-CD79b antibody wherein the affinity of the antibody in its bivalent form to CD79b (e.g., affinity of the antibody as an IgG to CD79b) is 0.12 nM or better. In another aspect, the invention provides a humanized anti-CD79b antibody wherein the affinity of the antibody in its bivalent form to CD79b (e.g., affinity of the antibody as an IgG to CD79b) is 0.14 nM or better. In another aspect, the invention provides a humanized anti-CD79b antibody wherein the affinity of the antibody in its bivalent form to CD79b (e.g., affinity of the antibody as an IgG to CD79b) is 0.16 nM or better. In another aspect, the invention provides a humanized anti-CD79b antibody wherein the affinity of the antibody in its bivalent form to CD79b (e.g., affinity of the antibody as an IgG to CD79b) is 0.18 nM or better. In another aspect, the invention provides a humanized anti-CD79b antibody wherein the affinity of the antibody in its bivalent form to CD79b (e.g., affinity of the antibody as an IgG to CD79b) is 0.2 nM or better. In another aspect, the invention provides a humanized anti-CD79b antibody wherein the affinity of the antibody in its bivalent form to CD79b (e.g., affinity of the antibody as an IgG to CD79b) is 0.22 nM or better. In another aspect, the invention provides a humanized anti-CD79b antibody wherein the affinity of the antibody in its bivalent form to CD79b (e.g., affinity of the antibody as an IgG to CD79b) is 0.24 nM or better. In another aspect, the invention provides a humanized anti-CD79b antibody wherein the affinity of the antibody in its bivalent form to CD79b (e.g., affinity of the antibody as an IgG to CD79b) is 0.26 nM or better. In another aspect, the invention provides a humanized anti-CD79b antibody wherein the affinity of the antibody in its bivalent form to CD79b (e.g., affinity of the antibody as an IgG to CD79b) is 0.28 nM or better. In another aspect, the invention provides a humanized anti-CD79b antibody wherein the affinity of the antibody in its bivalent form to CD79b (e.g., affinity of the antibody as an IgG to CD79b) is 0.30 nM or better. In another aspect, the invention provides a humanized anti-CD79b antibody wherein the affinity of the antibody in its bivalent form to CD79b (e.g., affinity of the antibody as an IgG to CD79b) is between 0.1 nM and 0.3 nM. In another aspect, the invention provides a humanized anti-CD79b antibody wherein the affinity of the antibody in its bivalent form to CD79b (e.g., affinity of the antibody as an IgG to CD79b) is between 0.12 nM and 0.28 nM. In another aspect, the invention provides a humanized anti-CD79b antibody wherein the affinity of the antibody in its bivalent form to CD79b (e.g., affinity of the antibody as an IgG to CD79b) is between 0.14 nM and 0.26 nM. In another aspect, the invention provides a humanized anti-CD79b antibody wherein the affinity of the antibody in its bivalent form to CD79b (e.g., affinity of the antibody as an IgG to CD79b) is between 0.16 nM and 0.24 nM. In another aspect, the invention provides a humanized anti-CD79b antibody wherein the affinity of the antibody in its bivalent form to CD79b (e.g., affinity of the antibody as an IgG to CD79b) is between 0.18 nM and 0.22 nM.

In another aspect, the invention provides a humanized anti-CD79b antibody wherein the affinity of the antibody in its bivalent form to CD79b (e.g., affinity of the antibody as an IgG to CD79b) is 0.5 nM. In a further aspect, the invention provides a humanized anti-CD79b antibody wherein the affinity of the antibody in its bivalent form to CD79b (e.g., affinity of the antibody as an IgG to CD79b) is 0.5 nM +/−0.1.

In another aspect, the invention provides a humanized anti-CD79b antibody wherein the affinity of the antibody in its bivalent form to CD79b (e.g., affinity of the antibody as an IgG to CD79b) is 0.4 nM or better. In another aspect, the invention provides a humanized anti-CD79b antibody wherein the affinity of the antibody in its bivalent form to CD79b (e.g., affinity of the antibody as an IgG to CD79b) is 0.5 nM or better. In another aspect, the invention provides a humanized anti-CD79b antibody wherein the affinity of the antibody in its bivalent form to CD79b (e.g., affinity of the antibody as an IgG to CD79b) is 0.6 nM or better. In another aspect, the invention provides a humanized anti-CD79b antibody wherein the affinity of the antibody in its bivalent form to CD79b (e.g., affinity of the antibody as an IgG to CD79b) is 0.7 nM or better. In another aspect, the invention provides a humanized anti-CD79b antibody wherein the affinity of the antibody in its bivalent form to CD79b (e.g., affinity of the antibody as an IgG to CD79b) is between 0.3 nM and 0.7 nM. In another aspect, the invention provides a humanized anti-CD79b antibody wherein the affinity of the antibody in its bivalent form to CD79b (e.g., affinity of the antibody as an IgG to CD79b) is between 0.4 nM and 0.6 nM. In another aspect, the invention provides a humanized anti-CD79b antibody wherein the affinity of the antibody in its bivalent form to CD79b (e.g., affinity of the antibody as an IgG to CD79b) is between 0.5 nM and 0.55 nM.

In one aspect, the monovalent affinity of the murine antibody to CD79b is substantially the same as the binding affinity of a Fab fragment comprising variable domain sequences of SEQ ID NO: 10 (FIGS. 7A-B) and SEQ ID NO: 14 (FIGS. 8A-B). In another aspect, the monovalent affinity of the murine antibody to CD79b is substantially the same as the binding affinity of a Fab fragment comprising variable domain sequences of an antibody generated from hybridoma deposited with the ATCC as HB11413 on Jul. 20, 1993 or chimeric antibody comprising the variable domains from antibody generated from hybridomas deposited with the ATCC as HB11413 on Jul. 20, 1993.

As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. For example, in one embodiment, if an antibody of the invention (A) has an affinity that is "3-fold lower" than the affinity of a reference antibody (M), then if the Kd value for A is 3x, the Kd value of M would be 1x, and the ratio of Kd of A to Kd of M would be 3:1. Conversely, in one embodiment, if an antibody of the invention (C) has an affinity that is "3-fold greater" than the affinity of a reference antibody (R), then if the Kd value for C is 1x, the Kd value of R would be 3x, and the ratio of Kd of C to Kd of R would be 1:3. Any of a number of assays known in the art, including those described herein, can be used to obtain binding affinity measurements, including, for example, Biacore, radioimmunoassay (RIA) and ELISA.

In one aspect, an antibody that binds to CD79b is provided, wherein the antibody comprises:

(a) at least one, two, three, four, five or six HVRs selected from the group consisting of:
(i) HVR-L1 comprising sequence A1-A15, wherein A1-A15 is KASQSVDYDGDSFLN (SEQ ID NO: 131)
(ii) HVR-L2 comprising sequence B1-B7, wherein B1-B7 is AASNLES (SEQ ID NO: 132)
(iii) HVR-L3 comprising sequence C1-C9, wherein C1-C9 is QQSNEDPLT (SEQ ID NO: 133)
(iv) HVR-H1 comprising sequence D1-D10, wherein D1-D10 is GYTFSSYWIE (SEQ ID NO: 134)
(v) HVR-H2 comprising sequence E1-E18, wherein E1-E18 is GEILPGGGDTNYNEIFKG (SEQ ID NO: 135) and
(vi) HVR-H3 comprising sequence F1-F10, wherein F1-F10 IS TRRVPVYFDY (SEQ ID NO: 136).

In one embodiment, HVR-L1 of an antibody of the invention comprises the sequence of SEQ ID NO: 131. In one embodiment, HVR-L2 of an antibody of the invention comprises the sequence of SEQ ID NO: 132. In one embodiment, HVR-L3 of an antibody of the invention comprises the sequence of SEQ ID NO: 133. In one embodiment, HVR-H1 of an antibody of the invention comprises the sequence of SEQ ID NO: 134. In one embodiment, HVR-H2 of an antibody of the invention comprises the sequence of SEQ ID NO: 135. In one embodiment, HVR-H3 of an antibody of the invention comprises the sequence of SEQ ID NO: 136. In one embodiment, an antibody of the invention comprising these sequences (in combination as described herein) is humanized or human.

In one aspect, an antibody that binds to CD79b is provided, wherein the antibody comprises:

(a) at least one, two, three, four, five or six HVRs selected from the group consisting of:
(i) HVR-L1 comprising sequence A1-A15, wherein A1-A15 is KASQSVDYDGDSFLN (SEQ ID NO: 131)
(ii) HVR-L2 comprising sequence B1-B7, wherein B1-B7 is AASNLES (SEQ ID NO: 132)
(iii) HVR-L3 comprising sequence C1-C9, wherein C1-C9 is QQSNEDPLT (SEQ ID NO: 133)
(iv) HVR-H1 comprising sequence D1-D10, wherein D1-D10 is GYTFSSYWIE (SEQ ID NO: 134)
(v) HVR-H2 comprising sequence E1-E18, wherein E1-E18 is GEILPGGGDTNYNEIFKG (SEQ ID NO: 135) and
(vi) HVR-H3 comprising sequence F1-F10, wherein F1-F10 IS TRRVPVYFDY (SEQ ID NO: 136); and
(b) at least one variant HVR wherein the variant HVR sequence comprises modification of at least one residue of the sequence depicted in SEQ ID NOs: 131, 132, 133, 134, 135 or 136. In one embodiment, HVR-L1 of an antibody of the invention comprises the sequence of SEQ ID NO: 131. In one embodiment, HVR-L2 of an antibody of the invention comprises the sequence of SEQ ID NO: 132. In one embodiment, HVR-L3 of an antibody of the invention comprises the sequence of SEQ ID NO: 133. In one embodiment, HVR-H1 of an antibody of the invention comprises the sequence of SEQ ID NO: 134. In one embodiment, HVR-H2 of an antibody of the invention comprises the sequence of SEQ ID NO: 135. In one embodiment, HVR-H3 of an antibody of the invention comprises the sequence of SEQ ID NO: 136. In one embodiment of the invention comprising these sequences (in combination as described herein) is humanized or human.

In one aspect, the invention provides an antibody comprising one, two, three, four, five or six HVRs, wherein each HVR comprises, consists or consists essentially of a sequence selected from the group consisting of SEQ ID NOs: 131, 132, 133, 134, 135, and 136, and wherein SEQ ID NO: 131 corresponds to an HVR-L1, SEQ ID NO: 132 corresponds to HVR-L2, SEQ ID NO: 133 corresponds to an HVR-L3, SEQ ID NO: 134 corresponds to an HVR-H1, SEQ ID NO: 135 corresponds to an HVR-H2, and SEQ ID NO: 136 corresponds to an HVR-H3. In one embodiment, an antibody of the invention comprises HVR-L1, HVR-L2, HVR-L3, HVR-H1, HVR-H2, and HVR-H3, wherein each, in order, comprises SEQ ID NO: 131, 132, 133, 134, 135 and 136.

Variant HVRs in an antibody of an invention can have modifications of one or more residues within the HVR. In one embodiment, a HVR-L1 variant comprises one substitution in the following positions: A4 (K), A9 (E or S) and A10 (A or S). In one embodiment, a HVR-L2 variant comprises 1-5 (1, 2, 3, 4, or 5) substitutions in any one or combination of the following positions: B2 (S or G), B3 (R or G), B4 (K, R, Y, I, H or Q), B5 (R), B6 (G, K, A, R, S or L) and B7 (R, N, T or G). In one embodiment, a HVR-L3 variant comprises 1-4 (1, 2, 3 or 4) substitutions in any one or combination of the following positions: C1 (N or D), C2 (N or P), C3 (D or R), C5 (S, K, A, Q, D, L or G), C6 (A, E or N), C7 (A), C8 (R) and C9 (N). In one embodiment, a HVR-H1 variant comprises 1-7 (1, 2, 3, 4, 5, 6 or 7) substitution in any one or combination of the following positions: D1 (P), D2 (F), D3 (P, S, Y, G or N), D4 (L or V), D5 (T, R, N, K, C, G or P), D6 (R, T, K or G), D8 (F), D9 (V OR L) and D10 (S, Q, N or D). In on embodiment, a HVR-H3 variant comprises 1-3 (1, 2 or 3) substitutions in any one or combination of the following positions: F4 (R or I), F6 (I or F), F7 (K, C, R, V or F), F8 (L), and F9 (S). Letter(s) in parenthesis following each position indicates an illustrative substitution (i.e., replacement) amino acid; as would be evident to one skilled in the art, suitability of other amino acids as substitution amino acids in the context described herein can be routinely assessed using techniques known in the art and/or described herein. In one embodiment, A9 in a variant HVR-L1 is E. In one embodiment, F6 in a variant HVR-H3 is I. In one embodiment, F7 in a variant HVR-H3 is R. In one embodiment, F8 in a variant HVR-H3 is L. In one embodiment an antibody of the invention comprises a variant HVR-H3 wherein F6 is I, F7 is R and F8 is L. In one embodiment an antibody of the invention comprises a variant HVR-L1 wherein A9 is E and a variant HVR-H3 wherein F6 is I, F7 is R and F8 is L. In one embodiment, A9 in a variant HVR-L1 is S. In one embodiment an antibody of the invention comprises a variant HVR-L1 wherein A9 is S and a variant HVR-H3 wherein F6 is I, F7 is R and F8 is L.

In one embodiment, an antibody of the invention comprises a variant HVR-L1 wherein A4 is K. In some embodiments, said variant HVR-L1 comprises HVR-L2, HVR-L3, HVR-H1, HVR-H2 and HVR-H3 wherein each comprises, in order, the sequence depicted in SEQ ID NOs: 132, 133, 134, 135 and 136. In some embodiments, said variant HVR-L1 antibody further comprises a HVR-L1 variant wherein A9 is E or S and/or A10 is A or S. In some embodiments, said variant HVR-L1 antibody further comprises a HVR-L3 variant wherein C6 is E or N and/or C7 is A. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiments of these antibodies, these antibodies further comprise a human κI light chain framework consensus sequence. In some embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F. In one embodiment of these antibodies, the human subgroup III heavy chain framework consensus sequence comprises substitution at position 48, 67, 69, 71, 73, 75, 78 and/or 80. In some embodiments of these antibodies, position (of the human subgroup III heavy chain framework consensus sequence) 48 is I, 67 is A, 69 is F, 71 is A, 73 is T, 75 is S, 78 is A and or 80 is M. In some embodiments of these antibodies, these antibodies further comprise a human κI light chain framework consensus sequence. In one embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F.

In one embodiment, an antibody of the invention comprises a variant HVR-L2 wherein B3 is R, B4 is K, B6 is G and B7 is R. In one embodiment, an antibody of the invention comprises a variant HVR-L2 wherein B3 is R, B4 is Y, B6 is K and B7 is R. In one embodiment, an antibody of the invention comprises a variant HVR-L2 wherein B3 is R B4 is K and B6 is G. In some embodiments, said variant HVR-L2 antibody further comprises HVR-L1, HVR-L3, HVR-H1, HVR-H2 and HVR-H3 wherein each comprises, in order, the sequence depicted in SEQ ID NOs: 131, 133, 134, 135 and 136. In some embodiments, said variant HVR-L2 antibody further comprises a HVR-L1 variant wherein A9 is E or S and/or A10 is A or S. In some embodiments, said variant HVR-L2 antibody further comprises a HVR-L3 variant wherein C6 is E or N and/or C7 is A. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiments of these antibodies, these antibodies further comprise a human κI light chain framework consensus sequence. In some embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F. In one embodiment of these antibodies, the human subgroup III heavy chain framework consensus sequence comprises substitution at position 48, 67, 69, 71, 73, 75, 78 and/or 80. In some embodiments of these antibodies, position (of the human subgroup III heavy chain framework consensus sequence) 48 is I, 67 is A, 69 is F, 71 is A, 73 is T, 75 is S, 78 is A and or 80 is M. In some embodiments of these antibodies, these antibodies further comprise a human κI light chain framework consensus sequence. In one embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F.

In one embodiment, an antibody of the invention comprises a variant HVR-L3 wherein C5 is K. In one embodiment, an antibody of the invention comprises a variant HVR-L3 wherein C5 is S. In some embodiments, said variant HVR-L3 antibody further comprises HVR-L1, HVR-L2, HVR-H1, HVR-H2 and HVR-H3 wherein each comprises, in order, the sequence depicted in SEQ ID NOs: 131, 132, 134, 135 and 136. In some embodiments, said variant HVR-L3 antibody further comprises a HVR-L1 variant wherein A9 is E or S and/or A10 is A or S. In some embodiments, said variant HVR-L3 antibody further comprises a HVR-L3 variant wherein C6 is E or N and/or C7 is A. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiments of these antibodies, these antibodies further comprise a human κI light chain frame-work consensus sequence. In some embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F. In one embodiment of these antibodies, the human subgroup III heavy chain framework consensus sequence comprises substitution at position 48, 67, 69, 71, 73, 75, 78 and/or 80. In some embodiments of these antibodies, position (of the human subgroup III heavy chain framework consensus sequence) 48 is I, 67 is A, 69 is F, 71 is A, 73 is T, 75 is S, 78 is A and or 80 is M. In some embodiments of these antibodies, these antibodies further comprise a human κI light chain framework consensus sequence. In one embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F.

In one embodiment, an antibody of the invention comprises a variant HVR-H1 wherein D3 is P, D5 is T, D6 is R and D10 is N. In one embodiment, an antibody of the invention comprises a variant HVR-H1 wherein D3 is P, D5 is N, D6 is R and D10 is N. In some embodiments, said variant HVR-H1 antibody further comprises HVR-L1, HVR-L2, HVR-L3, HVR-H2 and HVR-H3 wherein each comprises, in order, the sequence depicted in SEQ ID NOs: 131, 132, 133, 135 and 136. In some embodiments, said variant HVR-H1 antibody further comprises a HVR-L1 variant wherein A9 is E or S and/or A10 is A or S. In some embodiments, said variant HVR-H1 antibody further comprises a HVR-L3 variant wherein C6 is E or N and/or C7 is A. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiments of these antibodies, these antibodies further comprise a human κI light chain framework consensus sequence. In some embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F. In one embodiment of these antibodies, the human subgroup III heavy chain framework consensus sequence comprises substitution at position 48, 67, 69, 71, 73, 75, 78 and/or 80. In some embodiments of these antibodies, position (of the human subgroup III heavy chain framework consensus sequence) 48 is I, 67 is A, 69 is F, 71 is A, 73 is T, 75 is S, 78 is A and or 80 is M. In some embodiments of these antibodies, these antibodies further comprise a human κI light chain framework consensus sequence. In one embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F.

In one embodiment, an antibody of the invention comprises a variant HVR-H3 wherein F6 is I and F8 is L. In one embodiment, an antibody of the invention comprises a variant HVR-H3 wherein F6 is I, F7 is R and F8 is L. In some embodiments, said variant HVR-H3 antibody further comprises HVR-L1, HVR-L2, HVR-L3, HVR-H1 and HVR-H2 wherein each comprises, in order, the sequence depicted in SEQ ID NOs: 131, 132, 133, 134 and 135. In some embodiments, said variant HVR-H3 antibody further comprises a HVR-L1 variant wherein A9 is E or S and/or A10 is A or S. In some embodiments, said variant HVR-H3 antibody further comprises a HVR-L3 variant wherein C6 is E or N and/or C7 is A. In some embodiments, these antibodies further comprise a human subgroup III heavy chain framework consensus sequence. In one embodiment of these antibodies, the human subgroup III heavy chain framework consensus sequence comprises substitution at position 71, 73 and/or 78. In some embodiments of these antibodies, position (of the human subgroup III heavy chain framework consensus sequence) 71 is A, 73 is T and/or 78 is A. In one embodiment of these antibodies, the human subgroup III heavy chain framework consensus sequence comprises substitution at position 48, 67, 69, 71, 73 and/or 78. In some embodiments of these antibodies, position (of the human subgroup III heavy chain framework consensus sequence) 48 is I, 67 is A, 69 is F, 71 is A, 73 is T and/or 78 is A. In one embodiments of these antibodies, these antibodies further comprise a human κI light chain framework consensus sequence. In some embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F. In one embodiment of these antibodies, the human subgroup III heavy chain framework consensus sequence comprises substitution at position 48, 67, 69, 71, 73, 75, 78 and/or 80. In some embodiments of these antibodies, position (of the human subgroup III heavy chain framework consensus sequence) 48 is I, 67 is A, 69 is F, 71 is A, 73 is T, 75 is S, 78 is A and or 80 is M. In some embodiments of these antibodies, these antibodies further comprise a human κI light chain framework consensus sequence. In one embodiment of these antibodies, the framework human κI light chain framework consensus sequence comprises substitution at position 4 and/or 47. In some embodiments of these antibodies, position (of the human κI light chain framework consensus sequence) 4 is L and/or 47 is F.

In one aspect, the invention provides an antibody comprising one, two, three, four, five or all of the HVR sequences depicted in FIG. 9 (SEQ ID NOs: 17-21) and/or FIG. 10 (SEQ ID NOs: 22-106).

A therapeutic agent for use in a host subject preferably elicits little to no immunogenic response against the agent in said subject. In one embodiment, the invention provides such an agent. For example, in one embodiment, the invention provides a humanized antibody that elicits and/or is expected to elicit a human anti-mouse antibody response (HAMA) at a substantially reduced level compared to an antibody comprising the sequence of SEQ ID NO: 10 & 14 in a host subject. In another example, the invention provides a humanized antibody that elicits and/or is expected to elicit minimal or no human anti-mouse antibody response (HAMA). In one example, an antibody of the invention elicits anti-mouse antibody response that is at or less than a clinically-acceptable level.

A humanized antibody of the invention may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody of the invention comprises a human consensus framework sequence, which in one embodiment is the subgroup III consensus framework sequence. In one embodiment, an antibody of the invention comprises a variant subgroup III consensus framework sequence modified at least one amino acid position. For example, in one embodiment, a variant subgroup III consensus framework sequence may comprise a substitution at one or more of positions 71, 73 and/or 78. In one embodiment, said substitution is R71A, N73T and/or L78A, in any combination thereof. For example, in one embodiment, a variant subgroup III heavy chain framework consensus sequence comprises substitution at position 48, 67, 69, 71, 73 and/or 78. In one embodiment, said substitution is V48I, F67A, I69F, R71A, N73T and/or L78A. For example, in one embodiment, a variant subgroup III heavy chain framework consensus sequence comprises substitution at position 48, 67, 69, 71, 73, 75, 78 and/or 80. In one embodiment, said substitution is V48I, F67A, I69F, R71A, N73T, K75S, L78A and/or L80M. In one embodiment, the light chain variable domain of an antibody of the invention comprises a human consensus framework sequence, which in one embodiment is the id consensus framework sequence. In one embodiment, an antibody of the invention comprises a variant id consensus framework sequenced modified at least one amino acid position. For example, in one embodiment, a variant id consensus framework sequence may comprise a substitution at position 4. In one embodiment, said substitution is M4L. For example, in one embodiment, a variant id consensus framework sequence may comprise a substitution at position 4 and/or 47. In one embodiment, said substitution is M4L and/or L47F.

As is known in the art, and as described in greater detail herein below, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). The invention provides antibodies comprising modifications in these hybrid hypervariable positions. In one embodiment, these hypervariable positions include one or more positions 26-30, 33-35B, 47-49, 57-65, 93, 94 and 101-102 in a heavy chain variable domain. In one embodiment, these hybrid hypervariable positions include one or more of positions 24-29, 35-36, 46-49, 56 and 97 in a light chain variable domain. In one embodiment, an antibody of the invention comprises a human variant human subgroup consensus framework sequence modified at one or more hybrid hypervariable positions.

In one aspect, an antibody of the invention comprises a heavy chain variable domain comprising a variant human subgroup III consensus framework sequence modified at one or more of positions 26-30, 33-35, 48-49, 58, 60-63, 93 and 101. In one embodiment, the antibody comprises a G26P substitution. In one embodiment, the antibody comprises a F27Y substitution. In one embodiment, the antibody comprises a T28P, S, Y, G or N substitution. In one embodiment, the antibody comprises a F29L or F29V substitution. In one embodiment, the antibody comprises a S30T, R, N, K, C, G or P substitution. In one embodiment, the antibody comprises a A33W or A33F substitution. In one embodiment, the antibody comprises a M34I, V or L substitution. In one embodiment S35E, Q, N or D. In one embodiment, the antibody comprises a V48I substitution. In one embodiment, the antibody comprises a S49G substitution. In one embodiment, the antibody comprises a Y58N substitution. In one embodiment, the antibody comprises a A60N substitution. In one embodiment, the antibody comprises a D61E substitution. In one embodiment, the antibody comprises a S62I substitution. In one embodiment, the antibody comprises a V63F substitution. In one embodiment, the antibody comprises a A93T substitution. In one embodiment, the antibody comprises a D101S substitution.

In one aspect, an antibody of the invention comprises a light chain variable domain comprising a variant human kappa subgroup I consensus framework sequenced modified at one or more of positions 24, 27-29, 56 and 97. In one embodiment, the antibody comprises a R24K substitution. In one embodiment, the antibody comprises a Q27K substitution. In one embodiment, the antibody comprises a S28D or E substitution. In one embodiment, the antibody comprises a I29G, A or S substitution. In one embodiment, the antibody comprises a S56R, N, T or G substitution. In one embodiment, the antibody comprises a T97N substitution.

In one aspect, an antibody of the invention comprises a heavy chain variable domain comprising a variant human subgroup III consensus framework sequence modified at 1, 2, 3, 4, 5, 6, 7, 8, 9, 10, 11, 12, 13, 14, 15, 16 or all of positions 26-30, 33-35, 48-49, 58, 60-63, 93 and 101. In one embodiment, modification is selected from the group consisting of G26P, F27Y, T28P (S, Y, G or N), F29L (V), S30T (R, N, K, C, G or P), A33W (F), M34I (V or L), S35E (Q, N or D), V48I, S49G, Y58N, A6ON, D61E, S62I, V63F, A93T and D101 S. In some embodiments of the invention, an antibody of the invention comprises a variant subgroup III consensus framework sequence modified at position 48, 67, 69, 71, 73, 75, 78 and/or 80. In one embodiment, said substitution is V48I, F67A, I69F, R71A, N73T, K75S, L78A and/or L80M.

In one aspect, an antibody of the invention comprises a light chain variable domain comprising a variant human kappa subgroup I consensus framework sequence modified at 1, 2, 3, 4, 5 or all of positions 24, 27-29, 56 and 97. In one embodiment, modification is selected from the group consisting of R24K, Q27K, S28D (E), I29G (A or S), S56R (N, T or G) and T97N. In some embodiments of the invention, an antibody of the invention comprises a variant id consensus framework sequenced modified at position 4 and/or 47. In one embodiment, said substitution is M4L and/or L47F.

An antibody of the invention can comprise any suitable human or human consensus light chain framework sequences, provided the antibody exhibits the desired biological characteristics (e.g., a desired binding affinity). In one embodiment, an antibody of the invention comprises at least a portion (or all) of the framework sequence of human K light chain. In one embodiment, an antibody of the invention comprises at least a portion (or all) of human K subgroup I framework consensus sequence.

In one aspect, an antibody of the invention comprises a heavy and/or light chain variable domain comprising framework sequence depicted in SEQ ID NO: 9 (FIGS. 7A-B) and/or 13 (FIGS. 8A-B).

In one aspect, an antibody of the invention is a humanized anti-CD79b antibody conjugated to a cytotoxic agent. In one aspect, the humanized anti-CD79b antibody conjugated to a cytotoxic agent inhibits tumor progression in xenografts.

In one aspect, both the humanized antibody and chimeric antibody are monovalent. In one embodiment, both the humanized and chimeric antibody comprise a single Fab region linked to an Fc region. In one embodiment, the reference chimeric antibody comprises variable domain sequences depicted in FIGS. 7A-B (SEQ ID NO: 10) and FIGS. 8A-B (SEQ ID NO: 14) linked to a human Fc region. In one embodiment, the human Fc region is that of an IgG (e.g., IgG1, 2, 3 or 4).

In one aspect, the invention provides an antibody comprising a heavy chain variable domain comprising the HVR1-HC, HVR2-HC and/or HVR3-HC sequence depicted in FIG. 15 (SEQ ID NO: 164-166). In one embodiment, the variable domain comprises FR1-HC, FR2-HC, FR3-HC and/or FR4-HC sequence depicted in FIG. 15 (SEQ ID NO: 160-163). In one embodiment, the antibody comprises CH1 and/or Fc sequence depicted in FIG. 15 (SEQ ID NO: 167 and/or 168). In one embodiment, an antibody of the invention comprises a heavy chain variable domain comprising the HVR1-HC, HVR2-HC and/or HVR3-HC sequence (FIG. 15, SEQ ID NO: 164-166), and the FR1-HC, FR2-HC, FR3-HC and/or FR4-HC sequence (FIG. 15, SEQ ID NO: 160-163). In one embodiment, an antibody of the invention comprises a heavy chain variable domain comprising the HVR1-HC, HVR2-HC and/or HVR3-HC sequence (FIG. 15, SEQ ID NO: 164-166), and the CH1 and/or Fc sequence depicted in FIG. 15 (SEQ ID NO: 167 and/or 168) In one embodiment, an antibody of the invention comprises a heavy chain variable domain comprising the HVR1-HC, HVR2-HC and/or HVR3-HC sequence (FIG. 15, SEQ ID NO: 164-166), and the FR1-HC, FR2-HC, FR3-HC and/or FR4-HC sequence (FIG. 15, SEQ ID NO: 160-163), and the CH1 and/or Fc (FIG. 15, SEQ ID NO: 167 and/or 168).

In one aspect, the invention provides an antibody comprising a light chain variable domain comprising HVR1-LC, HVR2-LC and/or HVR3-LC sequence depicted in FIG. 15 (SEQ ID NO: 156-158). In one embodiment, the variable domain comprises FR1-LC, FR2-LC, FR3-LC and/or FR4-LC sequence depicted in FIG. 15 (SEQ ID NO: 152-155). In one embodiment, the antibody comprises CL1 sequence depicted in FIG. 15 (SEQ ID NO: 159). In one embodiment, the antibody of the invention comprises a light chain variable domain comprising the HVR1-LC, HVR2-LC and/or HVR3-LC sequence (SEQ ID NO: 156-158), and the FR1-LC, FR2-LC, FR3-LC and/or FR4-LC sequence (SEQ ID NO: 152-155) depicted in FIG. 15. In one embodiment, an antibody of the invention comprises a light chain variable domain comprising the HVR1-LC, HVR2-LC and/or HVR3-LC sequence (SEQ ID NO:156-158), and the CL1 sequence (SEQ ID NO: 159) depicted in FIG. 15. In one embodiment, an antibody of the invention comprises a light chain variable domain comprising the HVR1-LC, HVR2-LC and/or HVR3-LC sequence (SEQ ID NO: 156-158), and the FR1-LC, FR2-LC, FR3-LC and/or FR4-LC, (SEQ ID NO: 152-155) sequence depicted in FIG. 15, and the CL1 sequence depicted in FIG. 15 (SEQ ID NO: 159).

In one aspect, the invention provides an antibody comprising a heavy chain variable domain comprising the HVR1-HC, HVR2-HC and/or HVR3-HC sequence depicted in FIG. 16 (SEQ ID NO: 183-185). In one embodiment, the variable domain comprises FR1-HC, FR2-HC, FR3-HC and/or FR4-HC sequence depicted in FIG. 16 (SEQ ID NO: 179-182). In one embodiment, the antibody comprises CH1 and/or Fc sequence depicted in FIG. 16 (SEQ ID NO: 186 and/or 187). In one embodiment, an antibody of the invention comprises a heavy chain variable domain comprising the HVR1-HC, HVR2-HC and/or HVR3-HC sequence (FIG. 16, SEQ ID NO: 183-185), and the FR1-HC, FR2-HC, FR3-HC and/or FR4-HC sequence (FIG. 16, SEQ ID NO: 179-182). In one embodiment, an antibody of the invention comprises a heavy chain variable domain comprising the HVR1-HC, HVR2-HC and/or HVR3-HC sequence (FIG. 16, SEQ ID NO: 183-185), and the CH1 and/or Fc sequence depicted in FIG. 16 (SEQ ID NO: 186 and/or 187) In one embodiment, an antibody of the invention comprises a heavy chain variable domain comprising the HVR1-HC, HVR2-HC and/or HVR3-HC sequence (FIG. 16, SEQ ID NO: 183-185), and the FR1-HC, FR2-HC, FR3-HC and/or FR4-HC sequence (FIG. 16, SEQ ID NO: 179-182), and the CH1 and/or Fc (FIG. 16, SEQ ID NO: 186 and/or 187).

In one aspect, the invention provides an antibody comprising a light chain variable domain comprising HVR1-LC, HVR2-LC and/or HVR3-LC sequence depicted in FIG. 16 (SEQ ID NO: 175-177). In one embodiment, the variable domain comprises FR1-LC, FR2-LC, FR3-LC and/or FR4-LC sequence depicted in FIG. 16 (SEQ ID NO: 171-174). In one embodiment, the antibody comprises CL1 sequence depicted in FIG. 16 (SEQ ID NO: 178). In one embodiment, the antibody of the invention comprises a light chain variable domain comprising the HVR1-LC, HVR2-LC and/or HVR3-LC sequence (SEQ ID NO: 175-177), and the FR1-LC, FR2-LC, FR3-LC and/or FR4-LC sequence (SEQ ID NO: 171-174) depicted in FIG. 16. In one embodiment, an antibody of the invention comprises a light chain variable domain comprising the HVR1-LC, HVR2-LC and/or HVR3-LC sequence (SEQ ID NO: 175-177), and the CL1 sequence (SEQ ID NO: 178) depicted in FIG. 16. In one embodiment, an antibody of the invention comprises a light chain variable domain comprising the HVR1-LC, HVR2-LC and/or HVR3-LC sequence (SEQ ID NO: 175-177), and the FR1-LC, FR2-LC, FR3-LC and/or FR4-LC, (SEQ ID NO: 171-174) sequence depicted in FIG. 16, and the CL1 sequence depicted in FIG. 16 (SEQ ID NO: 178).

In one aspect, the invention provides an antibody comprising a heavy chain variable domain comprising the HVR1-HC, HVR2-HC and/or HVR3-HC sequence depicted in FIG. 17 (SEQ ID NO: 202-204). In one embodiment, the variable domain comprises FR1-HC, FR2-HC, FR3-HC and/or FR4-HC sequence depicted in FIG. 17 (SEQ ID NO: 198-201). In one embodiment, the antibody comprises CH1 and/or Fc sequence depicted in FIG. 17 (SEQ ID NO: 205 and/or 206). In one embodiment, an antibody of the invention comprises a heavy chain variable domain comprising the HVR1-HC, HVR2-HC and/or HVR3-HC sequence (FIG. 17, SEQ ID NO: 202-204), and the FR1-HC, FR2-HC, FR3-HC and/or FR4-HC sequence (FIG. 17, SEQ ID NO: 198-201). In one embodiment, an antibody of the invention comprises a heavy chain variable domain comprising the HVR1-HC, HVR2-HC and/or HVR3-HC sequence (FIG. 17, SEQ ID NO: 202-204), and the CH1 and/or Fc sequence depicted in FIG. 17 (SEQ ID NO: 205 and/or 206) In one embodiment, an antibody of the invention comprises a heavy chain variable domain comprising the HVR1-HC, HVR2-HC and/or HVR3-HC sequence (FIG. 17, SEQ ID NO: 202-204), and the FR1-HC, FR2-HC, FR3-HC and/or FR4-HC sequence (FIG. 17, SEQ ID NO: 198-201), and the CH1 and/or Fc (FIG. 17, SEQ ID NO: 205 and/or 206).

In one aspect, the invention provides an antibody comprising a light chain variable domain comprising HVR1-LC, HVR2-LC and/or HVR3-LC sequence depicted in FIG. 17 (SEQ ID NO: 194-196). In one embodiment, the variable domain comprises FR1-LC, FR2-LC, FR3-LC and/or FR4-LC sequence depicted in FIG. 17 (SEQ ID NO: 190-193). In one embodiment, the antibody comprises CL1 sequence depicted in FIG. 17 (SEQ ID NO: 197). In one embodiment, the antibody of the invention comprises a light chain variable domain comprising the HVR1-LC, HVR2-LC and/or HVR3-LC sequence (SEQ ID NO: 194-196), and the FR1-LC, FR2-LC, FR3-LC and/or FR4-LC sequence (SEQ ID NO: 190-193) depicted in FIG. 17. In one embodiment, an antibody of the invention comprises a light chain variable domain comprising the HVR1-LC, HVR2-LC and/or HVR3-LC sequence (SEQ ID NO: 194-196), and the CL1 sequence (SEQ ID NO: 197) depicted in FIG. 17. In one embodiment, an antibody of the invention comprises a light chain variable domain comprising the HVR1-LC, HVR2-LC and/or HVR3-LC sequence (SEQ ID NO: 194-196), and the FR1-LC, FR2-LC, FR3-LC and/or FR4-LC (SEQ ID NO: 190-193) sequence depicted in FIG. 17, and the CL1 sequence depicted in FIG. 17 (SEQ ID NO: 197).

In one aspect, the invention provides an antibody comprising a heavy chain variable domain comprising the HVR1-HC, HVR2-HC and/or HVR3-HC sequence depicted in FIG. 18 (SEQ ID NO: 221-223). In one embodiment, the variable domain comprises FR1-HC, FR2-HC, FR3-HC and/or FR4-HC sequence depicted in FIG. 18 (SEQ ID NO: 217-220). In one embodiment, the antibody comprises CH1 and/or Fc sequence depicted in FIG. 18 (SEQ ID NO: 224 and/or 225). In one embodiment, an antibody of the invention comprises a heavy chain variable domain comprising the HVR1-HC, HVR2-HC and/or HVR3-HC sequence (FIG. 18, SEQ ID NO: 221-223), and the FR1-HC, FR2-HC, FR3-HC and/or FR4-HC sequence (FIG. 18, SEQ ID NO: 217-220). In one embodiment, an antibody of the invention comprises a heavy chain variable domain comprising the HVR1-HC, HVR2-HC and/or HVR3-HC sequence (FIG. 18, SEQ ID NO: 221-223), and the CH1 and/or Fc sequence depicted in FIG. 18 (SEQ ID NO: 224 and/or 225) In one embodiment, an antibody of the invention comprises a heavy chain variable domain comprising the HVR1-HC, HVR2-HC and/or HVR3-HC sequence (FIG. 18, SEQ ID NO: 221-223), and the FR1-HC, FR2-HC, FR3-HC and/or FR4-HC sequence (FIG. 18, SEQ ID NO: 217-220), and the CH1 and/or Fc (FIG. 18, SEQ ID NO: 224 and/or 225).

In one aspect, the invention provides an antibody comprising a light chain variable domain comprising HVR1-LC, HVR2-LC and/or HVR3-LC sequence depicted in FIG. 18 (SEQ ID NO: 213-215). In one embodiment, the variable domain comprises FR1-LC, FR2-LC, FR3-LC and/or FR4-LC sequence depicted in FIG. 18 (SEQ ID NO: 209-212). In one embodiment, the antibody comprises CL1 sequence depicted in FIG. 18 (SEQ ID NO: 216). In one embodiment, the antibody of the invention comprises a light chain variable domain comprising the HVR1-LC, HVR2-LC and/or HVR3-LC sequence (SEQ ID NO: 213-215), and the FR1-LC, FR2-LC, FR3-LC and/or FR4-LC sequence (SEQ ID NO: 209-212) depicted in FIG. 18. In one embodiment, an antibody of the invention comprises a light chain variable domain comprising the HVR1-LC, HVR2-LC and/or HVR3-LC sequence (SEQ ID NO: 213-215), and the CL1 sequence (SEQ ID NO: 216) depicted in FIG. 18. In one embodiment, an antibody of the invention comprises a light chain variable domain comprising the HVR1-LC, HVR2-LC and/or HVR3-LC sequence (SEQ ID NO: 213-215), and the FR1-LC, FR2-LC, FR3-LC and/or FR4-LC (SEQ ID NO: 209-212) sequence depicted in FIG. 18, and the CL1 sequence depicted in FIG. 18 (SEQ ID NO: 216).

In one aspect, the antibodies of the invention include cysteine engineered antibodies where one or more amino acids of a parent antibody are replaced with a free cysteine amino acid as disclosed in WO2006/034488; US 2007/0092940 (herein incorporated by reference in its entirety). Any form of anti-CD79b antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered anti-CD79b antibodies of the invention include monoclonal antibodies, humanized or chimeric monoclonal antibodies, and antigen-binding fragments of antibodies, fusion polypeptides and analogs that preferentially bind cell-associated CD79b polypeptides. A cysteine engineered antibody may alternatively comprise an antibody comprising a cysteine at a position disclosed herein in the antibody or Fab, resulting from the sequence design and/or selection of the antibody, without necessarily altering a parent antibody, such as by phage display antibody design and selection or through de novo design of light chain and/or heavy chain framework sequences and constant regions. A cysteine engineered antibody comprises one or more free cysteine amino acids having a thiol reactivity value in the ranges of 0.6 to 1.0; 0.7 to 1.0 or 0.8 to 1.0. A free cysteine amino acid is a cysteine residue which has been engineered into the parent antibody and is not part of a disulfide bridge. Cysteine engineered antibodies are useful for attachment of cytotoxic and/or imaging compounds at the site of the engineered cysteine through, for example, a maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

In an aspect, a cysteine engineered anti-CD79b antibody of the invention comprises an engineered cysteine at any one of the following positions, where the position is numbered according to Kabat et al. in the light chain (see Kabat et al (1991) Sequences of Proteins of Immunological Interest, 5th Ed. Public Health Service, National Institutes of Health, Bethesda, Md.) and according to EU numbering in the heavy chain (including the Fc region) (see Kabat et al. (1991), supra), wherein the light chain constant region depicted by underlining in FIGS. 24A, 25A, 26A, 27A, 28, 48A and 49A begins at position 109 (Kabat numbering) and the heavy chain constant region depicted by underling in FIGS. 24B, 25B, 26B, 27B, 28B, 48B and 49B begins at position 118 (EU numbering). The position may also be referred to by its position in sequential numbering of the amino acids of the full length light chain or heavy chain shown in FIGS. 24-28, 48 and 49. According to one embodiment of the invention, an anti-CD79b antibody comprises an engineered cysteine at LC-V205C (Kabat number: Val 205; sequential number 209 in FIGS. 27A and 49A engineered to be Cys at that position). The engineered cysteine in the light chain is shown in bold, double underlined text in FIGS. 27A and 49A. According to one embodiment, an anti-CD79b antibody comprises an engineered cysteine at HC-A118C (EU number: Ala 118; Kabat number 114; sequential number 118 in FIG. 24B, 25B, 26B, 28B or 48B engineered to be Cys at that position). The engineered cysteine in the heavy chain is shown in bold, double underlined text in FIG. 24B, 25B, 26B, 28B or 48B. According to one embodiment, an anti-CD79b antibody comprises an engineered cysteine at Fc-S400C (EU number: Ser 400; Kabat number 396; sequential number 400 in FIG. 24B, 25B, 26B, 28B or 48B engineered to be Cys at that position). In other embodiments, the engineered cysteine of the heavy chain (including the Fc region) is at any one of the following positions (according to Kabat numbering with EU numbering in parenthesis): 5, 23, 84, 112, 114 (118 EU numbering), 116 (120 EU numbering), 278 (282 EU numbering), 371 (375 EU numbering) or 396 (400 EU numbering). Thus, changes in the amino acid at these positions for a parent humanized anti-CD79b antibody of the invention are: V5C, A23C, A84C, S112C, A114C (A118C EU Numbering), T116C (T120 C EU numbering), V278C (V282C EU numbering), S371C (S375C EU numbering) or S396C (S400C EU numbering). Thus, changes in the amino acid at these positions for a parent chimeric anti-CD79b antibody of the invention are: Q5C, K23C, S84C, S112C, A114C (A118C EU Numbering), T116C (T120C EU numbering), V278C (V282C EU numbering), S371C (S375C EU numbering) or S396C (S400C EU numbering). Thus, changes in the amino acid at these positions for a parent anti-cynoCD79b antibody of the invention are: Q5C, T23C, S84C, S112C, A114C (A118C EU Numbering), T116C (T120C EU numbering), V278C (V282C EU numbering), S371C (S375C EU numbering) or S396C (S400C EU numbering). In other embodiments, the engineered cysteine of the light chain is at any one of the following positions (according to Kabat numbering): 15, 110, 114, 121, 127, 168, 205. Thus, changes in the amino acid at these positions for a parent humanized anti-CD79b antibody of the invention are: V15C, V110C, S114C, S121C, S127C, S168C, or V205C. Thus, changes in the amino acid at these positions for a parent chimeric anti-CD79b antibody of the invention are: L15C, V110C, S114C, S121C, S127C, S168C, or V205C. Thus, changes in the amino acid at these positions for a parent anti-cynoCD79b antibody of the invention are: L15C, V110C, S114C, S121C, S127C, S168C, or V205C.

In one aspect, the invention includes a cysteine engineered anti-CD79b antibody comprises one or more free cysteine amino acids wherein the cysteine engineered anti-CD79b antibody binds to a CD79b polypeptide and is prepared by a process comprising replacing one or more amino acid residues of a parent anti-CD79b antibody by cysteine wherein the parent antibody comprises at least one HVR sequence selected from:

(a) HVR-L1 comprising sequence A1-A15, wherein A1-A15 is KASQSVDYDGDSFLN (SEQ ID NO: 131) or KASQSVDYEGDSFLN (SEQ ID NO: 137);

(b) HVR-L2 comprising sequence B1-B7, wherein B1-B7 is AASNLES (SEQ ID NO: 132)

(c) HVR-L3 comprising sequence C1-C9, wherein C1-C9 is QQSNEDPLT (SEQ ID NO: 133)

(d) HVR-H1 comprising sequence D1-D10, wherein D1-D10 is GYTFSSYWIE (SEQ ID NO: 134)

(e) HVR-H2 comprising sequence E1-E18, wherein E1-E18 is GEILPGGGDTNYNEIFKG (SEQ ID NO: 135) and (f) HVR-H3 comprising sequence F1-F10, wherein F1-F10 is TRRVPVYFDY (SEQ ID NO: 136) or TRRVPIRLDY (SEQ ID NO: 138).

In a certain aspect, the invention concerns a cysteine engineered anti-CD79b antibody, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99%, or 100% amino acid sequence identity, to a cysteine engineered antibody having a full-length amino acid sequence as disclosed herein, or a cysteine engineered antibody amino acid sequence lacking the signal peptide as disclosed herein.

In a yet further aspect, the invention concerns an isolated cysteine engineered anti-CD79b antibody comprising an amino acid sequence that is encoded by a nucleotide sequence that hybridizes to the complement of a DNA molecule encoding (a) a cysteine engineered antibody having a full-length amino acid sequence as disclosed herein, (b) a cysteine engineered antibody amino acid sequence lacking the signal peptide as disclosed herein, (c) an extracellular domain of a transmembrane cysteine engineered antibody protein, with or without the signal peptide, as disclosed herein, (d) an amino acid sequence encoded by any of the nucleic acid sequences disclosed herein or (e) any other specifically defined fragment of a full-length cysteine engineered antibody amino acid sequence as disclosed herein.

In a specific aspect, the invention provides an isolated cysteine engineered anti-CD79b antibody without the N-terminal signal sequence and/or without the initiating methionine and is encoded by a nucleotide sequence that encodes such an amino acid sequence as described in. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

Another aspect of the invention provides an isolated cysteine engineered anti-CD79b antibody which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the cysteine engineered antibody and recovering the cysteine engineered antibody from the cell culture.

In other aspects, the invention provides isolated anti-CD79b chimeric cysteine engineered antibodies comprising any of the herein described cysteine engineered antibody fused to a heterologous (non-CD79b) polypeptide. Examples of such chimeric molecules comprise any of the herein described cysteine engineered antibodies fused to a heterologous polypeptide such as, for example, an epitope tag sequence or a Fc region of an immunoglobulin.

The cysteine engineered anti-CD79b antibody may be a monoclonal antibody, antibody fragment, chimeric antibody, humanized antibody, single-chain antibody or antibody that competitively inhibits the binding of an anti-CD79b polypeptide antibody to its respective antigenic epitope. Antibodies of the present invention may optionally be conjugated to a growth inhibitory agent or cytotoxic agent such as a toxin, including, for example, an auristatin, a maytansinoid, a dolostatin derivative or a calicheamicin, an antibiotic, a radioactive isotope, a nucleolytic enzyme, or the like. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In other aspects of the present invention, the invention provides vectors comprising DNA encoding any of the herein described anti-CD79b antibodies and anti-CD79b cysteine engineered antibodies. Host cells comprising any such vector are also provided. By way of example, the host cells may be CHO cells, E. coli cells, or yeast cells. A process for producing any of the herein described polypeptides is further provided and comprises culturing host cells under conditions suitable for expression of the desired polypeptide and recovering the desired polypeptide from the cell culture.

Cysteine engineered antibodies may be useful in the treatment of cancer and include antibodies specific for cell surface and transmembrane receptors, and tumor-associated antigens (TAA). Such antibodies may be used as naked antibodies (unconjugated to a drug or label moiety) or as antibody-drug conjugates (ADC). Cysteine engineered antibodies of the invention may be site-specifically and efficiently coupled with a thiol-reactive reagent. The thiol-reactive reagent may be a multifunctional linker reagent, a capture label reagent, a fluorophore reagent, or a drug-linker intermediate. The cysteine engineered antibody may be labeled with a detectable label, immobilized on a solid phase support and/or conjugated with a drug moiety. Thiol reactivity may be generalized to any antibody where substitution of amino acids with reactive cysteine amino acids may be made within the ranges in the light chain selected from amino acid ranges: L10-L20, L105-L115, L109-L119, L116-L126, L122-L132, L163-L173, L200-L210; and within the ranges in the heavy chain selected from amino acid ranges: H1-H10, H18-H28, H79-H89, H107-H117, H109-H119, H111-H121, and in the selected from H270-H280, H366-H376, H391-401, where the numbering of amino acid positions begins at position 1 of the Kabat numbering system (Kabat et al. (1991) Sequences of Proteins of Immunological Interest, 5th Ed. Public Health Service, National Institutes of Health, Bethesda, Md.) and continues sequentially thereafter as disclosed in WO2006034488; US 2007/0092940. Thiol reactivity may also be generalized to certain domains of an antibody, such as the light chain constant domain (CL) and heavy chain constant domains, CH1, CH2 and CH3. Cysteine replacements resulting in thiol reactivity values of 0.6 and higher may be made in the heavy chain constant domains $\alpha$, $\delta$, $\epsilon$, $\gamma$, and $\mu$ of intact antibodies: IgA, IgD, IgE, IgG, and IgM, respectively, including the IgG subclasses: IgG1, IgG2, IgG3, IgG4, IgA, and IgA2. Such antibodies and their uses are disclosed in WO2006/034488; US 2007/0092940.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein, including but not limited to CD79b). Cysteine engineered anti-CD79b antibodies of the invention retain the antigen binding ability of their parent anti-CD79b antibody counterparts. Thus, cysteine engineered anti-CD79b antibodies of the invention are capable of binding, preferably specifically, to CD79b antigens including human anti-CD79b isoforms beta and/or alpha, including when such antigens are expressed on the surface of cells, including, without limitation, B cells.

In one aspect, antibodies of the invention may be conjugated with any label moiety which can be covalently attached to the antibody through a reactive moiety, an activated moiety, or a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labelled cysteine engineered antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

Radioisotopes (radionuclides), such $^{3}$H, $^{11}$C, $^{14}$C, $^{18}$F, $^{32}$P, $^{35}$S, $^{64}$Cu, $^{68}$Ga, $^{86}$Y, $^{99}$Tc, $^{111}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9):1137-1146).

Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al (2000) Proc. Natl. Acad. Sci. USA 97(4):1802-1807). DOTA-maleimide reagents react with the free cysteine amino acids of the cysteine engineered antibodies and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labelled antibodies can provide a marker of pathway activation by detection and quantitation of progressive accumulation of antibodies in tumor tissue (Albert et al (1998) Bioorg. Med. Chem. Left. 8:1207-1210). The conjugated radio-metals may remain intracellular following lysosomal degradation.

Metal-chelate complexes suitable as antibody labels for imaging experiments are disclosed: U.S. Pat. No. 5,342,606; U.S. Pat. No. 5,428,155; U.S. Pat. No. 5,316,757; U.S. Pat. No. 5,480,990; U.S. Pat. No. 5,462,725; U.S. Pat. No. 5,428,139; U.S. Pat. No. 5,385,893; U.S. Pat. No. 5,739,294; U.S. Pat. No. 5,750,660; U.S. Pat. No. 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in Current Protocols in Immunology, supra, for example. Fluorescent dyes and fluorescent label reagents include those which are commercially available from Invitrogen/Molecular Probes (Eugene, Oreg.) and Pierce Biotechnology, Inc. (Rockford, Ill.).

Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in Methods in Enzym. (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3', 5,5'-tetramethylbenzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review, see U.S. Pat. No. 4,275,149 and U.S. Pat. No. 4,318,980.

A label may be indirectly conjugated with an amino acid side chain, an activated amino acid side chain, a cysteine engineered antibody, and the like. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in Bioconjugate Techniques Academic Press, San Diego).

The antibody of the present invention may be employed in any known assay method, such as ELISA, competitive binding assays, direct and indirect sandwich assays, and immunoprecipitation assays (Zola, (1987) Monoclonal Antibodies: A Manual of Techniques, pp.147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, inmmunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372,907), apoptosis (Vermes, "A novel assay for apoptosis. Flow cytometric detection of phosphatidylserine expression on early apoptotic cells using fluorescein labelled Annexin V" (1995) J. Immunol Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Cross-linking, CRC Press, Boca Raton, Fla.); De Leon-Rodriguez et al (2004) Chem.Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

Labelling reagents typically bear reactive functionality which may react (i) directly with a cysteine thiol of a cysteine engineered antibody to form the labelled antibody, (ii) with a linker reagent to form a linker-label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g. TSTU (O-(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH (N,N',N'',N'''-tetramethyluronium 2-fluoro-hexafluorophosphate), PyBOP (benzotriazole-1-yl-oxy-tris-pyrrolidino-phosphonium hexafluorophosphate), EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Albumin Binding Peptide-Fab Compounds of the Invention:

In one aspect, the antibody of the invention is fused to an albumin binding protein. Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (US 20040001827, now abandoned). A series of albumin binding peptides were identified by phage display screening (Dennis et al. (2002) "Albumin Binding As A General Strategy For Improving The Pharmacokinetics Of Proteins" J Biol. Chem. 277:35035-35043; WO 01/45746). Compounds of the invention include ABP sequences taught by: (i) Dennis et al (2002) J Biol. Chem. 277:35035-35043 at Tables III and IV, page 35038; (ii) US 20040001827, now abandoned, at [0076] SEQ ID NOS: 9-22; and (iii) WO 01/45746 at pages 12-13, all of which are incorporated herein by reference. Albumin Binding (ABP)-Fabs are engineered by fusing an albumin binding peptide to the C-terminus of Fab heavy chain in 1:1 stoichiometric ratio (1 ABP/1 Fab). It was shown that association of these ABP-Fabs with albumin increased antibody half life by more than 25 fold in rabbits and mice. The above described reactive Cys residues can therefore be introduced in these ABP-Fabs and used for site-specific conjugation with cytotoxic drugs followed by in vivo animal studies.

Exemplary albumin binding peptide sequences include, but are not limited to the amino acid sequences listed in SEQ ID NOS: 246-250:

| | |
|---|---|
| CDKTHTGGGSQRLMEDICLPRWGCLWEDDF | SEQ ID NO: 246 |
| QRLMEDICLPRWGCLWEDDF | SEQ ID NO: 247 |
| QRLIEDICLPRWGCLWEDDF | SEQ ID NO: 248 |
| RLIEDICLPRWGCLWEDD | SEQ ID NO: 249 |
| DICLPRWGCLW | SEQ ID NO: 250 |

Antibody-Drug Conjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In another aspect, the invention further provides methods of using the immunoconjugates. In one aspect, an immunoconjugate comprises any of the above anti-CD79b antibodies covalently attached to a cytotoxic agent or a detectable agent.

In one aspect, a CD79b antibody of the invention binds to the same epitope on CD79b bound by another CD79b antibody. In another embodiment, a CD79b antibody of the invention binds to the same epitope on CD79b bound by the Fab fragment of, a monoclonal antibody generated from hybridomas deposited with the ATCC as HB11413 on Jul. 20, 1993, a monoclonal antibody comprising the variable domains of SEQ ID NO: 10 (FIGS. 7A-B) and SEQ ID NO: 14 (FIGS. 8A-B) or a chimeric antibody comprising the variable domain of either antibody generated from HB11413 hybridomas deposited with the ATCC on Jul. 20, 1993 and constant domains from IgG1, or the variable domains of monoclonal antibody comprising the sequences of SEQ ID NO: 10 (FIGS. 7A-B) and SEQ ID NO: 14 (FIGS. 8A-B). In another embodiment, a CD79b antibody of the invention binds to the same epitope on CD79b bound by another CD79b antibody (i.e., CB3.1 (BD Biosciences Catalog #555678; San Jose, Calif.), AT105-1 (AbD Serotec Catalog #MCA2208; Raleigh, N.C.), AT107-2 (AbD Serotec Catalog #MCA2209), anti-human CD79b antibody (BD Biosciences Catalog #557592; San Jose, Calif.)).

In another aspect, a CD79b antibody of the invention binds to an epitope on CD79b distinct from an epitope bound by another CD79b antibody. In another embodiment, a CD79b antibody of the invention binds to an epitope on CD79b distinct from an epitope bound by the Fab fragment of, monoclonal antibody generated from HB11413 hybridomas deposited with the ATCC on Jul. 20, 1993, monoclonal antibody comprising the variable domains of SEQ ID NO: 10 (FIGS. 7A-B) and SEQ ID NO: 14 (FIGS. 8A-B), or chimeric antibody comprising the variable domain of either antibody generated from HB11413 hybridomas deposited with the ATCC on Jul. 20, 1993 and constant domains from IgG1, or the variable domains of monoclonal antibody comprising the sequences of SEQ ID NO: 10 (FIGS. 7A-B) and SEQ ID NO: 14 (FIGS. 8A-B). In another embodiment, a CD79b antibody of the invention binds to an epitope on CD79b distinct from an epitope on CD79b bound by another CD79b antibody (i.e., CB3.1 (BD Biosciences Catalog #555678; San Jose, Calif.), AT105-1 (AbD Serotec Catalog #MCA2208; Raleigh, N.C.), AT107-2 (AbD Serotec Catalog #MCA2209), anti-human CD79b antibody (BD Biosciences Catalog #557592; San Jose, Calif.)).

In another aspect, a CD79b antibody of the invention is distinct from (i.e., it is not) a Fab fragment of, the monoclonal antibody generated from hybridomas deposited with the ATCC as HB11413 on Jul. 20, 1993, the monoclonal antibody comprising the variable domains of SEQ ID NO: 10 (FIGS. 7A-B) and SEQ ID NO: 14 (FIGS. 8A-B), or chimeric antibody comprising the variable domain of antibody generated from hybridomas deposited with the ATCC as HB11413 on Jul. 20, 1993 and constant domains from IgG1, or the variable domains of monoclonal antibody comprising the sequences of SEQ ID NO: 10 (FIGS. 7A-B) and SEQ ID NO: 14 (FIGS. 8A-B). In another embodiment, a CD79b antibody of the invention is distinct from (i.e., it is not) a Fab fragment of another CD79b antibody ((i.e., CB3.1 (BD Biosciences Catalog #555678; San Jose, Calif.), AT105-1 (AbD Serotec Catalog #MCA2208; Raleigh, N.C.), AT107-2 (AbD Serotec Catalog #MCA2209), anti-human CD79b antibody (BD Biosciences Catalog #557592; San Jose, Calif.)).

In one aspect, an antibody of the invention specifically binds to CD79b of a first animal species, and does not specifically bind to CD79b of a second animal species. In one embodiment, the first animal species is human and/or primate (e.g., cynomolgus monkey), and the second animal species is murine (e.g., mouse) and/or canine. In one embodiment, the first animal species is human. In one embodiment, the first animal species is primate, for example cynomolgus monkey. In one embodiment, the second animal species is murine, for example mouse. In one embodiment, the second animal species is canine.

In one aspect, the invention provides compositions comprising one or more antibodies of the invention and a carrier. In one embodiment, the carrier is pharmaceutically acceptable.

In one aspect, the invention provides nucleic acids encoding a CD79b antibody of the invention.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antibody of the invention. For example, the invention provides a method of making a CD79b antibody (which, as defined herein includes full length and fragments thereof), said method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more CD79b antibodies of the invention. In one embodiment, the composition comprises a nucleic acid of the invention. In one embodiment, a composition comprising an antibody further comprises a carrier, which in some embodiments is pharmaceutically acceptable. In one embodiment, an article of manufacture of the invention further comprises instructions for administering the composition (e.g., the antibody) to a subject.

In one aspect, the invention provides a kit comprising a first container comprising a composition comprising one or more CD79b antibodies of the invention; and a second container comprising a buffer. In one embodiment, the buffer is pharmaceutically acceptable. In one embodiment, a composition comprising an antagonist antibody further comprises a carrier, which in some embodiments is pharmaceutically acceptable. In one embodiment, a kit further comprises instructions for administering the composition (e.g., the antibody) to a subject.

In one aspect, the invention provides use of a CD79b antibody of the invention in the preparation of a medicament for the therapeutic and/or prophylactic treatment of a disease, such as a cancer, a tumor and/or a cell proliferative disorder. In one embodiment, cancer, tumor and/or cell proliferative disorder is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides use of a nucleic acid of the invention in the preparation of a medicament for the therapeutic and/or prophylactic treatment of a disease, such as a cancer, a tumor and/or a cell proliferative disorder. In one embodiment, cancer, tumor and/or cell proliferative disorder is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides use of an expression vector of the invention in the preparation of a medicament for the therapeutic and/or prophylactic treatment of a disease, such as a cancer, a tumor and/or a cell proliferative disorder. In one embodiment, cancer, tumor and/or cell proliferative disorder is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides use of a host cell of the invention in the preparation of a medicament for the therapeutic and/or prophylactic treatment of a disease, such as a cancer, a tumor and/or a cell proliferative disorder. In one embodiment, cancer, tumor and/or cell proliferative disorder is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides use of an article of manufacture of the invention in the preparation of a medicament for the therapeutic and/or prophylactic treatment of a disease, such as a cancer, a tumor and/or a cell proliferative disorder. In one embodiment, cancer, tumor and/or cell proliferative disorder is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides use of a kit of the invention in the preparation of a medicament for the therapeutic and/or prophylactic treatment of a disease, such as a cancer, a tumor and/or a cell proliferative disorder. In one embodiment, cancer, tumor and/or cell proliferative disorder is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides a method of inhibiting the growth of a cell that expresses CD79b, said method comprising contacting said cell with an antibody of the invention thereby causing an inhibition of growth of said cell. In one embodiment, the antibody is conjugated to a cytotoxic agent. In one embodiment, the antibody is conjugated to a growth inhibitory agent.

In one aspect, the invention provides a method of therapeutically treating a mammal having a cancerous tumor comprising a cell that expresses CD79b, said method comprising administering to said mammal a therapeutically effective amount of an antibody of the invention, thereby effectively treating said mammal. In one embodiment, the antibody is conjugated to a cytotoxic agent. In one embodiment, the antibody is conjugated to a growth inhibitory agent.

In one aspect, the invention provides a method for treating or preventing a cell proliferative disorder associated with increased expression of CD79b, said method comprising administering to a subject in need of such treatment an effective amount of an antibody of the invention, thereby effectively treating or preventing said cell proliferative disorder. In one embodiment, said proliferative disorder is cancer. In one embodiment, the antibody is conjugated to a cytotoxic agent. In one embodiment, the antibody is conjugated to a growth inhibitory agent.

In one aspect, the invention provides a method for inhibiting the growth of a cell, wherein growth of said cell is at least in part dependent upon a growth potentiating effect of CD79b, said method comprising contacting said cell with an effective amount of an antibody of the invention, thereby inhibiting the growth of said cell. In one embodiment, the antibody is conjugated to a cytotoxic agent. In one embodiment, the antibody is conjugated to a growth inhibitory agent.

In one aspect, the invention provides a method of therapeutically treating a tumor in a mammal, wherein the growth of said tumor is at least in part dependent upon a growth potentiating effect of CD79b, said method comprising contacting said cell with an effective amount of an antibody of the invention, thereby effectively treating said tumor. In one embodiment, the antibody is conjugated to a cytotoxic agent. In one embodiment, the antibody is conjugated to a growth inhibitory agent.

In one aspect, the invention provides a method of treating cancer comprising administering to a patient the pharmaceutical formulation comprising an immunoconjugate described herein, acceptable diluent, carrier or excipient. In one embodiment, the cancer is selected from the lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL) and mantle cell lymphoma. In one embodiment, the patient is administered a cytotoxic agent in combination with the antibody-drug conjugate compound.

In one aspect, the invention provides a method of inhibiting B cell proliferation comprising exposing a cell to an immunoconjugate comprising an antibody of the invention under conditions permissive for binding of the immunoconjugate to CD79b. In one embodiment, the B cell proliferation is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL) and mantle cell lymphoma. In one embodiment, the B cell is a xenograft. In one embodiment, the exposing takes place in vitro. In one embodiment, the exposing taxes place in vivo.

In one aspect, the invention provides a method of determining the presence of CD79b in a sample suspected of containing CD79b, said method comprising exposing said sample to an antibody of the invention, and determining binding of said antibody to CD79b in said sample wherein binding of said antibody to CD79b in said sample is indicative of the presence of said protein in said sample. In one embodiment, the sample is a biological sample. In a further embodiment, the biological sample comprises B cells. In one embodiment, the biological sample is from a mammal experiencing or suspected of experiencing a B cell disorder and/or a B cell proliferative disorder including, but not limited to, lymphoma, non-Hodgkin's lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL) and mantle cell lymphoma.

In one aspect, a method of diagnosing a cell proliferative disorder associated with an increase in cells, such as B cells, expressing CD79b is provided, the method comprising contacting a test cells in a biological sample with any of the above antibodies; determining the level of antibody bound to test cells in the sample by detecting binding of the antibody to CD79b; and comparing the level of antibody bound to cells in a control sample, wherein the level of antibody bound is normalized to the number of CD79b-expressing cells in the test and control samples, and wherein a higher level of antibody bound in the test sample as compared to the control sample indicates the presence of a cell proliferative disorder associated with cells expressing CD79b.

In one aspect, a method of detecting soluble CD79b in blood or serum, the method comprising contacting a test sample of blood or serum from a mammal suspected of experiencing a B cell proliferative disorder with an anti-CD79b antibody of the invention and detecting a increase in soluble CD79b in the test sample relative to a control sample of blood or serum from a normal mammal. In an embodiment, the method of detecting is useful as a method of diagnosing a B cell proliferative disorder associated with an increase in soluble CD79b in blood or serum of a mammal.

In one aspect, a method of binding an antibody of the invention to a cell that expresses CD79b, said method comprising contacting said cell with an antibody of the invention. In one embodiment, the antibody is conjugated to a cytotoxic agent. In one embodiment, the antibody is conjugated to a growth inhibitory agent.

Methods of the invention can be used to affect any suitable pathological state, for example, cells and/or tissues associated with expression of CD79b. In one embodiment, a cell that is targeted in a method of the invention is a hematopoietic cell. For example, a hematopoietic cell can be one selected from the group consisting of a lymphocyte, leukocyte, platelet, erythrocyte and natural killer cell. In one embodiment, a cell that is targeted in a method of the invention is a B cell or T cell. In one embodiment, a cell that is targeted in a method of the invention is a cancer cell. For example, a cancer cell can be one selected from the group consisting of a lymphoma cell, leukemia cell, or myeloma cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

As described herein, CD79b is a signaling component of the B cell receptor. Accordingly, in one embodiment of methods of the invention, a cell that is targeted (e.g., a cancer cell) is one in which CD79b is expressed as compared to a cell that does not express CD79b. In a further embodiment, the targeted cell is a cancer cell in which CD79b expression is enhanced as compared to a normal non-cancer cell of the same tissue type. In one embodiment, a method of the invention causes the death of a targeted cell.

In other aspects of the present invention, the invention provides vectors comprising DNA encoding any of the herein described antibodies. Host cell comprising any such vector are also provided. By way of example, the host cells may be CHO cells, E. coli cells, or yeast cells. A process for producing any of the herein described antibodies is further provided and comprises culturing host cells under conditions suitable for expression of the desired antibody and recovering the desired antibody from the cell culture.

In a still further aspect, the invention concerns a composition of matter comprising an anti-CD79b antibody as described herein, in combination with a carrier. Optionally, the carrier is a pharmaceutically acceptable carrier.

Another aspect of the present invention is directed to the use of an anti-CD79b polypeptide antibody as described herein, for the preparation of a medicament useful in the treatment of a condition which is responsive to the anti-CD79b polypeptide antibody.

Another aspect of the invention is a composition comprising a mixture of antibody-drug compounds of Formula I where the average drug loading per antibody is about 2 to about 5, or about 3 to about 4.

Another aspect of the invention is a pharmaceutical composition including a Formula I ADC compound, a mixture of Formula I ADC compounds, or a pharmaceutically acceptable salt or solvate thereof, and a pharmaceutically acceptable diluent, carrier, or excipient.

Another aspect provides a pharmaceutical combination comprising a Formula I ADC compound and a second compound having anticancer properties or other therapeutic effects.

Another aspect is a method for killing or inhibiting the proliferation of tumor cells or cancer cells comprising treating the cells with an amount of an antibody-drug conjugate of Formula I, or a pharmaceutically acceptable salt or solvate thereof, being effective to kill or inhibit the proliferation of the tumor cells or cancer cells.

Another aspect is a method of treating cancer comprising administering to a patient a therapeutically effective amount of a pharmaceutical composition including a Formula I ADC.

Another aspect includes articles of manufacture, i.e. kits, comprising an antibody-drug conjugate, a container, and a package insert or label indicating a treatment.

An aspect of the invention is a method for making a Formula I antibody drug conjugate compound comprising the steps of: (a) reacting an engineered cysteine group of the cysteine engineered antibody with a linker reagent to form antibody-linker intermediate Ab-L; and (b) reacting Ab-L with an activated drug moiety D; whereby the antibody-drug conjugate is formed; or comprising the steps of: (c) reacting a nucleophilic group of a drug moiety with a linker reagent to form drug-linker intermediate D-L; and (d) reacting D-L with an engineered cysteine group of the cysteine engineered antibody; whereby the antibody-drug conjugate is formed.

An aspect of the invention is an assay for detecting cancer cells comprising: (a) exposing cells to a cysteine engineered anti-CD79b antibody-drug conjugate; and (b) determining the extent of binding of the cysteine engineered anti-CD79b antibody-drug conjugate compound to the cells.

A. Anti-CD79b Antibodies

In one embodiment, the present invention provides anti-CD79b antibodies which may find use herein as therapeutic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol,* 5:256-262 (1993) and Pliickthun, *Immunol. Revs.* 130: 151-188 (1992).

In a further embodiment, monoclonal antibodies or antibody fragments can be isolated from antibody phage libraries generated using the techniques described in McCafferty et al., Nature, 348:552-554 (1990). Clackson et al., *Nature,* 352: 624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and CO sequences for the homologous murine sequences (U.S. Pat. No. 4,816,567; and Morrison, et al., *Proc. Natl Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-CD79b antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeye *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. Reduction or elimination of a HAMA response is a significant aspect of clinical development of suitable therapeutic agents. See, e.g., Khaxzaeli et al., J. Natl. Cancer Inst. (1988), 80:937; Jailers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

Thus, the VH acceptor human framework may comprise one, two, three or all of the following framework sequences:
FR1 comprising EVQLVESGGGLVQPGGSLRLSCAAS (SEQ ID NO: 143),
FR2 comprising WVRQAPGKGLEWV (SEQ ID NO: 144),
FR3 comprising FR3 comprises RFTISX$_1$DX$_2$SKNTX$_3$YLQMNSLRAEDTAVYYC (SEQ ID NO: 147), wherein
X$_1$ is A or R, X$_2$ is T or N, and X$_3$ is A or L,
FR4 comprising WGQGTLVTVSS (SEQ ID NO: 146).
Examples of VH consensus frameworks include:
human VH subgroup I consensus framework minus Kabat CDRs (SEQ ID NO: 108);
human VH subgroup I consensus framework minus extended hypervariable regions (SEQ ID NOs: 109-111);
human VH subgroup II consensus framework minus Kabat CDRs (SEQ ID NO: 112);
human VH subgroup II consensus framework minus extended hypervariable regions (SEQ ID NOs: 113-115);
human VH subgroup III consensus framework minus Kabat CDRs (SEQ ID NO: 116);
human VH subgroup III consensus framework minus extended hypervariable regions (SEQ ID NO: 117-119);
human VH acceptor framework minus Kabat CDRs (SEQ ID NO: 120);
human VH acceptor framework minus extended hypervariable regions (SEQ ID NOs: 121-122);
human VH acceptor 2 framework minus Kabat CDRs (SEQ ID NO: 123); or
human VH acceptor 2 framework minus extended hypervariable regions (SEQ ID NOs: 124-126).

In one embodiment, the VH acceptor human framework comprises one, two, three or all of the following framework sequences:
FR1 comprising EVQLVESGGGLVQPGGSLRLSCAAS (SEQ ID NO: 143),
FR2 comprising WVRQAPGKGLEWV (SEQ ID NO: 144),
FR3 comprising RFTISADTSKNTAYLQMNSLRAEDTAVYYC (SEQ ID NO: 145),
RFTISADTSKNTAYLQMNSLRAEDTAVYYCA (SEQ ID NO: 148),
RFTISADTSKNTAYLQMNSLRAEDTAVYYCAR (SEQ ID NO: 149),
RFTISADTSKNTAYLQMNSLRAEDTAVYYCS (SEQ ID NO: 150), or
RFTISADTSKNTAYLQMNSLRAEDTAVYYCSR (SEQ ID NO: 151)
FR4 comprising WGQGTLVTVSS (SEQ ID NO: 146).

The VL acceptor human framework may comprise one, two, three or all of the following framework sequences:

FR1 comprising DIQMTQSPSSLSASVGDRVTITC (SEQ ID NO: 139),

FR2 comprising WYQQKPGKAPKLLIY (SEQ ID NO: 140),

FR3 comprising GVPSRFSGSGSGTDFTLTISSLQPEDFATYYC (SEQ ID NO: 141),

FR4 comprising FGQGTKVEIKR (SEQ ID NO: 142).

Examples of VL consensus frameworks include:

human VL kappa subgroup I consensus framework (SEQ ID NO: 127);

human VL kappa subgroup II consensus framework (SEQ ID NO: 128);

human VL kappa subgroup III consensus framework (SEQ ID NO: 129); or human VL kappa subgroup IV consensus framework (SEQ ID NO: 130)

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35B (H1), 50-65, 47-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

In the examples herein, hypervariable region-grafted variants were generated by Kunkel mutagenesis of nucleic acid encoding the human acceptor sequences, using a separate oligonucleotide for each hypervariable region. Kunkel et al., *Methods Enzymol.* 154:367-382 (1987). Appropriate changes can be introduced within the framework and/or hypervariable region, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage (mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., *Proteins*, 8:309 (1990); Lowman and Wells, *Methods: A Companion to Methods in Enzymology*, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

| IUB CODES |
|---|
| G Guanine |
| A Adenine |
| T Thymine |
| C Cytosine |
| R (A or G) |
| Y (C or T) |
| M (A or C) |
| K (G or T) |
| S (C or G) |
| W (A or T) |
| H (A or C or T) |
| B (C or G or T) |
| V (A or C or G) |
| D (A or G or T) H |
| N (A or C or G or T) |

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA,* 75:5765 (1978).

The DNA template is generated by those vectors that are either derived from bacteriophage M13 vectors (the commercially available M13mp18 and Ml3mp19 vectors are suitable), or those vectors that contain a single-stranded phage origin of replication as described by Viera et al., *Meth. Enzymol.,* 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.,* 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, antigen binding may be restored during humanization of antibodies through the selection of repaired hypervariable regions (See application Ser. No. 11/061,841 filed Feb. 18, 2005, US 2006/0122377, now abandoned). The method includes incorporating non-human hypervariable regions onto an acceptor framework and further introducing one or more amino acid substitutions in one or more hypervariable regions without modifying the acceptor framework sequence. Alternatively, the introduction of one or more amino acid substitutions may be accompanied by modifications in the acceptor framework sequence.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-CD79b antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a CD79b protein as described herein. Other such antibodies may combine a CD79b binding site with a binding site for another protein. Alternatively, an anti-CD79b arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the CD79b-expressing cell. Bispecific antibodies may also be used to localize cytotoxic agents to cells which express CD79b. These antibodies possess a CD79b-binding arm and an arm which binds the cytotoxic agent (e.g., saporin, anti-interferon-a, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med. 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tuft et al., J. Immunol 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol* 148:2918-2922 (1992). Homodimeric antibodies with enhanced antitumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

9. Immunoconjugates

The invention also pertains to immunoconjugates (interchangeably referred to as "antibody-drug conjugates," or "ADCs") comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

In certain embodiments, an immunoconjugate comprises an antibody and a chemotherapeutic agent or other toxin. Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, auristatin peptides, such as monomethylauristatin (MMAE) (synthetic analog of dolastatin), maytansinoids, such as DM1, a trichothene, and CC1065, and the derivatives of these toxins that have toxin activity, are also contemplated herein.

Exemplary Immunoconjugates—Antibody-Drug Conjugates

An immunoconjugate (or "antibody-drug conjugate" ("ADC")) of the invention may be of Formula I, below, wherein an antibody is conjugated (i.e., covalently attached) to one or more drug moieties (D) through an optional linker (L). ADCs may include thioMAb drug conjugates ("TDC").

Ab-(L-D)$_p$     I

Accordingly, the antibody may be conjugated to the drug either directly or via a linker. In Formula I, p is the average number of drug moieties per antibody, which can range, e.g., from about 1 to about 20 drug moieties per antibody, and in certain embodiments, from 1 to about 8 drug moieties per antibody. The invention includes a composition comprising a mixture of antibody-drug compounds of Formula I where the average drug loading per antibody is about 2 to about 5, or about 3 to about 4.

a. Exemplary Linkers

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), and those resulting from conjugation with linker reagents: N-Succinimidyl 4-(2-pyridylthio) pentanoate ("SPP"), N-succinimidyl 4-(N-maleimidomethyl) cyclohexane-1 carboxylate ("SMCC", also referred to herein as "MCC"), and N-Succinimidyl (4-iodoacetyl) aminobenzoate ("SIAB"). Various linker components are known in the art, some of which are described below.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., Cancer Research 52:127-131 (1992); U.S. Pat. No. 5,208,020) may be used.

In certain embodiments, a linker is as shown in the following Formula II:

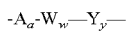  II wherein A is a stretcher unit, and a is an integer from 0 to 1; W is an amino acid unit, and w is an integer from 0 to 12; Y is a spacer unit, and y is 0, 1, or 2; and Ab, D, and p are defined as above for Formula I. Exemplary embodiments of such linkers are described in US 2005-0238649 A1, now U.S. Pat. No. 7,498,298, granted Mar. 3, 2009, which is expressly incorporated herein by reference.

In some embodiments, a linker component may comprise a "stretcher unit" that links an antibody to another linker component or to a drug moiety. Exemplary stretcher units are shown below (wherein the wavy line indicates sites of covalent attachment to an antibody):

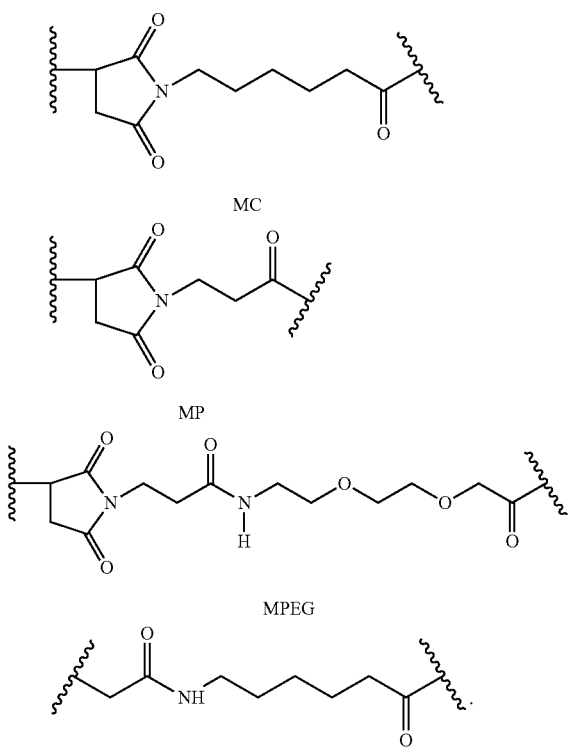

In some embodiments, a linker component may comprise an amino acid unit. In one such embodiment, the amino acid unit allows for cleavage of the linker by a protease, thereby facilitating release of the drug from the immunoconjugate upon exposure to intracellular proteases, such as lysosomal enzymes. See, e.g., Doronina et al. (2003) Nat. Biotechnol. 21:778-784. Exemplary amino acid units include, but are not limited to, a dipeptide, a tripeptide, a tetrapeptide, and a pentapeptide. Exemplary dipeptides include: valine-citrulline (vc or val-cit), alanine-phenylalanine (af or ala-phe); phenylalanine-lysine (fk or phe-lys); or N-methyl-valine-citrulline (Me-val-cit). Exemplary tripeptides include: glycine-valine-citrulline (gly-val-cit) and glycine-glycine-glycine (gly-gly-gly). An amino acid unit may comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some embodiments, a linker component may comprise a "spacer" unit that links the antibody to a drug moiety, either directly or by way of a stretcher unit and/or an amino acid unit. A spacer unit may be "self-immolative" or a "non-self-immolative." A "non-self-immolative" spacer unit is one in which part or all of the spacer unit remains bound to the drug moiety upon enzymatic (e.g., proteolytic) cleavage of the ADC. Examples of non-self-immolative spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an ADC containing a glycine-glycine spacer unit by a tumor-cell associated protease would result in release of a glycine-glycine-drug moiety from the remainder of the ADC. In one such embodiment, the glycine-glycine-drug moiety is then subjected to a separate hydrolysis step in the tumor cell, thus cleaving the glycine-glycine spacer unit from the drug moiety.

A "self-immolative" spacer unit allows for release of the drug moiety without a separate hydrolysis step. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. See, e.g., Hamann et al. (2005) Expert Opin. Ther. Patents (2005) 15:1087-1103. In one embodiment, the spacer unit is p-aminobenzyloxycarbonyl (PAB). In certain embodiments, the phenylene portion of a p-amino benzyl unit is substituted with Qm, wherein Q is —$C_1$-$C_8$ alkyl, —O—($C_1$-$C_8$ alkyl), -halogen, -nitro or -cyano; and m is an integer ranging from 0-4. Examples of self-immolative spacer units further include, but are not limited to, aromatic compounds that are electronically similar to p-aminobenzyl alcohol (see, e.g., US 2005/0256030 A1, now U.S. Pat. No. 7,375,078, granted May 20, 2008), such as 2-aminoimidazol-5-methanol derivatives (Hay et al. (1999) Bioorg. Med. Chem. Lett. 9:2237) and ortho- or para-aminobenzylacetals. Spacers can be used that undergo cyclization upon amide bond hydrolysis, such as substituted and unsubstituted 4-aminobutyric acid amides (Rodrigues et al., Chemistry Biology, 1995, 2, 223); appropriately substituted bicyclo[2.2.1] and bicyclo[2.2.2] ring systems (Storm, et al., J. Amer. Chem. Soc., 1972, 94, 5815); and 2-aminophenylpropionic acid amides (Amsberry, et al., J. Org. Chem., 1990, 55, 5867). Elimination of amine-containing drugs that are substituted at the a-position of glycine (Kingsbury, et al., J. Med. Chem., 1984, 27, 1447) are also examples of self-immolative spacers useful in ADCs.

In one embodiment, a spacer unit is a branched bis(hydroxymethyl)styrene (BHMS) unit as depicted below, which can be used to incorporate and release multiple drugs.

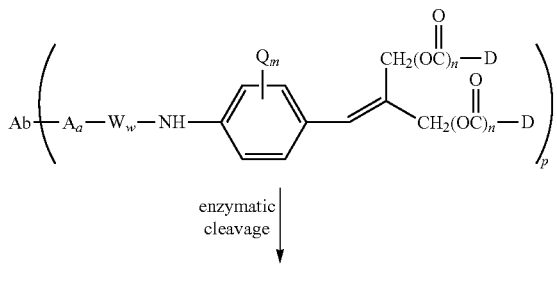

wherein Q is —$C_1$-$C_8$ alkyl, —O—($C_1$-$C_8$ alkyl), -halogen, -nitro or -cyano; m is an integer ranging from 0-4; n is 0 or 1; and p ranges raging from 1 to about 20.

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Exemplary linker components and combinations thereof are shown below in the context of ADCs of Formula II:

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through disulfide and non-disulfide linkers to antibodies, (iii) stable in plasma, and (iv) effective against a variety of tumor cell lines.

Maytansine compounds suitable for use as maytansinoid drug moieties are well known in the art and can be isolated from natural sources according to known methods or produced using genetic engineering and fermentation techniques (U.S. Pat. No. 6,790,952; US 2005/0170475, now U.S. Pat. No. 7,432,088, granted Oct. 7, 2008; Yu et al (2002) PNAS

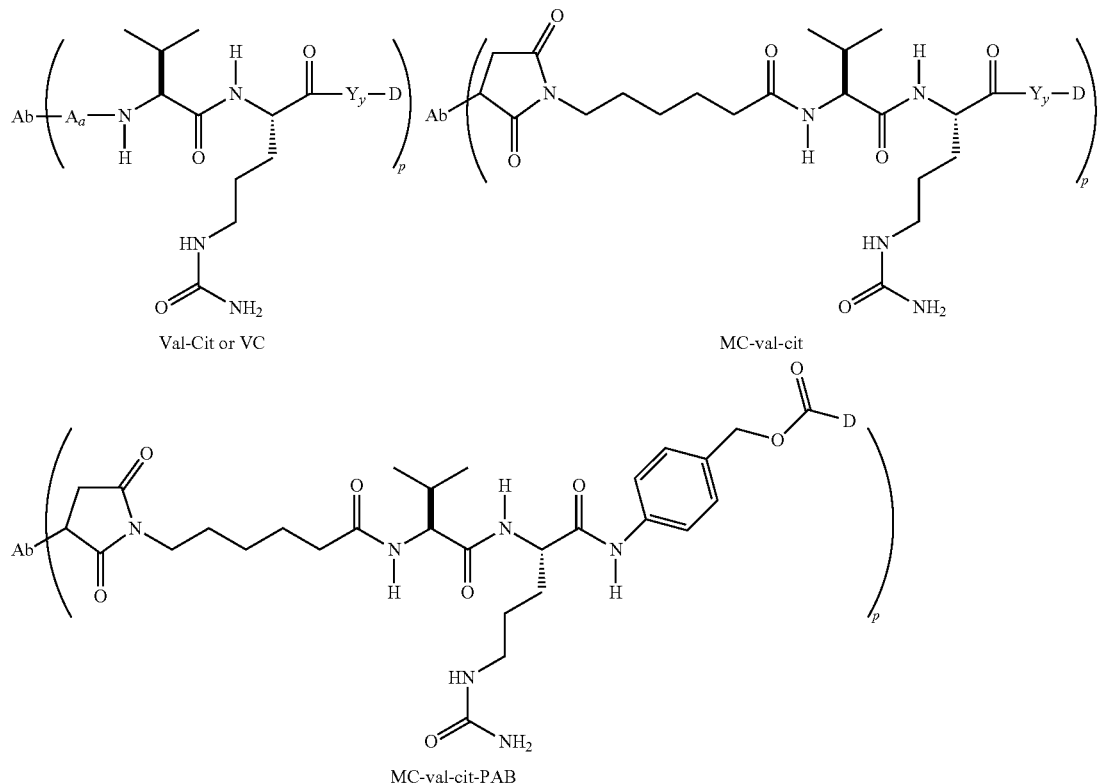

Val-Cit or VC

MC-val-cit

MC-val-cit-PAB

Linkers components, including stretcher, spacer, and amino acid units, may be synthesized by methods known in the art, such as those described in US 2005-0238649 A1, now U.S. Pat. No. 7,498,298, granted Mar. 3, 2009.

b. Exemplary Drug Moieties (1) Maytansine and Maytansinoids

In some embodiments, an immunoconjugate comprises an antibody conjugated to one or more maytansinoid molecules. Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

99:7968-7973). Maytansinol and maytansinol analogues may also be prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl) +/−C-19-dechloro (U.S. Pat. Nos. 4,361,650 and 4,307,016) (prepared by demethylation using Streptomyces or Actinomyces or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions.

Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2OR$)(U.S. Pat. No. 4,331,598); C-14-hydroxymethyl or acyloxymethyl ($CH_2OH$ or $CH_2OAc$) (U.S. Pat. No. 4,450,254) (prepared from Nocardia); C-15-hydroxy/acyloxy (U.S. Pat. No. 4,364,866) (prepared by the conversion of maytansinol by Streptomyces); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by Streptomyces); and 4,5-deoxy (U.S. Pat. No. 4,371,533) (prepared by the titanium trichloride/LAH reduction of maytansinol).

Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable (U.S. Pat. No. 5,208,020; US RE39151; U.S. Pat. No. 6,913,748; U.S. Pat. No. 7,368,565; US 2006/0167245, now U.S. Pat. No. 7,301,019, granted Nov. 27, 2007; US 2007/0037972, now U.S. Pat. No. 7,598,375 granted Oct. 6, 2009).

Maytansinoid drug moieties include those having the structure:

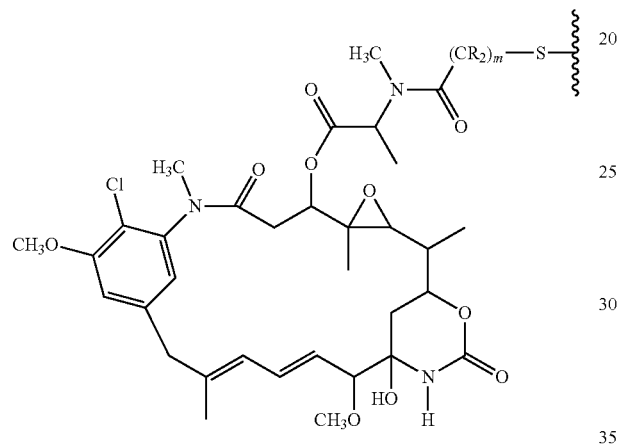

where the wavy line indicates the covalent attachment of the sulfur atom of the maytansinoid drug moiety to a linker of an ADC. R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; U.S. Pat. No. 7,276,497; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the compounds of the invention, i.e. any combination of R and S configurations at the chiral carbons of D. In one embodiment, the maytansinoid drug moiety will have the following stereochemistry:

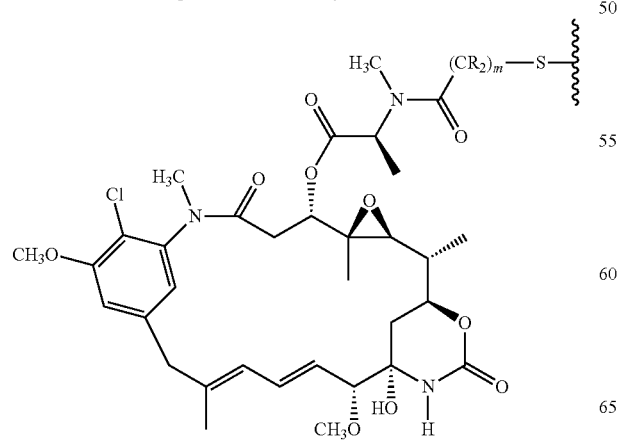

Exemplary embodiments of maytansinoid drug moieities include: DM1; DM3; and DM4, having the structures:

DM1

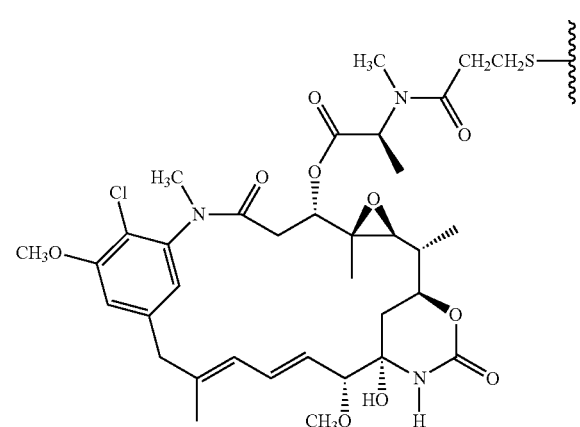

DM3

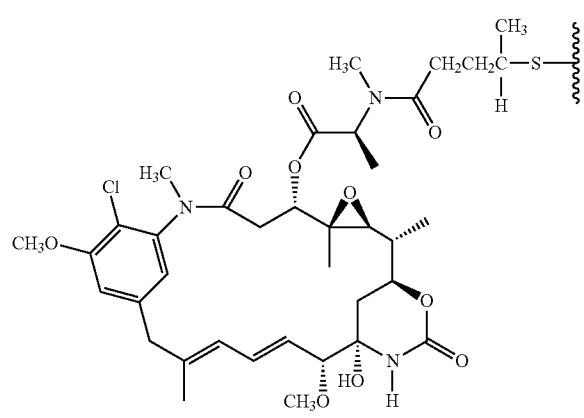

DM4

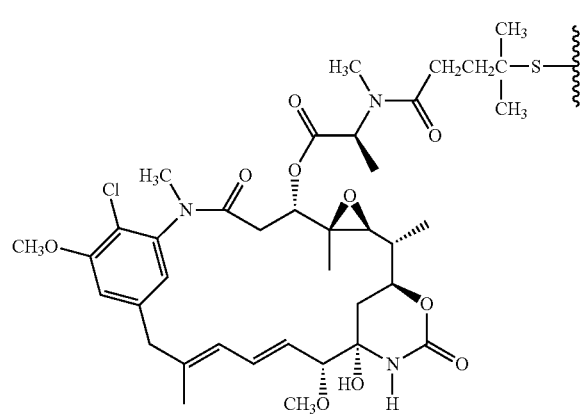

wherein the wavy line indicates the covalent attachment of the sulfur atom of the drug to a linker (L) of an antibody-drug conjugate. (WO 2005/037992; US 2005/0276812 A1, now abandoned).

Other exemplary maytansinoid antibody-drug conjugates have the following structures and abbreviations, (wherein Ab is antibody and p is 1 to about 8):

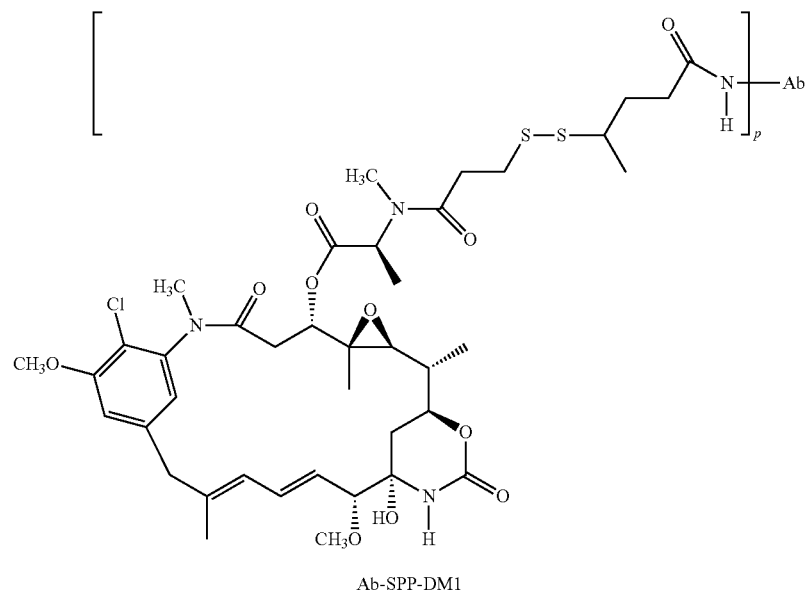
Ab-SPP-DM1
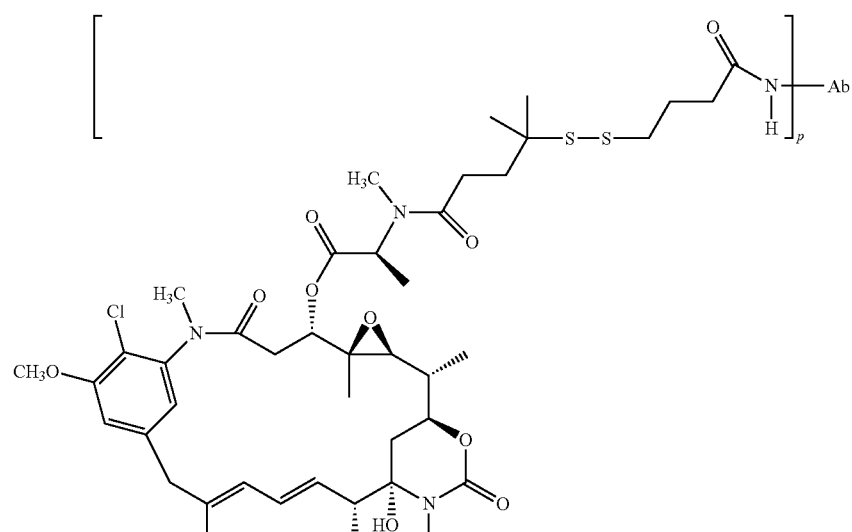
Ab-SPDB-DM4

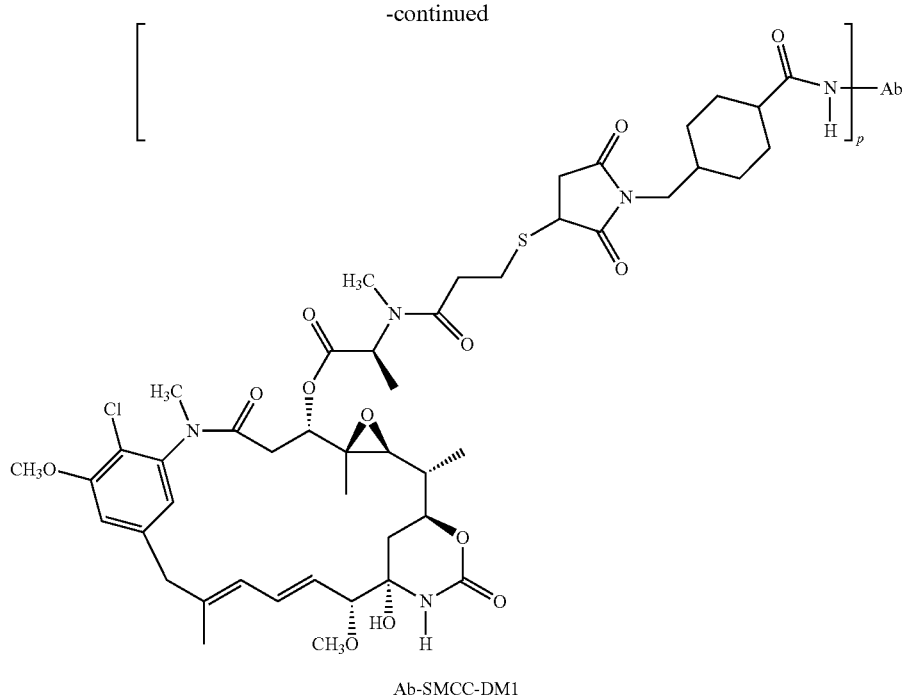

Ab-SMCC-DM1

Exemplary antibody-drug conjugates where DM1 is linked through a BMPEO linker to a thiol group of the antibody have the structure and abbreviation:

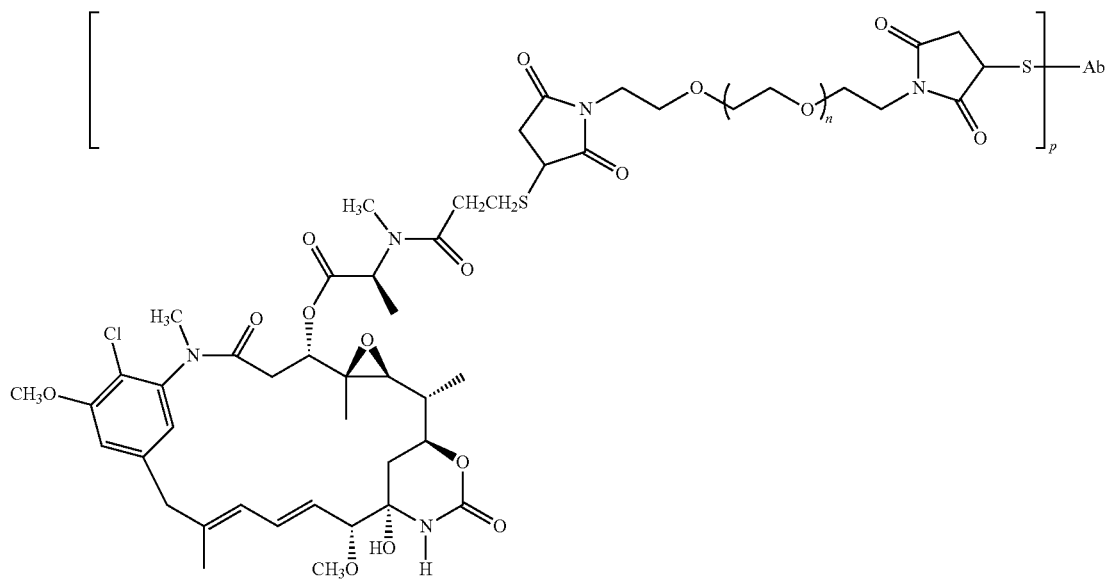

where Ab is antibody; n is 0, 1, or 2; and p is 1, 2, 3, or 4.

Immunoconjugates containing maytansinoids, methods of making the same, and their therapeutic use are disclosed, for example, in Erickson, et al (2006) Cancer Res. 66(8):4426-4433; U.S. Pat. Nos. 5,208,020, 5,416,064, US 2005/0276812 A1, now abandoned, and European Patent EP 0 425 235 B1, the disclosures of which are hereby expressly incorporated by reference.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). Maytansinoids can be synthesized by known techniques or isolated from natural sources. Suitable maytansinoids are disclosed, for example, in U.S. Pat. No. 5,208,020 and in the other patents and non-patent publications referred to hereinabove, such as maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1; Chari et al. *Cancer Research* 52:127-131 (1992); and US 2005/016993 A1, now U.S. Pat. No. 7,755,007, granted Jul. 13, 2010, the disclosures of which are hereby expressly incorporated by reference. Antibody-maytansinoid conjugates comprising the linker component SMCC may be prepared as disclosed in US 2005/0276812 A1, now abandoned, "Antibody-drug conjugates and Methods." The linkers comprise disulfide groups, thioether groups, acid labile groups, photolabile groups, peptidase labile groups, or esterase labile groups, as disclosed in the above-identified patents. Additional linkers are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In certain embodiments, the coupling agent is N-succinimidyl-3-(2-pyridyldithio) propionate (SPDP) (Carlsson et al., *Biochem. J.* 173:723-737 (1978)) or N-succinimidyl-4-(2-pyridylthio)pentanoate (SPP) to provide for a disulfide linkage.

The linker may be attached to the maytansinoid molecule at various positions, depending on the type of the link For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

(2) Auristatins and Dolastatins

In some embodiments, an immunoconjugate comprises an antibody conjugated to dolastatin or a dolastatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF (US 2005/0238649, now U.S. Pat. No. 7,498,298, granted Mar. 3, 2009, disclosed in Senter et al, Proceedings of the American Association for Cancer Research, Volume 45, Abstract Number 623, presented Mar. 28, 2004, the disclosure of which is expressly incorporated by reference in its entirety).

A peptidic drug moiety may be selected from Formulas $D_E$ and $D_F$ below:

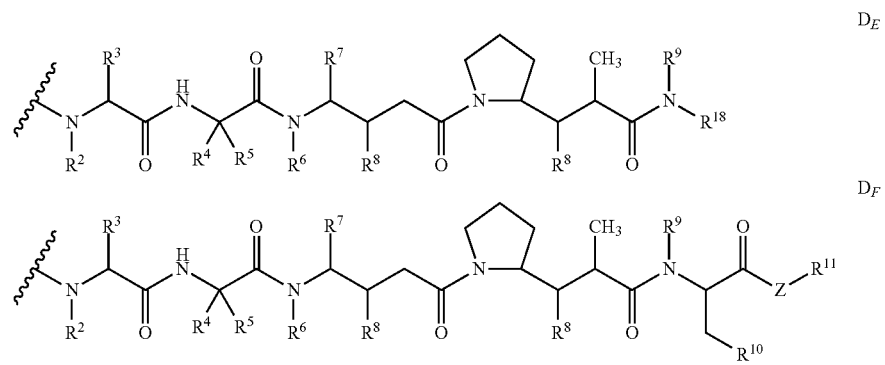

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_1$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl); $R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.
In one embodiment, $R^{10}$ is aryl.
In an exemplary embodiment, $R^{10}$ is -phenyl.
In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —CH$(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

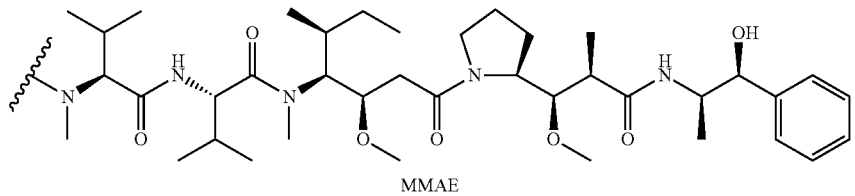 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula $D_F$ is MMAF, wherein the wavy line indicates the covalent attachment to a linker (L) of an antibody-drug conjugate (see US 2005/0238649, now U.S. Pat. No. 7,498,298, granted Mar. 3, 2009 and Doronina et al. (2006) *Bioconjugate Chem.* 17:114-124):

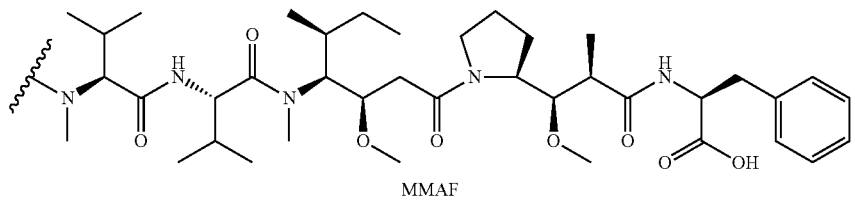

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Other drug moieties include the following MMAF derivatives, wherein the wavy line indicates the covalent attachment to a linker (L) of an antibody-drug conjugate:

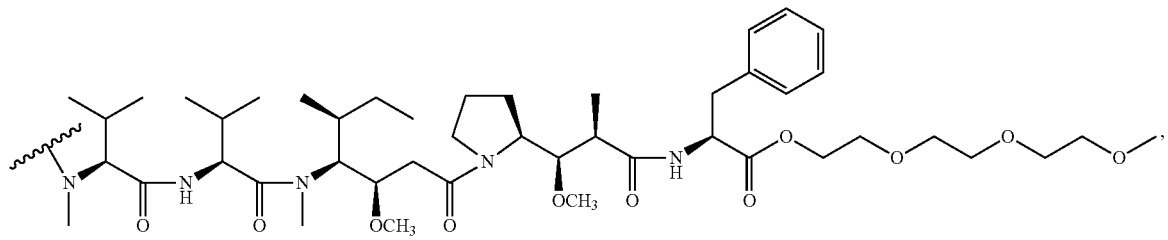

-continued
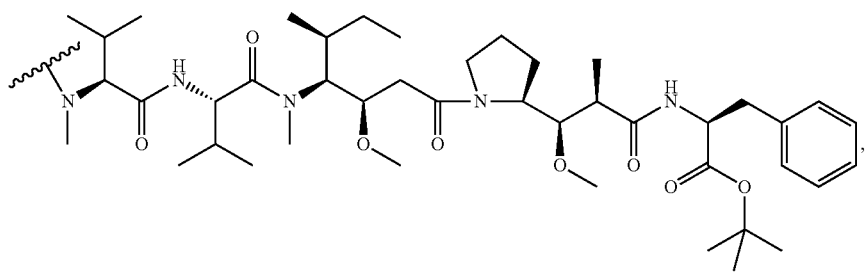
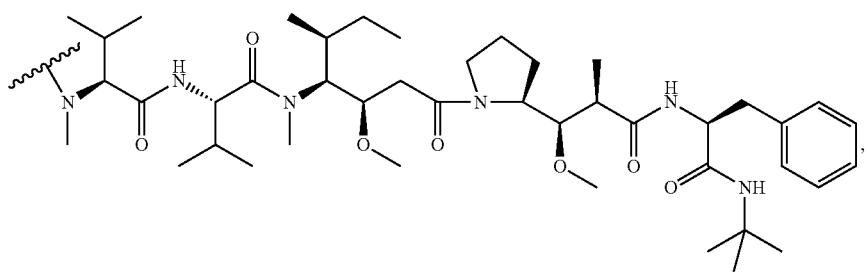
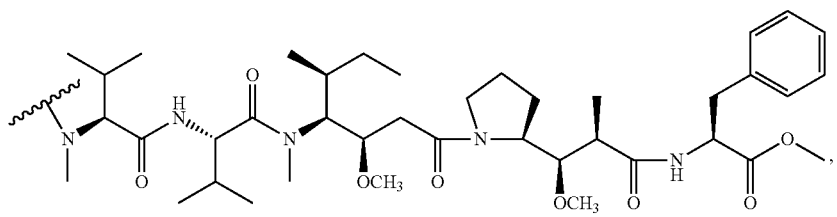
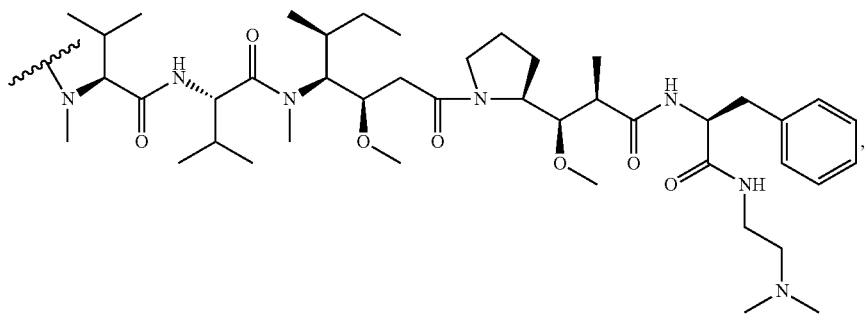
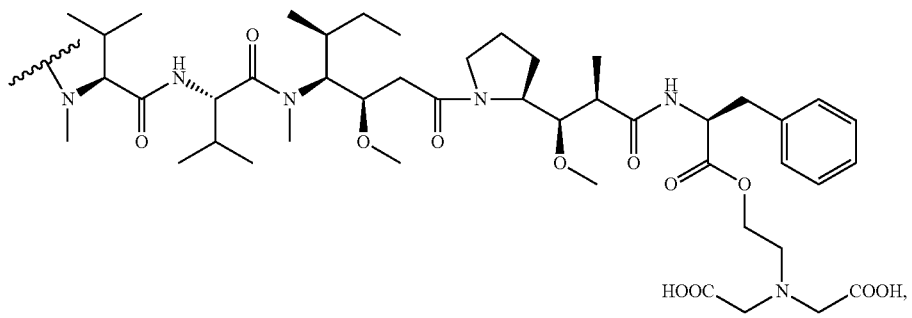
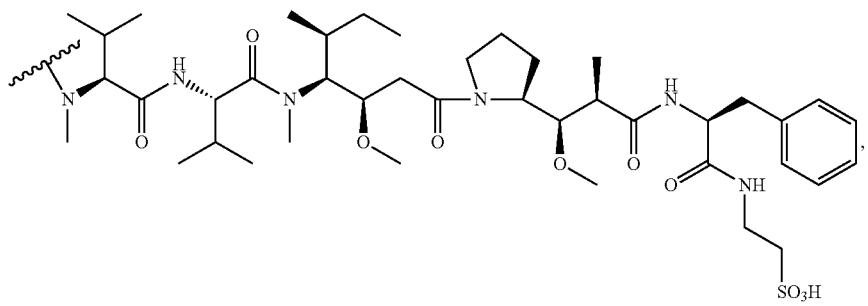

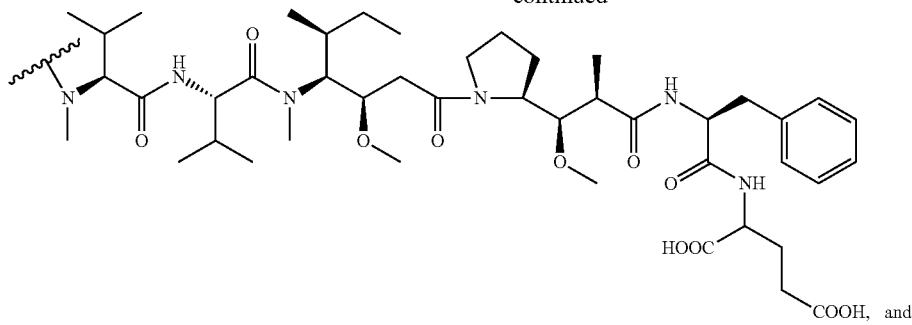

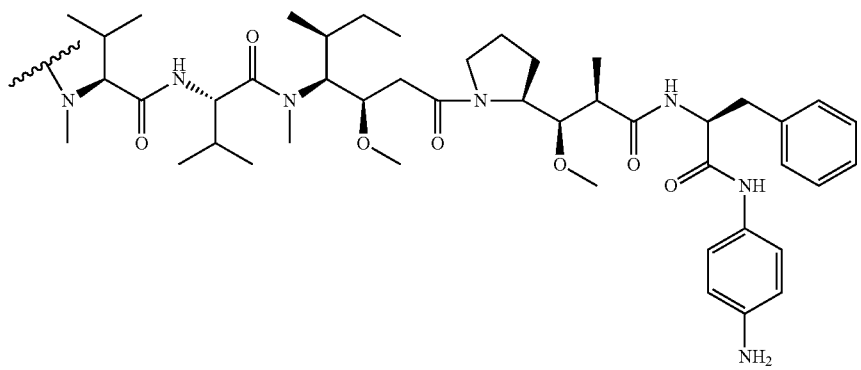

In one aspect, hydrophilic groups including but not limited to, triethylene glycol esters (TEG), as shown above, can be attached to the drug moiety at $R^{11}$. Without being bound by any particular theory, the hydrophilic groups assist in the internalization and non-agglomeration of the drug moiety.

Exemplary embodiments of ADCs of Formula I comprising an auristatin/dolastatin or derivative thereof are described in US 2005-0238649 and Doronina et al. (2006) *Bioconjugate Chem.* 17:114-124, which is expressly incorporated herein by reference. Exemplary embodiments of ADCs of Formula I comprising MMAE or MMAF and various linker components have the following structures and abbreviations (wherein "Ab" is an antibody; p is 1 to about 8, "Val-Cit" or "vc" is a valine-citrulline dipeptide; and "S" is a sulfur atom. It will be noted that in certain of the structural descriptions of sulfur linked ADC herein the antibody is represented as "Ab-S" merely to indicate the sulfur link feature and not to indicate that a particular sulfur atom bears multiple linker-drug moieties. The left parentheses of the following structures may also be placed to the left of the sulfur atom, between Ab and S, which would be an equivalent description of the ADC of the invention described throughout herein.

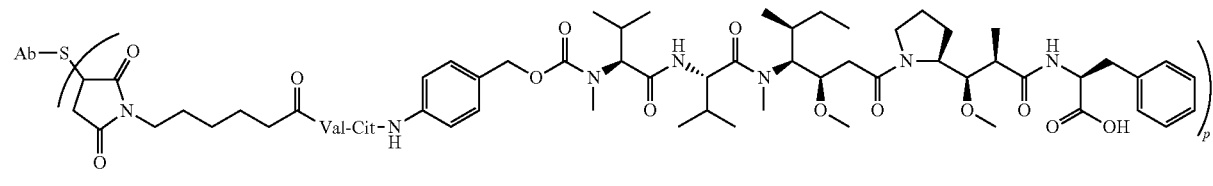

Ab-MC-vc-PAB-MMAF

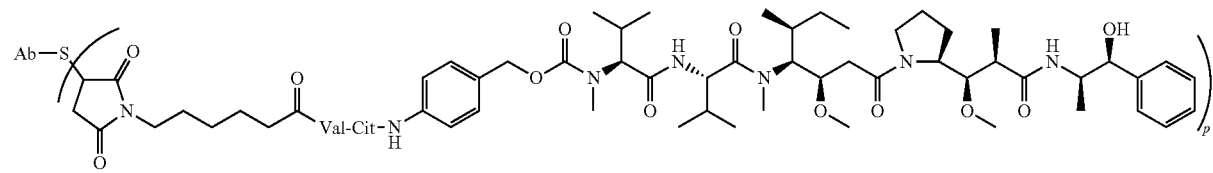

Ab-MC-vc-PAB-MMAE

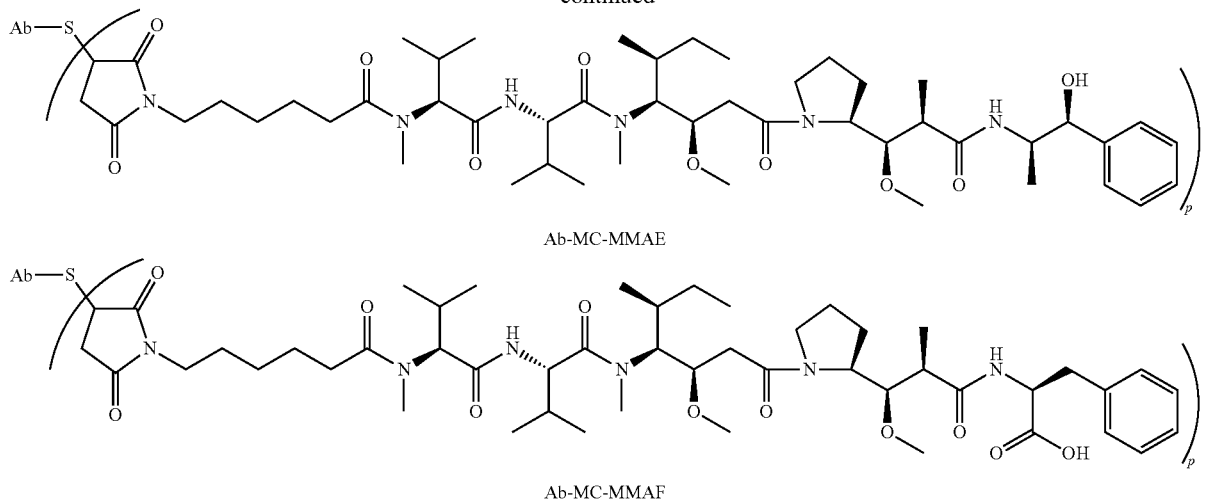

Ab-MC-MMAE

Ab-MC-MMAF

Exemplary embodiments of ADCs of Formula I comprising MMAF and various linker components further include Ab-MC-PAB-MMAF and Ab-PAB-MMAF. Interestingly, immunoconjugates comprising MMAF attached to an antibody by a linker that is not proteolytically cleavable have been shown to possess activity comparable to immunoconjugates comprising MMAF attached to an antibody by a proteolytically cleavable linker. See, Doronina et al. (2006) Bioconjugate Chem. 17:114-124. In such instances, drug release is believed to be effected by antibody degradation in the cell. Id.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. Auristatin/dolastatin drug moieties may be prepared according to the methods of: US 2005-0238649 A1, now U.S. Pat. No. 7,498,298, granted Mar. 3, 2009; U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat. Biotechnol. 21(7):778-784.

In particular, auristatin/dolastatin drug moieties of formula $D_F$, such as MMAF and derivatives thereof, may be prepared using methods described in US 2005-0238649 A1, now U.S. Pat. No. 7,498,298, granted Mar. 3, 2009, and Doronina et al. (2006) Bioconjugate Chem. 17:114-124. Auristatin/dolastatin drug moieties of formula $D_E$, such as MMAE and derivatives thereof, may be prepared using methods described in Doronina et al. (2003) Nat. Biotech. 21:778-784. Drug-linker moieties MC-MMAF, MC-MMAE, MC-vc-PAB-MMAF, and MC-vc-PAB-MMAE may be conveniently synthesized by routine methods, e.g., as described in Doronina et al. (2003) Nat. Biotech. 21:778-784, and Patent Application Publication No. US 2005/0238649 A1 now U.S. Pat. No. 7,498,298, granted Mar. 3, 2009, and then conjugated to an antibody of interest.

(3) Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998), and the aforementioned U.S. patents to American Cyanamid). Another antitumor drug to which the antibody can be conjugated is QFA, which is an antifolate. Both calicheamicin and QFA have intracellular sites of action and do not readily cross the plasma membrane. Therefore, cellular uptake of these agents through antibody-mediated internalization greatly enhances their cytotoxic effects.

c. Other Cytotoxic Agents

Other antitumor agents that can be conjugated to an antibody include BCNU, streptozocin, vincristine and 5-fluorouracil, the family of agents known collectively as the LL-E33288 complex, described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $P^{32}$, $Pb^{212}$ and radioactive isotopes of Lu. When the immunoconjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the immunoconjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) *Biochem. Biophys. Res. Commun.* 80:49-57 can be used to incorporate iodine-123. "Monoclonal Antibodies in Immunoscintigraphy" (Chatal, CRC Press 1989) describes other methods in detail.

In certain embodiments, an immunoconjugate may comprise an antibody conjugated to a prodrug-activating enzyme that converts a prodrug (e.g., a peptidyl chemotherapeutic agent, see WO 81/01145) to an active drug, such as an anti-cancer drug. Such immunoconjugates are useful in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. Enzymes may be covalently bound to antibodies by recombinant DNA techniques well known in the art. See, e.g., Neuberger et al., *Nature* 312:604-608 (1984).

d. Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis. Pharmaceutical formulations of Formula I antibody-drug conjugates may thus be a heterogeneous mixture of such conjugates with antibodies linked to 1, 2, 3, 4, or more drug moieties.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; or from about 3 to about 5. Indeed, it has been shown that for certain ADCs, the optimal ratio of drug moieties per antibody may be less than 8, and may be about 2 to about 5. See US 2005-0238649 A1, now U.S. Pat. No. 7,498,298, granted Mar. 3, 2009.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K.J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

e. Certain Methods of Preparing Immunconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in US 2005-0238649 A1, now U.S. Pat. No. 7,498,298, granted Mar. 3, 2009, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

The compounds of the invention expressly contemplate, but are not limited to, ADC prepared with the following cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A; see pages 467-498, 2003-2004 Applications Handbook and Catalog.

Immunoconjugates comprising an antibody and a cytotoxic agent may also be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Alternatively, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Exemplary Immunoconjugates—Thio-Antibody Drug Conjugates a. Preparation of Cysteine Engineered Anti-CD79b Antibodies DNA encoding an amino acid sequence variant of the cysteine engineered anti-CD79b antibodies and parent anti-CD79b antibodies of the invention is prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Ho et al (1989) Gene (Amst.) 77:51-59; Kunkel et al (1987) Proc. Natl. Acad. Sci. USA 82:488; Liu et al (1998) J. Biol. Chem. 273:20252-20260), PCR mutagenesis (Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733), and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M.J. and Smith, M. (1982) Nucl. Acids Res. 10:6487-6500). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993).

Phage display technology (McCafferty et al (1990) Nature 348:552-553) can be used to produce anti-CD79b human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell (Johnson et al (1993) Current Opinion in Structural Biology 3:564-571; Clackson et al (1991) Nature, 352:624-628; Marks et al (1991) J. Mol. Biol. 222:581-597; Griffith et al (1993) EMBO J. 12:725-734; U.S. Pat. No. 5,565,332; U.S. Pat. No. 5,573,905; U.S. Pat. No. 5,567,610; U.S. Pat. No. 5,229,275).

Anti-CD79b antibodies may be chemically synthesized using known oligopeptide synthesis methodology or may be prepared and purified using recombinant technology. The appropriate amino acid sequence, or portions thereof, may be produced by direct peptide synthesis using solid-phase techniques (Stewart et al., *Solid-Phase Peptide Synthesis*, (1969) W.H. Freeman Co., San Francisco, Calif.; Merrifield, (1963) J. Am. Chem. Soc., 85:2149-2154). In vitro protein synthesis may be performed using manual techniques or by automation. Automated solid phase synthesis may be accomplished, for instance, employing t-BOC or Fmoc protected amino acids and using an Applied Biosystems Peptide Synthesizer (Foster City, Calif.) using manufacturer's instructions. Various portions of the anti-CD79b antibody or CD79b polypeptide may be chemically synthesized separately and combined using chemical or enzymatic methods to produce the desired anti-CD79b antibody or CD79b polypeptide.

Various techniques have been developed for the production of antibody fragments. Traditionally, these fragments were derived via proteolytic digestion of intact antibodies (Morimoto et al (1992) Journal of Biochemical and Biophysical Methods 24:107-117; and Brennan et al (1985) Science, 229:81), or produced directly by recombinant host cells. Fab, Fv and ScFv anti-CD79b antibody fragments can all be expressed in and secreted from *E. coli*, thus allowing the facile production of large amounts of these fragments. Antibody fragments can be isolated from the antibody phage libraries discussed herein. Alternatively, Fab'-SH fragments can be directly recovered from *E. coli* and chemically coupled to form $F(ab')_2$ fragments (Carter et al (1992) Bio/Technology 10:163-167), or isolated directly from recombinant host cell culture. The anti-CD79b antibody may be a (scFv) single chain Fv fragment (WO 93/16185; U.S. Pat. No. 5,571,894; U.S. Pat. No. 5,587,458). The anti-CD79b antibody fragment may also be a "linear antibody" (U.S. Pat. No. 5,641,870). Such linear antibody fragments may be monospecific or bispecific.

The description below relates primarily to production of anti-CD79b antibodies by culturing cells transformed or transfected with a vector containing anti-CD79b antibody-encoding nucleic acid. DNA encoding anti-CD79b antibodies may be obtained from a cDNA library prepared from tissue believed to possess the anti-CD79b antibody mRNA and to express it at a detectable level. Accordingly, human anti-CD79b antibody or CD79b polypeptide DNA can be conveniently obtained from a cDNA library prepared from human tissue. The anti-CD79b antibody-encoding gene may also be obtained from a genomic library or by known synthetic procedures (e.g., automated nucleic acid synthesis).

The design, selection, and preparation methods of the invention enable cysteine engineered anti-CD79b antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London). The amount of free thiol in a protein may be estimated by the standard Ellman's assay. Immunoglobulin M is an example of a disulfide-linked pentamer, while immunoglobulin G is an example of a protein with internal disulfide bridges bonding the subunits together. In proteins such as this, reduction of the disulfide bonds with a reagent such as dithiothreitol (DTT) or selenol (Singh et al (2002) Anal. Biochem. 304:147-156) is required to generate the reactive free thiol. This approach may result in loss of antibody tertiary structure and antigen binding specificity.

The PHESELECTOR (Phage ELISA for Selection of Reactive Thiols) Assay allows for detection of reactive cysteine groups in antibodies in an ELISA phage format thereby assisting in the design of cysteine engineered antibodies (Junutula, J. R. et al. (2008) J Immunol Methods 332:41-52; WO 2006/034488; US 2007/0092940, now U.S. Pat. No. 7,521, 541, granted Apr. 21, 2009). The cysteine engineered antibody is coated on well surfaces, followed by incubation with phage particles, addition of HRP labeled secondary antibody, and absorbance detection. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

The PHESELECTOR assay allows screening of reactive thiol groups in antibodies. Identification of the A121C variant by this method is exemplary. The entire Fab molecule may be effectively searched to identify more ThioFab variants with reactive thiol groups. A parameter, fractional surface accessibility, was employed to identify and quantitate the accessibility of solvent to the amino acid residues in a polypeptide. The surface accessibility can be expressed as the surface area ($Å^2$) that can be contacted by a solvent molecule, e.g. water. The occupied space of water is approximated as a 1.4 Å radius sphere. Software is freely available or licensable (Secretary to CCP4, Daresbury Laboratory, Warrington, WA4 4AD, United Kingdom, Fax: (+44) 1925 603825, or by interne: www.ccp4.ac.uk/dist/html/INDEX.html) as the CCP4 Suite of crystallography programs which employ algorithms to calculate the surface accessibility of each amino acid of a protein with known x-ray crystallography derived coordinates ("The CCP4 Suite: Programs for Protein Crystallography" (1994) Acta. Cryst. D50:760-763). Two exemplary software modules that perform surface accessibility calculations are "AREAIMOL" and "SURFACE", based on the algorithms of B. Lee and F. M. Richards (1971) J.Mol.Biol. 55:379-400. AREAIMOL defines the solvent accessible surface of a protein as the locus of the centre of a probe sphere (representing a solvent molecule) as it rolls over the Van der Waals surface of the protein. AREAIMOL calculates the solvent accessible surface area by generating surface points on an extended sphere about each atom (at a distance from the atom centre equal to the sum of the atom and probe radii), and eliminating those that lie within equivalent spheres associated with neighboring atoms. AREAIMOL finds the solvent accessible area of atoms in a PDB coordinate file, and summarizes the accessible area by residue, by chain and for the whole molecule. Accessible areas (or area differences) for individual atoms can be written to a pseudo-PDB output file. AREAIMOL assumes a single radius for each element, and only recognizes a limited number of different elements.

AREAIMOL and SURFACE report absolute accessibilities, i.e. the number of square Angstroms (Å). Fractional surface accessibility is calculated by reference to a standard state relevant for an amino acid within a polypeptide. The reference state is tripeptide Gly-X-Gly, where X is the amino acid of interest, and the reference state should be an 'extended' conformation, i.e. like those in beta-strands. The extended conformation maximizes the accessibility of X. A calculated accessible area is divided by the accessible area in a Gly-X-Gly tripeptide reference state and reports the quotient, which is the fractional accessibility. Percent accessibility is fractional accessibility multiplied by 100. Another exemplary algorithm for calculating surface accessibility is based on the SOLV module of the program xsae (Broger, C., F. Hoffman-LaRoche, Basel) which calculates fractional accessibility of an amino acid residue to a water sphere based on the X-ray coordinates of the polypeptide. The fractional surface accessibility for every amino acid in an antibody may be calculated using available crystal structure information (Eigenbrot et al. (1993) J Mol Biol. 229:969-995).

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or other mammalian host cells, such as myeloma cells (U.S. Pat. No. 5,807,715; US 2005/0048572, now U.S. Pat. No. 7,608,429, granted Oct. 27, 2009; US 2004/0229310, now U.S. Pat. No. 7,575,893, granted Aug. 18, 2009) that do not otherwise produce the antibody protein, to obtain the synthesis of monoclonal antibodies in the recombinant host cells.

After design and selection, cysteine engineered antibodies, e.g. ThioFabs, with the engineered, highly reactive unpaired Cys residues, "free cysteine amino acids", may be produced by: (i) expression in a bacterial, e.g. E. coli, system (Skerra et al (1993) Curr. Opinion in Immunol. 5:256-262; Pliickthun (1992) Immunol Revs. 130:151-188) or a mammalian cell culture system (WO 01/00245), e.g. Chinese Hamster Ovary cells (CHO); and (ii) purification using common protein purification techniques (Lowman et al (1991) J. Biol. Chem. 266(17): 10982-10988).

The engineered Cys thiol groups react with electrophilic linker reagents and drug-linker intermediates to form cysteine engineered antibody drug conjugates and other labelled cysteine engineered antibodies. Cys residues of cysteine engineered antibodies, and present in the parent antibodies, which are paired and form interchain and intrachain disulfide bonds do not have any reactive thiol groups (unless treated with a reducing agent) and do not react with electrophilic linker reagents or drug-linker intermediates. The newly engineered Cys residue, can remain unpaired, and able to react with, i.e. conjugate to, an electrophilic linker reagent or drug-linker intermediate, such as a drug-maleimide. Exemplary drug-linker intermediates include: MC-MMAE, MC-MMAF, MC-vc-PAB-MMAE, and MC-vc-PAB-MMAF. The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) starting at the N-terminus, differs from the Kabat numbering scheme (bottom row) by insertions noted by a,b,c. Using the Kabat numbering system, the actual linear amino acid sequence may contain fewer or additional amino acids corresponding to a shortening of, or insertion into, a FR or CDR of the variable domain. The cysteine engineered heavy chain variant sites are identified by the sequential numbering and Kabat numbering schemes.

In one embodiment, the cysteine engineered anti-CD79b antibody is prepared by a process comprising:
(a) replacing one or more amino acid residues of a parent anti-CD79b antibody by cysteine; and
(b) determining the thiol reactivity of the cysteine engineered anti-CD79b antibody by reacting the cysteine engineered antibody with a thiol-reactive reagent.

The cysteine engineered antibody may be more reactive than the parent antibody with the thiol-reactive reagent.

The free cysteine amino acid residues may be located in the heavy or light chains, or in the constant or variable domains. Antibody fragments, e.g. Fab, may also be engineered with one or more cysteine amino acids replacing amino acids of the antibody fragment, to form cysteine engineered antibody fragments.

Another embodiment of the invention provides a method of preparing (making) a cysteine engineered anti-CD79b antibody, comprising:
(a) introducing one or more cysteine amino acids into a parent anti-CD79b antibody in order to generate the cysteine engineered anti-CD79b antibody; and
(b) determining the thiol reactivity of the cysteine engineered antibody with a thiol-reactive reagent; wherein the cysteine engineered antibody is more reactive than the parent antibody with the thiol-reactive reagent. Step (a) of the method of preparing a cysteine engineered antibody may comprise:
- (i) mutagenizing a nucleic acid sequence encoding the cysteine engineered antibody;
- (ii) expressing the cysteine engineered antibody; and
- (iii) isolating and purifying the cysteine engineered antibody.

Step (b) of the method of preparing a cysteine engineered antibody may comprise expressing the cysteine engineered antibody on a viral particle selected from a phage or a phagemid particle.

Step (b) of the method of preparing a cysteine engineered antibody may also comprise:
- (i) reacting the cysteine engineered antibody with a thiol-reactive affinity reagent to generate an affinity labelled, cysteine engineered antibody; and
- (ii) measuring the binding of the affinity labelled, cysteine engineered antibody to a capture media.

Another embodiment of the invention is a method of screening cysteine engineered antibodies with highly reactive, unpaired cysteine amino acids for thiol reactivity comprising:
- (a) introducing one or more cysteine amino acids into a parent antibody in order to generate a cysteine engineered antibody;
- (b) reacting the cysteine engineered antibody with a thiol-reactive affinity reagent to generate an affinity labelled, cysteine engineered antibody; and
- (c) measuring the binding of the affinity labelled, cysteine engineered antibody to a capture media; and
- (d) determining the thiol reactivity of the cysteine engineered antibody with the thiol-reactive reagent.

Step (a) of the method of screening cysteine engineered antibodies may comprise:
- (i) mutagenizing a nucleic acid sequence encoding the cysteine engineered antibody;
- (ii) expressing the cysteine engineered antibody; and
- (iii) isolating and purifying the cysteine engineered antibody.

Step (b) of the method of screening cysteine engineered antibodies may comprise expressing the cysteine engineered antibody on a viral particle selected from a phage or a phagemid particle.

Step (b) of the method of screening cysteine engineered antibodies may also comprise:
- (i) reacting the cysteine engineered antibody with a thiol-reactive affinity reagent to generate an affinity labelled, cysteine engineered antibody; and
- (ii) measuring the binding of the affinity labelled, cysteine engineered antibody to a capture media.

b. Cysteine Engineering of Anti-CD79b IgG Variants

Cysteine was introduced at the heavy chain 118 (EU numbering) (equivalent to heavy chain position 118, sequential numbering) site into the full-length, chimeric parent monoclonal anti-CD79b antibodies or at the light chain 205 (Kabat numbering) (equivalent to light chain position 209, sequential numbering) site into the full-length, chimeric parental monoclonal anti-CD79b antibodies by the cysteine engineering methods described herein.

Cysteine engineered antibodies with cysteine at heavy chain 118 (EU numbering) generated were: (a) thio-MA79b.v17-HC(A118C) with heavy chain sequence (SEQ ID NO: 228) and light chain sequence (SEQ ID NO: 229), FIG. 24; (b) thio-MA79b.v18-HC(A118C) with heavy chain sequence (SEQ ID NO: 230) and light chain sequence (SEQ ID NO: 231), FIG. 25; (c) thio-MA79b.v28-HC(A118C), with heavy chain sequence (SEQ ID NO: 232) and light chain sequence (SEQ ID NO: 233), FIG. 26; (d) thio-MA79b-HC (A118C) with heavy chain sequence (SEQ ID NO: 236) and light chain sequence (SEQ ID NO: 237), FIG. 28; and (e) thio-anti-cynoCD79b-HC(A118C) with heavy chain sequence (SEQ ID NO: 244) and light chain sequence (SEQ ID NO: 245), FIG. 48.

Cysteine engineered antibodies with cysteine at light chain 205 (Kabat numbering) generated were: (a) thio-MA79b-LC (V205C) with heavy chain sequence (SEQ ID NO: 234) and light chain sequence (SEQ ID NO: 235), FIG. 27 and (b) thio-anti-cynoCD79b(ch10D10)-LC(V205C) with heavy chain sequence (SEQ ID NO: 299) and light chain sequence (SEQ ID NO: 300), FIG. 49.

These cysteine engineered monoclonal antibodies were expressed in CHO (Chinese Hamster Ovary) cells by transient fermentation in media containing 1 mM cysteine.

According to one embodiment, humanized MA79b cysteine engineered anti-CD79b antibodies comprise one or more of the following heavy chain sequences with a free cysteine amino acid (SEQ ID NOs: 251-259, Table 2).

TABLE 2

Comparison of heavy chain Sequential, Kabat and EU numbering for humanized MA79b cysteine engineered anti-CD79b antibody variants

| SEQUENCE | SEQUENTIAL NUMBERING | KABAT NUMBERING | EU NUMBERING | SEQ ID NO: |
|---|---|---|---|---|
| EVQLCESGGG | V5C | V5C | | 251 |
| LRLSCCASGYT | A23C | A23C | | 252 |
| MNSLRCEDTAV | A88C | A84C | | 253 |
| TLVTVCSASTK | S116C | S112C | | 254 |
| VTVSSCSTKGP | A118C | A114C | A118C | 255 |
| VSSASCKGPSV | T120C | T116C | T120C | 256 |
| WYVDGCEVHNA | V282C | V278C | V282C | 257 |
| KGFYPCDIAVE | S375C | S371C | S375C | 258 |
| PPVLDCDGSFF | S400C | S396C | S400C | 259 |

According to one embodiment, chimeric MA79b cysteine engineered anti-CD79b antibodies comprise one or more of the following heavy chain sequences with a free cysteine amino acid (SEQ ID NOs: 260-268, Table 3).

TABLE 3

Comparison of heavy chain Sequential, Kabat and EU numbering for chMA79b cysteine engineered anti-CD79b antibody variants:

| SEQUENCE | SEQUENTIAL NUMBERING | KABAT NUMBERING | EU NUMBERING | SEQ ID NO: |
|---|---|---|---|---|
| EVQLCQSGAE | Q5C | Q5C | | 260 |
| VKISCCATGYT | K23C | K23C | | 261 |
| LSSLTCEDSAV | S88C | S84C | | 262 |
| TSVTVCSASTK | S116C | S112C | | 263 |
| VTVSSCSTKGP | A118C | A114C | A118C | 264 |

TABLE 3-continued

Comparison of heavy chain Sequential, Kabat and EU numbering for chMA79b cysteine engineered anti-CD79b antibody variants:

| SEQUENCE | SEQUENTIAL NUMBERING | KABAT NUMBERING | EU NUMBERING | SEQ ID NO: |
|---|---|---|---|---|
| VSSASCKGPSV | T120C | T116C | T120C | 265 |
| WYVDGCEVHNA | V282C | V278C | V282C | 266 |
| KGFYPCDIAVE | S375C | S371C | S375C | 267 |
| PPVLDCDGSFF | S400C | S396C | S400C | 268 |

According to one embodiment, anti-cynoCD79b (ch10D10) cysteine engineered anti-CD79b antibodies comprise one or more of the following heavy chain sequences with a free cysteine amino acid (SEQ ID NOs: 269-277, Table 4).

TABLE 4

Comparison of heavy chain Sequential, Kabat and EU numbering for anti-cynoCD79b(ch10D10) cysteine engineered anti-CD79b antibody variants:

| SEQUENCE | SEQUENTIAL NUMBERING | KABAT NUMBERING | EU NUMBERING | SEQ ID NO: |
|---|---|---|---|---|
| EVQLCESGPG | Q5C | Q5C | | 269 |
| LSLTCCVTGYS | T23C | T23C | | 270 |
| LNSVTCEDTAT | S88C | S84C | | 271 |
| TTLTVCSASTK | S111C | S112C | | 272 |
| LTVSSCSTKGP | A113C | A114C | A118C | 273 |
| VSSASCKGPSV | T115C | T116C | T120C | 274 |
| WYVDGCEVHNA | V282C | V278C | V282C | 275 |
| KGFYPCDIAVE | S370C | S371C | S375C | 276 |
| PPVLDCDGSFF | S395C | S396C | S400C | 277 |

According to one embodiment, humanized MA79b cysteine-engineered anti-CD79b antibodies comprise one or more of the following light chain sequences with a free cysteine amino acid (SEQ ID NOs: 278-284, Table 5).

TABLE 5

Comparison of light chain Sequential and Kabat numbering for humanized MA79b cysteine engineered anti-CD79b antibody variants

| SEQUENCE | SEQUENTIAL NUMBERING | KABAT NUMBERING | SEQ ID NO: |
|---|---|---|---|
| SLSASCGDRVT | V15C | V15C | 278 |
| EIKRTCAAPSV | V114C | V110C | 279 |
| TVAAPCVFIFP | S118C | S114C | 280 |
| FIFPPCDEQLK | S125C | S121C | 281 |
| DEQLKCGTASV | S131C | S127C | 282 |
| VTEQDCKDSTY | S172C | S168C | 283 |
| GLSSPCTKSFN | V209C | V205C | 284 |

According to one embodiment, chimeric MA79b cysteine-engineered anti-CD79b antibodies comprise one or more of the following light chain sequences with a free cysteine amino acid (SEQ ID NOs: 285-291, Table 6).

TABLE 6

Comparison of light chain Sequential and Kabat numbering for chimeric MA79b cysteine engineered anti-CD79b antibody variants

| SEQUENCE | SEQUENTIAL NUMBERING | KABAT NUMBERING | SEQ ID NO: |
|---|---|---|---|
| SLAVSCGQRAT | L15C | L15C | 285 |
| ELKRTCAAPSV | V114C | V110C | 286 |
| TVAAPCVFIFP | S118C | S114C | 287 |
| FIFPPCDEQLK | S125C | S121C | 288 |
| DEQLKCGTASV | S131C | S127C | 289 |
| VTEQDCKDSTY | S172C | S168C | 290 |
| GLSSPCTKSFN | V209C | V205C | 291 |

According to one embodiment, anti-cynoCD79b (ch10D10) cysteine-engineered anti-CD79b antibodies comprise one or more of the following light chain sequences with a free cysteine amino acid (SEQ ID NOs: 292-298, Table 7).

TABLE 7

Comparison of light chain Sequential and Kabat numbering for anti-cynoCD79b(ch10D10) cysteine engineered anti-CD79b antibody variants

| SEQUENCE | SEQUENTIAL NUMBERING | KABAT NUMBERING | SEQ ID NO: |
|---|---|---|---|
| SLAVSCGQRAT | L15C | L15C | 292 |
| EIKRTCAAPSV | V114C | V110C | 293 |
| TVAAPCVFIFP | S118C | S114C | 294 |
| FIFPPCDEQLK | S125C | S121C | 295 |
| DEQLKCGTASV | S131C | S127C | 296 |
| VTEQDCKDSTY | S172C | S168C | 297 |
| GLSSPCTKSFN | V209C | V205C | 298 | c. Labelled Cysteine Engineered Anti-CD79b Antibodies

Cysteine engineered anti-CD79b antibodies may be site-specifically and efficiently coupled with a thiol-reactive reagent. The thiol-reactive reagent may be a multifunctional linker reagent, a capture, i e affinity, label reagent (e.g. a biotin-linker reagent), a detection label (e.g. a fluorophore reagent), a solid phase immobilization reagent (e.g.

SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

The exemplary methods described here may be applied generally to the identification and production of antibodies, and more generally, to other proteins through application of the design and screening steps described herein.

Such an approach may be applied to the conjugation of other thiol-reactive reagents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The thiol-reactive reagent may be a drug moiety, a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

d. Uses of Cysteine Engineered Anti-CD79b Antibodies

Cysteine engineered anti-CD79b antibodies, and conjugates thereof may find use as therapeutic and/or diagnostic agents. The present invention further provides methods of preventing, managing, treating or ameliorating one or more symptoms associated with a B-cell related disorder. In particular, the present invention provides methods of preventing, managing, treating, or ameliorating one or more symptoms associated with a cell proliferative disorder, such as cancer, e.g., lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. The present invention still further provides methods for diagnosing a CD79b related disorder or predisposition to developing such a disorder, as well as methods for identifying antibodies, and antigen-binding fragments of antibodies, that preferentially bind B cell-associated CD79b polypeptides.

Another embodiment of the present invention is directed to the use of a cysteine engineered anti-CD79b antibody for the preparation of a medicament useful in the treatment of a condition which is responsive to a B cell related disorder.

e. Cysteine Engineered Antibody Drug Conjugates (Thio-Antibody Drug Conjugates (TDCs))

Another aspect of the invention is an antibody-drug conjugate compound comprising a cysteine engineered anti-CD79b antibody (Ab), and an auristatin drug moiety (D) wherein the cysteine engineered antibody is attached through one or more free cysteine amino acids by a linker moiety (L) to D; the compound having Formula I:

$$\text{Ab-(L-D)}_p \qquad \text{I}$$

where p is 1, 2, 3, or 4; and wherein the cysteine engineered antibody is prepared by a process comprising replacing one or more amino acid residues of a parent anti-CD79b antibody by one or more free cysteine amino acids.

Another aspect of the invention is a composition comprising a mixture of antibody-drug compounds of Formula I where the average drug loading per antibody is about 2 to about 5, or about 3 to about 4.

FIGS. 24-28 and 48-49 show embodiments of cysteine engineered anti-CD79b antibody drug conjugates (ADC) where an auristatin drug moiety is attached to an engineered cysteine group in: the light chain (LC-ADC) or the heavy chain (HC-ADC).

Potential advantages of cysteine engineered anti-CD79b antibody drug conjugates include improved safety (larger therapeutic index), improved PK parameters, the antibody inter-chain disulfide bonds are retained which may stabilize the conjugate and retain its active binding conformation, the sites of drug conjugation are defined, and the preparation of cysteine engineered antibody drug conjugates from conjugation of cysteine engineered antibodies to drug-linker reagents results in a more homogeneous product.

Linkers

"Linker", "Linker Unit", or "link" means a chemical moiety comprising a covalent bond or a chain of atoms that covalently attaches an antibody to a drug moiety. In various embodiments, a linker is specified as L. A "Linker" (L) is a bifunctional or multifunctional moiety which can be used to link one or more Drug moieties (D) and an antibody unit (Ab) to form antibody-drug conjugates (ADC) of Formula I. Antibody-drug conjugates (ADC) can be conveniently prepared using a Linker having reactive functionality for binding to the Drug and to the Antibody. A cysteine thiol of a cysteine engineered antibody (Ab) can form a bond with an electrophilic functional group of a linker reagent, a drug moiety or drug-linker intermediate.

In one aspect, a Linker has a reactive site which has an electrophilic group that is reactive to a nucleophilic cysteine present on an antibody. The cysteine thiol of the antibody is reactive with an electrophilic group on a Linker and forms a covalent bond to a Linker. Useful electrophilic groups include, but are not limited to, maleimide and haloacetamide groups.

Linkers include a divalent radical such as an alkyldiyl, an arylene, a heteroarylene, moieties such as: —$(CR_2)_n$O$(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Cysteine engineered antibodies react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773, and according to the protocol of Example 6.

The linker may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), N-succinimidyl 4-(2-pyridylthio)pentanoate ("SPP"), N-succinimidyl 4-(N-maleimidomethyl)cyclohexane-1 carboxylate ("SMCC"), N-Succinimidyl (4-iodo-acetyl)aminobenzoate ("SIAB"), ethyleneoxy —$CH_2CH_2$O— as one or more repeating units ("EO" or "PEO"). Additional linker components are known in the art and some are described herein.

In one embodiment, linker L of an ADC has the formula:

$$A_a\text{-}W_w\text{—}Y_y\text{—}$$

wherein:

-A- is a Stretcher unit covalently attached to a cysteine thiol of the antibody (Ab);

a is 0 or 1;

each —W— is independently an Amino Acid unit;

w is independently an integer ranging from 0 to 12;

—Y— is a Spacer unit covalently attached to the drug moiety; and y is 0, 1 or 2.

Stretcher Unit

The Stretcher unit (-A-), when present, is capable of linking an antibody unit to an amino acid unit (—W—). In this regard an antibody (Ab) has a functional group that can form a bond with a functional group of a Stretcher. Useful functional groups that can be present on an antibody, either naturally or via chemical manipulation include, but are not limited to, sulfhydryl (—SH), amino, hydroxyl, carboxy, the anomeric hydroxyl group of a carbohydrate, and carboxyl. In one aspect, the antibody functional groups are sulfhydryl or amino. Sulfhydryl groups can be generated by reduction of an intramolecular disulfide bond of an antibody. Alternatively, sulfhydryl groups can be generated by reaction of an amino group of a lysine moiety of an antibody using 2-iminothiolane (Traut's reagent) or another sulfhydryl generating reagent. In one embodiment, an antibody (Ab) has a free cysteine thiol group that can form a bond with an electrophilic functional group of a Stretcher Unit. Exemplary stretcher units in Formula I conjugates are depicted by Formulas II and III, wherein Ab-, —W—, —Y—, -D, w and y are as defined above, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—$(C_3$-$C_8$ carbocyclyl), $(C_3$-$C_8$ carbocyclyl)-$(CH_2)_r$, $C_3$-$C_8$ heterocyclyl, $(CH_2)_r$—$(C_3$-$C_8$ heterocyclyl), —$(C_3$-$C_8$ heterocyclyl)-$(CH_2)_r$—, —$(CH_2)_rC(O)NR^b(CH_2)_r$—, —$(CH_2CH_2O)_r$—, —$(CH_2CH_2O)_r$—$CH_2$—, —$(CH_2)_rC(O)NR^b(CH_2CH_2O)_r$—, —$(CH_2)_rC(O)NR^b(CH_2CH_2O)_r$—$CH_2$—, —$(CH_2CH_2O)_rC(O)NR^b(CH_2CH_2O)_r$—, —$(CH_2CH_2O)_rC(O)NR^b(CH_2CH_2O)_r$—$CH_2$—, and —$(CH_2CH_2O)_rC(O)NR^b(CH_2)_r$—; where $R^b$ is H, $C_1$-$C_6$ alkyl, phenyl, or benzyl; and r is independently an integer ranging from 1-10.

Arylene includes divalent aromatic hydrocarbon radicals of 6-20 carbon atoms derived by the removal of two hydrogen atoms from the aromatic ring system. Typical arylene groups include, but are not limited to, radicals derived from benzene, substituted benzene, naphthalene, anthracene, biphenyl, and the like.

Heterocyclyl groups include a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2 H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbocyclyl groups include a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

It is to be understood from all the exemplary embodiments of Formula I ADC such as II-VI, that even where not denoted expressly, from 1 to 4 drug moieties are linked to an antibody (p=1-4), depending on the number of engineered cysteine residues.

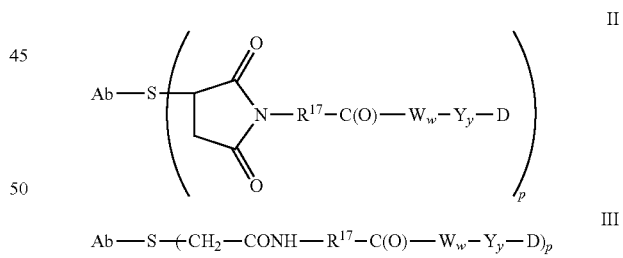

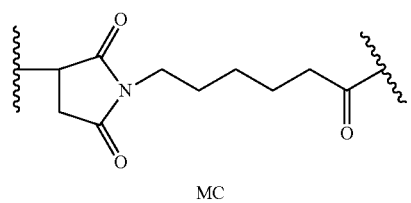 [SMILES: *C(=O)CCCCCN1C(=O)CC(*)C1=O]

An illustrative Formula II Stretcher unit is derived from maleimido-caproyl (MC) wherein $R^{17}$ is —$(CH_2)_5$—:

An illustrative Stretcher unit of Formula II, and is derived from maleimido-propanoyl (MP) wherein $R^{17}$ is —$(CH_2)_2$—:

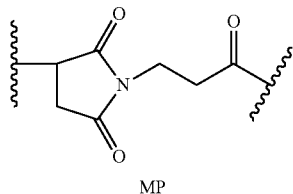

MP

Another illustrative Stretcher unit of Formula II wherein $R^{17}$ is —$(CH_2CH_2O)_r$—$CH_2$— and r is 2:

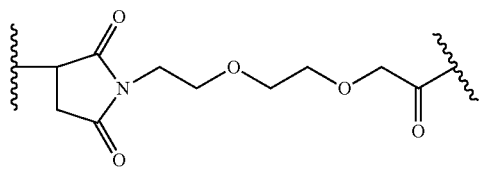

Another illustrative Stretcher unit of Formula II wherein $R^{17}$ is —$(CH_2)_rC(O)NR^b(CH_2CH_2O)_r$—$CH_2$— where $R^b$ is H and each r is 2:

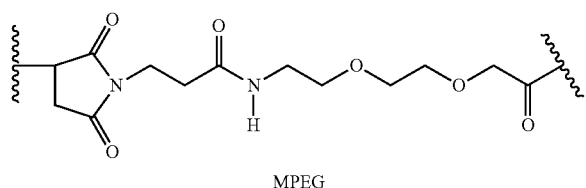

MPEG

An illustrative Stretcher unit of Formula III wherein $R^{17}$ is —$(CH_2)_5$—:

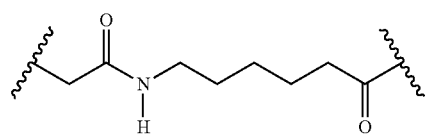

In another embodiment, the Stretcher unit is linked to the cysteine engineered anti-CD79b antibody via a disulfide bond between the engineered cysteine sulfur atom of the antibody and a sulfur atom of the Stretcher unit. A representative Stretcher unit of this embodiment is depicted by Formula IV, wherein $R^{17}$, Ab-, —W—, —Y—, -D, w and y are as defined above.

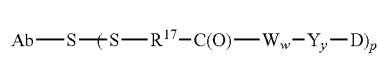

IV

In yet another embodiment, the reactive group of the Stretcher contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted by Formulas Va and Vb, wherein —$R^{17}$—, Ab-, —W—, —Y—, -D, w and y are as defined above;

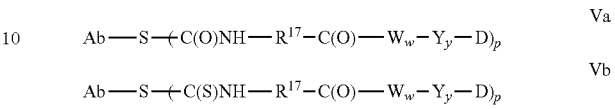

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Amino Acid Unit

The linker may comprise amino acid residues. The Amino Acid unit (—$W_w$—), when present, links the antibody (Ab) to the drug moiety (D) of the cysteine engineered antibody-drug conjugate (ADC) of the invention.

—$W_w$— is a dipeptide, tripeptide, tetrapeptide, pentapeptide, hexapeptide, heptapeptide, octapeptide, nonapeptide, decapeptide, undecapeptide or dodecapeptide unit Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

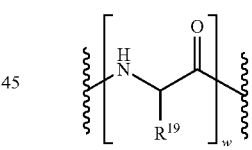

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

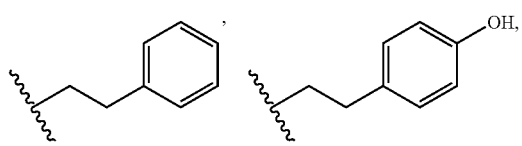

-continued

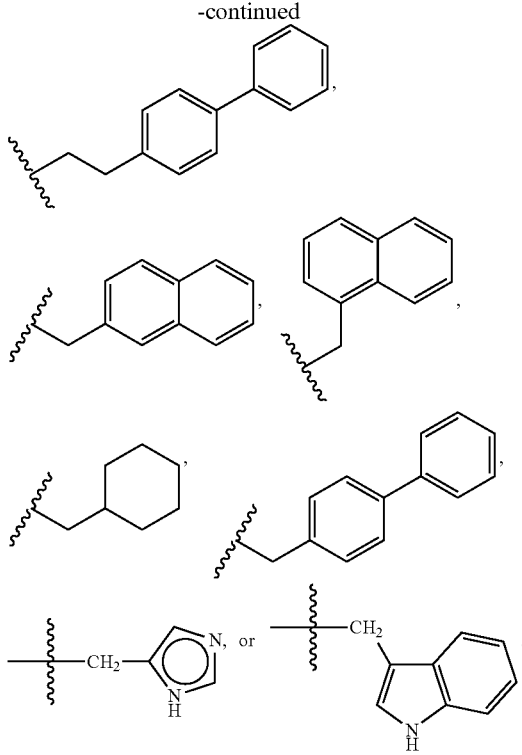

When $R^{19}$ is other than hydrogen, the carbon atom to which $R^{19}$ is attached is chiral. Each carbon atom to which $R^{19}$ is attached is independently in the (S) or (R) configuration, or a racemic mixture Amino acid units may thus be enantiomerically pure, racemic, or diastereomeric.

Exemplary —$W_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline.

The Amino Acid unit can be enzymatically cleaved by one or more enzymes, including a tumor-associated protease, to liberate the Drug moiety (-D), which in one embodiment is protonated in vivo upon release to provide a Drug (D). Amino acid linker components can be designed and optimized in their selectivity for enzymatic cleavage by a particular enzymes, for example, a tumor-associated protease, cathepsin B, C and D, or a plasmin protease.

Spacer Unit

The Spacer unit (—$Y_y$—), when present (y=1 or 2), links an Amino Acid unit (—$W_w$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y=0). Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the antibody-drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-Ww-. In one embodiment, an independent hydrolysis reaction takes place within the target cell, cleaving the glycine-Drug moiety bond and liberating the Drug.

In another embodiment, —$Y_y$— is a p-aminobenzylcarbamoyl (PAB) unit whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

Exemplary embodiments of a non self-immolative Spacer unit (—Y—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —Y— is a PAB group that is linked to —$W_w$— via the amino nitrogen atom of the PAB group, and connected directly to -D via a carbonate, carbamate or ether group, where the ADC has the exemplary structure:

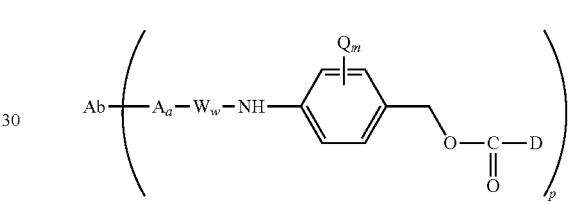

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237), heterocyclic PAB analogs (US 2005/0256030, now U.S. Pat. No. 7,375,078, granted May 20, 2008), beta-glucuronide (WO 2007/011968), and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

Exemplary Spacer units (—$Y_y$—) are represented by Formulas X-XII:

X

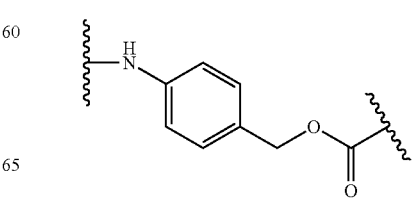

XI

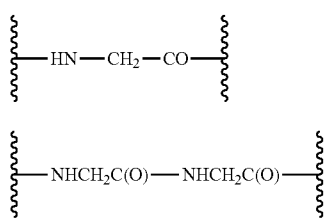

XII

Dendritic Linkers

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker. Exemplary embodiments of branched, dendritic linkers include 2,6-bis(hydroxymethyl)-p-cresol and 2,4,6-tris(hydroxymethyl)-phenol dendrimer units (WO 2004/01993; Szalai et al (2003) J. Amer. Chem. Soc. 125: 15688-15689; Shamis et al (2004) J. Amer. Chem. Soc. 126: 1726-1731; Amir et al (2003) Angew. Chem. Int. Ed. 42:4494-4499).

In one embodiment, the Spacer unit is a branched bis (hydroxymethyl)styrene (BHMS), which can be used to incorporate and release multiple drugs, having the structure:

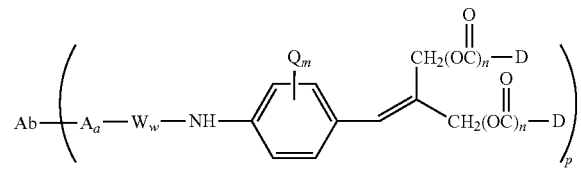

comprising a 2-(4-aminobenzylidene)propane-1,3-diol dendrimer unit (WO 2004/043493; de Groot et al (2003) Angew. Chem. Int. Ed. 42:4490-4494), wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to 4.

Exemplary embodiments of the Formula I antibody-drug conjugate compounds include XIIIa (MC), XIIIb (val-cit), XIIIc (MC-val-cit), and XIIId (MC-val-cit-PAB):

XIIIa

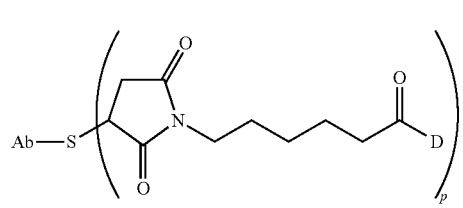

XIIIb

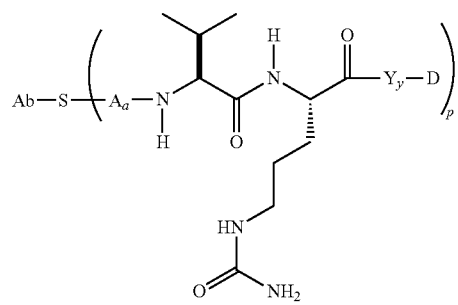

XIIIc

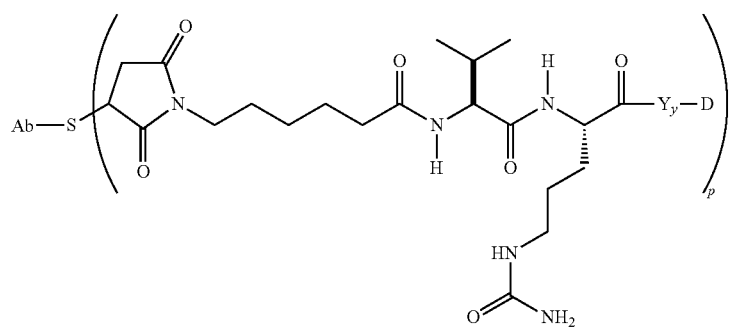

-continued

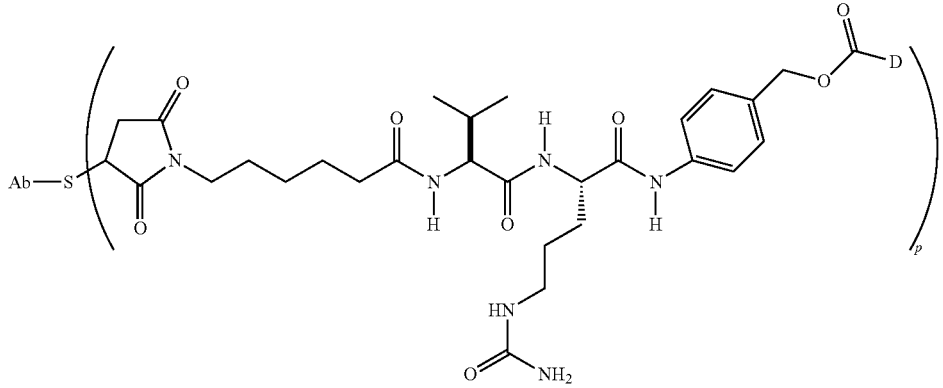

XIIId

Other exemplary embodiments of the Formula Ia antibody-drug conjugate compounds include XIVa-e:

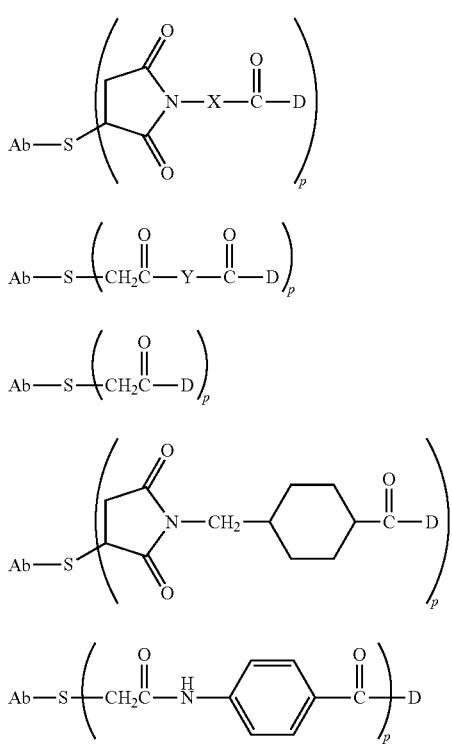

XIVa

XIVb

XIVc

XIVd

XIVe where X is:

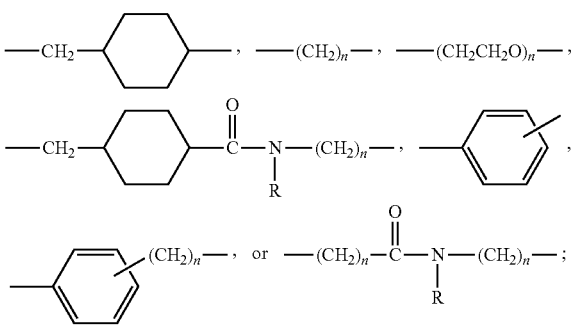

Y is:

and R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry. Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to carboxyls, hydroxyls, para-nitrophenylcarbonate, isothiocyanate, and leaving groups, such as O-mesyl, O-tosyl, —Cl, —Br, —I; or maleimide.

For example, a charged substituent such as sulfonate ($—SO_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

Linker Reagents

Conjugates of the antibody and auristatin may be made using a variety of bifunctional linker reagents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The antibody drug conjugates may also be prepared with linker reagents: BMPEO, BMPS, EMCS, GMBS, HBVS, LC-SMCC, MBS, MPBH, SBAP, SIA, SIAB, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, 1,8-bis-maleimidodiethyleneglycol (BM(PEO)$_2$), and 1,11-bis-maleimidotriethyleneglycol (BM(PEO)$_3$), which are commercially available from Pierce Biotechnology, Inc., ThermoScientific, Rockford, Ill., and other reagent suppliers. Bis-maleimide reagents allow the attachment of the thiol group of a cysteine engineered antibody to a thiol-containing drug moiety, label, or linker intermediate, in a sequential or concurrent fashion. Other functional groups besides maleimide, which are reactive with a thiol group of a cysteine engineered antibody, drug moiety, label, or linker intermediate include iodoacetamide, bromoacetamide, vinyl pyridine, disulfide, pyridyl disulfide, isocyanate, and isothiocyanate.

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189, now U.S. Pat. No. 7,553,816, granted Jun. 30, 2009; US2003096743, now U.S. Pat. No. 7,091,186, granted Aug. 15, 2006; WO 03/026577; WO 03/043583; and WO 04/032828.

Stretchers of formula (Ma) can be introduced into a Linker by reacting the following linker reagents with the N-terminus of an Amino Acid unit:

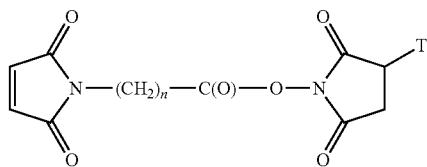

where n is an integer ranging from 1-10 and T is —H or —SO$_3$Na;

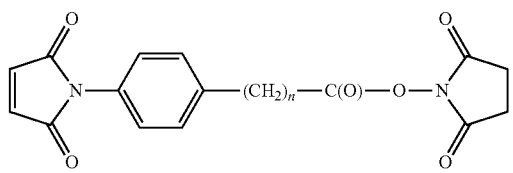

where n is an integer ranging from 0-3;

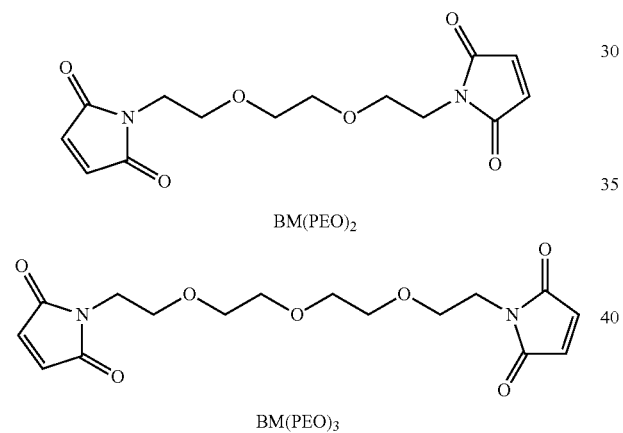

BM(PEO)$_2$

BM(PEO)$_3$

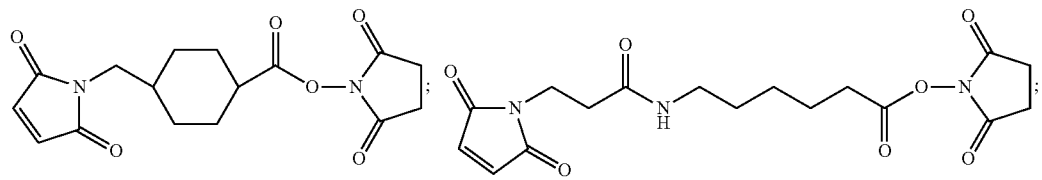

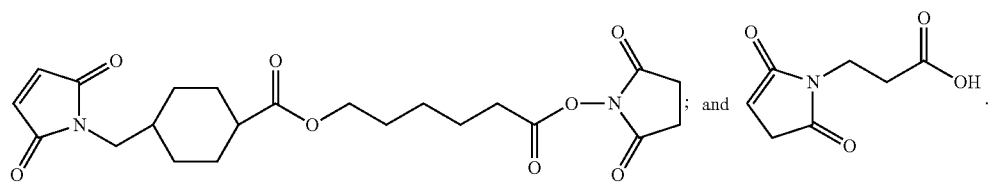

Stretcher units of can be introduced into a Linker by reacting the following bifunctional reagents with the N-terminus of an Amino Acid unit:

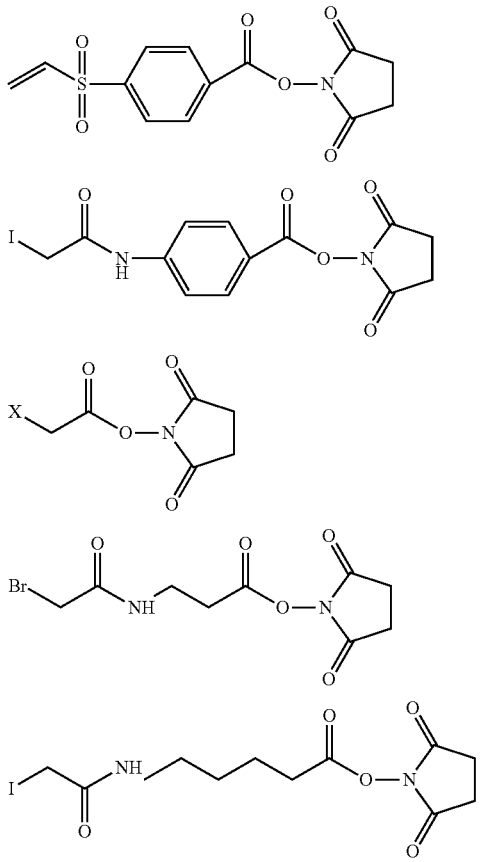

where X is Br or I.

Stretcher units of formula can also be introduced into a Linker by reacting the following bifunctional reagents with the N-terminus of an Amino Acid unit:

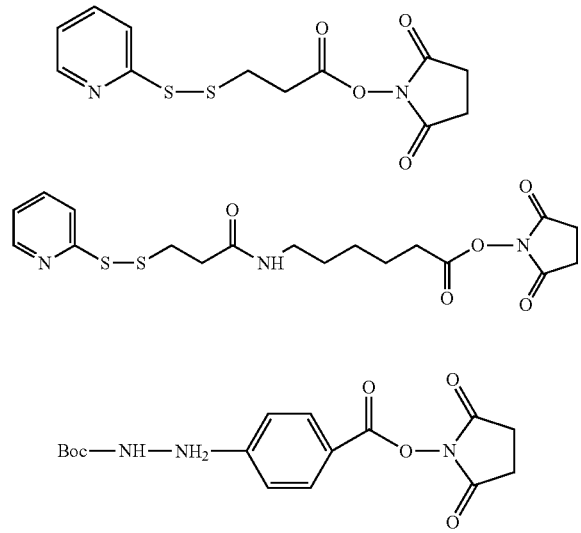

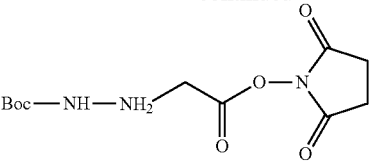

An exemplary valine-citrulline (val-cit or vc) dipeptide linker reagent having a maleimide Stretcher and a para-aminobenzylcarbamoyl (PAB) self-immolative Spacer has the structure:

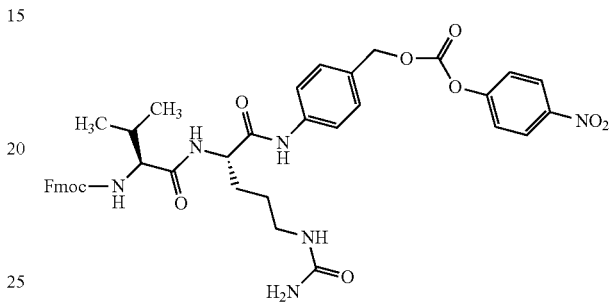

An exemplary phe-lys(Mtr, mono-4-methoxytrityl) dipeptide linker reagent having a maleimide Stretcher unit and a PAB self-immolative Spacer unit can be prepared according to Dubowchik, et al. (1997) Tetrahedron Letters, 38:5257-60, and has the structure:

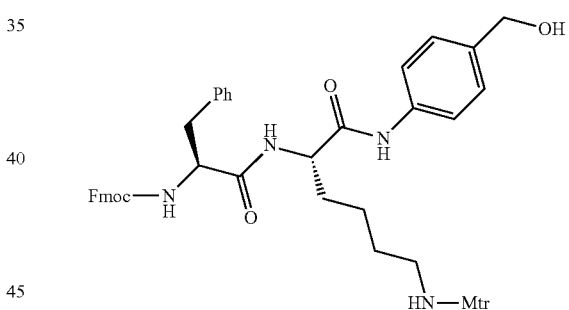

Preparation of Cysteine Engineered Anti-CD79b Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.), followed by reoxidation to reform interchain and intrachain disulfide bonds (Example 5). For example, full length, cysteine engineered monoclonal antibodies (ThioMabs) expressed in CHO cells are reduced with about a 50 fold molar excess of TCEP for 3 hrs at 37° C. to reduce disulfide bonds in cysteine adducts which may form between the newly introduced cysteine residues and the cysteine present in the culture media. The reduced ThioMab is diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate ($CuSO_4$) at room temperature, overnight. Alternatively, dehydroascorbic acid (DHAA) is an effective oxidant to reestablish the intrachain disulfide groups of the cysteine engineered antibody after reductive cleavage of the cysteine adducts. Other oxidants, i.e. oxidizing agents, and oxidizing conditions, which are known in the art may be used. Ambient air oxidation is also effective. This mild, partial reoxidation step forms intrachain disulfides efficiently with high fidelity and preserves the thiol groups of the newly introduced cysteine residues. An approximate 10 fold excess of drug-linker intermediate, e.g. MC-vc-PAB-MMAE, was added, mixed, and let stand for about an hour at room temperature to effect conjugation and form the anti-CD79b antibody-drug conjugate. The conjugation mixture was gel filtered and loaded and eluted through a HiTrap S column to remove excess drug-linker intermediate and other impurities.

Figure 23:
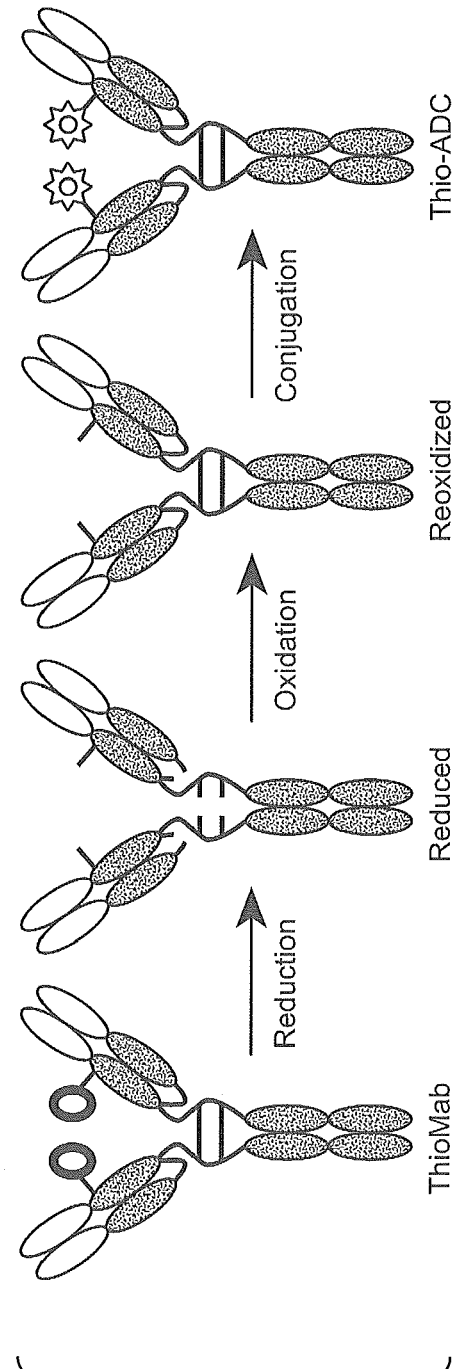
FIG. 23 shows the steps of: (i) reducing cysteine disulfide adducts and interchain and intrachain disulfides in a cysteine engineered anti-CD79b antibody (ThioMab) with reducing agent TCEP (tris(2-carboxyethyl)phosphine hydrochloride); (ii) partially oxidizing, i.e. reoxidation to reform interchain and intrachain disulfides, with dhAA (dehydroascorbic acid); and (iii) conjugation of the reoxidized antibody with a drug-linker intermediate to form a cysteine anti-CD79b drug conjugate (ADC).

FIG. 23 shows the general process to prepare a cysteine engineered antibody expressed from cell culture for conjugation. When the cell culture media contains cysteine, disulfide adducts can form between the newly introduced cysteine amino acid and cysteine from media. These cysteine adducts, depicted as a circle in the exemplary ThioMab (left) in FIG. 23, must be reduced to generate cysteine engineered antibodies reactive for conjugation. Cysteine adducts, presumably along with various interchain disulfide bonds, are reductively cleaved to give a reduced form of the antibody with reducing agents such as TCEP. The interchain disulfide bonds between paired cysteine residues are reformed under partial oxidation conditions with copper sulfate, DHAA, or exposure to ambient oxygen. The newly introduced, engineered, and unpaired cysteine residues remain available for reaction with linker reagents or drug-linker intermediates to form the antibody conjugates of the invention. The ThioMabs expressed in mammalian cell lines result in externally conjugated Cys adduct to an engineered Cys through —S—S— bond formation. Hence the purified ThioMabs are treated with the reduction and reoxidation procedures as described in Example 5 to produce reactive ThioMabs. These ThioMabs are used to conjugate with maleimide containing cytotoxic drugs, fluorophores, and other labels.

10. Immunoliposomes

The anti-CD79b antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. Certain Methods of Making Antibodies

1. Screening for Anti-CD79b Antibodies with the Desired Properties

Techniques for generating antibodies that bind to CD79b polypeptides have been described above. One may further select antibodies with certain biological characteristics, as desired.

The growth inhibitory effects of an anti-CD79b antibody of the invention may be assessed by methods known in the art, e.g., using cells which express a CD79b polypeptide either endogenously or following transfection with the CD79b gene. For example, appropriate tumor cell lines and CD79b-transfected cells may be treated with an anti-CD79b monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-CD79b antibody of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. The tumor cell may be one that overexpresses a CD79b polypeptide. The anti-CD79b antibody will inhibit cell proliferation of a CD79b-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-CD79b antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an anti-CD79b antibody which induces cell death, loss of membrane integrity as indicated by, e.g., propidium iodide (PI), trypan blue or 7AAD uptake may be assessed relative to control. A PI uptake assay can be performed in the absence of complement and immune effector cells. CD79b polypeptide-expressing tumor cells are incubated with medium alone or medium containing the appropriate anti-CD79b antibody (e.g, at about 10 µg/ml). The cells are incubated for a 3 day time period. Following each treatment, are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those anti-CD79b antibodies that induce statistically significant levels of cell death as determined by PI uptake may be selected as cell death-inducing anti-CD79b antibodies.

To screen for antibodies which bind to an epitope on a CD79b polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody binds the same site or epitope as a known anti-CD79b antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a CD79b polypeptide can be used in competition assays with the test antibodies or with a test antibody and an antibody with a characterized or known epitope.

2. Certain Library Screening Methods

Anti-CD79b antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. (2001) in Methods in Molecular Biology 178:1-37 (O'Brien et al., ed., Human Press, Totowa, N.J.), and in certain embodiments, in Lee et al. (2004) J. Mol. Biol. 340:1073-1093.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-CD79b antibodies of the invention can be obtained by designing a suitable antigen screening procedure to select for the phage clone of interest followed by construction of a full length anti-CD79b antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-CD79b clones is desired, the subject is immunized with CD79b to generate an antibody response, and spleen cells and/or circulating B cells other peripheral blood lymphocytes (PBLs) are recovered for library construction. In a preferred embodiment, a human antibody gene fragment library biased in favor of anti-CD79b clones is obtained by generating an anti-CD79b antibody response in transgenic mice carrying a functional human immunoglobulin gene array (and lacking a functional endogenous antibody production system) such that CD79b immunization gives rise to B cells producing human antibodies against CD79b. The generation of human antibody-producing transgenic mice is described below.

Additional enrichment for anti-CD79b reactive cell populations can be obtained by using a suitable screening procedure to isolate B cells expressing CD79b-specific membrane bound antibody, e.g., by cell separation using CD79b affinity chromatography or adsorption of cells to fluorochrome-labeled CD79b followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which CD79b is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by $E.\ coli$ transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about $10^{-9}$ M or less.

Screening of the libraries can be accomplished by various techniques known in the art. For example, CD79b can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized CD79b under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci USA, 88: 7978-7982 (1991), or by alkali, e.g. as described in Marks et al., J. Mol. Biol., 222: 581-597 (1991), or by CD79b antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for CD79b. However, random mutation of a selected antibody (e.g. as performed in some affinity maturation techniques) is likely to give rise to many mutants, most binding to antigen, and a few with higher affinity. With limiting CD79b, rare high affinity phage could be competed out. To retain all higher affinity mutants, phages can be incubated with excess biotinylated CD79b, but with the biotinylated CD79b at a concentration of lower molarity than the target molar affinity constant for CD79b. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity Conditions used in washing phages bound to a solid phase can also be manipulated to discriminate on the basis of dissociation kinetics.

Anti-CD79b clones may be selected based on activity. In certain embodiments, the invention provides anti-CD79b antibodies that bind to living cells that naturally express CD79b. In one embodiment, the invention provides anti-CD79b antibodies that block the binding between a CD79b ligand and CD79b, but do not block the binding between a CD79b ligand and a second protein. Fv clones corresponding to such anti-CD79b antibodies can be selected by (1) isolating anti-CD79b clones from a phage library as described above, and optionally amplifying the isolated population of phage clones by growing up the population in a suitable bacterial host; (2) selecting CD79b and a second protein against which blocking and non-blocking activity, respectively, is desired; (3) adsorbing the anti-CD79b phage clones to immobilized CD79b; (4) using an excess of the second protein to elute any undesired clones that recognize CD79b-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-CD79b antibody derived from a hybridoma can also be modified, for example, by substituting the coding sequence for human heavy- and light-chain constant domains in place of homologous murine sequences derived from the hybridoma clone (e.g. as in the method of Morrison et al., Proc. Natl. Acad. Sci. USA, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

C. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328:457-458 (1987)). Antibody-abzyme conjugates can be prepared as described herein for delivery of the abzyme to a tumor cell population.

The enzymes of this invention can be covalently bound to the anti-CD79b antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature 312:604-608 (1984).

D. Anti-CD79b Antibody

In addition to the anti-CD79b antibodies described herein, it is contemplated that anti-CD79b antibody variants can be prepared. Anti-CD79b antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-CD79b antibody, such as changing the number or position of glycosylation sites or altering the membrane anchoring characteristics.

Variations in the anti-CD79b antibodies described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-CD79b antibody. Guidance in determining which amino acid residue may be inserted, substituted or deleted without adversely affecting the desired activity may be found by comparing the sequence of the anti-CD79b antibody with that of homologous known protein molecules and minimizing the number of amino acid sequence changes made in regions of high homology Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-CD79b antibody fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-CD79b antibody.

Anti-CD79b antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-CD79b antibody fragments share at least one biological and/or immunological activity with the native anti-CD79b antibody disclosed herein.

In particular embodiments, conservative substitutions of interest are shown in Table 8 under the heading of preferred substitutions. If such substitutions result in a change in biological activity, then more substantial changes, denominated exemplary substitutions in Table 8, or as further described below in reference to amino acid classes, are introduced and the products screened.

TABLE 8

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the anti-CD79b antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the anti-CD79b antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Any cysteine residue not involved in maintaining the proper conformation of the anti-CD79b antibody also may be substituted, generally with serine, to improve the oxidative stability of the molecule and prevent aberrant crosslinking. Conversely, cysteine bond(s) may be added to the anti-CD79b antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and CD79b polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-CD79b antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-CD79b antibody.

E. Modifications of Anti-CD79b Antibodies

Covalent modifications of anti-CD79b antibodies are included within the scope of this invention. One type of covalent modification includes reacting targeted amino acid residues of an anti-CD79b antibody with an organic derivatizing agent that is capable of reacting with selected side chains or the N- or C-terminal residues of the anti-CD79b antibody. Derivatization with bifunctional agents is useful, for instance, for crosslinking anti-CD79b antibody to a water-insoluble support matrix or surface for use in the method for purifying anti-CD79b antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the anti-CD79b antibody included within the scope of this invention comprises altering the native glycosylation pattern of the antibody or polypeptide. "Altering the native glycosylation pattern" is intended for purposes herein to mean deleting one or more carbohydrate moieties found in native sequence anti-CD79b antibody (either by removing the underlying glycosylation site or by deleting the glycosylation by chemical and/or enzymatic means), and/or adding one or more glycosylation sites that are not present in the native sequence anti-CD79b antibody. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-CD79b antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-CD79b antibody (for O-linked glycosylation sites). The anti-CD79b antibody amino acid sequence may optionally be altered through changes at the DNA level, particularly by mutating the DNA encoding the anti-CD79b antibody at preselected bases such that codons are generated that will translate into the desired amino acids.

Another means of increasing the number of carbohydrate moieties on the anti-CD79b antibody is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the anti-CD79b antibody may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of anti-CD79b antibody comprises linking the antibody to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The anti-CD79b antibody of the present invention may also be modified in a way to form chimeric molecules comprising an anti-CD79b antibody fused to another, heterologous polypeptide or amino acid sequence.

In one embodiment, such a chimeric molecule comprises a fusion of the anti-CD79b antibody with a tag polypeptide which provides an epitope to which an anti-tag antibody can selectively bind. The epitope tag is generally placed at the amino- or carboxyl-terminus of the anti-CD79b antibody. The presence of such epitope-tagged forms of the anti-CD79b antibody can be detected using an antibody against the tag polypeptide. Also, provision of the epitope tag enables the anti-CD79b antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9 E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the anti-CD79b antibody with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-CD79b antibody in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

F. Preparation of Anti-CD79b Antibodies

The description below relates primarily to production of anti-CD79b antibodies by culturing cells transformed or transfected with a vector containing anti-CD79b antibody-encoding nucleic acid. It is, of course, contemplated that alternative methods, which are well known in the art, may be employed to prepare anti-CD79b antibodies. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-CD79b antibody may be chemically synthesized separately and combined using chemical or enzymatic methods to produce the desired anti-CD79b antibody.

1. Isolation of DNA Encoding Anti-CD79b Antibody

DNA encoding anti-CD79b antibody may be obtained from a cDNA library prepared from tissue believed to possess the anti-CD79b antibody mRNA and to express it at a detectable level. Accordingly, human anti-CD79b antibody DNA can be conveniently obtained from a cDNA library prepared from human tissue. The anti-CD79b antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding anti-CD79b antibody is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-CD79b antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation, which means introduction of DNA into the host so that the DNA is replicable, either as an extrachromosomal or by chromosomal integrant, are known to the ordinarily skilled artisan, for example, $CaCl_2$, $CaPO_4$, liposome-mediated, polyethylene-gycol/DMSO and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells.

a. Prokaryotic Host Cells

Suitable prokaryotes include but are not limited to archaebacteria and eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, *Rhizobia*, *Vitreoscilla*, *Paracoccus* and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 (Bachmann, *Cellular and Molecular Biology*, vol. 2 (Washington, D.C.: American Society for Microbiology, 1987), pp. 1190-1219; ATCC Deposit No. 27,325) may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT $kan^r$; *E. coli* W3110 strain 37D6, which has the complete genotype tonA ptr3 phoA E15 (argF-lac)169 degP ompT rbs7 ilvG $kan^r$; *E. coli* W3110 strain 40B4, which is strain 37D6 with a non-kanamycin resistant degP deletion mutation; *E. coli* W3110 strain 33D3 having genotype W3110 ΔfhuA (ΔtonA) ptr3 lac Iq lacL8 ΔompTΔ(nmpc-fepE) degP41 $kan^R$ (U.S. Pat. No. 5,639,635) and an *E. coli* strain having mutant periplasmic protease disclosed in U.S. Pat. No. 4,946,783 issued 7 Aug. 1990. Other strains and derivatives thereof, such as *E. coli* 294 (ATCC 31,446), *E. coli* B, *E. coli*$_\lambda$ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

b. Eukaryotic Host Cells

In addition to prokaryotes, eukaryotic microbes such as filamentous fungi or yeast are suitable cloning or expression hosts for anti-CD79b antibody-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula.* A list of specific species that are exemplary of this class of yeasts may be found in C. Anthony, *The Biochemistry of Methylotrophs,* 269 (1982).

Suitable host cells for the expression of glycosylated anti-CD79b antibody are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for anti-CD79b antibody production and cultured in conventional nutrient media modified as appropriate for inducing promoters, selecting transformants, or amplifying the genes encoding the desired sequences.

3. Selection and Use of a Replicable Vector

For recombinant production of an antibody of the invention, the nucleic acid (e.g., cDNA or genomic DNA) encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The CD79b may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-CD79b antibody-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

a. Prokaryotic Host Cells

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides.

In general, plasmid vectors containing replicon and control sequences which are derived from species compatible with the host cell are used in connection with these hosts. Both expression and cloning vectors contain a nucleic acid sequence that enables the vector to replicate in one or more selected host cells, as well as marking sequences which are capable of providing phenotypic selection in transformed cells. Such sequences are well known for a variety of bacteria, yeast, and viruses. The origin of replication from the plasmid pBR322, which contains genes encoding ampicillin (Amp) and tetracycline (Tet) resistance and thus provides easy means for identifying transformed cells, is suitable for most Gram-negative bacteria, the 2µ plasmid origin is suitable for yeast, and various viral origins (SV40, polyoma, adenovirus, VSV or BPV) are useful for cloning vectors in mammalian cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters recognized by a variety of potential host cells are well known. Promoters suitable for use with prokaryotic hosts include the PhoA promoter, the β-galactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776] and hybrid promoters such as the tac [deBoer et al., *Proc. Natl. Acad. Sci. USA,* 80:21-25 (1983)] or the trc promoter. Promoters for use in bacterial systems also will contain a Shine-Dalgarno (S.D.) sequence operably linked to the DNA encoding anti-CD79b antibody. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

b. Eukaryotic Host Cells

The vector components generally include, but are not limited to, one or more of the following: a signal sequence, an origin of replication, one or more marker genes, an enhancer element, a promoter, and a transcription termination sequence.

(1) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(2) Origin of replication

Generally, an origin of replication component is not needed for mammalian expression vectors. For example, the SV40 origin may typically be used only because it contains the early promoter.

(3) Selection Gene Component

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

An example of suitable selectable markers for mammalian cells are those that enable the identification of cells competent to take up the anti-CD79b antibody-encoding nucleic acid, such as DHFR or thymidine kinase, metallothionein-I and -II, preferably primate metallothionein genes, adenosine deaminase, ornithine decarboxylase, etc. An appropriate host cell when wild-type DHFR is employed is the CHO cell line deficient in DHFR activity (e.g., ATCC CRL-9096), prepared and propagated as described by Urlaub et al., Proc. Natl. Acad. Sci. USA, 77:4216 (1980). For example, cells transformed with the DHFR selection gene are first identified by culturing all of the transformants in a culture medium that contains methotrexate (Mtx), a competitive antagonist of DHFR. Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

(4) Promoter Component

Expression and cloning vectors usually contain a promoter operably linked to the anti-CD79b antibody-encoding nucleic acid sequence to direct mRNA synthesis. Promoters recognized by a variety of potential host cells are well known.

Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-CD79b antibody transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(5) Enhancer Element Component

Transcription of a DNA encoding the anti-CD79b antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the anti-CD79b antibody coding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-CD79b antibody. One useful transcription termination component is the bovine growth hormone polyadenylation region. See WO94/11026 and the expression vector disclosed therein.

Still other methods, vectors, and host cells suitable for adaptation to the synthesis of anti-CD79b antibody in recombinant vertebrate cell culture are described in Gething et al., *Nature,* 293:620-625 (1981); Mantei et al., *Nature,* 281:40-46 (1979); EP 117,060; and EP 117,058.

4. Culturing the Host Cells

The host cells used to produce the anti-CD79b antibody of this invention may be cultured in a variety of media.

a. Prokaryotic Host Cells

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

b. Eukaryotic Host Cells

Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102: 255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence CD79b polypeptide or against a synthetic peptide based on the DNA sequences provided herein or against exogenous sequence fused to CD79b DNA and encoding a specific antibody epitope.

6. Purification of Anti-CD79b Antibody

Forms of anti-CD79b antibody may be recovered from culture medium or from host cell lysates. If membrane-bound, it can be released from the membrane using a suitable detergent solution (e.g. Triton-X 100) or by enzymatic cleavage. Cells employed in expression of anti-CD79b antibody can be disrupted by various physical or chemical means, such as freeze-thaw cycling, sonication, mechanical disruption, or cell lysing agents.

It may be desired to purify anti-CD79b antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-CD79b antibody. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular anti-CD79b antibody produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

G. Pharmaceutical Formulations

The antibody-drug conjugates (ADC) of the invention may be administered by any route appropriate to the condition to be treated. The ADC will typically be administered parenterally, i.e. infusion, subcutaneous, intramuscular, intravenous, intradermal, intrathecal and epidural.

For treating these cancers, in one embodiment, the antibody-drug conjugate is administered via intravenous infusion. The dosage administered via infusion is in the range of about 1 $\mu g/m^2$ to about 10,000 $\mu g/m^2$ per dose, generally one dose per week for a total of one, two, three or four doses. Alternatively, the dosage range is of about 1 $\mu g/m^2$ to about 1000 $\mu g/m^2$, about 1 $\mu g/m^2$ to about 800 $\mu g/m^2$, about 1 $\mu g/m^2$ to about 600 $\mu g/m^2$, about 1 $\mu g/m^2$ to about 400 $\mu g/m^2$, about 10 $\mu g/m^2$ to about 500 $\mu g/m^2$, about 10 $\mu g/m^2$ to about 300 $\mu g/m^2$, about 10 $\mu g/m^2$ to about 200 $\mu g/m^2$, and about 1 $\mu g/m^2$ to about 200 $\mu g/m^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until remission of the tumor or symptoms of the lymphoma, leukemia being treated. Administration may continue after remission or relief of symptoms is achieved where such remission or relief is prolonged by such continued administration.

The invention also provides a method of alleviating an autoimmune disease, comprising administering to a patient suffering from the autoimmune disease, a therapeutically effective amount of a humanized MA79b antibody-drug conjugate of any one of the preceding embodiments. In preferred embodiments the antibody is administered intravenously or subcutaneously. The antibody-drug conjugate is administered intravenously at a dosage in the range of about 1 $\mu g/m^2$ to about 100 mg/m$^2$ per dose and in a specific embodiment, the dosage is 1 $\mu g/m^2$ to about 500 $\mu g/m^2$. The dose may be administered once per day, once per week, multiple times per week, but less than once per day, multiple times per month but less than once per day, multiple times per month but less than once per week, once per month or intermittently to relieve or alleviate symptoms of the disease. Administration may continue at any of the disclosed intervals until relief from or alleviation of symptoms of the autoimmune disease being treated. Administration may continue after relief from or alleviation of symptoms is achieved where such alleviation or relief is prolong by such continued administration.

The invention also provides a method of treating a B cell disorder comprising administering to a patient suffering from a B cell disorder, such as a B cell proliferative disorder (including without limitation lymphoma and leukemia) or an autoimmune disease, a therapeutically effective amount of a humanized MA79b antibody of any one of the preceding embodiments, which antibody is not conjugated to a cytotoxic molecule or a detectable molecule. The antibody will typically be administered in a dosage range of about 1 $\mu g/m^2$ to about 1000 mg/m$^2$.

In one aspect, the invention further provides pharmaceutical formulations comprising at least one anti-CD79b antibody of the invention and/or at least one immunoconjugate thereof and/or at least one anti-CD79b antibody-drug conjugate of the invention. In some embodiments, a pharmaceutical formulation comprises (1) an antibody of the invention and/or an immunoconjugate thereof, and (2) a pharmaceutically acceptable carrier. In some embodiments, a pharmaceutical formulation comprises (1) an antibody of the invention and/or an immunoconjugate thereof, and optionally, (2) at least one additional therapeutic agent. Additional therapeutic agents include, but are not limited to, those described below. The ADC will typically be administered parenterally, i.e. infusion, subcutaneous, intramuscular, intravenous, intradermal, intrathecal and epidural.

Therapeutic formulations comprising an anti-CD79b antibody or CD79b immunoconjugate used in accordance with the present invention are prepared for storage by mixing the antibody or immunoconjugate, having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). Pharmaceutical formulations to be used for in vivo administration are generally sterile. This is readily accomplished by filtration through sterile filtration membranes.

The formulations herein may also contain more than one active compound as necessary for the particular indication being treated, preferably those with complementary activities that do not adversely affect each other. For example, in addition to an anti-CD79b antibody, it may be desirable to include in the one formulation, an additional antibody, e.g., a second anti-CD79b antibody which binds a different epitope on the CD79b polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

An antibody may be formulated in any suitable form for delivery to a target cell/tissue. For example, antibodies may be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

The formulations to be used for in vivo administration must be sterile. This is readily accomplished by filtration through sterile filtration membranes.

H. Treatment with Anti-CD79b Antibodies

To determine CD79b expression in the cancer, various detection assays are available. In one embodiment, CD79b polypeptide overexpression may be analyzed by immunohistochemistry (IHC). Parrafin embedded tissue sections from a tumor biopsy may be subjected to the IHC assay and accorded a CD79b protein staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for CD79b polypeptide expression may be characterized as not overexpressing CD79b, whereas those tumors with 2+ or 3+ scores may be characterized as overexpressing CD79b.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of CD79b overexpression in the tumor.

CD79b overexpression or amplification may be evaluated using an in vivo detection assay, e.g., by administering a molecule (such as an antibody) which binds the molecule to be detected and is tagged with a detectable label (e.g., a radioactive isotope or a fluorescent label) and externally scanning the patient for localization of the label.

As described above, the anti-CD79b antibodies of the invention have various non-therapeutic applications. The anti-CD79b antibodies of the present invention can be useful for staging of CD79b polypeptide-expressing cancers (e.g., in radioimaging). The antibodies are also useful for purification or immunoprecipitation of CD79b polypeptide from cells, for detection and quantitation of CD79b polypeptide in vitro, e.g., in an ELISA or a Western blot, to kill and eliminate CD79b-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-CD79b antibody therapy may be especially desirable in elderly patients who do not tolerate the toxicity and side effects of chemotherapy well and in metastatic disease where radiation therapy has limited usefulness. The tumor targeting anti-CD79b antibodies of the invention are useful to alleviate CD79b-expressing cancers upon initial diagnosis of the disease or during relapse. For therapeutic applications, the anti-CD79b antibody can be used alone, or in combination therapy with, e.g., hormones, antiangiogens, or radiolabelled compounds, or with surgery, cryotherapy, and/or radiotherapy. Anti-CD79b antibody treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-CD79b antibody in conjunction with treatment with the one or more of the preceding chemotherapeutic agents. In particular, combination therapy with palictaxel and modified derivatives (see, e.g., EP0600517) is contemplated. The anti-CD79b antibody will be administered with a therapeutically effective dose of the chemotherapeutic agent. In another embodiment, the anti-CD79b antibody is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-CD79b antibody conjugated with a cytotoxic agent is administered to the patient. Preferably, the immunoconjugate bound to the CD79b protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-CD79b antibodies or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Other therapeutic regimens may be combined with the administration of the anti-CD79b antibody. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-CD79b antibody or antibodies, with administration of an antibody directed against another tumor antigen associated with the particular cancer.

In another embodiment, the therapeutic treatment methods of the present invention involves the combined administration of an anti-CD79b antibody (or antibodies), and one or more chemotherapeutic agents or growth inhibitory agents, including co-administration of cocktails of different chemotherapeutic agents, or other cytotoxic agent(s) or other therapeutic agent(s) which also inhibits tumor growth. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-CD79b antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy (e.g. external beam irradiation or therapy with a radioactive labeled agent, such as an antibody), before, simultaneously with, or post antibody therapy. Suitable dosages for any of the above co-administered agents are those presently used and may be lowered due to the combined action (synergy) of the agent and anti-CD79b antibody.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-CD79b antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

The anti-CD79b antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-CD79b antibodies of the invention are also contemplated, specifically including the in vivo tumor targeting and any cell proliferation inhibition or cytotoxic characteristics.

Methods of producing the above antibodies are described in detail herein.

The present anti-CD79b antibodies are useful for treating a CD79b-expressing cancer or alleviating one or more symptoms of the cancer in a mammal. Such a cancer includes, but is not limited to, hematopoietic cancers or blood-related cancers, such as lymphoma, leukemia, myeloma or lymphoid malignancies, but also cancers of the spleen and cancers of the lymph nodes. More particular examples of such B-cell associated cancers, including for example, high, intermediate and low grade lymphomas (including B cell lymphomas such as, for example, mucosa-associated-lymphoid tissue B cell lymphoma and non-Hodgkin's lymphoma, mantle cell lymphoma, Burkitt's lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia, such as B cell leukemia (CD5+ B lymphocytes), myeloid leukemia, such as acute myeloid leukemia, chronic myeloid leukemia, lymphoid leukemia, such as acute lymphoblastic leukemia and myelodysplasia), and other hematological and/or B cell- or T-cell-associated cancers. The cancers encompass metastatic cancers of any of the preceding. The antibody is able to bind to at least a portion of the cancer cells that express CD79b polypeptide in the mammal. In a preferred embodiment, the antibody is effective to destroy or kill CD79b-expressing tumor cells or inhibit the growth of such tumor cells, in vitro or in vivo, upon binding to CD79b polypeptide on the cell. Such an antibody includes a naked anti-CD79b antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-CD79b antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-CD79b antibody of the invention, and a carrier. For the purposes of treating cancer, compositions can be administered to the patient in need of such treatment, wherein the composition can comprise one or more anti-CD79b antibodies present as an immunoconjugate or as the naked antibody. In a further embodiment, the compositions can comprise these antibodies in combination with other therapeutic agents such as cytotoxic or growth inhibitory agents, including chemotherapeutic agents. The invention also provides formulations comprising an anti-CD79b antibody of the invention, and a carrier. In one embodiment, the formulation is a therapeutic formulation comprising a pharmaceutically acceptable carrier.

Another aspect of the invention is isolated nucleic acids encoding the anti-CD79b antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a CD79b polypeptide-expressing cancer or alleviating one or more symptoms of the cancer in a mammal, comprising administering a therapeutically effective amount of an anti-CD79b antibody to the mammal. The antibody therapeutic compositions can be administered short term (acute) or chronic, or intermittent as directed by physician. Also provided are methods of inhibiting the growth of, and killing a CD79b polypeptide-expressing cell.

The invention also provides kits and articles of manufacture comprising at least one anti-CD79b antibody. Kits containing anti-CD79b antibodies find use, e.g., for CD79b cell killing assays, for purification or immunoprecipitation of CD79b polypeptide from cells. For example, for isolation and purification of CD79b, the kit can contain an anti-CD79b antibody coupled to beads (e.g., sepharose beads). Kits can be provided which contain the antibodies for detection and quantitation of CD79b in vitro, e.g., in an ELISA or a Western blot. Such antibody useful for detection may be provided with a label such as a fluorescent or radiolabel.

I. Antibody-Drug Conjugate Treatments

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

The ADC compounds which are identified in the animal models and cell-based assays can be further tested in tumor-bearing higher primates and human clinical trials. Human clinical trials can be designed to test the efficacy of the anti- CD79b monoclonal antibody or immunoconjugate of the invetion in patients experiencing a B cell proliferative disorder including without limitation lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma. The clinical trial may be designed to evaluate the efficacy of an ADC in combinations with known therapeutic regimens, such as radiation and/or chemotherapy involving known chemotherapeutic and/or cytotoxic agents.

Generally, the disease or disorder to be treated is a hyperproliferative disease such as a B cell proliferative disorder and/or a B cell cancer. Examples of cancer to be treated herein include, but are not limited to, B cell proliferative disorder is selected from lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

The cancer may comprise CD79b-expressing cells, such that the ADC of the present invention are able to bind to the cancer cells. To determine CD79b expression in the cancer, various diagnostic/prognostic assays are available. In one embodiment, CD79b overexpression may be analyzed by IHC. Parrafin-embedded tissue sections from a tumor biopsy may be subjected to the IHC assay and accorded a CD79b protein staining intensity criteria with respect to the degree of staining and in what proportion of tumor cells examined.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-ErbB2 antibody. Other dosage regimens may be useful. The progress of this therapy is easily monitored by conventional techniques and assays.

J. Combination Therapy

An antibody-drug conjugate (ADC) of the invention may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an ADC of the invention may also have a therapeutically effective amount of a chemotherapeutic agent such as a tubulin-forming inhibitor, a topoisomerase inhibitor, or a DNA binder.

In one aspect, the first compound is an anti-CD79b ADC of the invention and the second compound is an anti-CD20 antibody (either a naked antibody or an ADC). In one embodiment the second compound is an anti-CD20 antibody rituximab (Rituxan®) or 2H7 (Genentech, Inc., South San Francisco, Calif.). Another antibodies useful for combined immunotherapy with anti-CD79b ADCs of the invention includes without limitation, anti-VEGF (e.g, Avastin®).

Other therapeutic regimens may be combined with the administration of an anticancer agent identified in accordance with this invention, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (Oncovin™), prednisolone, CHOP, CVP, or COP, or immunotherapeutics such as anti-CD20 (e.g., Rituxan®) or anti-VEGF (e.g., Avastin®).

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an ADC involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

K. Articles of Manufacture and Kits

Another embodiment of the invention is an article of manufacture containing materials useful for the treatment, prevention and/or diagnosis of CD79b-expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosing the cancer condition and may have a sterile access port (for example the container may be an intravenous solution bag or a vial having a stopper pierceable by a hypodermic injection needle). At least one active agent in the composition is an anti-CD79b antibody of the invention. The label or package insert indicates that the composition is used for treating cancer. The label or package insert will further comprise instructions for administering the antibody composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for CD79b-expressing cell killing assays, for purification or immunoprecipitation of CD79b polypeptide from cells. For isolation and purification of CD79b polypeptide, the kit can contain an anti-CD79b antibody coupled to beads (e.g., sepharose beads). Kits can be provided which contain the antibodies for detection and quantitation of CD79b polypeptide in vitro, e.g., in an ELISA or a Western blot. As with the article of manufacture, the kit comprises a container and a label or package insert on or associated with the container. The container holds a composition comprising at least one anti-CD79b antibody of the invention. Additional containers may be included that contain, e.g., diluents and buffers, control antibodies. The label or package insert may provide a description of the composition as well as instructions for the intended in vitro or detection use.

L. Uses for CD79b Polypeptides

This invention encompasses methods of screening compounds to identify those that mimic the CD79b polypeptide (agonists) or prevent the effect of the CD79b polypeptide (antagonists). Screening assays for antagonist drug candidates are designed to identify compounds that bind or complex with the CD79b polypeptides encoded by the genes identified herein, or otherwise interfere with the interaction of the encoded polypeptides with other cellular proteins, including e.g., inhibiting the expression of CD79b polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a CD79b polypeptide encoded by a nucleic acid identified herein under conditions and for a time sufficient to allow these two components to interact.

In binding assays, the interaction is binding and the complex formed can be isolated or detected in the reaction mixture. In a particular embodiment, the CD79b polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the CD79b polypeptide and drying. Alternatively, an immobilized antibody, e.g., a monoclonal antibody, specific for the CD79b polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular CD79b polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a CD79b polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the CD79b polypeptide may be added to a cell along with the compound to be screened for a particular activity and the ability of the compound to inhibit the activity of interest in the presence of the CD79b polypeptide indicates that the compound is an antagonist to the CD79b polypeptide. Alternatively, antagonists may be detected by combining the CD79b polypeptide and a potential antagonist with membrane-bound CD79b polypeptide receptors or recombinant receptors under appropriate conditions for a competitive inhibition assay. The CD79b polypeptide can be labeled, such as by radioactivity, such that the number of CD79b polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Current Protocols in Immun., 1(2): Chapter 5 (1991). Preferably, expression cloning is employed wherein polyadenylated RNA is prepared from a cell responsive to the CD79b polypeptide and a cDNA library created from this RNA is divided into pools and used to transfect COS cells or other cells that are not responsive to the CD79b polypeptide. Transfected cells that are grown on glass slides are exposed to labeled CD79b polypeptide. The CD79b polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled CD79b polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled CD79b polypeptide in the presence of the candidate compound. The ability of the compound to enhance or block this interaction could then be measured.

More specific examples of potential antagonists include an oligonucleotide that binds to the fusions of immunoglobulin with CD79b polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the CD79b polypeptide that recognizes the receptor but imparts no effect, thereby competitively inhibiting the action of the CD79b polypeptide.

Antibodies specifically binding a CD79b polypeptide identified herein, as well as other molecules identified by the screening assays disclosed hereinbefore, can be administered for the treatment of various disorders, including cancer, in the form of pharmaceutical compositions.

If the CD79b polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

M. Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

N. Method of Screening

Yet another embodiment of the present invention is directed to a method of determining the presence of a CD79b polypeptide in a sample suspected of containing the CD79b polypeptide, wherein the method comprises exposing the sample to an antibody drug conjugate thereof, that binds to the CD79b polypeptide and determining binding of the antibody drug conjugate thereof, to the CD79b polypeptide in the sample, wherein the presence of such binding is indicative of the presence of the CD79b polypeptide in the sample. Optionally, the sample may contain cells (which may be cancer cells) suspected of expressing the CD79b polypeptide. The antibody drug conjugate thereof, employed in the method may optionally be detectably labeled, attached to a solid support, or the like.

Another embodiment of the present invention is directed to a method of diagnosing the presence of a tumor in a mammal, wherein the method comprises (a) contacting a test sample comprising tissue cells obtained from the mammal with an antibody drug conjugate thereof, that binds to a CD79b polypeptide and (b) detecting the formation of a complex between the antibody drug conjugate thereof, and the CD79b polypeptide in the test sample, wherein the formation of a complex is indicative of the presence of a tumor in the mammal. Optionally, the antibody drug conjugate thereof, is detectably labeled, attached to a solid support, or the like, and/or the test sample of tissue cells is obtained from an individual suspected of having a cancerous tumor.

IV. Further Methods of Using Anti-CD79b Antibodies and Immunoconjugates

A. Diagnostic Methods and Methods of Detection

In one aspect, anti-CD79b antibodies and immunoconjugates of the invention are useful for detecting the presence of CD79b in a biological sample. The term "detecting" as used herein encompasses quantitative or qualitative detection. In certain embodiments, a biological sample comprises a cell or tissue. In certain embodiments, such tissues include normal and/or cancerous tissues that express CD79b at higher levels relative to other tissues, for example, B cells and/or B cell associated tissues.

In one aspect, the invention provides a method of detecting the presence of CD79b in a biological sample. In certain embodiments, the method comprises contacting the biological sample with an anti-CD79b antibody under conditions permissive for binding of the anti-CD79b antibody to CD79b, and detecting whether a complex is formed between the anti-CD79b antibody and CD79b.

In one aspect, the invention provides a method of diagnosing a disorder associated with increased expression of CD79b. In certain embodiments, the method comprises contacting a test cell with an anti-CD79b antibody; determining the level of expression (either quantitatively or qualitatively) of CD79b by the test cell by detecting binding of the anti-CD79b antibody to CD79b; and comparing the level of expression of CD79b by the test cell with the level of expression of CD79b by a control cell (e.g., a normal cell of the same tissue origin as the test cell or a cell that expresses CD79b at levels comparable to such a normal cell), wherein a higher level of expression of CD79b by the test cell as compared to the control cell indicates the presence of a disorder associated with increased expression of CD79b. In certain embodiments, the test cell is obtained from an individual suspected of having a disorder associated with increased expression of CD79b. In certain embodiments, the disorder is a cell proliferative disorder, such as a cancer or a tumor.

Exemplary cell proliferative disorders that may be diagnosed using an antibody of the invention include a B cell disorder and/or a B cell proliferative disorder including, but not limited to, lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In certain embodiments, a method of diagnosis or detection, such as those described above, comprises detecting binding of an anti-CD79b antibody to CD79b expressed on the surface of a cell or in a membrane preparation obtained from a cell expressing CD79b on its surface. In certain embodiments, the method comprises contacting a cell with an anti-CD79b antibody under conditions permissive for binding of the anti-CD79b antibody to CD79b, and detecting whether a complex is formed between the anti-CD79b antibody and CD79b on the cell surface. An exemplary assay for detecting binding of an anti-CD79b antibody to CD79b expressed on the surface of a cell is a "FACS" assay.

Certain other methods can be used to detect binding of anti-CD79b antibodies to CD79b. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-CD79b antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, (3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, anti-CD79b antibodies are immobilized on an insoluble matrix. Immobilization entails separating the anti-CD79b antibody from any CD79b that remains free in solution. This conventionally is accomplished by either insolubilizing the anti-CD79b antibody before the assay procedure, as by adsorption to a water-insoluble matrix or surface (Bennich et al., U.S. Pat. No. 3,720,760), or by covalent coupling (for example, using glutaraldehyde crosslinking), or by insolubilizing the anti-CD79b antibody after formation of a complex between the anti-CD79b antibody and CD79b, e.g., by immunoprecipitation.

Any of the above embodiments of diagnosis or detection may be carried out using an immunoconjugate of the invention in place of or in addition to an anti-CD79b antibody.

B. Therapeutic Methods

An antibody or immunoconjugate of the invention may be used in, for example, in vitro, ex vivo, and in vivo therapeutic methods. In one aspect, the invention provides methods for inhibiting cell growth or proliferation, either in vivo or in vitro, the method comprising exposing a cell to an anti-CD79b antibody or immunoconjugate thereof under conditions permissive for binding of the immunoconjugate to CD79b. "Inhibiting cell growth or proliferation" means decreasing a cell's growth or proliferation by at least 10%, 20%, 30%, 40%, 50%, 60%, 70%, 80%, 90%, 95%, or 100%, and includes inducing cell death. In certain embodiments, the cell is a tumor cell. In certain embodiments, the cell is a B cell. In certain embodiments, the cell is a xenograft, e.g., as exemplified herein.

In one aspect, an antibody or immunoconjugate of the invention is used to treat or prevent a B cell proliferative disorder. In certain embodiments, the cell proliferative disorder is associated with increased expression and/or activity of CD79b. For example, in certain embodiments, the B cell proliferative disorder is associated with increased expression of CD79b on the surface of a B cell. In certain embodiments, the B cell proliferative disorder is a tumor or a cancer. Examples of B cell proliferative disorders to be treated by the antibodies or immunoconjugates of the invention include, but are not limited to, lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one aspect, the invention provides methods for treating a B cell proliferative disorder comprising administering to an individual an effective amount of an anti-CD79b antibody or immunoconjugate thereof. In certain embodiments, a method for treating a B cell proliferative disorder comprises administering to an individual an effective amount of a pharmaceutical formulation comprising an anti-CD79b antibody or anti-CD79b immunoconjugate and, optionally, at least one additional therapeutic agent, such as those provided below. In certain embodiments, a method for treating a cell proliferative disorder comprises administering to an individual an effective amount of a pharmaceutical formulation comprising 1) an immunoconjugate comprising an anti-CD79b antibody and a cytotoxic agent; and optionally, 2) at least one additional therapeutic agent, such as those provided below.

In one aspect, at least some of the antibodies or immunoconjugates of the invention can bind CD79b from species other than human. Accordingly, antibodies or immunoconjugates of the invention can be used to bind CD79b, e.g., in a cell culture containing CD79b, in humans, or in other mammals having a CD79b with which an antibody or immunoconjugate of the invention cross-reacts (e g chimpanzee, baboon, marmoset, cynomolgus and rhesus monkeys, pig or mouse). In one embodiment, an anti-CD79b antibody or immunoconjugate can be used for targeting CD79b on B cells by contacting the antibody or immunoconjugate with CD79b to form an antibody or immunoconjugate-antigen complex such that a conjugated cytotoxin of the immunoconjugate accesses the interior of the cell. In one embodiment, the CD79b is human CD79b.

In one embodiment, an anti-CD79b antibody or immunoconjugate can be used in a method for binding CD79b in an individual suffering from a disorder associated with increased CD79b expression and/or activity, the method comprising administering to the individual the antibody or immunoconjugate such that CD79b in the individual is bound. In one embodiment, the bound antibody or immunoconjugate is internalized into the B cell expressing CD79b. In one embodiment, the CD79b is human CD79b, and the individual is a human individual. Alternatively, the individual can be a mammal expressing CD79b to which an anti-CD79b antibody binds. Still further the individual can be a mammal into which CD79b has been introduced (e.g., by administration of CD79b or by expression of a transgene encoding CD79b).

An anti-CD79b antibody or immunoconjugate can be administered to a human for therapeutic purposes. Moreover, an anti-CD79b antibody or immunoconjugate can be administered to a non-human mammal expressing CD79b with which the antibody cross-reacts (e.g., a primate, pig, rat, or mouse) for veterinary purposes or as an animal model of human disease. Regarding the latter, such animal models may be useful for evaluating the therapeutic efficacy of antibodies or immunoconjugates of the invention (e.g., testing of dosages and time courses of administration).

Antibodies or immunoconjugates of the invention can be used either alone or in combination with other compositions in a therapy. For instance, an antibody or immunoconjugate of the invention may be co-administered with at least one additional therapeutic agent and/or adjuvant. In certain embodiments, an additional therapeutic agent is a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (Oncovin™), prednisolone, CHOP, CVP, or COP, or immunotherapeutics such as anti-CD20 (e.g., Rituxan®) or anti-VEGF (e.g., Avastin®), wherein the combination therapy is useful in the treatment of cancers and/or B cell disorders such as B cell proliferative disorders including lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody or immunoconjugate is suitably administered by pulse infusion, particularly with declining doses of the antibody or immunoconjugate. Dosing can be by any suitable route, e.g. by injections, such as intravenous or subcutaneous injections, depending in part on whether the administration is brief or chronic.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents, such as chemotherapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 mg/kg to 100 mg/kg (e.g. 0.1 mg/kg-20 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) of antibody or immunoconjugate may be administered to the patient. Such doses may be administered intermittently, e.g. every week or every three weeks (e.g. such that the patient receives from about two to about twenty, or e.g. about six doses of the antibody or immunoconjugate). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

C. Activity Assays

Anti-CD79b antibodies and immunoconjugates of the invention may be characterized for their physical/chemical properties and/or biological activities by various assays known in the art.

1. Activity assays

In one aspect, assays are provided for identifying anti-CD79b antibodies or immunoconjugates thereof having biological activity. Biological activity may include, e.g., the ability to inhibit cell growth or proliferation (e.g., "cell killing" activity), or the ability to induce cell death, including programmed cell death (apoptosis). Antibodies or immunoconjugates having such biological activity in vivo and/or in vitro are also provided.

In certain embodiments, an anti-CD79b antibody or immunoconjugate thereof is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol Meth. 160:81-88, U.S. Pat. No. 6,602,677. The assay may be conducted in 96- or 384-well format, making it amenable to automated high-throughput screening (HTS). See Cree et al (1995) AntiCancer Drugs 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) J. Immunol. Meth. 65:55-63, and Zhang et al. (2005) Cancer Res. 65:3877-3882.

In one aspect, an anti-CD79b antibody is tested for its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) Cytotechnology, 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. Cells are seeded at a density of $3 \times 10^6$ per dish in 100×20 mm dishes and allowed to attach overnight. The medium is removed and replaced with fresh medium alone or medium containing various concentrations of the antibody or immunoconjugate. The cells are incubated for a 3-day time period. Following treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 µg/ml). Samples are analyzed using a FACSCAN™ flow cytometer and FACSCONVERT™ CellQuest software (Becton Dickinson). Antibodies or immunoconjugates which induce statistically significant levels of cell death as determined by PI uptake are thus identified.

In one aspect, an anti-CD79b antibody or immunoconjugate is tested for its ability to induce apoptosis (programmed cell death) in vitro. An exemplary assay for antibodies or immunconjugates that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 µg/ml of the antibody or immunoconjugate. Following a three-day incubation period, monolayers are washed with PBS and detached by trypsinization. Cells are then centrifuged, resuspended in $Ca^{2+}$ binding buffer, and aliquoted into tubes as discussed in the preceding paragraph. Tubes then receive labeled annexin (e.g. annexin V-FITC) (1 µg/ml). Samples are analyzed using a FACSCAN™ flow cytometer and FACSCONVERT™ CellQuest software (BD Biosciences). Antibodies or immunoconjugates that induce statistically significant levels of annexin binding relative to control are thus identified. Another exemplary assay for antibodies or immunconjugates that induce apoptosis is a histone DNA ELISA colorimetric assay for detecting internucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express CD79b or that have been engineered to express CD79b. Such cells include tumor cells that overexpress CD79b relative to normal cells of the same tissue origin. Such cells also include cell lines (including tumor cell lines) that express CD79b and cell lines that do not normally express CD79b but have been transfected with nucleic acid encoding CD79b.

In one aspect, an anti-CD79b antibody or immunoconjugate thereof is tested for its ability to inhibit cell growth or proliferation in vivo. In certain embodiments, an anti-CD79b antibody or immunoconjugate thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., a SCID mouse. An antibody or immunoconjugate of the invention is administered to the animal. The ability of the antibody or immunoconjugate to inhibit or decrease tumor growth is measured. In certain embodiments of the above xenograft system, the human tumor cells are tumor cells from a human patient. Such cells useful for preparing xenograft models include human leukemia and lymphoma cell lines, which include without limitation the BJAB-luc cells (an EBV-negative Burkitt's lymphoma cell line transfected with the luciferase reporter gene), Ramos cells (ATCC, Manassas, Va., CRL-1923), SuDHL-4 cells (DSMZ, Braunschweig, Germany, AAC 495), DoHH2 cells (see Kluin-Neilemans, H. C. et al., Leukemia 5:221-224 (1991), and Kluin-Neilemans, H. C. et al., Leukemia 8:1385-1391 (1994)), Granta-519 cells (see Jadayel, D. M. et al, Leukemia 11(1):64-72 (1997)). In certain embodiments, the human tumor cells are introduced into a suitably immunocompromised non-human animal by subcutaneous injection or by transplantation into a suitable site, such as a mammary fat pad.

2. Binding Assays and Other Assays

In one aspect, an anti-CD79b antibody is tested for its antigen binding activity. For example, in certain embodiments, an anti-CD79b antibody is tested for its ability to bind to CD79b expressed on the surface of a cell. A FACS assay may be used for such testing.

In one aspect, competition assays may be used to identify a monoclonal antibody that competes with murine MA79b antibody, humanized MA79b.v17 antibody and/or humanized MA79b.v18 and/or humanized MA79b.v28 and/or humanized MA79b.v32 antibody for binding to CD79b. In certain embodiments, such a competing antibody binds to the same epitope (e.g., a linear or a conformational epitope) that is bound by murine MA79b antibody, humanized MA79bv.17 antibody and/or humanized MA79b.v18 antibody and/or humanized MA79b.v28 and/or humanized MA79b.v32. Exemplary competition assays include, but are not limited to, routine assays such as those provided in Harlow and Lane (1988) Antibodies: A Laboratory Manual ch.14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In an exemplary competition assay, immobilized CD79b is incubated in a solution comprising a first labeled antibody that binds to CD79b (e.g., murine MA79b antibody, humanized MA79b.v17 antibody and/or humanized MA79b.v18 antibody and/or humanized MA79b.v28 and/or humanized MA79b.v32) and a second unlabeled antibody that is being tested for its ability to compete with the first antibody for binding to CD79b. The second antibody may be present in a hybridoma supernatant. As a control, immobilized CD79b is incubated in a solution comprising the first labeled antibody but not the second unlabeled antibody. After incubation under conditions permissive for binding of the first antibody to CD79b, excess unbound antibody is removed, and the amount of label associated with immobilized CD79b is measured. If the amount of label associated with immobilized CD79b is substantially reduced in the test sample relative to the control sample, then that indicates that the second antibody is competing with the first antibody for binding to CD79b. In certain embodiments, immobilized CD79b is present on the surface of a cell or in a membrane preparation obtained from a cell expressing CD79b on its surface.

In one aspect, purified anti-CD79b antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In one embodiment, the invention contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). Clq binding assays may also be carried out to confirm that the antibody is unable to bind Clq and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. Antibodies used in the examples include commercially available antibodies and include, but are not limited to, anti-CD79b (antibody purchased from Biomeda (Foster City, Calif.) or BDbioscience (San Diego, Calif.) or Ancell (Bayport, Minn.)), anti-CD79b (generated from hybridomas deposited with the ATCC as HB11413 on Jul. 20, 1993), and chimeric anti-CD79b antibodies (comprising variable domains from antibodies generated from hybridomas deposited with the ATCC as HB11413 on Jul. 20, 1993). The source of those cells identified in the following examples, and throughout the specification, by ATCC accession numbers, is the American Type Culture Collection, Manassas, Va.

Example 1

Generation of Humanized Anti-CD79b Antibody

Residue numbers are according to Kabat (Kabat et al., *Sequences of proteins of immunological interest*, 5th Ed., Public Health Service, National Institutes of Health, Bethesda, Md. (1991)). Single letter amino acid abbreviations are used. DNA degeneracies are represented using the IUB code (N=A/C/G/T, D=A/G/T, V=A/C/G, B=C/G/T, H=A/C/T, K=G/T, M=A/C, R=A/G, S=G/C, W=A/T, Y=C/T).

A. Humanized Anti-CD79b Antibody Graft

Various humanized anti-CD79b antibodies were generated. The VL and VH domains from murine MA79b antibody (MA79b) (Roswell Park Cancer Institute; Okazaki et al., *Blood*, 81:84-94 (1993)) were aligned with the human consensus VL kappa I (huKI) and human subgroup III consensus VH (huIII) domains. To make the HVR graft, the acceptor VH framework, which differs from the human subgroup III consensus VH domain at 3 positions: R71A, N73T, and L78A (Carter et al., Proc. Natl. Acad. Sci. USA 89:4285 (1992)) was used. Hypervariable regions from murine MA79b (MA79b) were engineered into the acceptor human consensus framework to generate a direct HVR-graft of MA79b (herein referred to as "MA79b graft" or "MA79b-graft" or "MA79b-grafted 'humanized' antibody" or "huMA79b-graft"). In the VL domain the following regions were grafted to the human consensus acceptor: positions 24-34 (L1), 50-56 (L2) and 89-97 (L3) (FIGS. 7A-B). In the VH domain, positions 26-35 (H1), 49-65 (H2) and 93-102 (H3) were grafted (FIGS. 8A-B). MacCallum et al. (MacCallum et al., *J. Mol. Biol.*, 262: 732-745 (1996)) analyzed antibody and antigen complex crystal structures and found positions 49, 93 and 94 of the heavy chain are part of the contact region and are thus included in the definition of HVR-H2 and HVR-H3 when humanizing antibodies.

The direct-graft variant (huMA79b-graft) was generated by Kunkel mutagenesis, as both the Fab displayed on phage and as an IgG, using a separate oligonucleotide for each hypervariable region. Correct clones were assessed by DNA sequencing.

B. Humanized Anti-CD79b Antibody Graft Variants

Anti-CD79b antibody graft variants which included mutational diversity in the hypervariable regions of the MA79b-grafted "humanized" antibody were generated using phage libraries. The anti-CD79b antibody graft variants included either a single position variation in the HVRs (FIG. 9) or multiple position variations in the HVRs (FIG. 10).

C. Phage Selection

For phage selection, the extracellular domain of CD79b (huCD79b$_{ecd}$) (2 µg/ml) was immobilized in PBS on MaxiSorp microtiter plates (Nunc) overnight at 4° C. Plates were blocked for at least 1 h using Casein Blocker (Pierce). Phage were harvested from the culture supernatant and suspended in PBS containing 0.5% BSA and 0.05% Tween 20 (PBSBT). Following addition of the phage library and phage selection for 2 h, microtiter wells were washed extensively with PBS containing 0.05% Tween 20 (PBST) to remove unbound phage and bound phage were eluted by incubating the wells with 100 mM HCl for 30 min. Selection stringency may be increased during successive rounds of selection by increasing the number of washes with PBST or by incubating with soluble huCD79b$_{ecd}$ for increasing time periods prior to elution.

Eluted phage were neutralized with 1 M Tris, pH 8 and amplified using XL1-Blue cells and M13/KO7 helper phage and grown overnight at 37° C. in 2YT, 50 µg/ml carbenacillin. The titers of phage eluted from a target containing well were compared to titers of phage recovered from a non-target containing well to assess enrichment.

D. Fab Production and IgG Production

To express Fab protein for affinity measurements, a stop codon was introduced between the heavy chain and g3 in the phage display vector. Clones were transformed into *E. coli* 34B8 cells and grown in Complete C.R.A.P. media at 30° C. (Presta et al. *Cancer Res.* 57: 4593-4599 (1997)). Cells were harvested by centrifugation, suspended in PBS, 100 µM PMSF, 100 µM benzamidine, 2.4 mM EDTA and broken open using a microfluidizer. Fab was purified with Protein G affinity chromatography.

For screening purposes, IgG variants were initially produced in 293 cells. Vectors coding for VL and VH (25 µg) were transfected into 293 cells using the FuGene system. 500 µl of FuGene was mixed with 4.5 ml of DMEM media containing no FBS and incubated at room temperature for 5 min. Each chain (25 µg) was added to this mixture and incubated at room temperature for 20 min and then transferred to a flask for transfection overnight at 37° C. in 5% $CO_2$. The following day the media containing the transfection mixture was removed and replaced with 23 ml PS04 media with 0.1 ml/L trace elements (A0934) and 10 mg/L insulin (A0940). Cells were incubated for an additional 5 days after which the media was harvested at 1000 rpm for 5 min and sterile filtered using a 0.22 µm low protein-binding filter. Samples could be stored at 4° C. after addition of 2.5 ml 0.1% PMSF for every 125 ml of media.

E. Affinity Determination (Biacore Analysis)

For affinity determination of the MA79b-grafted "humanized" antibody variants, the extracellular domain of human CD79b (huCD79b$_{ecd}$) was expressed in CHO cells alone or as a Fc fusion (huCD79b$_{ecd}$-Fc) and purified by conventional means. In addition, a 16 amino acid peptide (ARSEDRYRNPKGSACK) (SEQ ID NO: 16) containing the epitope for MA79b was synthesized by conventional means.

Characterization of the epitope for MA79b antibody (labeled as "test peptide" in FIG. 19) was previously disclosed in U.S. application Ser. No. 11/462,336, filed Aug. 3, 2006, US 2007/0207142, now abandoned. The epitope for MA79b was located in the extracellular peptide region distal to the transmembrane domain and was present in the full-length and truncated forms of human CD79b (Cragg, *Blood*, 100(9): 3068-76 (2002)), which have been described in normal and malignant B cells (Hashimoto, S. et al., *Mol. Immunol.*, 32(9): 651-9 (1995); Alfarano et al., *Blood*, 93(7): 2327-35 (1999)). The truncated form of CD79b lacks the entire extracellular Ig-like domain (the extracellular Ig-like domain that is not present in the spliced truncated form of CD79b is boxed in FIG. 19).

Binding of Fab and IgG variants of MA79b, the MA79b-grafted "humanized" antibody or MA79b-grafted "humanized" antibody variants to immobilized huCD79b$_{ecd}$ or huCD79b-Fc or the 16 amino acid peptide containing the epitope for MA79b was measured by surface plasma resonance. Affinity determinations were performed by surface plasmon resonance using a BIAcore™-2000. The antigen, huCD79b$_{ecd}$ or huCD79b-Fc was immobilized (approximately 50-200 RU) in 10 mM sodium acetate pH 4.8 on a CM5 sensor chip. Due to a large avidity effect, affinity measurements were sensitive to the amount of huCD79b$_{ecd}$ immobilized. For this reason, affinities, determined for samples run on different days, were normalized to MA79b that was run along side as a standard. In experiments that measured binding to the 16 amino acid peptide containing the epitope for MA79b (ARSEDRYRNPKGSACK) (SEQ ID NO: 16), the biotinylated peptide was captured (approximately 20 RU) on a streptavidin coated sensor chip. Purified MA79b-grafted "humanized" antibody variant (as Fab or IgG) (a 2-fold serial dilution of 0.5 to 1000 nM in PBST) was injected at a flow rate of 30 μL/min. Each sample was analyzed with 4-minute association and 10-minute disassociation. After each injection the chip was regenerated using 10 mM Glycine pH 1.7.

Binding response was corrected by subtracting a control flow cell from MA79b-grafted "humanized" antibody variant (as Fab or IgG) flow cells. A 1:1 Languir model of simultaneous fitting of k$_{on}$ and k$_{off}$ was used for kinetics analysis.

F. Binding Analysis (FACS Analysis)

To further determine binding of the Fab variants of MA79b-grafted "humanized" antibody or antibody variants, binding of Fab and/or IgG variants to DoHH-2 cells were analyzed using FACS analysis. Further, binding of MA79b-grafted "humanized" antibody variants to BJAB-luciferase cells was analyzed using FACS analysis.

For FACS analysis of Fab variants of MA79b-grafted "humanized" antibody variants (MA79b-grafted "humanized" antibody (IgG version used as a control)), DoHH-2 cells (1×10$^6$ in 100 μl volume) were first incubated with or without 1 μg of original mouse anti-CD79b monoclonal antibody (MA79b) for 30 minutes, before adding 1 μg of individual Fab variant (or control antibody). PE conjugated mouse anti-human Ig, kappa light chain (clone G20-193, BD Biosciences, San Diego, Calif.) was used as the secondary detecting antibody, since all the Fab variants bear kappa light chain and DoHH-2 cells do not express kappa light chain on the cell surface.

For additional FACS analysis of IgG variants of MA79b-grafted "humanized" antibody variants (IgG version of chMA79b used as a control), 1.0 μg, 0.1 μg or 0.01 μg of antibody was titrated per million cells of BJAB-luciferase cells. PE conjugated mouse anti-human Ig was used as the secondary detecting antibody.

G. Affinity Determination (Scatchard Analysis)

To further determine binding of the IgG variants having changes in HVR-L2 and HVR-H3 (huMA79b L2/H3), binding of iodinated IgG variants to BJAB cells expressing human CD79b and cynomologous CD79b was analyzed and Scatchard analysis was performed.

For Scatchard analysis, 0.5 nM I$^{125}$ labeled MA79b or huMA79b L2/H3 was competed against unlabeled MA79b or huMA79b L2/H3, respectively, ranging from 50 to 0.02 nM (12 step 1:2 serial dilution) in the presence of a transfected BJAB line stably expressing cynomologous-CD79b and endogenous human-CD79b. After a four hour incubation at 4° C., cells were washed and cell pellet counts were read by a gamma counter (1470 WIZARD Automatic Gamma Counter; Perkin Elmer, Walthem, Mass.). All points were done in triplicate and counted for 10 minutes. The average CPM was used for Kd calculation using the New Ligand (Genentech, South San Francisco, Calif.) program.

Results and Discussion

A. Results of Generation of Humanized anti-CD79b Antibody

The human acceptor framework used for the generation of humanized anti-CD79b antibody comprises the consensus human kappa I VL domain and a variant of the human subgroup III consensus VH domain. The variant VH domain has 3 changes from the human consensus: R71A, N73T and L78A. The VL and VH domains of MA79b were aligned with the human kappa I and subgroup III domains; each HVR was identified and then grafted into the human acceptor framework to generate a HVR graft that could be displayed as a Fab on phage (FIGS. 7 and 8).

Phage displaying the MA79b-graft as a Fab bound to immobilized huCD79b$_{ecd}$ (data not shown). However, when the huMA79b-graft sequence was expressed as an IgG, FACS analysis of its affinity for huCD79b$_{ecd}$ indicated that binding affinity had been reduced by over 100-fold (data not shown) and Biacore analysis indicated a loss of over 50-fold (FIG. 11).

1. CDR Repair

MA79b-grafted "humanized" antibody variants that were able to bind to immobilized huCD79b$_{ecd}$ with the following sequence changes were identified.

Only sequence changes targeting HVRs in VL were observed in the libraries containing single position changes and are shown in FIG. 9 (for L1 mutations: Q27K (SEQ ID NO: 17; SPL-2 mutation), (for L2 mutations: L54R (SEQ ID NO: 18), E55K (SEQ ID NO: 19)), and (for L3 mutations: E93S (SEQ ID NO: 20; SPL-5 mutation), E93K (SEQ ID NO: 21)).

Only sequence changes targetting HVRs in L2, L3, H1 and H3 were observed in the libraries containing multiple position changes and are shown in FIG. 10 (for L2 mutations: S52R, N53K, E55G and S56R (SEQ ID NO: 22; L2-2 mutation); N53R (SEQ ID NO: 23); S52R, N53K, E55G and S56N (SEQ ID NO: 24); S52R, N53K, E55K and S56R (SEQ ID NO: 25); S52R, N53Y, E55K and S56R (SEQ ID NO: 26; L2-29 mutation); S52R, N53K and E55K (SEQ ID NO: 27); S52R, N53K and E55A (SEQ ID NO: 28); S52G, N53I, E55A and S56R (SEQ ID NO: 29); S52R, N53K, E55R (SEQ ID NO: 30); S52R, N53K and E55G (SEQ ID NO: 31; L2-38 mutation); S52R, N53H, E55K and S56R (SEQ ID NO: 32); A51S, S52R, N53Y, E55S and S56R (SEQ ID NO: 33); A51G, N53K, E55L and S56R (SEQ ID NO: 34); L54R and E55K (SEQ ID NO: 35); N53K and E55G (SEQ ID NO: 36); S52R, N53Y, E55R and S56R (SEQ ID NO: 37); S52R, N53R, E55R and S56T (SEQ ID NO: 38); S52R, N53R, E55G and S56R (SEQ ID NO: 39); S52R, N53Q, L54R, E55K and S56R (SEQ ID NO: 40); S52R, N53K, E55L and S56R (SEQ ID NO: 41); S52R, N53K, E55K and S56N (SEQ ID NO: 42); S52R, N53K, E55G and S56T (SEQ ID NO: 43); S52R, N53K, E55G and S56G (SEQ ID NO: 44); and S52R, N53K, E55A and S56R (SEQ ID NO: 45)), (for L3 mutations: E93A (SEQ ID NO: 46); E93Q (SEQ ID NO: 47); no mutation (SEQ ID NO: 48); E93D (SEQ ID NO: 49); E93L (SEQ ID NO: 50); Q89N, Q90N, E93G and T97N (SEQ ID NO: 51); Q90P, S91D, D94A and L96R (SEQ ID NO: 52); Q89D, S91R and E93A (SEQ ID NO: 53)), (for H1 mutations: T28P, S30T, S31R and E35S (SEQ ID NO: 54); T28P, S30R and E35Q (SEQ ID NO: 55); T28P, S30T and E35N (SEQ ID NO: 56); T28P, S30T, S31R and E36N (SEQ ID NO: 57; H1-6 mutation)); S30N, S31R and E35N (SEQ ID NO: 58); T28S and S30K (SEQ ID NO: 59); G26P, T28S, F29L, S30C, S31T, W33F and E35D (SEQ ID NO: 60); T28Y and S30T (SEQ ID NO: 61); T28P, S30G, S31R, I34V and E35N (SEQ ID NO: 62); S30K and S31K (SEQ ID NO: 63); T28P, S30T and E35Q (SEQ ID NO: 64); T28P, S30R and S31R (SEQ ID NO: 65); T28P, F29V, S30G, S31R and E35S (SEQ ID NO: 66); T28P, S30N, S31R and E35N (SEQ ID NO: 67; H1-1 mutation); T28G, S30T and E35S (SEQ ID NO: 68); S30T, I34L and E35S (SEQ ID NO: 69); S30T (SEQ ID NO: 70); S31G and E35N (SEQ ID NO: 71); S30R, S31R and E35N (SEQ ID NO: 72); T28S, S30R and E35N (SEQ ID NO: 73); T28S, S30R, S31R and E35N (SEQ ID NO: 74); T28S, S30R and S31R (SEQ ID NO: 75); T28S, S30P, I34L and E35Q (SEQ ID NO: 76); T28P, S30T and S31R (SEQ ID NO: 77); T28P and S31G (SEQ ID NO: 78); T28P, S30R and E35S (SEQ ID NO: 79); T28P, S30R and E35N (SEQ ID NO: 80); T28P, S30R and S31G (SEQ ID NO: 81); T28P, S30N and S31R (SEQ ID NO: 82); T28P, S30N, S31G and E35N (SEQ ID NO: 83); T28N, F29V, I34L and E35S (SEQ ID NO: 84); Y27F, T28P, S30T and E35S (SEQ ID NO: 85); and Y27F, T28P, S30N, S31R and E35N (SEQ ID NO: 86)) and (for H3 mutations: V98I and F100L (SEQ ID NO: 87; H3-12 mutation); no mutation (SEQ ID NO: 88); Y99K and F100L (SEQ ID NO: 89); F100L (SEQ ID NO: 90); V98I (SEQ ID NO: 91); V98F, Y99C and F100L (SEQ ID NO: 92); F100L (SEQ ID NO: 93); V98I, Y99R and F100L (SEQ ID NO: 94; H3-10 mutation); V98I, Y99K and F100L (SEQ ID NO: 95); V98I and Y99R (SEQ ID NO: 96); V98I (SEQ ID NO: 97); D101S (SEQ ID NO: 98); Y99V and F100L (SEQ ID NO: 99); Y99R and F100L (SEQ ID NO: 100); Y99R (SEQ ID NO: 101); Y99F and F100L (SEQ ID NO: 102); V98I and F100L (SEQ ID NO: 103); V98I (SEQ ID NO: 104); V96R, Y99C and F100L (SEQ ID NO: 105); and V96I (SEQ ID NO: 106)).

Select clones were reformatted as Fab for analysis by FACS and as IgG for further analysis by Biacore and Scatchard.

a. Affinity Determination (Biacore Analysis)

As shown in FIG. 11, showing Biacore analysis, this CDR-repair approach identified many individual sequence changes that improve the affinity of the MA79b-grafted "humanized" antibody. The surface plasmon resonance assays showed that although none of the tested variants with single HVR changes had an affinity similar to MA79b, the combination of changes identified in HVR-L2 and HVR-H3 (MA79b-grafted "humanized" antibody variant L2/H3; also referred to herein as huMA79b L2/H3) led to a variant with similar affinity (FIG. 11) as MA79b when binding to immobilized huCD79b$_{ecd}$ or huCD79b$_{ecd}$-Fc or the 16 amino acid peptide containing the epitope for MA79b as determined by Biacore analysis.

Analysis of monomeric binding (Fab) versus dimeric binding (IgG) of MA79b to antigen (huCD79b$_{ecd}$-Fc) (FIG. 11, row 1, compare Fab to IgG columns) suggested that a 100-fold avidity component present in MA79b may be lacking in the affinity improved variants. Specifically, in the MA79b-grafted "humanized" antibody variant L2-2 (also referred herein to as huMA79b L2-2) which demonstrates a 5-fold improvement in monomeric binding compared to MA79b (FIG. 11, rows 1 and 3, compare Fab columns), no apparent affinity is gained upon reformatting huMA79b L2-2 as an IgG) (FIG. 11, row 4, compare Fab to IgG columns). In addition, the initial MA79b HVR grafted-"humanized" antibody (huMA79b graft) demonstrates the loss of this avidity component in binding (FIG. 11, row 2, compare Fab to IgG columns). The ability to enhance binding through avidity may be desirable in binding cell surface antigens.

b. Affinity Determination (Scatchard Analysis)

As assessed by Scatchard analysis, this CDR-repair approach identified many individual sequence changes that improved the affinity of the MA79b-grafted "humanized" antibody. Specifically, the cell binding assays showed that the affinity of MA79b and MA79b-grafted "humanized" antibody variant L2/H3 (huMA79b L2/H3) (reformatted as IgG) for binding BJAB cells stably expressing cynomologous CD79b and endogenous human CD79b was with Kd values of 0.63 nM (MA79b; Kd=0.63±0.14 nM) and 0.52 nM (huMA79b L2/H3; Kd=0.52±0.1 nM), respectively (data not shown), as determined by Scatchard analysis.

c. Binding Determination (FACS Analysis)

As assessed by FACS analysis, this CDR-repair approach identified many individual sequence changes that improved the binding of the MA79b-grafted "humanized" antibody (huMA79b graft) to DoHH-2 cells (data not shown). Specifically, FACS analysis of Fab variants (L2-2, H3-10 and H1-1 mutations) identified from the SP and 6 SR libraries to DoHH-2 cells showed binding of the Fab variants and huMA79b graft (formatted as an IgG) to DoHH-2 cells (data not shown). Further, FACS analysis of the Fab variants showed that binding of the Fab variants to DoHH-2 cells was blocked by pre-incubation with murine anti-CD79b monoclonal antibody (MA79b) (data not shown).

2. Framework Repair

HVR sequence changes introduced into HVR-L2 of the huMA79b L2/H3 variant were radically different from those observed in any human germline. The huMA79b L2/H3 variant, when conjugated to DM1, was observed to be effective at inhibiting tumor growth in an in vivo mouse xenograft model (Table 9). Since analysis of monomeric binding (Fab) versus dimeric binding (IgG) of huMA79b L2/H3 variant to antigen showed a loss of avidity (FIG. 11), framework repair was performed as described below.

To explore the role of framework positions in dimeric antigen binding, an "all framework" positions variant was constructed in which potentially important murine framework positions were incorporated into the MA79b HVR-grafted "humanized" antibody (huMA79b graft). This variant (referred to in FIG. 12 as "all framework"), lacking any HVR changes, possessed similar dimeric binding affinity to chimeric MA79b antibody (chMA79b) (FIG. 12) as assessed by Biacore Analysis and Scatchard analysis.

IgG variants, including murine framework residues at positions 4 and/or 47 (VL) and/or positions 47, 48, 67, 69, 71, 73, 74, 78 and/or 80 (VH) were generated to determine the minimum set of framework positions needed to maintain high affinity, dimeric binding (FIG. 12). Murine framework residues are shown in FIGS. 7A-B (SEQ ID NO: 10) and FIGS. 8A-B (SEQ ID NO: 14). Framework positions 47 in VL, and 75 and 80 in VH were found dispensable as evidenced by MA79b-grafted "humanized" antibody variant 17 (huMA79b.v17) (FIG. 12, row labeled as 17).

MA79b-grafted "humanized" antibody variant 18 (MA79b.v18; FIG. 12, row labeled as 18), which includes murine framework residues at positions 4 in VL, and 48, 67, 69, 71, 73 and 78 in VH and further includes changes in HVR-H3 (referred to in FIG. 12 as "H3-10" and described above as H3-10 mutation), including V98I, Y99R and F100L, showed an additional 2-fold improvement (FIG. 12, row labeled as 28) in dimeric binding when compared to variant 17 (FIG. 12, row labeled as 17).

To avoid potential manufacturing issues, a potential iso-aspartic acid forming site (Asp-Gly) in HVR-L1 of the MA79b-grafted "humanized" antibody variants was eliminated by converting D28 to Glu (glutamic acid) (D28E; see variant 28; also referred to herein as "huMA79b.v28"; FIG. 12, row labeled as 28). Other substitutions for stability in VL of the MA79b-grafted "humanized" antibody variants were also tolerated including D28 to Ser (serine) (D28E; see variant 32; also referred to herein as "huMA79b.v32"; FIG. 12, row labeled as 32).

MA79b-grafted "humanized" antibody variant 28 (huMA79b.v28; FIG. 12, row labeled as 28), which includes: (1) murine framework residues at positions 4 in VL, and 48, 67, 69, 71, 73 and 78 in VH, (2) further includes changes in HVR-H3 (referred to in FIG. 12 as "H3-10" and described above as H3-10 mutation), including V98I, Y99R and F100L, and (3) even further includes changes in HVR-L1 (D28E, described above) were characterized via Biacore analysis.

MA79b-grafted "humanized" antibody variant 32 (MA79b.v32; FIG. 12, row labeled as 32), which includes: (1) murine framework residues at positions 4 in VL, and 48, 67, 69, 71, 73 and 78 in VH, (2) further includes changes in HVR-H3 (referred to in FIG. 12 as "H3-10" and described above as H3-10 mutation), including V98I, Y99R and F100L, and (3) even further includes changes in HVR-L1 (D28S, described above) were characterized via Biacore analysis.

a. Affinity Determination (Biacore Analysis)

As shown in FIG. 12, showing Biacore analysis, this framework-repair approach identified many individual sequence changes that improve affinity of the MA79b-grafted "humanized" antibody to huCD79b$_{ecd}$. The surface plasmon resonance assays showed that a MA79b-grafted "humanized" antibody variant 28 (huMA79b.v28; with murine framework positions 4 in VL, 48, 67, 69, 71, 73 and 78 in VH, as well as the H3-10 mutation in HVR-H3 (V98I, Y99R and F100L (also described above) and a D28E mutation in HVR-L1 (for stability, see description above); FIG. 12, row labeled as 28) and a MA79b-grafted "humanized" antibody variant (huMA79b.v32; with murine framework positions 4 in VL, 47, 48, 67, 69, 71, 73 and 78 in VH, as well as the H3-10 mutation in HVR-H3 (V98I, Y99R and F100L (also described above) and a D28S mutation in HVR-L1 (for stability, see description below); FIG. 12, row labeled as 32) had affinity equivalent to chimeric MA79b antibody (chMA79b) when binding to immobilized huCD79b$_{ecd}$ as determined by Biacore analysis.

b. Affinity Determination (Scatchard Analysis)

As assessed by Scatchard analysis, similar to the Biacore analysis, this framework-repair approach identified many individual sequence changes that improve the affinity of the MA79b-grafted "humanized" antibody (huMA79b graft). The cell binding assays showed that the affinity of MA79b, MA79b-grafted "humanized" antibody variant 28 (huMA79b.v28; see FIG. 12, row labeled as 28) (reformatted as IgG), and MA79b-grafted "humanized" antibody variant 32 (huMA79b.v32; see FIG. 12, row labeled as 32) for binding BJAB cells stably expressing cynomologous CD79b and endogenous human CD79b was with Kd values of 0.63 nM (MA79b; Kd=0.63±0.14 nM), 0.44 nM (huMA79b.v28; Kd=0.44±0.04 nM), and 0.24 nM (huMA79b.v32; Kd=0.24±0.02 nM), respectively (data not shown), as determined by Scatchard analysis.

c. Binding Determination (FACS Analysis)

As assessed by FACS analysis, this framework-repair approach identified many individual sequence changes that improve the binding of the MA79b-grafted "humanized" antibody (huMA79b graft) to BJAB-luciferase cells (data not shown). Specifically, FACS analysis of IgG variants of MA79b-grafted "humanized" antibody variants (variants huMA79b.v28 and huMA79b.v32) to BJAB-luciferase cells showed binding to BJAB-luciferase cells (data not shown).

B. Discussion of Generation of Humanized Anti-CD79b Antibodies

Starting from a graft of the 6 murine MA79b HVRs (defined as positions 24-34 (L1), 50-56 (L2), 89-97 (L3), 26-35 (H1), 49-65 (H2) and 93-102 (H3)) into the human consensus Kappa I VL and subgroup III VH (containing A71, T73 and A78), CDR repair was used to identify changes in HVRs 1-6 that improve binding affinity. HVR sequence changes identified in FIGS. 10 and 11 or combinations of these changes led to humanized variants of MA79b with affinities similar to MA79b.

Alternatively, framework repair was used to recapture dimeric binding avidity by the addition of framework positions 4 in VL, and 48, 67, and 69 in VH to the huMA79b graft (which includes murine framework residues at 71, 73 and 78 of VH) (FIG. 12; MA79b-grafted "humanized" antibody variant 17 (huMA79b.v17)). The affinity of these framework mutation variants for huCD79b$_{ecd}$ antigen was further enhanced by the addition of 3 changes in HVR-H3: V98I, Y99R and F100L (FIG. 12; MA79b-grafted "humanized" antibody variant 18 (huMA79b.v18)). A potential iso-aspartic acid forming site in HVR-L1 was eliminated with a D28E mutation (FIG. 12; MA79b-grafted "humanized" antibody variant 28 (huMA79b.v28)).

Example 2

Generation of Anti-CD79b Antibody Drug Conjugates (ADCs)

To test the efficacy of IgG variants of MA79b-grafted "humanized" antibody variants, the MA79b-grafted "humanized" antibody variants were conjugated to drugs, such as DM1. The variants conjugated to DM1 included the variants having changes in HVR-L2 and HVR-H3 (huMA79b L2/H3), huMA79b.v17, huMA79b.v18, huMA79b.v28 and huMA79b.v32.

The drugs used for generation of antibody drug conjugates (ADCs) for anti-CD79b antibodies included maytansinoid DM1 and dolastatin10 derivatives monmethylauristatin E (MMAE) and monomethylauristatin F (MMAF). (US 2005/0276812, now abandoned; US 2005/0238649, now U.S. Pat. No. 7,498,298, granted Mar. 3, 2009; Doronina et al., *Bioconjug. Chem.*, 17:114-123 (2006); Doronina et al., *Nat. Biotechnol.*, 21: 778-784 (2003); Erickson et al., *Cancer Res.*, 66: 4426-4433 (2006), all of which are herein incorporated by reference in their entirety). Linkers useful for generation of the ADCs are BMPEO, SPP or SMCC (also referred to herein as "MCC") for DM1 and MC or MC-vc-PAB for MMAE and MMAF. For DM1, the antibodies were linked to the thio group of DM1 and through the -amino group of lysine using the linker reagent SMCC. Alternatively, for DM1, the antibodies were linked to DM1 through the e-amino group of lysine using the SPP linker. SPP(N-succinimidyl 4-(2'-pyridldithio) pentanoate) reacts with the epsilon amino group of lysines to leave a reactive 2-pyridyl disulfide linker on the protein. With SPP linkers, upon reaction with a free sulfhydral (e.g. DM1), the pyridyl group is displaced, leaving the DM1 attached via a reducible disulfide bond. DM1 attached via a SPP linker is released under reducing conditions (i.e., for example, within cells) while DM1 attached via the SMCC linker is resistant to cleavage in reducing conditions. Further, SMCC-DM1 ADCs induce cell toxicity if the ADC is internalized and targeted to the lysosome causing the release of lysine-N-DM1, which is an effective anti-mitotic agent inside the cell, and when released from the cell, lysine-N-DM1 is non-toxic (Erickson et al., *Cancer Res.*, 66: 4426-4433

(2006)) For MMAE and MMAF, the antibodies were linked to MMAE or MMAF through the cysteine by maleeimidocaproyl-valine-citruline (vc)-p-aminobenzyloxycarbonyl (MC-vc-PAB). For MMAF, the antibodies were alternatively linked to MMAF through the cysteine by maleeimidocaproyl (MC) linker. The MC-vc-PAB linker is cleavable by intercellular proteases such as cathepsin B and when cleaved, releases free drug (Doronina et al., *Nat. Biotechnol.*, 21: 778-784 (2003)) while the MC linker is resistant to cleavage by intracellular proteases.

Antibody drug conjugates (ADCs) for anti-CD79b, using SMCC and DM1, were generated similar to the procedure described in US 2005/0276812, now abandoned. Anti-CD79b purified antibodies were buffer-exchanged into a solution containing 50 mM potassium phosphate and 2 mM EDTA, pH 7.0. SMCC (Pierce Biotechnology, Rockford, Ill.) was dissolved in dimethylacetamide (DMA) and added to the antibody solution to make a final SMCC/Ab molar ratio of 10:1. The reaction was allowed to proceed for three hours at room temperature with mixing. The SMCC-modified antibody was subsequently purified on a GE Healthcare HiTrap desalting column (G-25) equilibrated in 35 mM sodium citrate with 150 mM NaCl and 2 mM EDTA, pH 6.0. DM1, dissolved in DMA, was added to the SMCC antibody preparation to give a molar ratio of DM1 to antibody of 10:1. The reaction was allowed to proceed for 4-20 hrs at room temperature with mixing. The DM1-modified antibody solution was diafiltered with 20 volumes of PBS to remove unreacted DM1, sterile filtered, and stored at 4 degrees C. Typically, a 40-60% yield of antibody was achieved through this process. The preparation was usually >95% monomeric as assessed by gel filtration and laser light scattering. Since DM1 has an absorption maximum at 252 nm, the amount of drug bound to the antibody could be determined by differential absorption measurements at 252 and 280 nm. Typically, the drug to antibody ratio was 3 to 4.

Antibody drug conjugates (ADCs) for anti-CD79b antibodies described herein using SPP-DM1 linkers may be generated similar to the procedure described in US 2005/0276812, now abandoned. Anti-CD79b purified antibodies are buffer-exchanged into a solution containing 50 mM potassium phosphate and 2 mM EDTA, pH 7.0 SPP (Immunogen) was dissolved in DMA and added to the antibody solution to make a final SPP/Ab molar ratio of approximately 10:1, the exact ratio depending upon the desired drug loading of the antibody. A 10:1 ratio will usually result in a drug to antibody ratio of approximately 3-4. The SPP is allowed to react for 3-4 hours at room temperature with mixing. The SPP-modified antibody is subsequently purified on a GE Healthcare HiTrap desalting column (G-25) equilibrated in 35 mM sodium citrate with 150 mM NaCl and 2 mM EDTA, pH 6.0 or phosphate buffered saline, pH 7.4. DM1 is dissolved in DMA and added to the SPP antibody preparation to give a molar ratio of DM1 to antibody of 10:1, which results in a 3-4 fold molar excess over the available SPP linkers on the antibody. The reaction with DM1 is allowed to proceed for 4-20 hrs at room temperature with mixing. The DM1-modified antibody solution is diafiltered with 20 volumes of PBS to remove unreacted DM1, sterile filtered, and stored at 4 degrees C. Typically, yields of antibody of 40-60% or greater are achieved with this process. The antibody-drug conjugate is usually >95% monomeric as assessed by gel filtration and laser light scattering. The amount of bound drug is determined by differential absorption measurements at 252 and 280 nm as described for the preparation of SMCC-DM1 conjugates (described above).

Antibody drug conjugates (ADC) for anti-CD79b antibodies described herein using MC-MMAF, MC-MMAE, MC-val-cit (vc)-PAB-MMAE or MC-val-cit (vc)-PAB-MMAF drug linkers may also be generated similar to the procedure described in US 2005/0238649, now U.S. Pat. No. 7,498,298, granted Mar. 3, 2009. Purified anti-CD79b antibody is dissolved in 500 mM sodium borate and 500 mM sodium chloride at pH 8.0 and further treated with an excess of 100 MM dithiothreitol (DTT). After incubation at 37 degrees C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody is dissolved in PBS was chilled on ice. The drug linker, for example, MC-val-cit (vc)-PAB-MMAE, in DMSO, is dissolved in acetonitrile and water, and added to the chilled reduced antibody in PBS. After an hour incubation, an excess of maleimide is added to quench the reaction and cap any unreacted antibody thiol groups. The reaction mixture is concentrated by centrifugal ultrafiltration and the antibody drug conjugate, is purified and desalted by elution through G25 resin in PBS, filtered through 0.2 m filters under sterile conditions, and frozen for storage.

Antibody drug conjugates (using anti-CD79b antibodies described herein) were diluted at 2×10 g/ml in assay medium. Conjugates were linked with crosslinkers SMCC (alternative disulfide linker may be used for SPP to maytansinoid DM1 toxin) (See US 2005/0276812, now abandoned and US 2005/0238649, now U.S. Pat. No. 7,498,298, Granted Mar. 3, 2009). Further, conjugates may be linked with MC-valine-citrulline (vc)-PAB or MC to dolastatin1 0 derivatives, monomethylauristatin E (MMAE) toxin or monomethylauristatin F (MMAF) toxin (See U.S. application Ser. Nos. 11/141,344, filed May 31, 2005, now abandoned, and U.S. application Ser. No. 10/983,340, filed Nov. 5, 2004, now U.S. Pat. No. 7,498,298, granted Mar. 3, 2009). Negative controls included HERCEPTIN® (trastuzumab) (anti-HER2) based conjugates (SMCC-DM1 or SPP-DM1 or MC-vc-MMAE or MC-vc-MMAF). Positive controls may include free L-DM1 equivalent to the conjugate loading dose. Samples were vortexed to ensure homogenous mixture prior to dilution.

Anti-CD79b antibodies for drug conjugation included chimeric MA79b antibodies (chMA79b) and huMA79b L2/H3 antibody variant and huMA79b.v17, huMA79b.v18, huMA79b.v28 and huMA79b.v32 described herein (see Example 1). Further antibodies for conjugation may include any antibodies described herein (see Example 1).

Example 3

In Vivo Tumor Cell Killing Assay

A. Xenografts

To test the efficacy of IgG variants of MA79b-grafted "humanized" antibody variants having changes in HVR-L2 and HVR-H3 (huMA79b L2/H3), the huMA79b L2/H3 variant was conjugated to DM1 and the effect of the conjugated variant on tumors in mice were analyzed.

Specifically, the ability of the antibodies to regress tumors in multiple xenograft models, including RAMOS cells, BJAB cells (Burkitt's lymphoma cell line that contain the t(2;8) (p112;q24) (IGK-MYC) translocation, a mutated p53 gene and are Epstein-Barr virus (EBV) negative) (Drexler, H. G., The Leukemia-Lymphoma Cell Line Facts Book, San Diego: Academic Press, 2001)), Granta 519 cells (mantle cell lymphoma cell line that contains the t(11;14)(q13;q32) (BCL1-IGH) translocation that results in the over-expression of cyclin D1 (BCL1), contains P16INK4B and P16INK4A deletions and are EBV positive) (Drexler, H. G., *The Leukemia-Lymphoma Cell Line Facts Book*, San Diego: Academic Press, 2001)), U698M cells (lymphoblastic lymphosarcoma B cell line; (Drexler, H. G., *The Leukemia-Lymphoma Cell Line Facts Book*, San Diego: Academic Press, 2001) and DoHH2 cells (follicular lymphoma cell line that contains the translocation characteristic of follicular lymphoma t(14;18)(q32;q21) that results in the over-expression of Bc1-2 driven by the Ig heavy chain, contains the P16INK4A deletion, contains the t(8;14)(q24;q32) (IGH-MYC) translocation and are EBV negative) (Drexler, H. G., *The Leukemia-Lymphoma Cell Line Facts Book*, San Diego: Academic Press, 2001)), may be examined.

For analysis of efficacy of MA79b-grafted "humanized" antibody variants, female CB17 ICR SCID mice (6-8 weeks of age from Charles Rivers Laboratories; Hollister, Calif.) were inoculated subcutaneously with $2 \times 10^7$ BJAB-luciferase cells or Granta-519 cells via injection into the flanks of CB17 ICR SCID mice and the xenograft tumors were allowed to grow to an average of 200 mm$^2$. Day 0 refers to the day the tumors were an average of 200 mm$^2$ and when the first/or only dose of treatment was administered, unless indicated specifically below. Tumor volume was calculated based on two dimensions, measured using calipers, and was expressed in mm$^3$ according to the formula: $V=0.5a \times b^2$, where a and b are the long and the short diameters of the tumor, respectively. Data collected from each experimental group were expressed as mean±SE. Groups of 10 mice were treated with a single intravenous (i.v.) dose of between 50 µg and 210 µg of antibody-linked drug/m$^2$ mouse (corresponding to ~1-4 mg/kg of mouse) with MA79b-grafted "humanized" antibody variants or control antibody-drug conjugates. Tumors were measured either once or twice a week throughout the experiment. Body weights of mice were measured either once or twice a week throughout the experiment. Mice were euthanized before tumor volumes reached 3000 mm$^3$ or when tumors showed signs of impending ulceration. All animal protocols were approved by an Institutional Animal Care and Use Committee (IACUC).

Linkers between the antibody and the toxin that were used were thioether crosslinker SMCC for DM1. Additional linkers may include disulfide linker SPP or thioether crosslinker SMCC for DM1 or MC or MC-valine-citrulline(vc)-PAB or (a valine-citrulline (vc)) dipeptide linker reagent) having a maleimide component and a para-aminobenzylcarbamoyl (PAB) self-immolative component for monomethylauristatin E (MMAE) or monomethylauristan F (MMAF). Toxins used were DM1. Additional toxins may include MMAE or MMAF.

CD79b antibodies for this experiment included chimeric MA79b (chMA79b) antibodies as described in U.S. application Ser. No. 11/462,336, filed Aug. 3, 2006, now abandoned, as well as MA79b-grafted "humanized" antibody variants described herein (see Example 1A). Additional antibodies may include commercially available antibodies, including anti-CD79b antibody, and MA79b monoclonal antibodies generated from hybridomas deposited with the ATCC as HB11413 on Jul. 20, 1993.

Negative controls included anti-HER2 (HERCEPTIN® (trastuzumab)) based conjugates (SMCC-DM1).

B. Results

1. BJAB-Luciferase Xenografts

Figure 20:
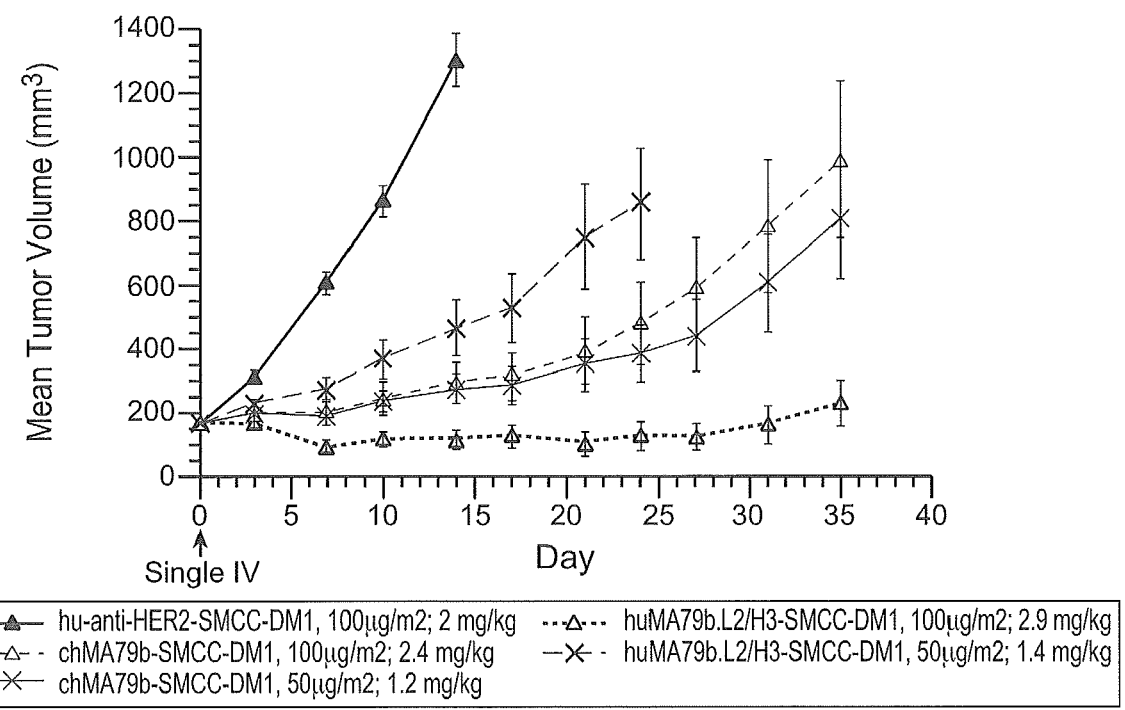
FIG. 20 is a graph of inhibition of in vivo tumor growth in a BJAB-luciferase xenograft model which shows that administration of anti-CD79b antibodies ((a) chMA79b-SMCC-DM1, drug load was approximately 2.9 (Table 9) and (b) huMA79b L2/H3-SMCC-DM1, drug load was approximately 2.4 (Table 9)) to SCID mice having human B cell tumors significantly inhibited tumor growth. Controls included Herceptin® (trastuzumab)-SMCC-DM1 (anti-HER2-SMCC-DM1).

In a 35 day time course with drug conjugates and doses as shown in Table 9, MA79b-grafted "humanized" antibody variant L2/H3 (huMA79b L2/H3 variant) (reformatted as IgG) and chimeric anti-CD79b antibody (chMA79b) conjugated to DM1 (huMA79b L2/H3-SMCC-DM1 and chMA79b-SMCC-DM1, respectively), showed inhibition of tumor growth in SCID mice with BJAB-luciferase tumors compared to negative control, HERCEPTIN® (trastuzumab)-SMCC-DM1 (anti-HER2-SMCC-DM1). ADCs were administered in a single dose (as indicated in Table 9) at day 0 for all ADCs and controls. Specifically, the huMA79b L2/H3-SMCC-DM1 antibodies (reformatted as IgG) and chMA79b-SMCC-DM1 significantly inhibited tumor growth (FIG. 20). Further, in Table 9, the number of mice out of the total number of mice tested showing PR=Partial Regression (where the tumor volume at any time after administration dropped below 50% of the tumor volume measured at day 0) or CR=Complete Remission (where the tumor volume at any time after administration dropped to 0 mm$^3$) are indicated.

TABLE 9

| Antibody administered (Treatment) | PR | CR | Dose Drug - DM1 (µg/m$^2$) | Dose Ab (mg/kg) | Drug ratio (Drug/Ab) |
|---|---|---|---|---|---|
| Control anti-HER2-SMCC-DM1 | 0/10 | 0/10 | 100 | 2 | 3.3 |
| chMA79b-SMCC-DM1 | 3/10 | 3/10 | 100 | 2.4 | 2.9 |
| chMA79b-SMCC-DM1 | 1/10 | 0/10 | 50 | 1.2 | 2.9 |
| huMA79b L2/H3-SMCC-DM1 | 2/10 | 0/10 | 100 | 2.9 | 2.4 |
| huMA79b L2/H3-SMCC-DM1 | 0/10 | 0/10 | 50 | 1.4 | 2.4 |

2. Granta-519 Xenografts

Figure 21A:
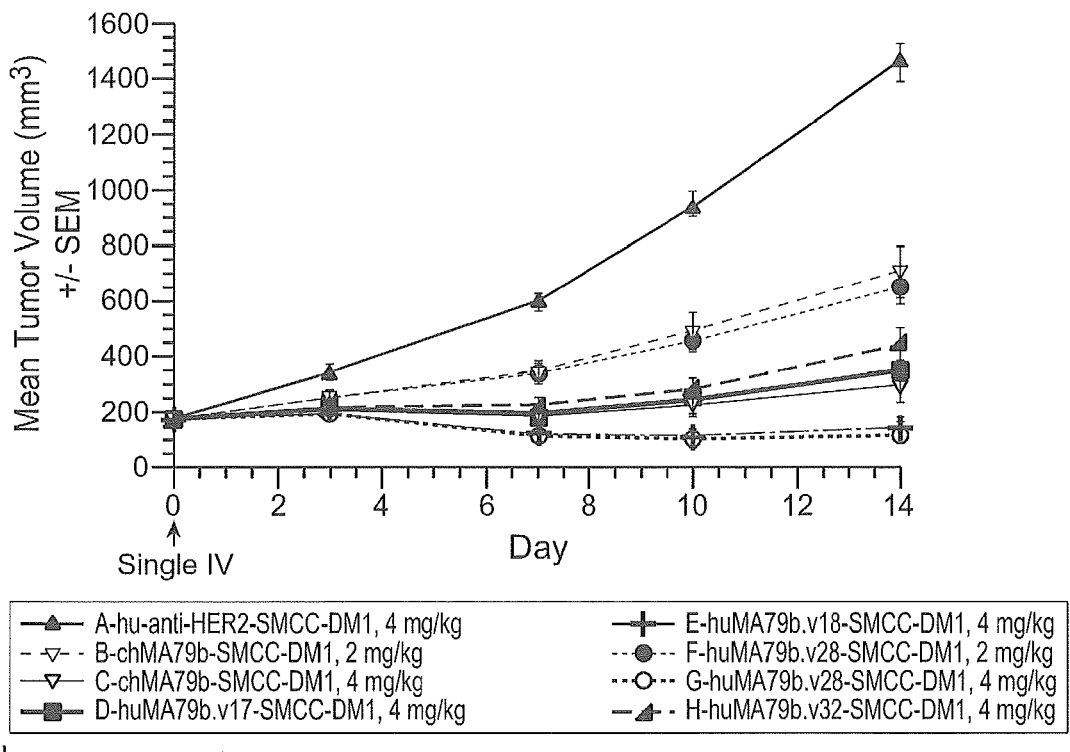
FIG. 21A is a graph of inhibition of in vivo tumor growth in a Granta-519 (Human Mantle Cell Lymphoma) xenograft model which shows that administration of anti-CD79b antibodies ((a) chMA79b-SMCC-DM1, drug load was approximately 3.6 (Table 10), (b) huMA79b.v17-SMCC-DM1, drug load was approximately 3.4 (Table 10), (c) huMA79b.v28-SMCC-DM1, drug load was approximately 3.3 or 3.4 (Table 10), (d) huMA79b.v18-SMCC-DM1, drug load was approximately 3.4 (Table 10) and (e) huMA79b.v32-SMCC-DM1, drug load was approximately 2.9 (Table 10)) to SCID mice having human B cell tumors significantly inhibited tumor growth. Controls included Herceptin® (trastuzumab)-SMCC-DM1 (anti-HER2-SMCC-DM1).

In a 14 day time course with drug conjugates and doses as shown in Table 10, MA79b-grafted "humanized" antibody variant 17, variant 18, variant 28 and variant 32 (huMA79b.v17, huMA79b.v18, huMA79b.v28 and huMA79b.v32, respectively) (reformatted as IgG) and chimeric anti-CD79b antibody (chMA79b) conjugated to DM1 (huMA79b.v17-SMCC-DM1, huMA79b.v18-SMCC-DM1, huMA79b.v28-SMCC-DM1, huMA79b.v32-SMCC-DM1 and chMA79b-SMCC-DM1, respectively), showed inhibition of tumor growth in SCID mice with Granta-519 tumors compared to negative control, HERCEPTIN® (trastuzumab)-SMCC-DM1 (anti-HER2-SMCC-DM1). ADCs were administered in a single dose (as indicated in Table 10) at day 0 for all ADCs and controls. Specifically, the huMA79b.v28-SMCC-DM1, huMA79b.v32-SMCC-DM1, huMA79b.v17-SMCC-DM1 and huMA79b.v18-SMCC-DM1 antibodies (reformatted as IgG) and chMA79b-SMCC-DM1 significantly inhibited tumor growth (FIG. 21A).

Figure 21B:
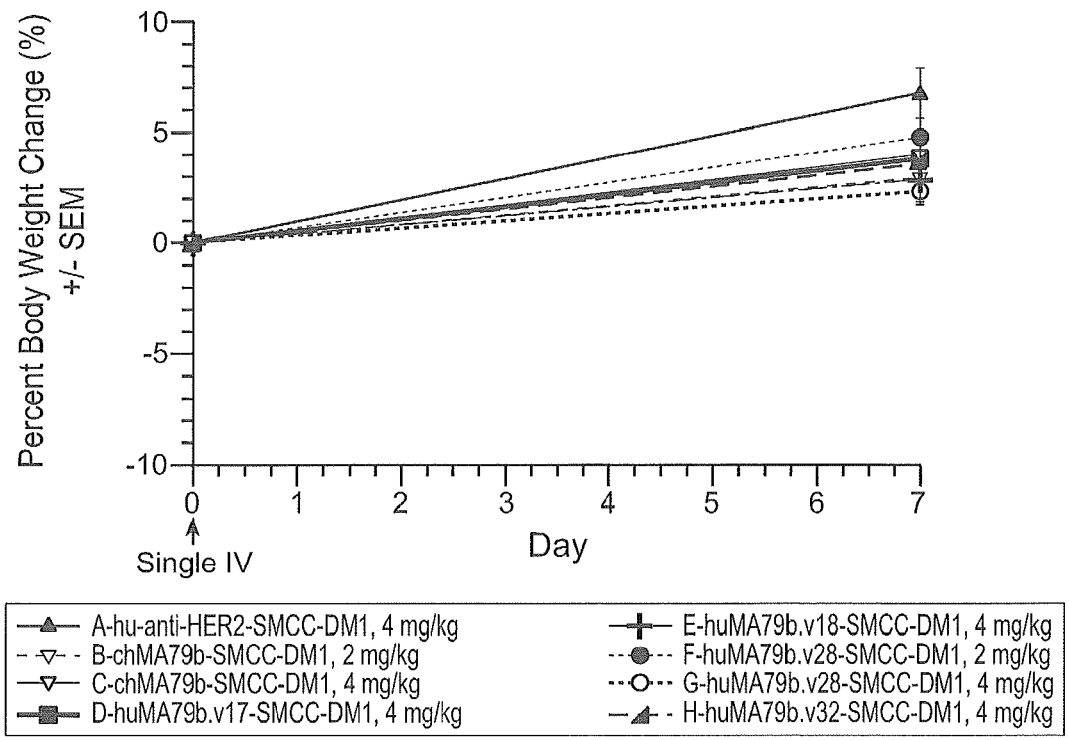
FIG. 21B is a plot of percent weight change in the mice from the Granta-519 xenograft study (FIG. 21A and Table 10) showing that there was no significant change in weight during the first 7 days of the study. "hu" refers to humanized antibody and "ch" refers to chimeric antibody.
Figure 22:
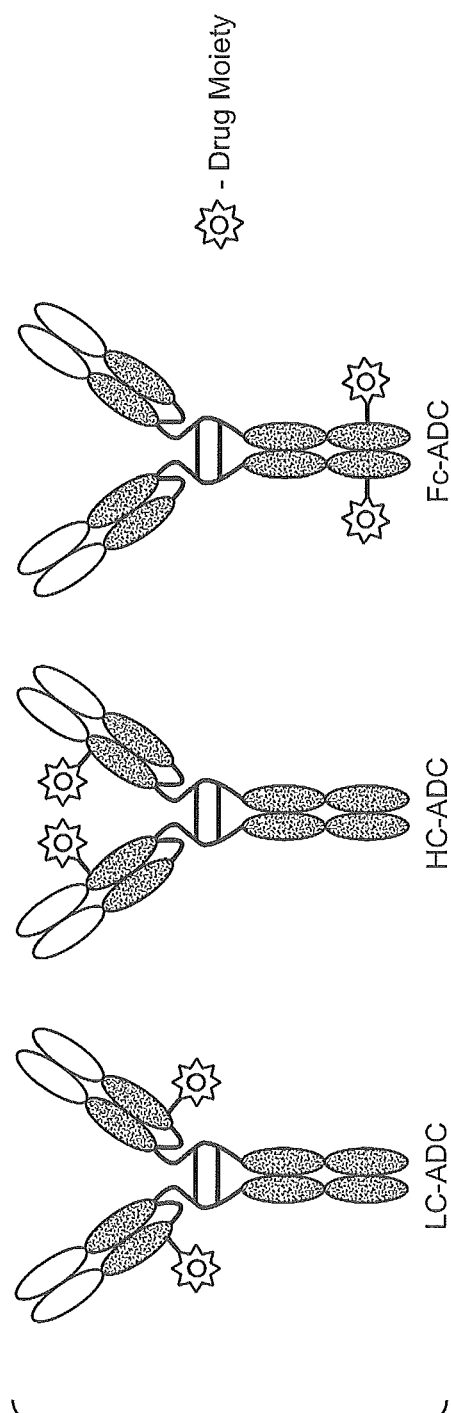
FIG. 22 shows depictions of cysteine engineered anti-CD79b antibody drug conjugates (ADC) where a drug moiety is attached to an engineered cysteine group in: the light chain (LC-ADC); the heavy chain (HC-ADC); and the Fc region (Fc-ADC).

Further, treatment with huMA79b.v28-SMCC-DM1, huMA79b.v32-SMCC-DM1, huMA79b.v17-SMCC-DM1, huMA79b.v18-SMCC-DM1 and chMA79b-SMCC-DM1 and control HERCEPTIN® (trastuzumab)-SMCC-DM1 (anti-HER2-SMCC-DM1) did not result in a decrease in percent body weight of the mice (FIG. 21B). Even further, in Table 10, the number of mice out of the total number of ten mice tested showing PR=Partial Regression (where the tumor volume at any time after administration dropped below 50% of the tumor volume measured at day 0) or CR=Complete Remission (where the tumor volume at any time after administration dropped to 0 mm$^3$) are indicated.

TABLE 10

| Antibody administered (Treatment) | PR | CR | Dose Drug - DM1 (μg/m²) | Dose Ab (mg/kg) | Drug ratio (Drug/Ab) |
|---|---|---|---|---|---|
| Control anti-HER2-SMCC-DM1 | 0/10 | 0/10 | 208 | 4 | 3.4 |
| chMA79b-SMCC-DM1 | 0/10 | 0/10 | 107 | 2 | 3.6 |
| chMA79b-SMCC-DM1 | 1/10 | 0/10 | 213 | 4 | 3.6 |
| huMA79b.v17-SMCC-DM1 | 0/10 | 0/10 | 202 | 4 | 3.4 |
| huMA79b.v18-SMCC-DM1 | 4/10 | 0/10 | 196 | 4 | 3.3 |
| huMA79b.v28-SMCC-DM1 | 0/10 | 0/10 | 101 | 2 | 3.4 |
| huMA79b.v28-SMCC-DM1 | 2/10 | 2/10 | 202 | 4 | 3.4 |
| huMA79b.v32-SMCC-DM1 | 0/10 | 0/10 | 172 | 4 | 2.9 |

In light of the ability of MA79b-grafted "humanized" antibody ADCs to significantly inhibit tumor progression in xenografts, CD79b molecules may be excellent targets for therapy of tumors in mammals, including B-cell associated cancers, such as lymphomas (i.e. Non-Hodgkin's Lymphoma), leukemias (i.e. chronic lymphocytic leukemia), and other cancers of hematopoietic cells. Further, MA79b-grafted "humanized" ADCs are useful for reducing in vivo tumor growth of tumors, including B-cell associated cancers, such as lymphomas (i.e. Non-Hodgkin's Lymphoma), leukemias (i.e. chronic lymphocytic leukemia), and other cancers of hematopoietic cells.

Example 4

CD79b Antibody Colocalization

To determine where MA79b-grafted "humanized" antibodies and antibody variants are delivered upon internalization into the cell, colocalization studies of the anti-CD79b antibodies internalized into B-cell lines may be assessed in Ramos cell lines. LAMP-1 is a marker for late endosomes and lysosomes (Kleijmeer et al., *Journal of Cell Biology*, 139(3): 639-649 (1997); Hunziker et al., *Bioessays*, 18:379-389 (1996); Mellman et al., *Annu. Rev. Dev. Biology*, 12:575-625 (1996)), including MHC class II compartments (MIICs), which is a late endosome/lysome-like compartment. HLA-DM is a marker for MIICs.

Ramos cells are incubated for 3 hours at 37° C. with 1 μg/ml MA79b-grafted "humanized" antibodies and antibody variants, FcR block (Miltenyi) and 25 μg/ml Alexa647-Transferrin (Molecular Probes) in complete carbonate-free medium (Gibco) with the presence of 10 μg/ml leupeptin (Roche) and 5 μM pepstatin (Roche) to inhibit lysosomal degradation. Cells are then washed twice, fixed with 3% paraformaldehyde (Electron Microscopy Sciences) for 20 minutes at room temperature, quenched with 50 mM NH4Cl (Sigma), permeabilized with 0.4% Saponin/2% FBS/1% BSA for 20 minutes and then incubated with 1 μg/ml Cy3 anti-mouse (Jackson Immunoresearch) for 20 minutes. The reaction is then blocked for 20 minutes with mouse IgG (Molecular Probes), followed by a 30 minute incubation with Image-iT FX Signal Enhancer (Molecular Probes). Cells are finally incubated with Zenon Alexa488-labeled mouse anti-LAMP1 (BD Pharmingen), a marker for both lysosomes and MIIC (a lysosome-like compartment that is part of the MHC class II pathway), for 20 minutes, and post-fixed with 3% PFA. Cells are resuspended in 20 μl saponin buffer and allowed to adhere to poly-lysine (Sigma) coated slides prior to mounting a coverglass with DAPI-containing VectaShield (Vector Laboratories). For immunofluorescence of the MIIC or lysosomes, cells are fixed, permeabilized and enhanced as above, then co-stained with Zenon labeled Alexa555-HLA-DM (BD Pharmingen) and Alexa488-Lamp1 in the presence of excess mouse IgG as per the manufacturer's instructions (Molecular Probes).

Accordingly, colocalization of MA79b-grafted "humanized" antibodies or antibody variants with MIIC or lysosomes of B-cell lines as assessed by immunofluorescence may indicate the molecules as excellent agents for therapy of tumors in mammals, including B-cell associated cancers, such as lymphomas (i.e. Non-Hodgkin's Lymphoma), leukemias (i.e. chronic lymphocytic leukemia), and other cancers of hematopoietic cells.

Example 5

Preparation of Cysteine Engineered Anti-CD79b Antibodies

Preparation of cysteine engineered anti-CD79b antibodies was performed as disclosed herein.

DNA encoding the MA79b antibody (light chain, SEQ ID NO: 4, FIG. 4; and heavy chain, SEQ ID NO: 5, FIG. 5), was mutagenized by methods disclosed herein to modify the light chain and heavy chain. DNA encoding the MA79b antibody (heavy chain, SEQ ID NO: 5; FIG. 5) may also be mutagenized by methods disclosed herein to modify the Fc region of the heavy chain.

DNA encoding the huMA79b.v17 antibody (heavy chain, SEQ ID NO: 304, FIG. 15) was mutagenized by methods disclosed herein to modify the heavy chain. DNA encoding the huMA79b.v17 antibody (light chain, SEQ ID NO: 303; FIG. 15; and heavy chain, SEQ ID NO: 304; FIG. 15), may also be mutagenized by methods disclosed herein to modify the light chain or the Fc region of the heavy chain.

DNA encoding the huMA79b.v18 antibody (heavy chain, SEQ ID NO: 306, FIG. 16) was mutagenized by methods disclosed herein to modify the heavy chain. DNA encoding the huMA79b.v18 antibody (light chain, SEQ ID NO: 305; FIG. 16; and heavy chain, SEQ ID NO: 306; FIG. 16), may also be mutagenized by methods disclosed herein to modify the light chain or the Fc region of the heavy chain.

DNA encoding the huMA79b.v28 antibody (heavy chain, SEQ ID NO: 308, FIG. 17), was mutagenized by methods disclosed herein to modify the heavy chain. DNA encoding the huMA79b.v28 antibody (light chain, SEQ ID NO: 307, FIG. 17; and heavy chain, SEQ ID NO: 308, FIG. 17), may also be mutagenized by methods disclosed herein to modify the light chain or the Fc region of the heavy chain.

DNA encoding the huMA79b.v32 antibody (light chain, SEQ ID NO: 310, FIG. 18; and heavy chain, SEQ ID NO: 309, FIG. 18) may be mutagenized by methods disclosed herein to modify the light chain and heavy chain.

DNA encoding the anti-cyno CD79b antibody (light chain, SEQ ID NO: 241; FIG. 45 and heavy chain, SEQ ID NO: 243, FIG. 47), was mutagenized by methods disclosed herein to modify the light chain heavy chain. DNA encoding the anti-cyno CD79b antibody (heavy chain, SEQ ID NO: 243, FIG. 47), may also be mutagenized by methods disclosed herein to modify the Fc region of the heavy chain.

In the preparation of the cysteine engineered anti-CD79b antibodies, DNA encoding the light chain was mutagenized to substitute cysteine for valine at Kabat position 205 in the light chain (sequential position 209) as shown in FIG. 27

(light chain SEQ ID NO: 235 of MA79b thioMAb) and FIG. 49 (light chain SEQ ID NO: 300 of thioMAb anti-cyno CD79b (chi10D10)). DNA encoding the heavy chain was mutagenized to substitute cysteine for alanine at EU position 118 in the heavy chain (sequential position 118; Kabat number 114) as shown in FIG. 48 (heavy chain SEQ ID NO: 244 of thioMAb anti-cyno CD79b (ch10D10) antibody), FIG. 28 (heavy chain SEQ ID NO: 236 of MA79b thioMAb), FIG. 24 (heavy chain SEQ ID NO: 228 of thioMAb huMA79b.v17), FIG. 25 (heavy chain SEQ ID NO: 230 of thioMAb huMA79b.v18) and in FIG. 26 (heavy chain SEQ ID NO: 232 of thioMAb huMA79b.v28). The Fc region of anti-CD79b antibodies may be mutagenized to substitute cysteine for serine at EU position 400 in the heavy chain Fc region (sequential position 400; Kabat number 396) as shown in Table 2-4.

A. Preparation of Cysteine Engineered Anti-CD79b Antibodies for Conjugation by Reduction and Reoxidation Full length, cysteine engineered anti-CD79b monoclonal antibodies (ThioMabs) expressed in CHO cells and purified on a protein A affinity chromatography followed by a size exclusion chromatography. The purified antibodies are reconstituted in 500 mM sodium borate and 500 mM sodium chloride at about pH 8.0 and reduced with about a 50-100 fold molar excess of 1 mM TCEP (tris(2-carboxyethyl)phosphine hydrochloride; Getz et al (1999) Anal. Biochem. Vol 273:73-80; Soltec Ventures, Beverly, Mass.) for about 1-2 hrs at 37° C. The reduced ThioMab is diluted and loaded onto a HiTrap S column in 10 mM sodium acetate, pH 5, and eluted with PBS containing 0.3M sodium chloride. The eluted reduced ThioMab is treated with 2 mM dehydroascorbic acid (dhAA) at pH 7 for 3 hours, or 2 mM aqueous copper sulfate ($CuSO_4$) at room temperature overnight. Ambient air oxidation may also be effective. The buffer is exchanged by elution over Sephadex G25 resin and eluted with PBS with 1 mM DTPA. The thiol/Ab value is estimated by determining the reduced antibody concentration from the absorbance at 280 nm of the solution and the thiol concentration by reaction with DTNB (Aldrich, Milwaukee, Wis.) and determination of the absorbance at 412 nm.

Example 6

Preparation of Cysteine Engineered Anti-CD79b Antibody Drug Conjugates by Conjugation of Cysteine Engineered Anti-CD79b Antibodies And Drug-Linker Intermediates After the reduction and reoxidation procedures of Example 5, the cysteine engineered anti-CD79b antibody is reconstituted in PBS (phosphate buffered saline) buffer and chilled on ice. About 1.5 molar equivalents relative to engineered cysteines per antibody of an auristatin drug linker intermediate, such as MC-MMAE (maleimidocaproyl-monomethyl auristatin E), MC-MMAF, MC-val-cit-PAB-MMAE, or MC-val-cit-PAB-MMAF, with a thiol-reactive functional group such as maleimido, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The reaction mixture is concentrated by centrifugal ultrafiltration and the cysteine engineered anti-CD79b antibody drug conjugate is purified and desalted by elution through G25 resin in PBS, filtered through 0.2 μm filters under sterile conditions, and frozen for storage.

Preparation of huMA79b.v18-HC(A118C) thioMAb-BM-PEO-DM1 was performed as follows. The free cysteine on huMA79b.v18-HC(A118C) thioMAb was modified by the bis-maleimido reagent BM(PEO)3 (Pierce Chemical), leaving an unreacted maleimido group on the surface of the antibody. This was accomplished by dissolving BM(PEO)3 in a 50% ethanol/water mixture to a concentration of 10 mM and adding a tenfold molar excess of BM(PEO)3 to a solution containing huMA79b.v18-HC(A118C) thioMAb in phosphate buffered saline at a concentration of approximately 1.6 mg/ml (10 micromolar) and allowing it to react for 1 hour. Excess BM(PEO)3 was removed by gel filtration (HiTrap column, Pharmacia) in 30 mM citrate, pH 6 with 150 mM NaCl buffer. An approximate 10 fold molar excess DM1 dissolved in dimethyl acetamide (DMA) was added to the huMA79b.v18-HC(A118C) thioMAb-BMPEO intermediate. Dimethylformamide (DMF) may also be employed to dissolve the drug moiety reagent. The reaction mixture was allowed to react overnight before gel filtration or dialysis into PBS to remove unreacted drug. Gel filtration on S200 columns in PBS was used to remove high molecular weight aggregates and furnish purified huMA79b.v18-HC(A118C) thioMAb-BMPEO-DM1.

By the same protocols, thio control hu-anti-HER2-HC (A118C)-BMPEO-DM1, thio control hu-anti-HER2-HC (A118C)-MC-MMAF, thio contol hu-anti-HER2-HC (A118C)-MCvcPAB-MMAE and thio control anti-CD22-HC(A118C)-MC-MMAF were generated.

By the procedures above, the following cysteine engineered anti-CD79b antibody drug conjugates (TDCs) were prepared and tested:

1. thio huMA79b.v18-HC(A118C)-MC-MMAF by conjugation of A118C thio huMA79b.v18-HC(A118C) and MC-MMAF;
2. thio huMA79b.v18-HC(A118C)-BMPEO-DM1 by conjugation of A118C thio huMA79b.v18-HC(A118C) and BMPEO-DM1;
3. thio huMA79b.v18-HC(A118C)-MCvcPAB-MMAE by conjugation of A118C thio huMA79b.v18-HC(A118C) and MC-val-cit-PAB-MMAE;
4. thio huMA79b.v28-HC(A118C)-MC-MMAF by conjugation of A118C thio huMA79b.v28-HC(A118C) and MC-MMAF;
5. thio huMA79b.v28-HC(A118C)-BMPEO-DM1 by conjugation of thio huMA79b.v28-HC(A118C) and BMPEO-DM1;
6. thio huMA79b.v28-HC(A118C)-MC-val-cit-PAB-MMAE by conjugation of thio huMA79b.v28-HC(A118C) and MC-val-cit-PAB-MMAE;
7. thio anti-cynoCD79b (ch10D10)-HC(A118C)-MC-MMAF by conjugation of A118C thio anti-cynoCD79b (ch10D10)-HC(A118C) and MC-MMAF;
8. thio anti-cynoCD79b (ch10D10)-HC(A118C)-BMPEO-DM1 by conjugation of A118C thio anti-cynoCD79b (ch10D10)-HC(A118C) and BMPEO-DM1;
9. thio anti-cynoCD79b (ch10D10)-HC(A118C)-MCvc-PAB-MMAE by conjugation of A118C thio anti-cynoCD79b (ch10D10)-HC(A118C) and MC-val-cit-PAB-MMAE;
10. thio MA79b-HC(A118C)-MC-MMAF by conjugation of thio MA79b-HC(A118C) and MC-MMAF; and
11. thio MA79b-LC(V205C)-MC-MMAF by conjugation of thio MA79b-LC(V205C) and MC-MMAF.

Example 7

Characterization of Binding Affinity of Cysteine Engineered ThioMAb Drug Conjugates to Cell Surface Antigen The binding affinity of thio huMA79b.v18, thio huMA79b.v28 drug conjugates and thio MA79b drug conjugates to CD79b expressed on BJAB-luciferase cells was determined by FACS analysis. Further, the binding affinity of thio anti-cynoCD79b(ch10D10) drug conjugates to CD79b expressed on BJAB cells expressing cynoCD79b was determined by FACS analysis.

Figure 31A:
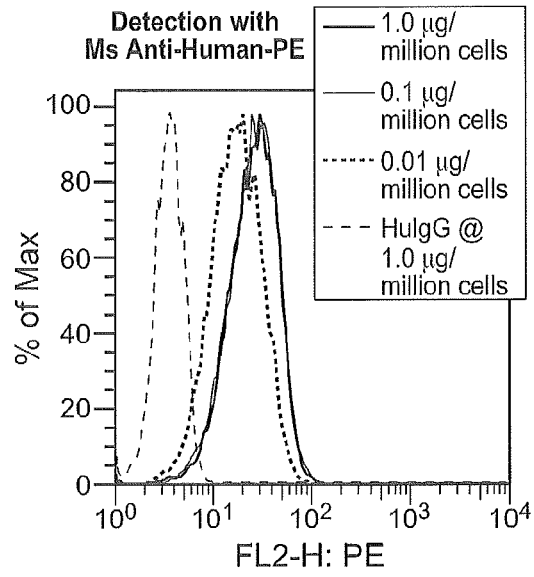
FIGS. 31A-D are FACS plots indicating that binding of anti-CD79b thioMAb drug conjugates (TDCs) of the invention bind to CD79b expressed on the surface of BJAB-luciferase cells is similar for (A) naked (unconjugated) HC (A118C) thioMAb variants of huMA79b.v28 and conjugated HC (A118C) thioMAb variants of huMA79b.v28 with the different drug conjugates shown ((B) MMAE, (C) DM1 and (D) MMAF)). Detection was with MS anti-human-PE. "Thio" refers to cysteine-engineered antibody while "hu" refers to humanized antibody.
Figure 31B:
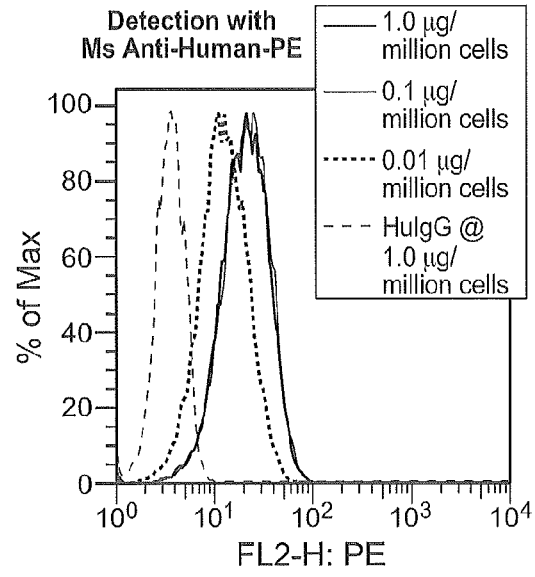
Figure 31C:
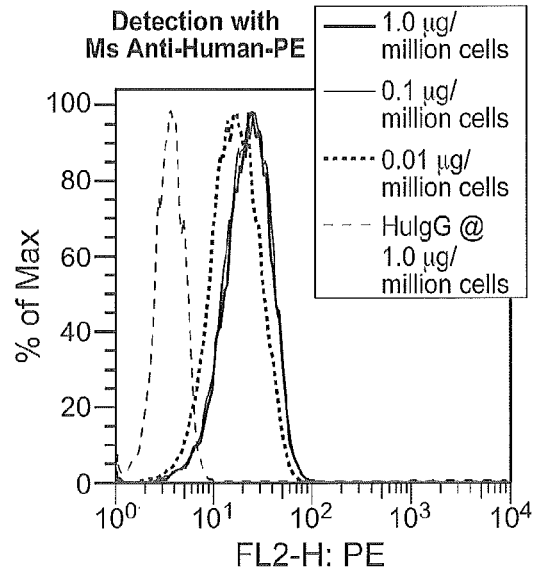
Figure 31D:
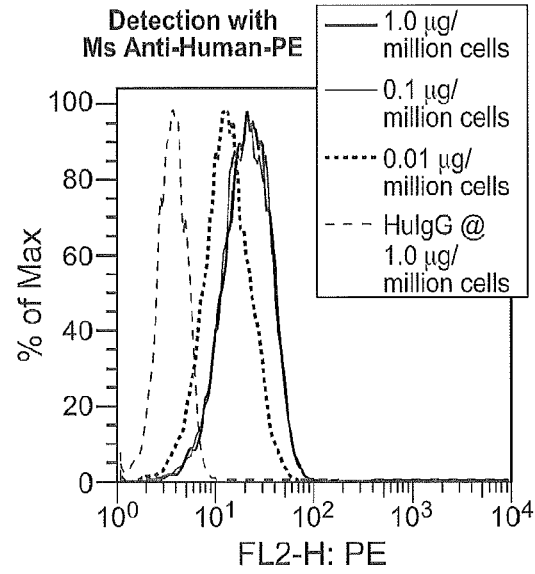
Figure 32A:
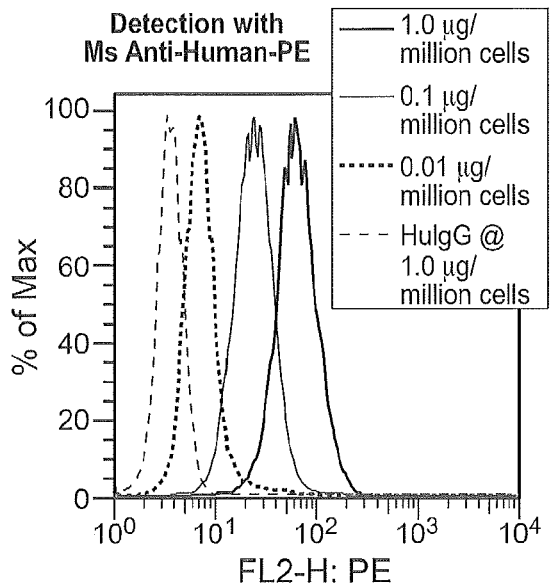
FIGS. 32A-D are FACS plots indicating that binding of anti-cynoCD79b thioMAb drug conjugates (TDCs) of the invention bind to CD79b expressed on the surface of BJAB-cells expressing cynoCD79b is similar for (A) naked (unconjugated) HC(A118C) thioMAb variants of anti-cynoCD79b (ch10D10) and conjugated HC(A118C) thioMAb variants of anti-cynoCD79b (ch10D10) with the different drug conjugates shown ((B) MMAE, (C) DM1 and (D) MMAF)). Detection was with MS anti-huIgG-PE. "Thio" refers to cysteine-engineered antibody.
Figure 32B:
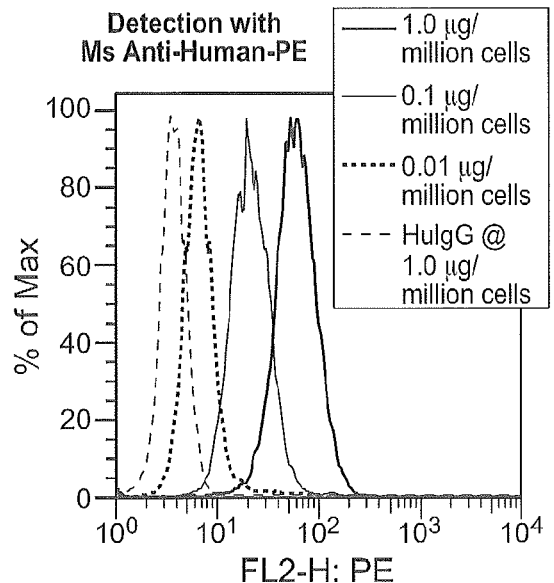
Figure 32C:
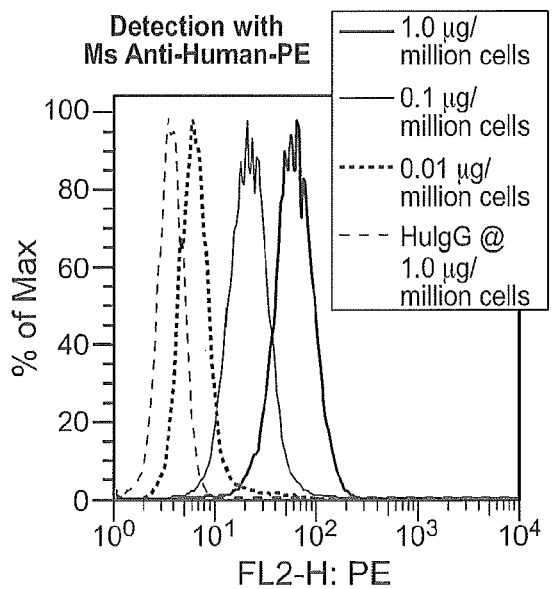
Figure 32D:
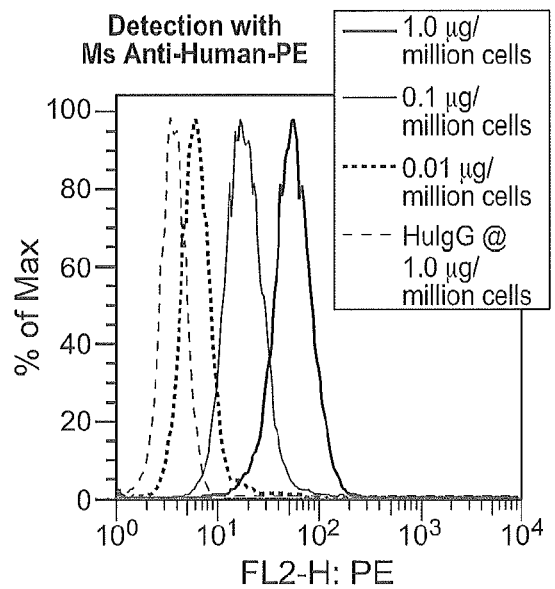

Briefly, approximately 1×10$^6$ cells in 100 µl were contacted with varying amounts (1.0 µg, 01. µg or 0.01 µg of Ab per million cells of BJAB-luciferase cells or BJAB cells expressing cynoCD79b (for anti-cynoCD79b thioMAbs)) of one of the following anti-CD79b thioMAb drug conjugates or naked (unconjugated Ab as a control): (1) thio MA79b-LC (V205C)-MC-MMAF or (2) thio MA79b-HC(A118C)-MC-MMAF (FIGS. 29A-B, respectively); (3) thio huMA79b.v18-HC(A118C)-MC-MMAF, (4) thio huMA79b.v18-HC(A118C)-MC-vcPAB-MMAE or (5) thio huMA79b.v18-HC(A118C)-BMPEO-DM1 (FIGS. 30B-D, respectively); (6) thio huMA79b.v28-HC(A118C)-MCvcPAB-MMAE, (7) thio huMA79b.v28-HC(A118C)-BMPEO-DM1, or (8) thio huMA79b.v28-HC(A118C)-MC-MMAF (see FIGS. 31B-31D, respectively); or (9) thio anti-cynoCDb79(ch10D10)-HC(A118C)-MCvcPAB-MMAE, (10) thio anti-cynoCD79b (ch10D10)-HC(A118C)-BMPEO-DM1 or (11) thio anti-cynoCD79b(ch10D10)-HC(A118C)-MC-MMAF (see FIGS. 32B-32D, respectively). PE conjugated mouse anti-human Ig was used as the secondary detecting antibody (BD Cat #555787).

Anti-CD79b antibody bound to the cell surface was detected using PE conjugated mouse anti-human Ig. The plots of FIGS. 29-32 indicate that antigen binding was approximately the same for all of the thioMAb drug conjugates tested.

Example 8

Figure 41A:
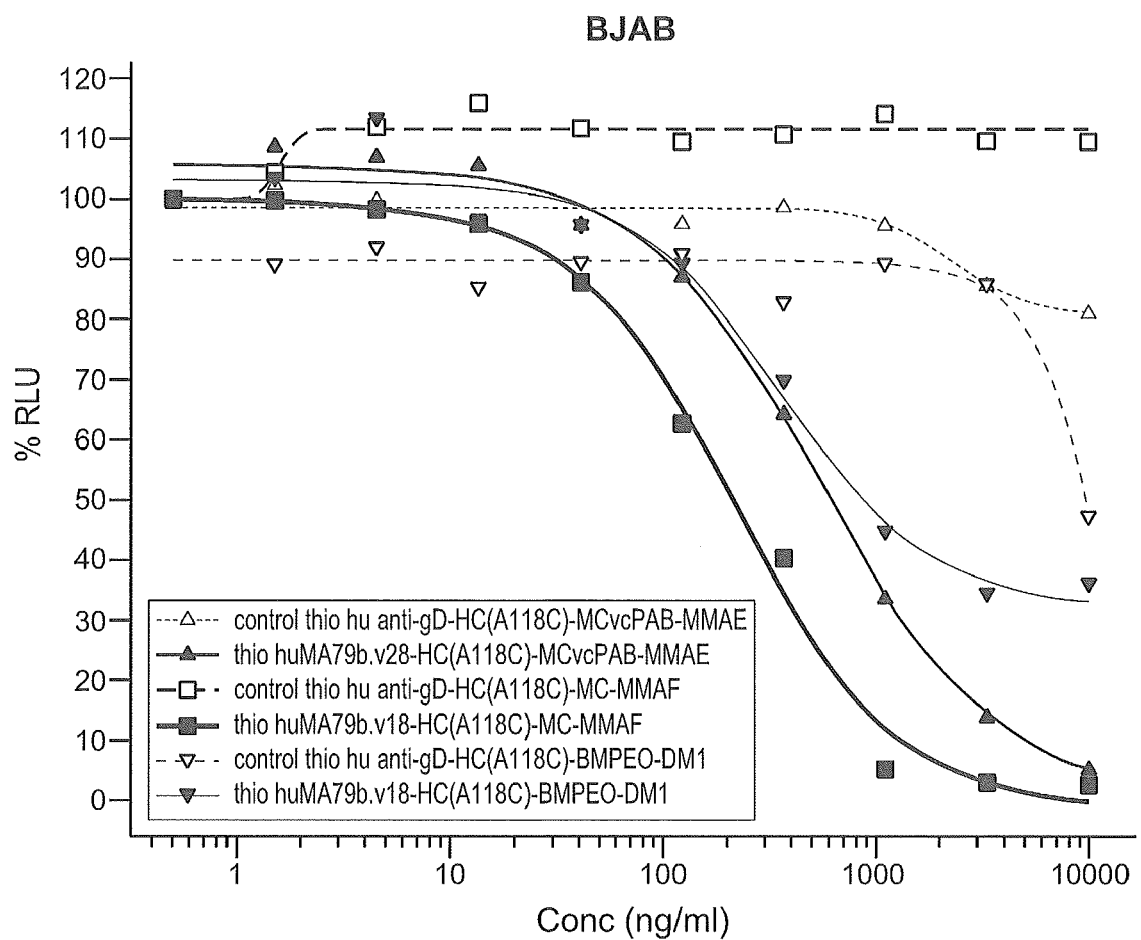
FIG. 41 shows a plot of in vitro cell proliferation assay results with (A) BJAB, (B) Granta-519 or (C) WSU-DLCL2 tumor cells, treated with varying concentrations 0.001 to 10000 ng of TDC per ml, including: (1) control thio hu anti-gD-HC(A118C)-MCvcPAB-MMAE, 2.0 MMAE/Ab loading, (2) control thio hu anti-gD-HC(A118C)-MC-MMAF, 2.1 MMAF/Ab loading, (3) control thio hu anti-gD-HC(A118C)-BMPEO-DM1, 2.1 DM1/Ab loading, (4) thio huMA79b.v18-HC(A118C)-MC-MMAF, 1.91 MMAF/Ab loading, (5) thio huMA79b.v18-HC(A118C)-BMPEO-DM1, 1.8 DM1/Ab loading, and (6) thio huMA79b.v28-HC(A118 C)-MCvcPAB-MMAE, 2.0 MMAE/Ab loading. "Thio" refers to cysteine-engineered antibody while "hu" refers to humanized antibody. "gD" refers to glycoprotein D.
Figure 41B:
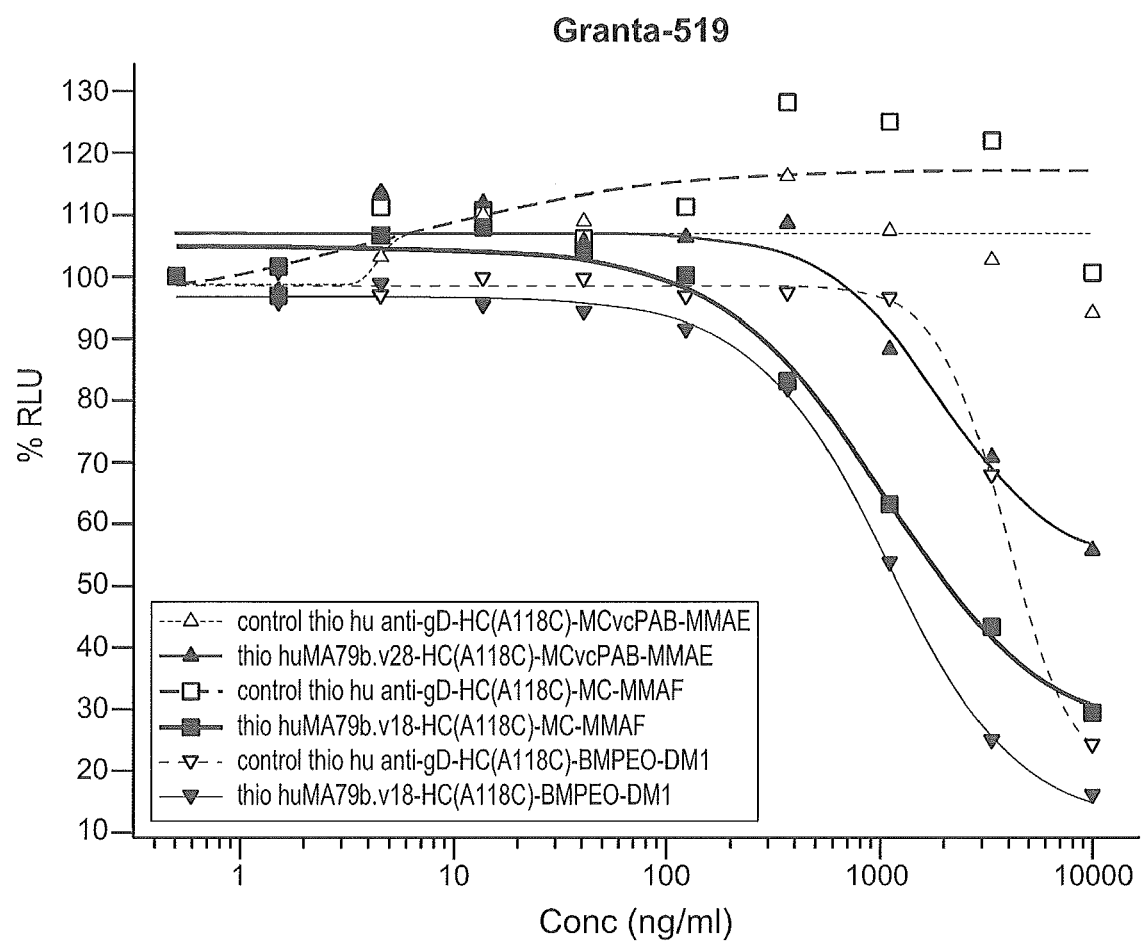
Figure 41C:
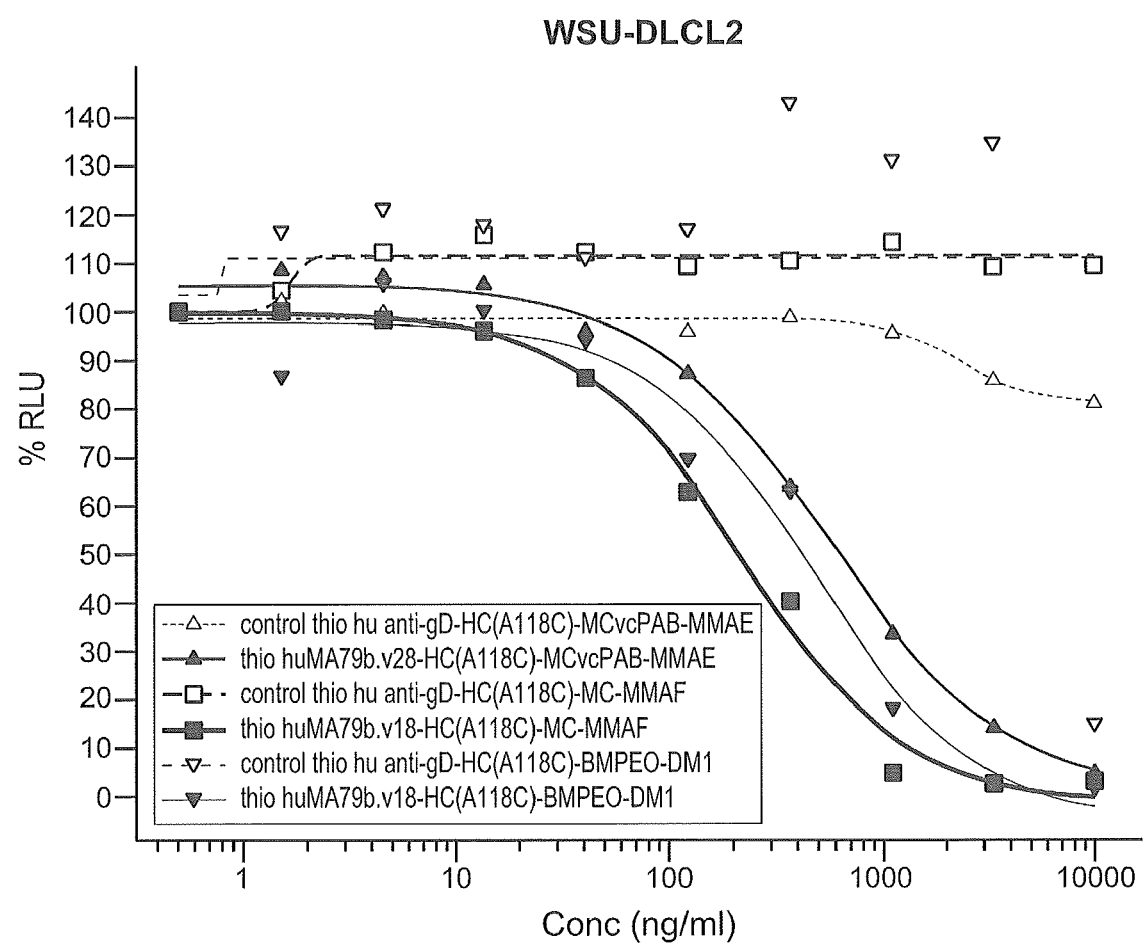

Assay for In Vitro Cell Proliferation Reduction by Anti-CD79b ThioMab Drug Conjugates The in vitro potency of anti-CD79b ThioMAb-drug conjugates (including thio huMA79b.v18-HC(A118C)-MCM-MAF, thio huMA79b.v28-HC(A118C)-MCvcPAB-MMAE and thio huMA79b.v18-HC(A118C)-BMPEO-DM1), was measured by a cell proliferation assay (FIG. 41A, BJAB-luciferase; FIG. 41B, Granta-519; FIG. 41C, WSU-DLCL2). The CellTiter-Glo® Luminescent Cell Viability Assay is a commercially available (Promega Corp., Madison, Wis.), homogeneous assay method based on the recombinant expression of *Coleoptera luciferase* (U.S. Pat. No. 5,583,024; U.S. Pat. No. 5,674,713; U.S. Pat. No. 5,700,670). This cell proliferation assay determines the number of viable cells in culture based on quantitation of the ATP present, an indicator of metabolically active cells (Crouch et al., *J. Immunol. Metho.*, 160: 81-88 (1993); U.S. Pat. No. 6,602,677). The CellTiter-Glo® Assay was conducted in 96 well format, making it amenable to automated high-throughput screening (HTS) (Cree et al., *AntiCancer Drugs*, 6:398-404 (1995)). The homogeneous assay procedure involves adding the single reagent (The CellTiter-Glo® Reagent) directly to cells cultured in serum-supplemented medium.

The homogeneous "add-mix-measure" format results in cell lysis and generation of a luminescent signal proportional to the amount of ATP present. The substrate, Beetle Luciferin, is oxidatively decarboxylated by recombinant firefly luciferase with concimatant conversion of ATP to AMP and generation of photons. Viable cells are reflected in relative luminescence units (RLU). Data can be recorded by luminometer or CCD camera imaging device. The luminescence output is presented as RLU, measured over time. % RLU is normalized RLU percentage compared to a "non-drug-conjugate" control. Alternatively, photons from luminescence can be counted in a scintillation counter in the presence of a scintillant. The light units can be represented then as CPS (counts per second).

Efficacy of thioMAb-drug conjugates were measured by a cell proliferation assay employing the following protocol, adapted from CellTiter Glo Luminescent Cell Viability Assay, Promega Corp. Technical bulletin TB288; Mendoza et al., *Cancer Res.*, 62: 5485-5488 (2002)):

1. An aliquot of 40 µl of cell culture containing about 3000 BJAB, Granta-519 or WSU-DLCL2 cells in medium was deposited in each well of a 384-well, opaque-walled plate.
2. TDC (ThioMab Drug Conjugate) (10 µl) was added to quadruplicate experimental wells to final concentration of 10000, 3333, 1111, 370, 123, 41, 13.7, 4.6 or 1.5 ng/mL, with "non-drug conjugate" control wells receiving medium alone, and incubated for 3 days.
3. The plates were equilibrated to room temperature for approximately 30 minutes.
4. CellTiter-Glo Reagent (50 µl) was added.
5. The contents were mixed for 2 minutes on an orbital shaker to induce cell lysis.
6. The plate was incubated at room temperature for 10 minutes to stabilize the luminescence signal.
7. Luminescence was recorded and reported in graphs as % RLU (relative luminescence units). Data from cells incubated with drug-conjugate-free medium were plotted at 0.51 ng/ml. Media: BJAB, Granta-519 and WSU-DLCL2 cells grow in RPMI1640/10% FBS/2 mM glutamine.

Example 9

Assay for Inhibition of In Vivo Tumor Growth by Anti-CD79b ThioMab Drug Conjugates A. Granta-519 (Human Mantle Cell Lymphoma)

In a similar study, using the same xenograft study protocol as disclosed in the Example 3 (see above), varying the drug conjugates and doses administered, the efficacy of thioMAb drug conjugates in Granta-519 xenografts (Human Mantle Cell Lymphoma) in CB17 SCID mice was studied. The drug conjugates and doses (administered at day 0 for all ADCs and controls) are shown in Table 11, below.

The control Ab was hu-anti-HER2-MC-MMAF or MA79b-MC-MMAF. The control HC(A118C) thioMAb was thio hu-anti-HER2-HC(A118C)-MMAF thioMAb. The results are shown in Table 11 and FIG. 33.

Figure 33A:
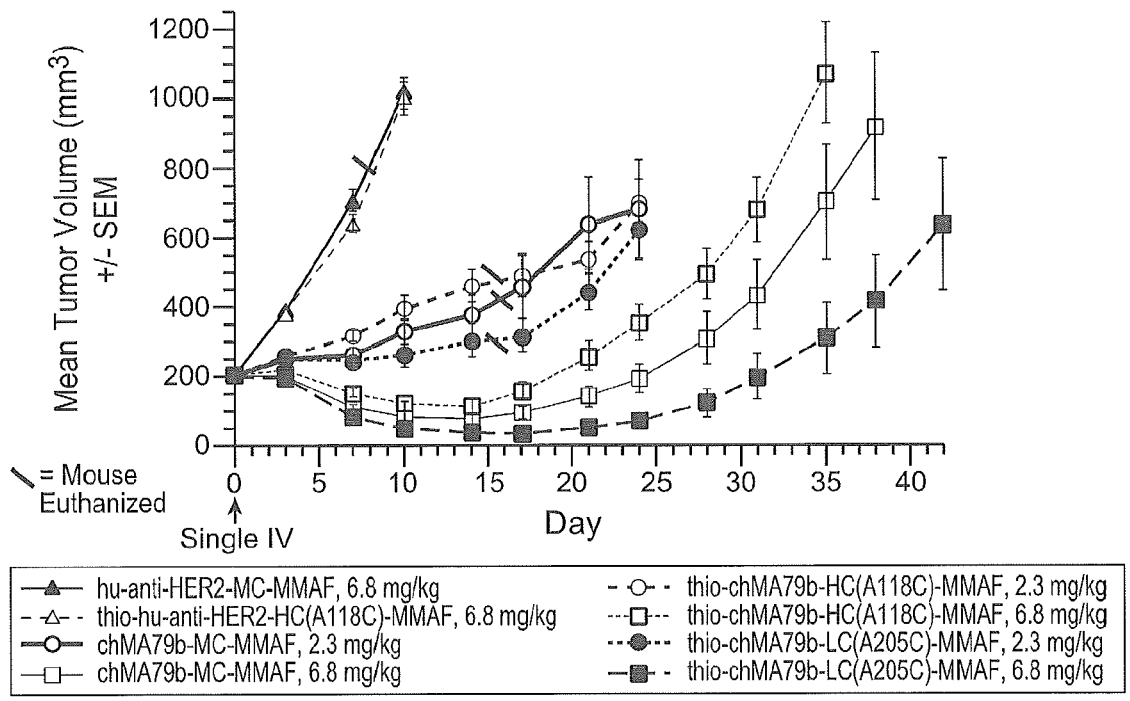
FIG. 33A is a graph of inhibition of in vivo tumor growth in a Granta-519 (Human Mantle Cell Lymphoma) xenograft model which shows that administration of anti-CD79b TDCs which varied by position of the engineered cysteine (LC (V205C) or HC (A118C)) and/or different drug doses to SCID mice having human B cell tumors significantly inhibited tumor growth. Xenograft models treated with thio chMA79b-HC(A118C)-MC-MMAF, drug load was approximately 1.9 (Table 11) or thio chMA79b-LC(V205C)-MC-MMAF, drug load was approximately 1.8 (Table 11) showed a significant inhibition of tumor growth during the study. Controls included hu-anti-HER2-MC-MMAF and thio hu-anti-HER2-HC(A118C)-MC-MMAF and chMA79b-MC-MMAF.
Figure 33B:
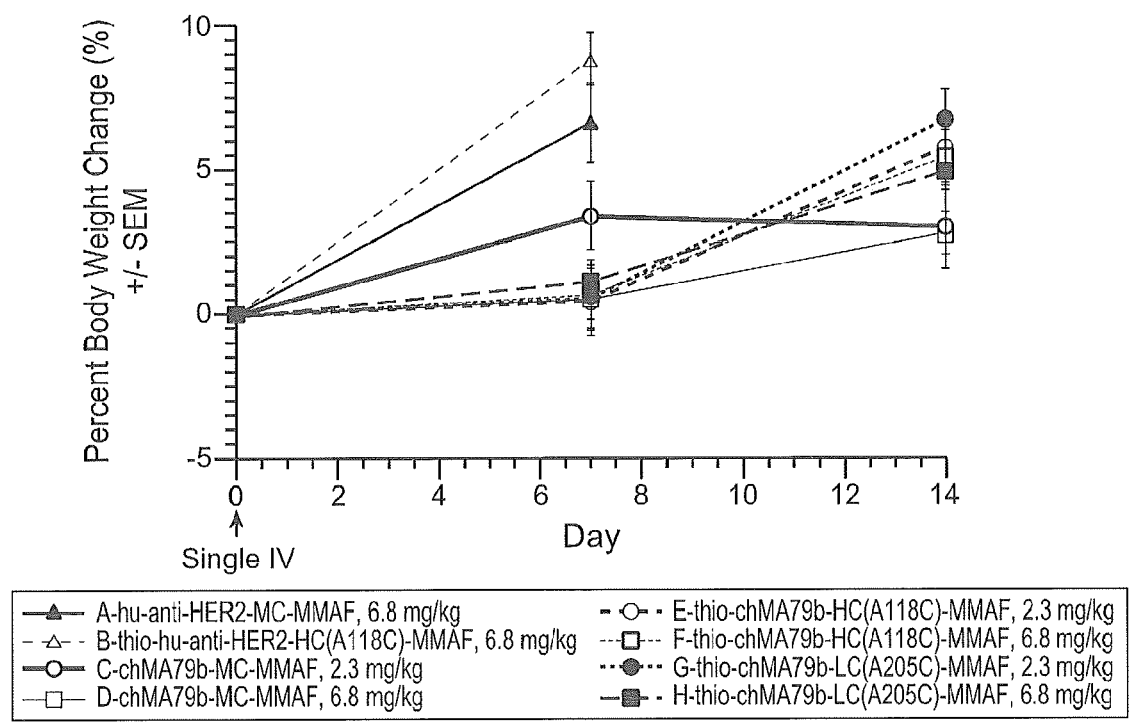
FIG. 33B is a plot of percent weight change in the mice from the Granta-519 xenograft study (FIG. 33A and Table 11) showing that there was no significant change in weight during the first 14 days of the study. "Thio" refers to cysteine-engineered antibody while "hu" refers to humanized antibody.

FIG. 33A is a graph plotting changes in mean tumor volume over time in the Granta-519 xenograft in CB17 SCID mice treated with the heavy chain A118C or light chain V205C anti-CD79b TDCs, at doses as shown in Table 11. Specifically, administration of thio chMA79b-HC(A118C)-MC-MMAF and thio chMA79b-LC(V205C)-MC-MMAF showed inhibition of tumor growth when compared to the negative controls (anti-hu-HER2-MC-MMAF and thio-hu-anti-HER2-HC(A118C)-MC-MMAF. Other controls included MA79b-MC-MMAF.

Further, in the same study, the percent body weight change in the first 14 days was determined in each dosage group. The results (FIG. 33B) indicated administration of these thioMAb drug conjugates did not result in a significant decrease in percent body weight or weight loss during this time.

Even further, in Table 11, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm³) are indicated and NA=not applicable. (DAR=Drug to Antibody Ratio)

TABLE 11

In Vivo Tumor Volume Reduction,
Thio chMA79b-HC(A118C) or thio chMA79b-LC(V205C)
MMAF Conjugate Administration
In Granta-519 Xenografts in CB17 SCID Mice

| Antibody administered | PR | CR | Dose MMAF (µg/m²) | Dose Ab (mg/kg) | DAR (Drug/Ab) |
|---|---|---|---|---|---|
| Control hu-anti-HER2-MC-MMAF | 0/8 | 0/8 | 413 | 6.8 | 4.0 |
| Thio Control hu-anti-HER2-HC(A118C)-MC-MMAF | 0/9 | 0/9 | 191 | 6.8 | 1.85 |
| Control chMA79b-MC-MMAF | 1/8 | 0/8 | 100 | 2.3 | 3.0 |
| Control chMA79b-MC-MMAF | 8/9 | 1/9 | 300 | 6.8 | 3.0 |
| Thio chMA79b-HC(A118C)-MC-MMAF | 0/8 | 0/8 | 63 | 2.3 | 1.9 |
| Thio chMA79b-HC(A118C)-MC-MMAF | 4/9 | 0/9 | 190 | 6.8 | 1.9 |
| Thio chMA79b-LC(V205C)-MC-MMAF | 0/8 | 0/8 | 60 | 2.3 | 1.8 |
| Thio chMA79b-LC(V205C)-MC-MMAF | 5/9 | 4/9 | 180 | 6.8 | 1.8 |

B. BJAB-Luciferase (Burkitt's Lymphoma) Xenografts

In a similar study, using the same xenograft study protocol as disclosed in Example 3 (above), varying the drug conjugates and doses administered, efficacy of additional drug conjugates were tested in BJAB-luciferase xenografts (Burkitt's Lymphoma) in CB17 SCID mice. The drug conjugates and doses (administered at day 0 for all ADCs and controls) are shown in Table 12, below.

The control antibody was huMA79b.v28 (conjugated to SMCC-DM1). The control HC (A118C) thioMAb was thio hu-anti-HER2-HC(A118C) antibody thioMAb (conjugated to BMPEO-DM1, MC-MMAF or MCvcPAB-MMAE), thio huMA79b.v28-HC(A118C) thioMAb or thio hu-anti-CD22 (10F4v3)-HC(A118C) thioMAb (conjugated to MC-MMAF). The results are shown in Table 12 and FIG. 34, below.

Figure 34A:
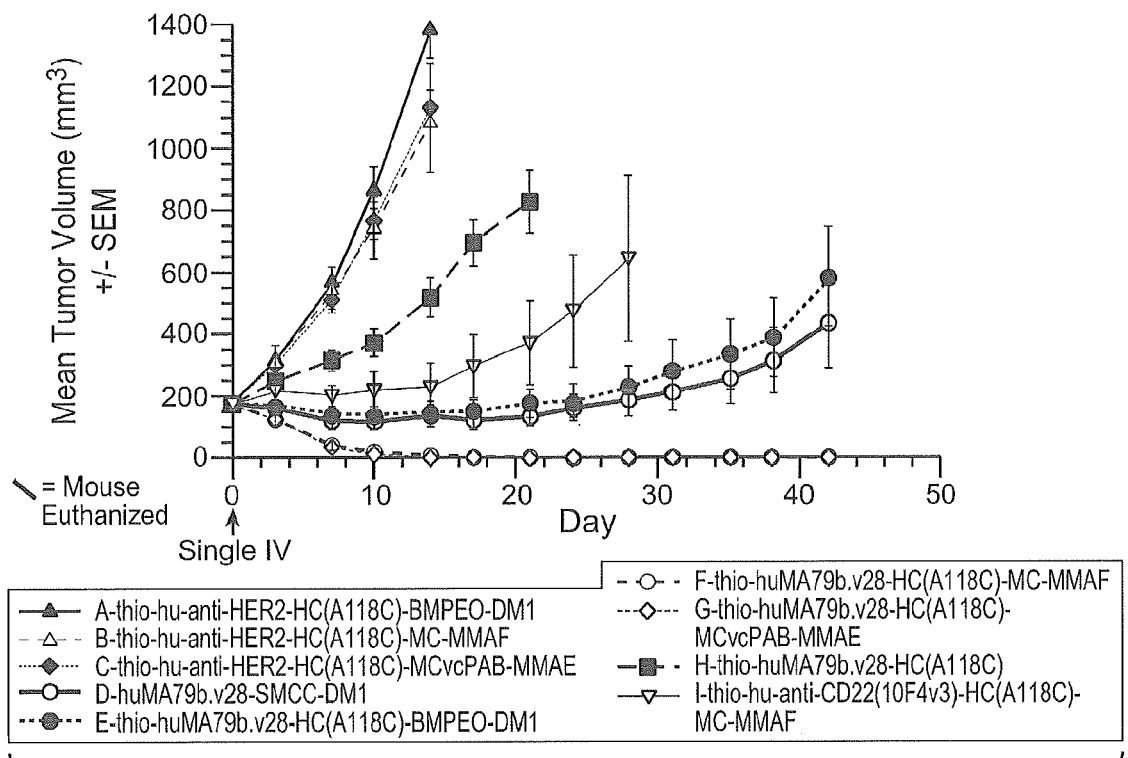
FIG. 34A is a graph of inhibition of in vivo tumor growth in a BJAB-luciferase (Burkitt's Lymphoma) xenograft model which shows that administration of anti-CD79b TDCs conjugated to different linker drug moieties (MCvcPAB-MMAE, BMPEO-DM1 or MC-MMAF) to SCID mice having human B cell tumors, significantly inhibited tumor growth. Xenograft models treated with thio huMA79b.v28-HC(A118C)-MCvcPAB-MMAE, drug load was approximately 1.87 (Table 12), thio huMA79b.v28-HC(A118C)-BMPEO-DM1, drug load was approximately 1.85 (Table 12), or thio huMA79b.v28-HC(A118C)-MC-MMAF, drug load was approximately 1.95 (Table 12), showed a significant inhibition of tumor growth during the study. Controls included anti-HER2 controls (thio hu-anti-HER2-HC(A118C)-BMPEO-DM1, thio hu-anti-HER2-HC(A118C)-MC-MMAF, thio hu-anti-HER2-HC(A118C)-MCvcPAB-MMAE), huMA79b.v28 controls (huMA79b.v28-SMCC-DM1 and thio huMA79b.v28-HC(A118C)) and anti-CD22 controls (thio hu-anti-CD22(10F4v3)-HC(A118C)-MC-MMAF).
Figure 34B:
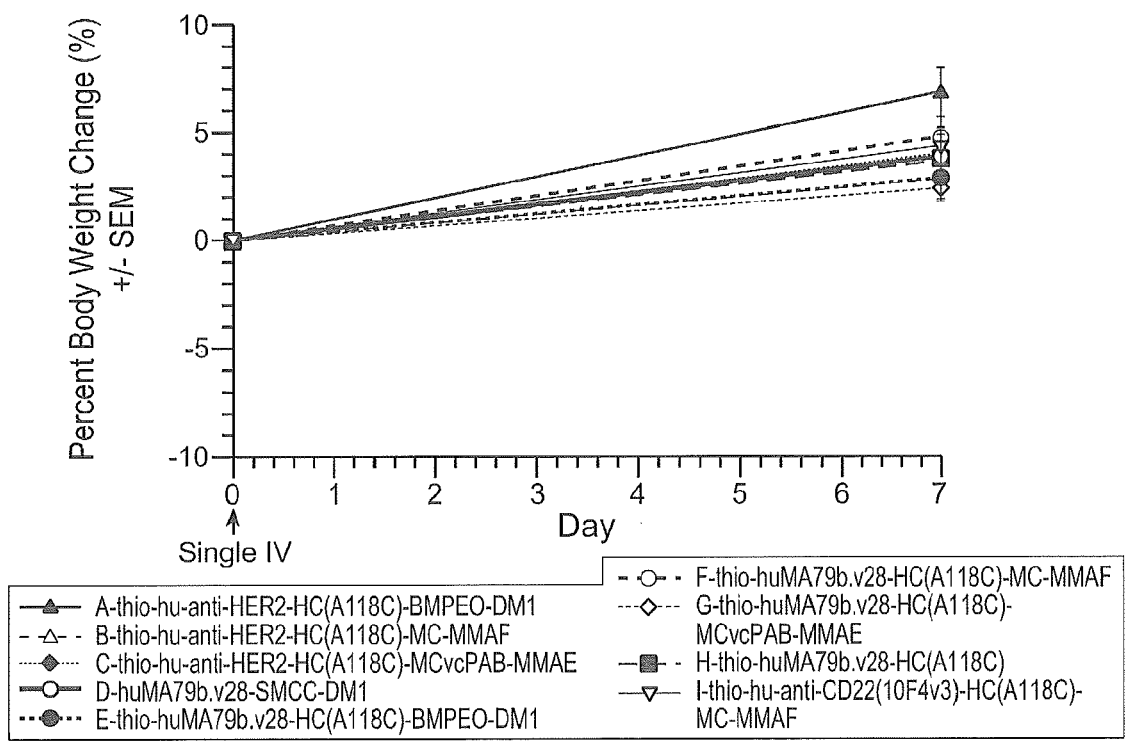
FIG. 34B is a plot of percent weight change in the mice from the BJAB-luciferase xenograft study (FIG. 34A and Table 12) showing that there was no significant change in weight during the first 7 days of the study. "Thio" refers to cysteine-engineered antibody while "hu" refers to humanized antibody.

FIG. 34A is a graph plotting changes in mean tumor volume over time in the BJAB-luciferase xenografts in CB17 SCID mice treated with the huMA79b.v28-HC(A118C) thioMAb drug conjugates as shown in Table 12. Specifically, administration of the thio huMA79b.v28-HC(A118C)-BMPEO-DM1, thio-huMA79b.v28-HC(A118C)-MC-MMAF and thio huMA79b.v28-HC(A118C)-MCvcPAB-MMAE thioMAb drug conjugate showed an inhibition in tumor growth when compared to the negative control antibody drug conjugates (thio-hu-anti-HER2-HC(A118C)-BMPEO-DM1, thio-hu-anti-HER2-HC(A118C)-MC-MMAF and thio-hu-anti-HER2-HC(A118C)-MCvcPAB-MMAE). Other controls were thio-huMA79b.v28-HC(A118C), huMA79b.v28-SMCC-DM1 and thio-hu-anti-CD22 (10F4v3)-HC(A118C)-MC-MMAF.

Further, in the same study, the percent body weight change in the first 7 days was determined in each dosage group. The results (FIG. 34B) indicated administration of these thioMAb drug conjugates did not cause a significant decrease in percent body weight or weight loss during this time.

Even further, in Table 12, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm³) are indicated and NA=not applicable. (DAR=Drug to Antibody Ratio)

TABLE 12

In Vivo Tumor Volume Reduction,
Thio HuMA79b.v28-HC(A118C) MMAE,
MMAF, and DM1 Conjugate Administration
In BJAB-Luciferase Xenografts in CB17 SCID Mice

| Antibody administered | PR | CR | Dose MMAF, MMAE or DM1 (µg/m²) | Dose Ab (mg/kg) | DAR (Drug/Ab) |
|---|---|---|---|---|---|
| Thio Control hu-anti-HER2-HC(A118C)-BMPEO-DM1 | 0/10 | 0/10 | 57 | 2 | 1.86 |
| Thio Control hu-anti-HER2-HC(A118C)-MC-MMAF | 1/10 | 0/10 | 58 | 2 | 1.9 |
| Thio Control hu-anti-HER2-HC(A118C)-MCvcPAB-MMAE | 0/10 | 0/10 | 46 | 2 | 1.55 |
| Control huMA79b.v28-SMCC-DM1 | 2/10 | 3/10 | 101 | 2 | 3.4 |
| Thio huMA79b.v28-HC(A118C)-BMPEO-DM1 | 3/10 | 2/10 | 55 | 2 | 1.85 |
| Thio huMA79b.v28-HC(A118C)-MC-MMAF | 0/10 | 10/10 | 57 | 2 | 1.95 |
| Thio huMA79b.v28-HC(A118C)-MCvcPAB-MMAE | 0/10 | 10/10 | 54 | 2 | 1.87 |
| Thio Control huMA79b.v28-HC(A118C) | 0/10 | 0/10 | NA | 2 | NA |
| Thio Control hu-anti-CD22(10F4v3)-HC(A118C)-MC-MMAF | 1/10 | 4/10 | 59 | 2 | 1.96 |

C. WSU-DLCL2 (Diffuse Large Cell Lymphoma) Xenografts)

In a similar study, using the same xenograft study protocol as disclosed in the Example 3 (see above), varying the drug conjugates and doses administered, the efficacy of thioMAb drug conjugates in follicular lymphoma WSU-DLCL2 xenografts (Diffuse Large Cell Lymphoma) in CB17 SCID mice was studied. The drug conjugates and doses are shown in Table 13, below.

The control antibody was huMA79b.v28 (conjugated to SMCC-DM1). The control HC(A118C) thioMAb was thio hu-anti-HER2-HC(A118C) antibody thioMAb (conjugated to BMPEO-DM1, MC-MMAF or MCvcPAB-MMAE), thio huMA79b.v28-HC(A118C) thioMAb or thio anti-CD22 10F4v3-HC(A118C) thioMAb (conjugated to MC-MMAF). The results are shown in Table 13, below.

Figure 35A:
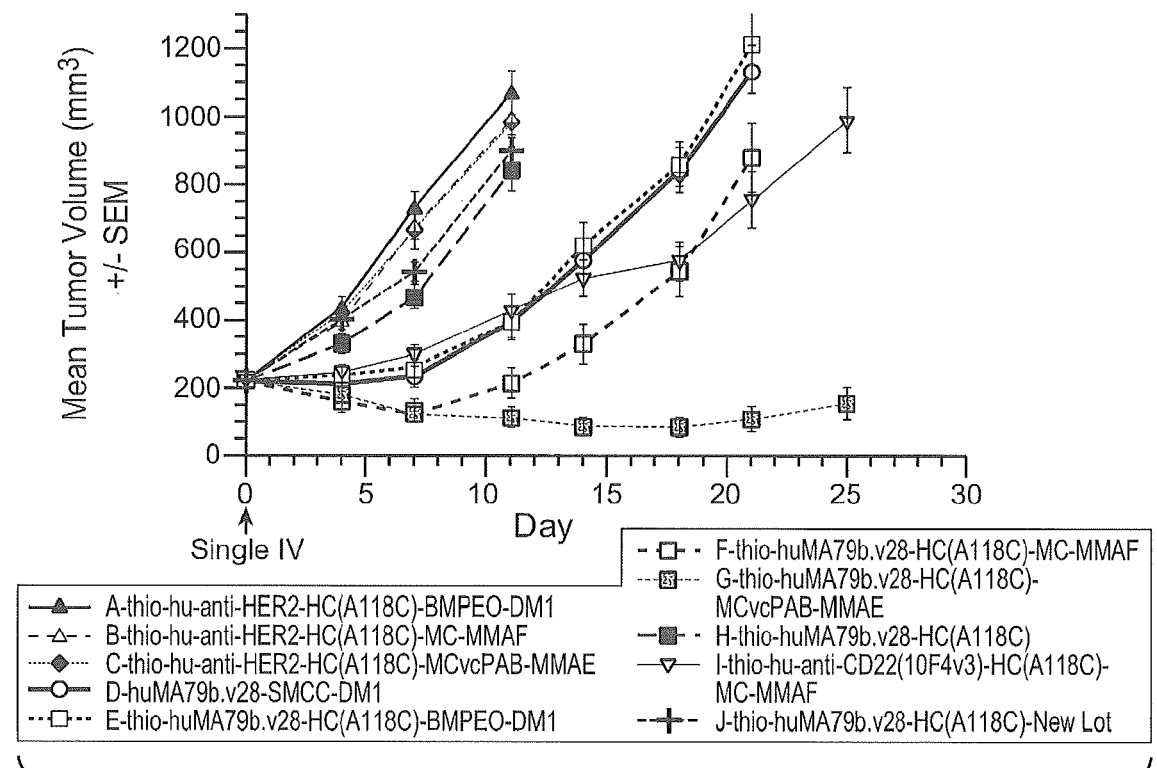
FIG. 35A is a graph of inhibition of in vivo tumor growth in a WSU-DLCL2 (Diffuse Large Cell Lymphoma) xenograft model which shows that administration of anti-CD79b TDCs conjugated to different linker drug moieties (MCvcPAB-MMAE, BMPEO-DM1 or MC-MMAF) to SCID mice having human B cell tumors significantly inhibited tumor growth. Xenograft models treated with thio huMA79b.v28-HC(A118C)-MCvcPAB-MMAE, drug load was approximately 1.87 (Table 13), thio huMA79b.v28-HC(A118C)-BMPEO-DM1, drug load was approximately 1.85 (Table 13), or thio huMA79b.v28-HC(A118C)-MC-MMAF, drug load was approximately 1.95 (Table 13), showed a significant inhibition of tumor growth during the study. Controls included anti-HER2 controls (thio hu-anti-HER2-HC(A118C)-BMPEO-DM1, thio hu-anti-HER2-HC(A118C)-MC-MMAF, thio hu-anti-HER2-HC(A118C)-MCvcPAB-MMAE), huMA79b.v28 controls (huMA79b.v28-SMCC-DM1 and thio huMA79b.v28-HC(A118C)) and anti-CD22 controls (thio hu-anti-CD22(10F4v3)-HC(A118C)-MC-MMAF).

FIG. 35A is a graph plotting changes in mean tumor volume over time in the WSU-DLCL2 (Diffuse Large Cell Lymphoma) xenograft in CB17 SCID mice treated with the heavy chain A118C anti-CD79b TDCs, at doses as shown in Table 13. Specifically, administration of thio huMA79b.v28-HC(A118C)-BMPEO-DM1, thio huMA79b.v28-HC(A118C)-MC-MMAF and thio huMA79b.v28-HC(A118C)-MCvc-PAB-MMAE showed inhibition of tumor growth when compared to the negative controls (thio-hu-anti-HER2-HC(A118C)-BMPEO-DM1, thio-hu-anti-HER2-HC(A118C)-MC-MMAF, thio-hu-anti-HER2-HC(A118C)-MCvcPAB-MMAE, thio-huMA79b.v28-HC(A118C)). Other controls included thio-huMA79b.v28-HC(A118C), huMA79b.v28-SMCC-DM1 and thio hu-anti-CD22(10F4v3)-HC(A118C)-MC-MMAF.

The thio huMA79b.v28-HC(A118C)-MCvcPAB-MMAE TDC appeared to be the most efficacious of the test agents in this study.

Figure 35B:
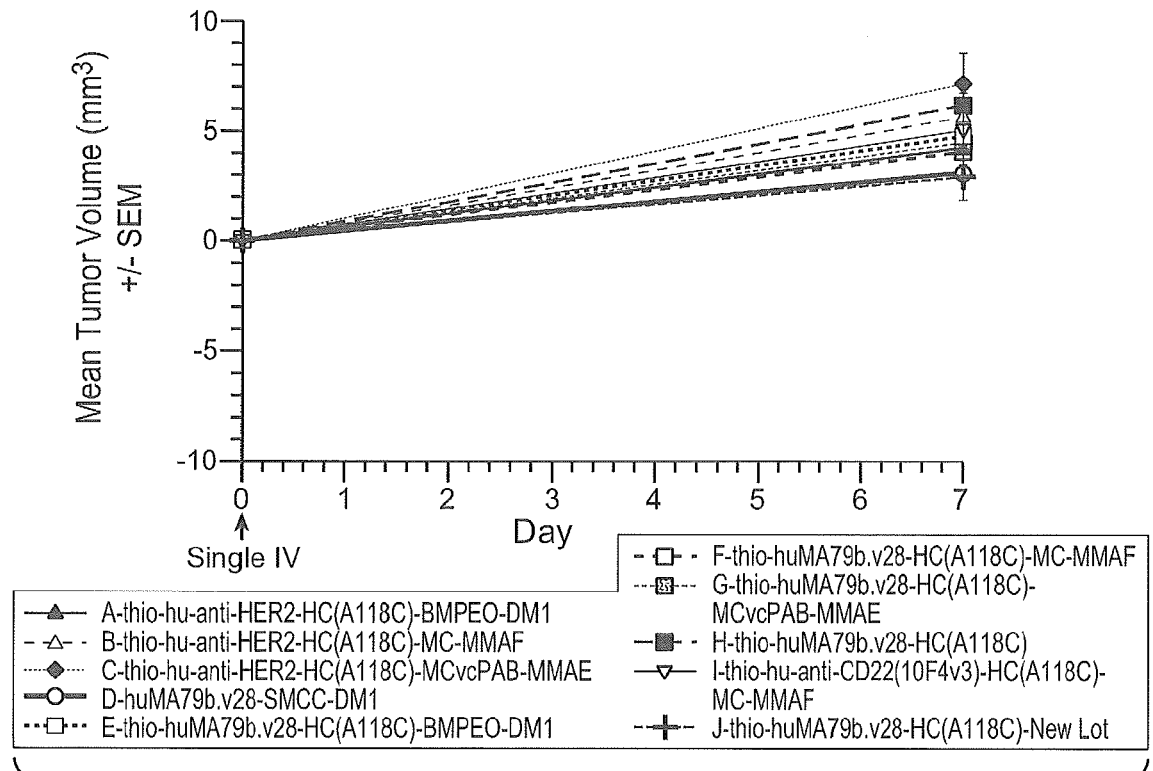
FIG. 35B is a plot of percent weight change in the mice from the WSU-DLCL2 xenograft study (FIG. 35A and Table 13) showing that there was no significant change in weight during the first 7 days of the study. "Thio" refers to cysteine-engineered antibody while "hu" refers to humanized antibody.

Further, in the same study, the percent body weight change in the first 7 days was determined in each dosage group. The results (FIG. 35B) indicated administration of these thioMAb drug conjugates did not cause a significant decrease in percent body weight or weight loss during this time.

Even further, in Table 13, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm³) are indicated and NA=not applicable. (DAR=Drug to Antibody Ratio)

D. DOHH2 (Follicular Lymphoma) Xenografts

In a similar study, using the same xenograft study protocol as disclosed in Example 3 (see above), varying the drug conjugates and doses administered, the ability of the thioMAb drug conjugates to reduce B-cell tumor volume in DOHH2 xenograft models in CB17 SCID mice was studied. The drug conjugates and doses (administered at day 0 for all ADCs and controls) are shown in Table 14, below.

Figure 36:
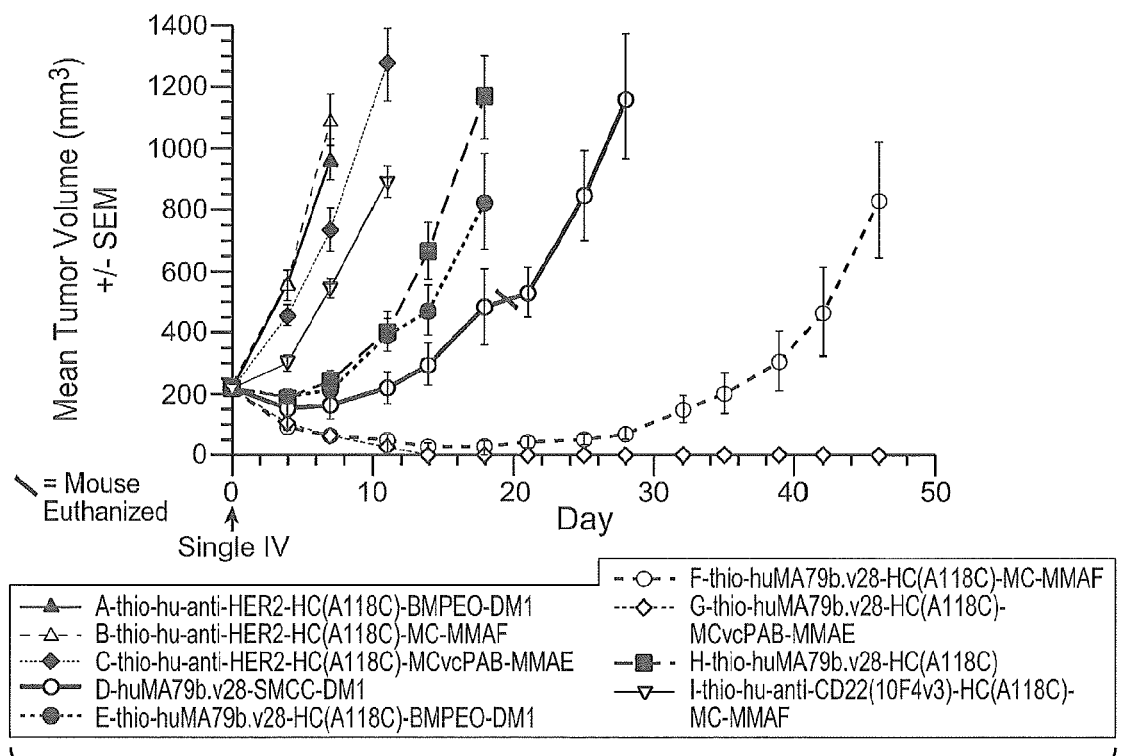
FIG. 36 is a graph of inhibition of in vivo tumor growth in a DOHH2 (Follicular Lymphoma) xenograft model which shows that administration of anti-CD79b TDCs conjugated to different linker drug moieties (BMPEO-DM1, MC-MMAF or MCvcPAB-MMAE) to SCID mice having human B cell tumors significantly inhibited tumor growth. Xenograft models treated with thio huMA79b.v28-BMPEO-DM1 (drug load was approximately 1.85 (Table 14)), thio huMA79b.v28-MC-MMAF (drug load was approximately 1.95 (Table 14)) or thio MA79b-HC(A118C)-MCvcPAB-MMAE (drug load was approximately 1.87 (Table 14)) showed a significant inhibition of tumor growth during the study. Controls included anti-HER2 controls (thio hu-anti-HER2-HC(A118C)-BMPEO-DM1, thio hu-anti-HER2-HC(A118C)-MC-MMAF, thio hu-anti-HER2-HC(A118C)-MCvcPAB-MMAE), huMA79b.v28 controls (huMA79b.v28-SMCC-DM1 and thio huMA79b.v28-HC(A118C)) and anti-CD22 controls (thio hu-anti-CD22(10F4v3)-HC(A118C)-MC-MMAF). "Thio" refers to cysteine-engineered antibody while "hu" refers to humanized antibody.

The control Ab was huMA79b.v28 (conjugated to SMCC-DM1). The control HC(A118C) thioMAb was thio hu-anti-HER2-HC(A118C) thioMAb (conjugated to BMPEO-DM1, MC-MMAF or MCvcPAB-MMAE), thio huMA79b.v28-HC(A118C) thioMab and thio hu-anti-CD22-HC(A118C) (conjugated to MC-MMAF). The results are shown in Table 14 and FIG. 36.

FIG. 36A is a graph plotting changes in mean tumor volume over time in the DOHH2 cell xenograft in CB17 SCID mice treated with heavy chain A118C TDCs, at doses as shown in Table 14. Specifically, administration of the thio huMA79b.v28-HC-(A118C)-BMPEO-DM1, thio huMA79b.v28-HC(A118C)-MC-MMAF and thio huMA79b.v28-HC(A118C)-MCvcPAB-MMAE thioMAb drug conjugates at the doses shown in Table 14 showed an inhibition in tumor growth when compared to the negative control drug conjugates (Thio Control hu-anti-HER2-HC(A118C)-BMPEO-DM1, Thio Control hu-anti-HER2-HC(A118C)-MC-MMAF, Thio Control hu-anti-HER2-HC(A118C)-MCvcPAB-MMAE. Other controls included Thio Control huMA79b.v28-HC(A118C), Thio Control anti-CD22-HC(A118C)-MC-MMAF and Thio Control huMA79b.v28-HC(A118C) and Control huMA79b.v28-SMCC-DM1.

Even further, in Table 14, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm³) are indicated and NA=not applicable. (DAR=Drug to Antibody Ratio)

TABLE 13

In Vivo Tumor Volume Reduction,
Thio HuMA79b.v28-HC(A118C) MMAE, MMAF, and DM1 Conjugate Administration
In WSU-DLCL2 Xenografts in CB17 SCID Mice

| Antibody administered | PR | CR | Dose MMAF, MMAE or DM1 (μg/m²) | Dose Ab (mg/kg) | DAR (Drug/Ab) |
|---|---|---|---|---|---|
| Thio Control hu-anti-HER2-HC(A118C)-BMPEO-DM1 | 0/10 | 0/10 | 114 | 4 | 1.86 |
| Thio Control hu-anti-HER2-HC(A118C)-MC-MMAF | 0/10 | 0/10 | 115 | 4 | 1.9 |
| Thio Control hu-anti-HER2-HC(A118C)-MCvcPAB-MMAE | 0/10 | 0/10 | 92 | 4 | 1.55 |
| Control huMA79b.v28-SMCC-DM1 | 1/10 | 0/10 | 202 | 4 | 3.4 |
| Thio huMA79b.v28-HC(A118C)-BMPEO-DM1 | 0/10 | 0/10 | 110 | 4 | 1.85 |
| Thio huMA79b.v28-HC(A118C)-MC-MMAF | 3/10 | 1/10 | 115 | 4 | 1.95 |
| Thio huMA79b.v28-HC(A118C)-MCvcPAB-MMAE | 4/10 | 3/10 | 108 | 4 | 1.87 |
| Thio Control huMA79b.v28-HC(A118C) | 0/10 | 0/10 | NA | 4 | NA |
| Thio Control 10F4v3-HC(A118C)-MC-MMAF | 1/10 | 0/10 | 118 | 4 | 1.96 |
| Thio Control huMA79b.v28-HC(A118C) | 0/10 | 0/10 | NA | 4 | NA |

TABLE 14

In Vivo Tumor Volume Reduction,
Thio HuMA79b.v28-HC(A118C) DM1, MMAF and MMAE Conjugate Administration
In DOHH2 Xenografts in CB17 SCID Mice

| Antibody administered | PR | CR | Dose MMAF or DM1 (μg/m²) | Dose Ab (mg/kg) | DAR (Drug/Ab) |
|---|---|---|---|---|---|
| Thio Control hu-anti-HER2-HC(A118C)-BMPEO-DM1 | 0/9 | 0/9 | 114 | 4 | 1.86 |
| Thio Control hu-anti-HER2-HC(A118C)-MC-MMAF | 0/9 | 0/9 | 115 | 4 | 1.9 |
| Thio Control hu-anti-HER2-HC(A118C)-MCvcPAB-MMAE | 0/9 | 0/9 | 92 | 4 | 1.55 |
| Control huMA79b.v28-SMCC-DM1 | 1/8 | 1/8 | 202 | 4 | 3.4 |
| Thio huMA79b.v28-HC(A118C)-BMPEO-DM1 | 1/9 | 1/9 | 110 | 4 | 1.85 |
| Thio huMA79b.v28-HC(A118C)-MC-MMAF | 5/9 | 4/9 | 115 | 4 | 1.95 |
| Thio huMA79b.v28-HC(A118C)-MCvcPAB-MMAE | 0/9 | 9/9 | 108 | 4 | 1.87 |
| Thio Control huMA79b.v28-HC(A118C) | 1/9 | 0/9 | NA | 4 | NA |
| Thio Control anti-CD22-HC(A118C)-MC-MMAF | 0/9 | 0/9 | 118 | 4 | 1.96 |

E. BJAB-Luciferase (Burkitt's Lymphoma) Xenografts

In a similar study, using the same xenograft study protocol as disclosed in Example 3, varying the antibody drug conjugates and doses administered, the efficacy of drug conjugates in BJAB-luciferase (Burkitt's Lymphoma) xenografts in CB17 SCID mice was studied. The drug conjugates and doses (administered at day 0 for all ADCs and controls) are shown in Table 15, below.

The control antibody was vehicle (buffer (for ADC) alone). The control HC (A118C) thioMAb was thio hu-anti-HER2-HC(A118C) antibody thioMAb (conjugated to BMPEO-DM1, MCvcPAB-MMAE or MC-MMAF), thio huMA79b.v28-HC(A118C) thioMAb or thio anti-CD22 anti-HER2-HC(A118C)-MCvcPAB-MMAE, thio-anti-HER2-HC(A118C)-MC-MMAF). Other controls included thio huMA79b.v28-HC(A118C) and thio-10F4v3-HC(A118C)-MC-MMAF.

Even further, in Table 15, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm³) are indicated and NA=not applicable. (DAR=Drug to Antibody Ratio)

TABLE 15

In Vivo Tumor Volume Reduction,
Thio HuMA79b.v28-HC(A118C) MMAE, MMAF, and DM1 Conjugate Administration
In BJAB-Luciferase Xenografts in CB17 SCID Mice

| Antibody administered | PR | CR | Dose MMAF, MMAE or DM1 (μg/m²) | Dose Ab (mg/kg) | DAR (Drug/Ab) |
|---|---|---|---|---|---|
| Control vehicle | 0/10 | 0/10 | NA | NA | NA |
| Thio Control hu-anti-HER2-HC(A118C)-BMPEO-DM1 | 0/10 | 1/10 | 57 | 2 | 1.86 |
| Thio Control hu-anti-HER2-HC(A118C)-MCvcPAB-MMAE | 0/10 | 0/10 | 23 | 1 | 1.55 |
| Thio Control hu-anti-HER2-HC(A118C)-MC-MMAF | 0/10 | 0/10 | 29 | 1 | 1.9 |
| Thio huMA79b.v28-HC(A118C)-BMPEO-DM1 | 2/10 | 0/10 | 27 | 1 | 1.85 |
| Thio huMA79b.v28-HC(A118C)-BMPEO-DM1 | 4/10 | 0/10 | 55 | 2 | 1.85 |
| Thio huMA79b.v28-HC(A118C)-MCvcPAB-MMAE | 4/10 | 1/10 | 27 | 1 | 1.9 |
| Thio huMA79b.v28-HC(A118C)-MC-MMAF | 3/8 | 1/8 | 28 | 1 | 1.9 |
| Thio Control huMA79b.v28-HC(A118C) | 0/10 | 0/10 | NA | 1 | NA |
| Thio Control 10F4v3-HC(A118C)-MC-MMAF | 0/10 | 1/10 | 30 | 1 | 1.96 |

10F4v3-HC(A118C) thioMAb (conjugated to MC-MMAF). The results are shown in Table 15, below.

Figure 37:
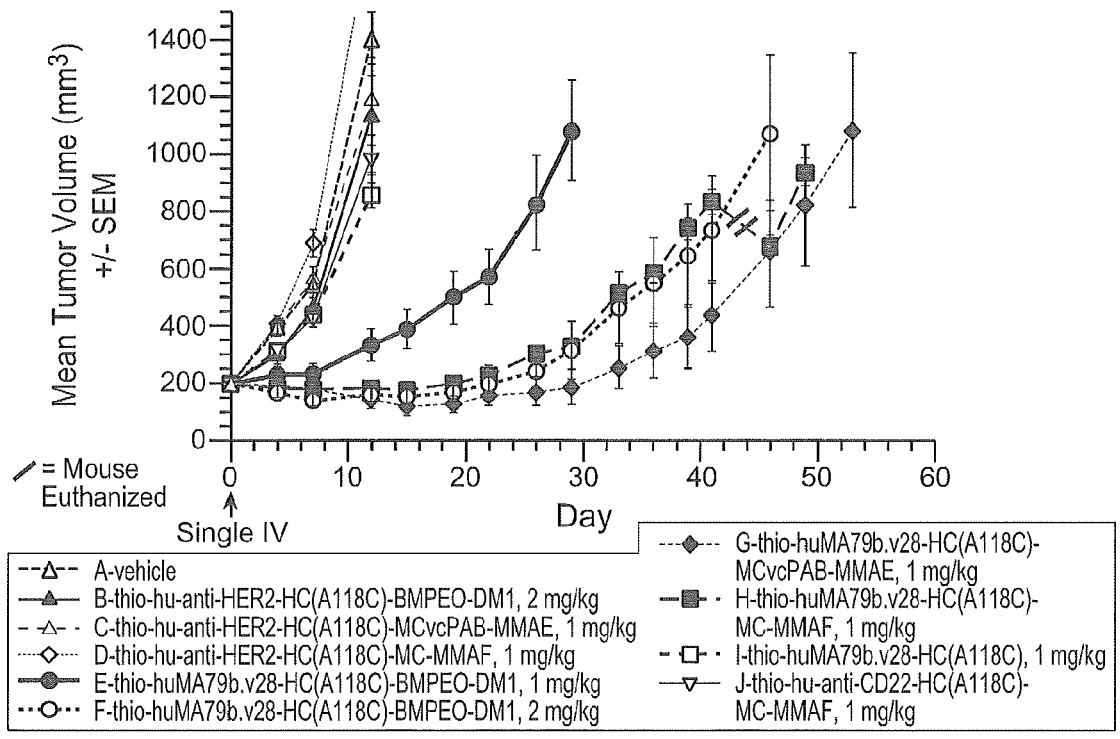
FIG. 37 is a graph of inhibition of in vivo tumor growth in a BJAB-luciferase (Burkitt's Lymphoma) xenograft model which shows that administration of anti-CD79b TDCs conjugated to different linker drug moieties (MCvcPAB-MMAE, BMPEO-DM1 or MC-MMAF) and/or administered at different doses as shown to SCID mice having human B cell tumors, significantly inhibited tumor growth. Xenograft models treated with thio huMA79b.v28-HC(A118C)-BMPEO-DM1, drug load was approximately 1.85 (Table 15), thio huMA79b.v28-HC(A118C)-MCvcPAB-MMAE, drug load was approximately 1.9 (Table 15), or thio huMA79b.v28-HC(A118C)-MC-MMAF, drug load was approximately 1.9 (Table 15) showed a significant inhibition of tumor growth during the study. Controls included vehicle (buffer alone), anti-HER2 controls (thio hu-anti-HER2-HC(A118C)-BMPEO-DM1, thio hu-anti-HER2-HC(A118C)-MC-MMAF, thio hu-anti-HER2-HC(A118C)-MCvcPAB-MMAE), huMA79b.v28 controls (thio huMA79b.v28-HC(A118C)) and anti-CD22 controls (thio hu-anti-CD22(10F4v3)-HC(A118C)-MC-MMAF). "Thio" refers to cysteine-engineered antibody while "hu" refers to humanized antibody.

FIG. 37A is a graph plotting changes in mean tumor volume over time in the BJAB-luciferase xenograft in CB17 SCID mice treated with the heavy chain A118C anti-CD79b TDCs, at doses as shown in Table 15. Specifically, administration of thio huMA79b.v28-HC(A118C)-BMPEO-DM1, thio huMA79b.v28-HC(A118C)-MCvcPAB-MMAE and thio huMA79b.v28-HC(A118C)-MC-MMAF showed inhibition of tumor growth when compared to the negative controls (thio-anti-HER2-HC(A118C)-BMPEO-DM1, thio- F. Granta-519 (Human Mantle Cell Lymphoma) Xenografts In a similar study, using the same xenograft study protocol as disclosed in Example 3 (see above), varying the drug conjugates and doses administered, the efficacy of thioMAb drug conjugates in Granta-519 xenografts (Human Mantle Cell Lymphoma in CB17 SCID mice was studied. The drug conjugates and doses (administered at day 0 for all ADCs and controls) are shown in Table 16, below.

The control HC(A118C) thioMAb was thio hu-anti-HER2-HC(A118C) thioMAb (conjugated to BMPEO-DM1 or MC-MMAF). The results are shown in Table 16 and FIG. 38.

Figure 38A:
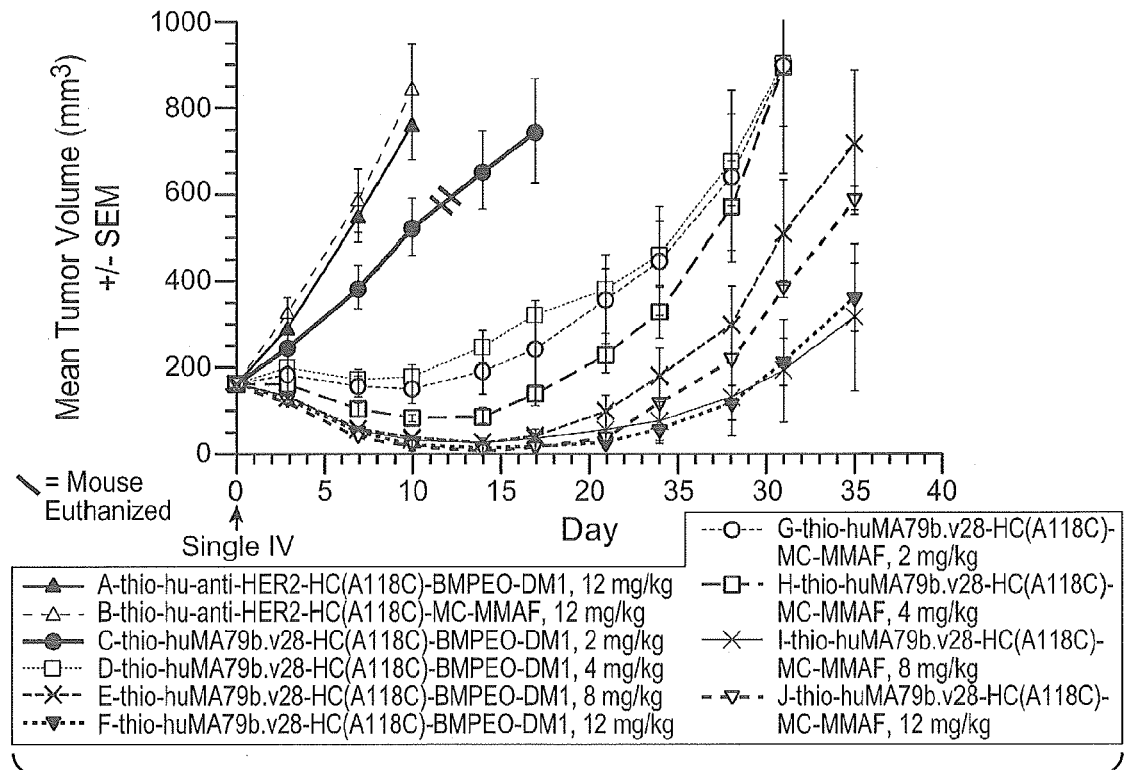
FIG. 38A is a graph of inhibition of in vivo tumor growth in a Granta-619 (Human Mantle Cell Lymphoma) xenograft model which shows that administration of anti-CD79b TDCs conjugated to different linker drug moieties (BMPEO-DM1 or MC-MMAF) and/or administered at different doses as shown to SCID mice having human B cell tumors, significantly inhibited tumor growth. Xenograft models treated with thio huMA79b.v28-HC(A118C)-BMPEO-DM1, drug load was approximately 1.85 (Table 16), or thio huMA79b.v28-HC(A118C)-MC-MMAF, drug load was approximately 1.95 (Table 16), showed significant inhibition of tumor growth during the study. Controls included anti-HER2 controls (thio hu-anti-HER2-HC(A118C)-BMPEO-DM1, thio hu-anti-HER2-HC(A118C)-MC-MMAF).
Figure 38B:
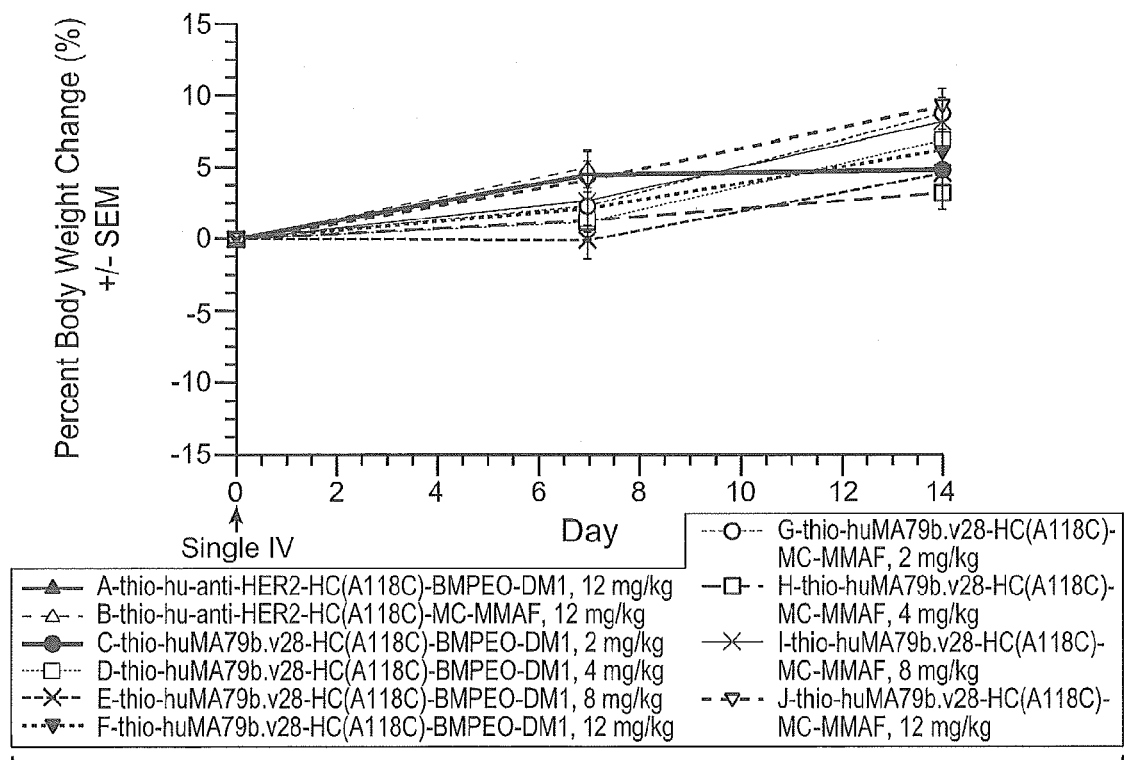
FIG. 38B is a plot of percent weight change in the mice from the Granta-519 xenograft study (FIG. 38A and Table 16) showing that there was no significant change in weight during the first 14 days of the study. "Thio" refers to cysteine-engineered antibody while "hu" refers to humanized antibody.

FIG. 38A is a graph plotting changes in mean tumor volume over time in the Granta 519 xenograft in CB17 SCID mice treated with the heavy chain A118C anti-CD79b TDCs, at doses as shown in Table 16. Specifically, the administration of the thio huMA79b.v28-HC-(A118C)-BMPEO-DM1 and thio huMA79b.v28-HC(A118C)-MC-MMAF thioMAb drug conjugates at the doses shown in Table 16 showed an inhibition in tumor growth when compared to the control drug conjugates.

Further, in the same study, the percent body weight change in the first 14 days was determined in each dosage group. The results (FIG. 38B) indicated administration of these thioMAb drug conjugates did not result in a decrease in percent body weight or cause weight loss during this time.

In Table 16, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm$^3$) are indicated. (DAR=Drug to Antibody Ratio)

TABLE 16

In Vivo Tumor Volume Reduction,
Thio HuMA79b.v28-HC(A118C) DM1 and MMAF Conjugate Administration
In Granta-519 Xenografts in CB17 SCID Mice

| Antibody administered | PR | CR | Dose MMAF or DM1 (μg/m$^2$) | Dose Ab (mg/kg) | DAR (Drug/Ab) |
|---|---|---|---|---|---|
| Thio Control hu-anti-HER2-HC(A118C)-BMPEO-DM1 | 0/8 | 0/8 | 342 | 12 | 1.86 |
| Thio Control hu-anti-HER2-HC(A118C)-MC-MMAF | 0/8 | 0/8 | 346 | 12 | 1.9 |
| Thio huMA79b.v28-HC(A118C)-BMPEO-DM1 | 0/6 | 0/6 | 55 | 2 | 1.85 |
| Thio huMA79b.v28-HC(A118C)-BMPEO-DM1 | 0/8 | 0/8 | 110 | 4 | 1.85 |
| Thio huMA79b.v28-HC(A118C)-BMPEO-DM1 | 4/8 | 4/8 | 219 | 8 | 1.85 |
| Thio huMA79b.v28-HC(A118C)-BMPEO-DM1 | 3/8 | 5/8 | 329 | 12 | 1.85 |
| Thio huMA79b.v28-HC(A118C)-MC-MMAF | 1/8 | 1/8 | 57 | 2 | 1.95 |
| Thio huMA79b.v28-HC(A118C)-MC-MMAF | 2/8 | 1/8 | 115 | 4 | 1.95 |
| Thio huMA79b.v28-HC(A118C)-MC-MMAF | 6/8 | 2/8 | 229 | 8 | 1.95 |
| Thio huMA79b.v28-HC(A118C)-MC-MMAF | 4/8 | 4/8 | 344 | 12 | 1.95 |

G. WSU-DLCL2 (Diffuse Large Cell Lymphoma) Xenografts

In a similar study, using the same xenograft study protocol as disclosed in Example 3 (see above), varying the drug conjugates and doses administered, the efficacy of thioMAb drug conjugates in WSU-DLCL2 xenografts (Diffuse Large Cell Lymphoma) in CB17 SCID mice was studied. The drug conjugates and doses (administered at day 0 for all ADCs and controls) are shown in Table 17, below.

The control antibody was vehicle (buffer (for ADC) alone). The control thio MAbs were thio hu-anti-HER2-HC(A118C) antibody thioMAbs (conjugated to BMPEO-DM1, MCvc-PAB-MMAE or MC-MMAF). The results are shown in Table 17 and FIG. 39.

Figure 39:
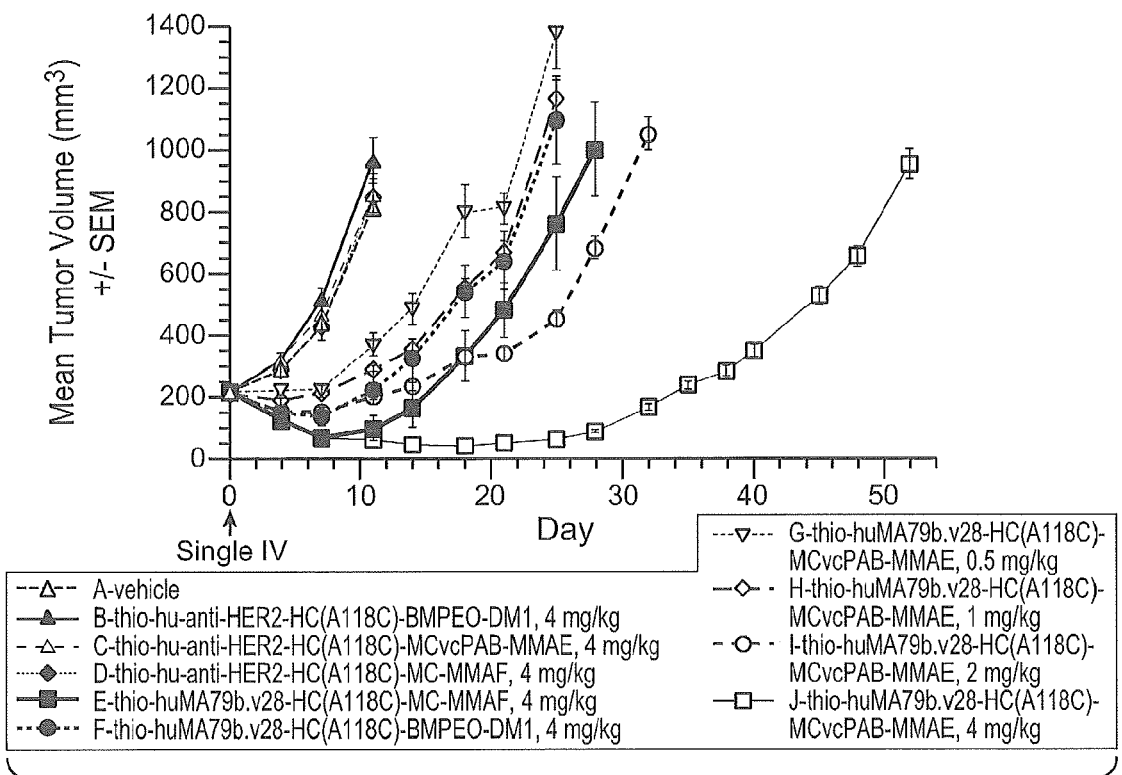
FIG. 39 is a graph of inhibition of in vivo tumor growth in a WSU-DLCL2 (Diffuse Large Cell Lymphoma) xenograft model which shows that administration of anti-CD79b TDCs conjugated to different linker drug moieties (BMPEO-DM1, MC-MMAF or MCvcPAB-MMAE) and/or administered at different doses as shown to SCID mice having human B cell tumors, significantly inhibited tumor growth. Xenograft models treated with thio huMA79b.v28-HC(A118C)-BMPEO-DM1, drug load was approximately 1.85 (Table 17), thio huMA79b.v28-HC(A118C)-MC-MMAF, drug load was approximately 1.9 (Table 17) or thio huMA79b.v28-HC(A118C)-MCvcPAB-MMAE, drug load was approximately 1.9 (Table 17), showed significant inhibition of tumor growth during the study. Controls included vehicle (buffer alone) and anti-HER2 controls (thio hu-anti-HER2-HC(A118C)-BMPEO-DM1, thio hu-anti-HER2-HC(A118C)-MC-MMAF, thio hu-anti-HER2-HC(A118C)-MCvcPAB-MMAE). "Thio" refers to cysteine-engineered antibody while "hu" refers to humanized antibody.

FIG. 39 is a graph plotting changes in mean tumor volume over time in the WSU-DLCL2 xenograft in CB17 SCID mice treated with the heavy chain A118C anti-CD79b TDCs, at doses as shown in Table 17. Specifically, administration of thio huMA79b.v28-HC(A118C)-BMPEO-DM1, thio huMA79b.v28-HC(A118C)-MC-MMAF and thio huMA79b.v28-HC(A118C)-MCvcPAB-MMAE (at Ab dose of 0.5, 1.0 mg/kg, 2.0 mg/kg and 4.0 mg/kg) showed inhibition of tumor growth when compared to the negative controls (thio-hu-anti-HER2-HC(A118C)-BMPEO-DM1, thio-hu-anti-HER2-HC(A118C)-MCvcPAB-MMAE, thio-hu-anti-HER2-HC(A118C)-MC-MMAF and A-vehicle).

Even further, in Table 17, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm$^3$) are indicated and NA=not applicable. (DAR=Drug to Antibody Ratio)

TABLE 17

In Vivo Tumor Volume Reduction,
Thio HuMA79b.v28-HC(A118C) MMAE, MMAF, and DM1 Conjugate Administration
In WSU-DLCL2 Xenografts in CB17 SCID Mice

| Antibody administered | PR | CR | Dose MMAF, MMAE or DM1 ($\mu g/m^2$) | Dose Ab (mg/kg) | DAR (Drug/Ab) |
|---|---|---|---|---|---|
| Control vehicle | 0/9 | 0/9 | NA | NA | NA |
| Thio Control hu-anti-HER2-HC(A118C)-BMPEO-DM1 | 0/9 | 0/9 | 114 | 4 | 1.86 |
| Thio Control hu-anti-HER2-HC(A118C)-MCvcPAB-MMAE | 0/9 | 0/9 | 92 | 4 | 1.55 |
| Thio Control hu-anti-HER2-HC(A118C)-MC-MMAF | 0/9 | 0/9 | 115 | 4 | 1.9 |
| Thio huMA79b.v28-HC(A118C)-MC-MMAF | 5/9 | 2/9 | 112 | 4 | 1.9 |
| Thio huMA79b.v28-HC(A118C)-BMPEO-DM1 | 4/9 | 0/9 | 110 | 4 | 1.85 |
| Thio huMA79b.v28-HC(A118C)-MCvcPAB-MMAE | 1/9 | 0/9 | 14 | 0.5 | 1.9 |
| Thio huMA79b.v28-HC(A118C)-MCvcPAB-MMAE | 0/9 | 0/9 | 27 | 1.0 | 1.9 |
| Thio huMA79b.v28-HC(A118C)-MCvcPAB-MMAE | 2/9 | 1/9 | 55 | 2.0 | 1.9 |
| Thio huMA79b.v28-HC(A118C)-MCvcPAB-MMAE | 1/9 | 7/9 | 110 | 4.0 | 1.9 |

H. Granta-519 (Human Mantle Cell Lymphoma) Xenografts

In a similar study, using the same xenograft study protocol as disclosed in Example 3 (see above), varying the drug conjugates and doses administered, the efficacy of thioMAb drug conjugates in Granta-519 xenografts (Human Mantle Cell Lymphoma) in CB17 SCID mice was studied. The drug conjugates and doses (administered at day 0 for all ADCs and controls) are shown in Table 18, below.

The control thio MAbs were thio hu-anti-HER2-HC (A118C) (conjugated to BMPEO-DM1) and thio hu-anti-HER2-HC(A118C)-MCvcPAB-MMAE antibody thioMAbs. The results are shown in Table 18, below.

Figure 40:
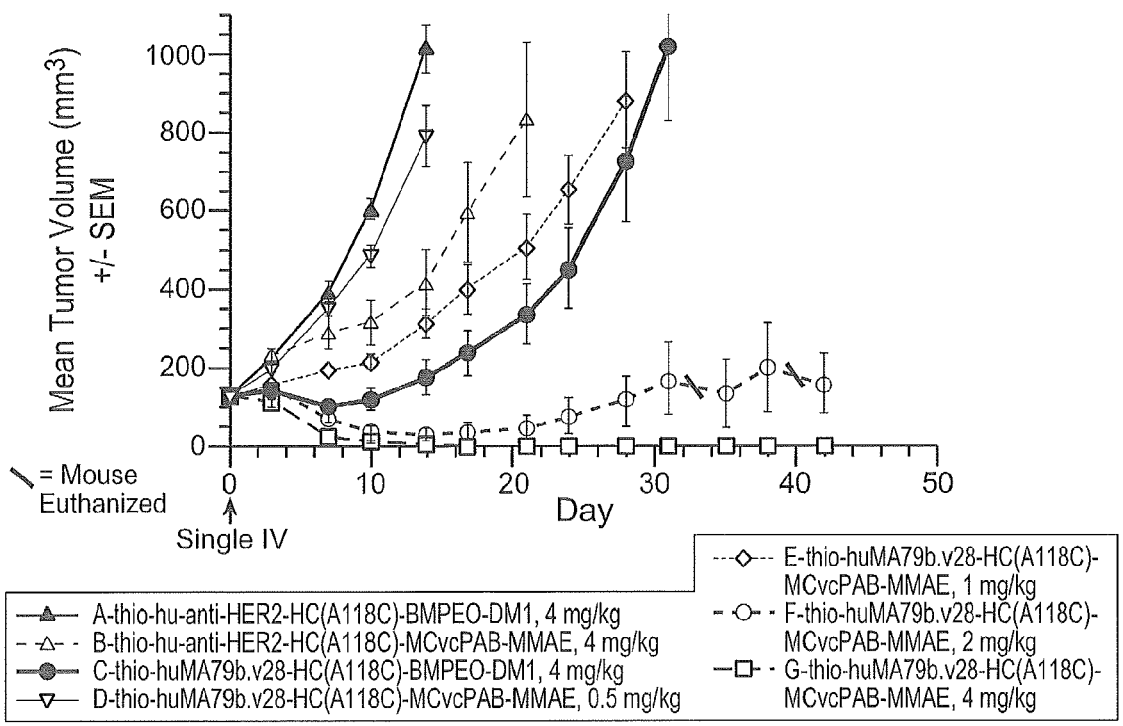
FIG. 40 is a graph of inhibition of in vivo tumor growth in a Granta-519 (Human Mantle Cell Lymphoma) xenograft model which shows that administration of anti-CD79b TDCs conjugated to different linker drug moieties (BMPEO-DM1 or MCvcPAB-MMAE) and/or administered at different doses as shown to SCID mice having human B cell tumors, significantly inhibited tumor growth. Xenograft models treated with thio huMA79b.v28-HC(A118C)-BMPEO-DM1, drug load was approximately 1.85 (Table 18) or thio huMA79b.v28-HC(A118C)-MCvcPAB-MMAE, drug load was approximately 1.87 (Table 18), showed significant inhibition of tumor growth during the study. Controls included anti-HER2 controls (thio hu-anti-HER2-HC(A118C)-BMPEO-DM1, thio hu-anti-HER2-HC(A118C)-MCvcPAB-MMAE). "Thio" refers to cysteine-engineered antibody while "hu" refers to humanized antibody.

FIG. 40A is a graph plotting changes in mean tumor volume over time in the Granta-519 xenograft in CB17 SCID mice treated with the heavy chain A118C anti-CD79b TDCs, at doses as shown in Table 18. Specifically, administration of thio huMA79b.v28-HC(A118C)-BMPEO-DM1 and thio huMA79b.v28-HC(A118C)-MCvcPAB-MMAE (at Ab dose of 1.0 mg/kg, 2.0 mg/kg and 4.0 mg/kg) showed inhibition of tumor growth when compared to the negative controls (thio-anti-HER2-HC(A118C)-BMPEO-DM1 and thio-anti-HER2-HC(A118C)-MCvcPAB-MMAE.

Even further, in Table 18, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 $mm^3$) are indicated and NA=not applicable. (DAR=Drug to Antibody Ratio)

TABLE 18

In Vivo Tumor Volume Reduction,
Thio HuMA79b.v28-HC(A118C) DM1 and MMAE Conjugate Administration
In Granta-519 Xenografts in CB17 SCID Mice

| Antibody administered | PR | CR | Dose MMAF, MMAE or DM1 ($\mu g/m^2$) | Dose Ab (mg/kg) | DAR (Drug/Ab) |
|---|---|---|---|---|---|
| Thio Control hu-anti-HER2-HC(A118C)-BMPEO-DM1 | 0/10 | 0/10 | 114 | 4 | 1.86 |
| Thio Control hu-anti-HER2-HC(A118C)-MCvcPAB-MMAE | 2/10 | 1/10 | 92 | 4 | 1.55 |
| Thio huMA79b.v28-HC(A118C)-BMPEO-DM1 | 3/10 | 0/10 | 110 | 4 | 1.85 |
| Thio huMA79b.v28-HC(A118C)-MCvcPAB-MMAE | 0/10 | 1/10 | 13 | 0.5 | 1.87 |
| Thio huMA79b.v28-HC(A118C)-MCvcPAB-MMAE | 1/10 | 0/10 | 27 | 1.0 | 1.87 |
| Thio huMA79b.v28-HC(A118C)-MCvcPAB-MMAE | 1/10 | 7/10 | 54 | 2.0 | 1.87 |
| Thio huMA79b.v28-HC(A118C)-MCvcPAB-MMAE | 0/10 | 10/10 | 108 | 4.0 | 1.87 |

I. BJAB-CynoCD79b Xenografts

In a similar study, using the same xenograft study protocol as disclosed in Example 3 (see above), varying the drug conjugates and doses administered, the efficacy of thioMAb drug conjugates in BJAB (Burkitt's Lymphoma) cells expressing cynoCD79b (BJAB-cynoCD79b) xenografts in CB17 SCID was studied. The drug conjugates and doses (administered at day 0 for all ADCs and controls) are shown in Table 18, below.

The control Ab was vehicle (buffer alone). The control thio MAbs were thio-hu-anti-HER2-HC(A118C)-BMPEO-DM1, thio-hu-anti-HER2-HC(A118C)-MC-MMAF and thio-hu-anti-HER2-HC(A118C)-MCvcPAB-MMAE antibody thioMAbs. The results are shown in Table 19 and FIG. 50.

Figure 50:
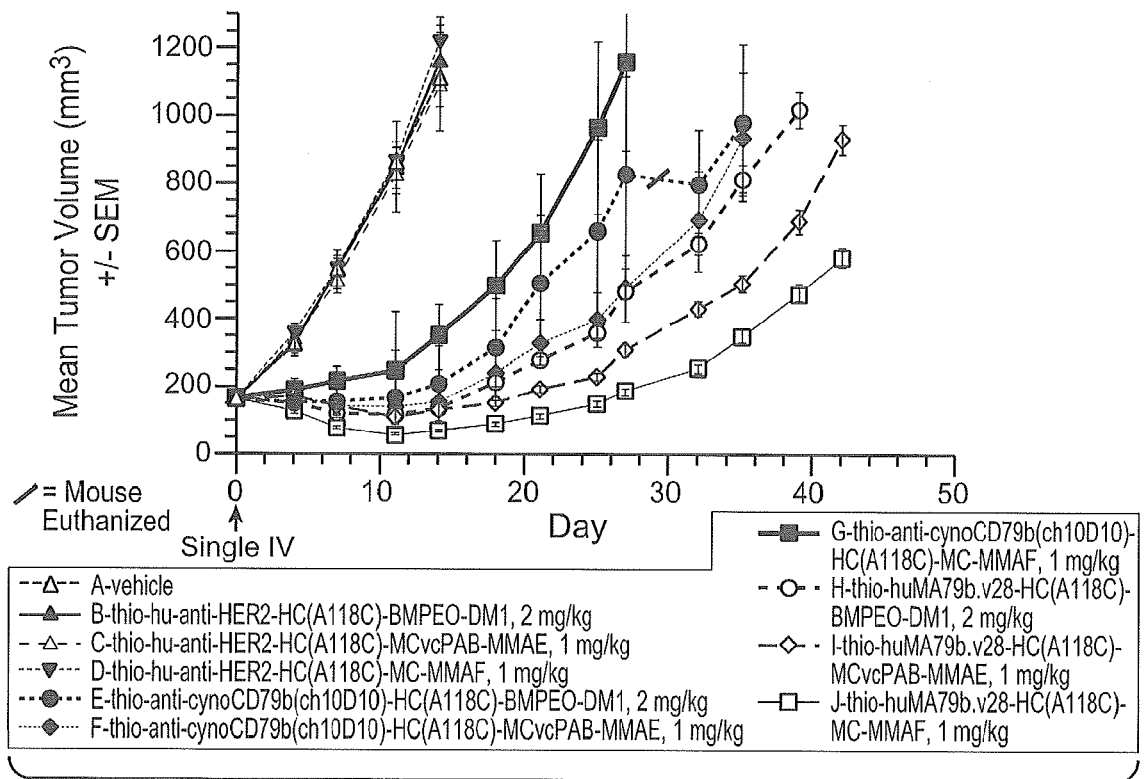
FIG. 50 is a graph of inhibition of in vivo tumor growth in a BJAB-cynoCD79b (BJAB cells expressing cynoCD79b) (Burkitt's Lymphoma) xenograft model which shows that administration of anti-CD79b TDCs conjugated to different linker drug moieties (BMPEO-DM1, MC-MMAF or MCvc-PAB-MMAE) to SCID mice having human B cell tumors, significantly inhibited tumor growth. Xenograft models treated with thio huMA79b.v28-HC(A118C)-BMPEO-DM1, drug load was approximately 1.85 (Table 19), thio huMA79b.v28-HC(A118C)-MC-MMAF, drug load was approximately 1.9 (Table 19), or thio huMA79b.v28-HC(A118C)-MCvcPAB-MMAE, drug load was approximately 1.9 (Table 19), thio anti-cyno CD79b (ch10D10)-HC(A118C)-BMPEO-DM1, drug load was approximately 1.8 (Table 19), thio anti-cyno CD79b (ch10D10)-HC(A118C)-MC-MMAF, drug load was approximately 1.9 (Table 19) or thio anti-cyno CD79b (ch10D10)-HC(A118C)-MCvcPAB-MMAE, drug load was approximately 1.86 (Table 19), showed significant inhibition of tumor growth during the study. Controls included anti-HER2 controls (thio hu-anti-HER2-HC(A118C)-BMPEO-DM1, thio hu-anti-HER2-HC(A118C)-MCvcPAB-MMAE, thio hu-anti-HER2-HC(A118C)-MC-MMAF). "Thio" refers to cysteine-engineered antibody while "hu" refers to humanized antibody.

FIG. 50 is a graph plotting inhibition of tumor growth over time in the BJAB-cynoCD79b xenograft in CB17 SCID mice treated with the heavy chain A118C anti-CD79b TDCs, at doses as shown in Table 19. Specifically, Administration of thio huMA79b.v28-HC(A118C)-BMPEO-DM1, thio huMA79b.v28-HC(A118C)-MCvcPAB-MMAE and thio huMA79b.v28-HC(A118C)-MC-MMAF as well as thio-anti-cynoCD79b(ch10D10)-HC(A118C)-BMPEO-DM1, thio-anti-cynoCD79b(ch10D10)-HC(A118C)-MCvcPAB-MMAE and thio-anti-cynoCD79b(ch10D10)-HC(A118C)-MC-MMAF showed inhibition of tumor growth when compared to the negative controls (thio-anti-HER2-HC(A118C)-BMPEO-DM1, thio-anti-HER2-HC(A118C)-MCvcPAB-MMAE and thio-anti-HER2-HC(A118C)-MC-MMAF and A-vehicle).

Even further, in Table 19, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm$^3$) are indicated and NA=not applicable. (DAR=Drug to Antibody Ratio)

TABLE 19

In Vivo Tumor Volume Reduction,
Thio anti-cyno CD79b(ch10D10)-HC(A118C) DM1, MMAF or MMAE or
Thio HuMA79b.v28 DM1, MMAF or MMAE Conjugate Administration
In BJAB-cynoCD79b Xenografts in CB17 SCID Mice

| Antibody administered | PR | CR | Dose MMAF, MMAE or DM1 (μg/m²) | Dose Ab (mg/kg) | DAR (Drug/Ab) |
|---|---|---|---|---|---|
| Control vehicle | 0/9 | 0/9 | NA | NA | NA |
| Thio Control hu-anti-HER2-HC(A118C)-BMPEO-DM1 | 0/9 | 0/9 | 57 | 2 | 1.86 |
| Thio Control hu-anti-HER2-HC(A118C)-MCvcPAB-MMAE | 0/9 | 0/9 | 23 | 1 | 1.55 |
| Thio Control hu-anti-HER2-HC(A118C)-MC-MMAF | 0/9 | 0/9 | 29 | 1 | 1.9 |
| Thio anti-cynoCD79b(ch10D10)-HC(A118C)-BMPEO-DM1 | 3/8 | 1/8 | 53 | 2 | 1.8 |
| Thio anti-cynoCD79b(ch10D10)-HC(A118C)-MCvcPAB-MMAE | 1/9 | 2/9 | 27 | 1 | 1.86 |
| Thio anti-cynoCD79b(ch10D10)-HC(A118C)-MC-MMAF | 0/9 | 1/9 | 28 | 1 | 1.9 |
| Thio huMA79b.v28-HC(A118C)-BMPEO-DM1 | 3/9 | 0/9 | 55 | 2 | 1.85 |
| Thio huMA79b.v28-HC(A118C)-MCvcPAB-MMAE | 2/9 | 2/9 | 27 | 1 | 1.9 |
| Thio huMA79b.v28-HC(A118C)-MC-MMAF | 7/9 | 1/9 | 28 | 1 | 1.9 |

J. BJAB-CynoCD79b Xenografts

In a similar study, using the same xenograft study protocol as disclosed in Example 3 (see above), varying the drug conjugates and doses administered, the efficacy of thioMAb drug conjugates in BJAB (Burkitt's Lymphoma) expressing cynoCD79b (BJAB cynoCD79b) xenograft in CB17 SCID mice was studied. The drug conjugates and doses (administered at day 0 for all ADCs and controls) are shown in Table 19, below.

The control thio MAbs was thio-hu-anti-HER2-HC(A118C)-BMPEO-DM1, thio-huMA79b.v28-HC(A118C), and thio-anti-cynoCD79b(ch10D10)-HC(A118C) antibody thioMAbs. The results are shown in Table 20 and FIG. 51.

Figure 51:
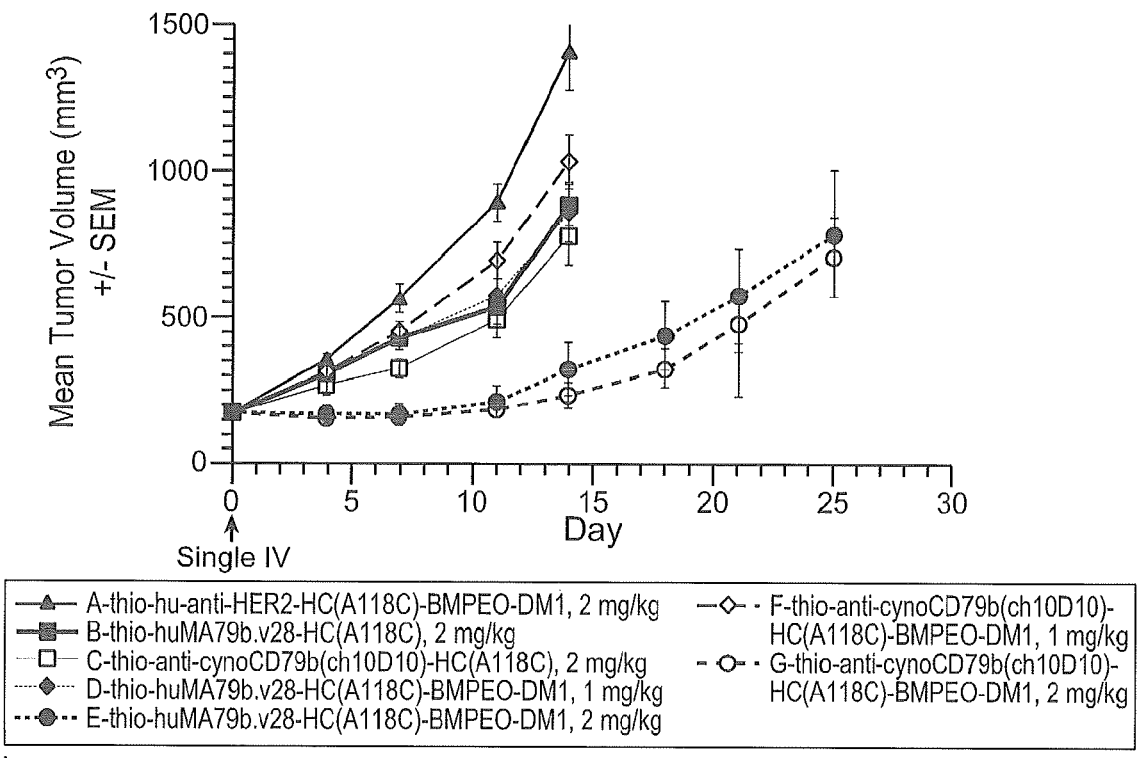
FIG. 51 is a graph of inhibition of in vivo tumor growth in a BJAB-cynoCD79b (BJAB cells expressing cynoCD79b) (Burkitt's Lymphoma) xenograft model which shows that administration of anti-CD79b TDCs with BMPEO-DM1 linker drug moiety administered at different doses as shown, to SCID mice having human B cell tumors, significantly inhibited tumor growth. Xenograft models treated with thio huMA79b.v28-HC(A118C)-BMPEO-DM1, drug load was approximately 1.85 (Table 20) or thio anti-cyno (ch10D10)-HC(A118C)-BMPEO-DM1, drug load was approximately 1.8 (Table 20), showed significant inhibition of tumor growth during the study. Controls included anti-HER2 controls (thio hu-anti-HER2-HC(A118C)-BMPEO-DM1) and huMA79b.v28 controls (thio huMA79b.v28-HC(A118C) and anti-cynoCD79b(ch10D10) controls (thio anti-cunoCD79b(ch10D10)-HC(A118C)). "Thio" refers to cysteine-engineered antibody while "hu" refers to humanized antibody.

FIG. 51 is a graph plotting inhibition of tumor growth over time in the BJAB-cynoCD79b xenograft in CB17 SCID mice treated with the heavy chain A118C anti-CD79b TDCs, at doses as shown in Table 20. Specifically, administration of thio huMA79b.v28-HC(A118C)-BMPEO-DM1 as well as thio-anti-cynoCD79b(ch10D10)-HC(A118C)-BMPEO-DM1 showed inhibition of tumor growth when compared to the negative controls (thio-anti-HER2-HC(A118C)-BMPEO-DM1. Other controls included thio-hu-MA79b.v28-HC(A118C) and thio-anti-cynoCD79b(ch10D10)-HC(A118C).

The results are shown in Table 20, below. In Table 20, the number of mice out of the total number tested showing PR=Partial Regression (where the tumor volume at any time after administration dropped below 50% of the tumor volume measured at day 0) or CR=Complete Remission (where the tumor volume at any time after administration dropped to 0 mm$^3$) are indicated and NA=not applicable. (DAR=Drug to Antibody Ratio)

TABLE 20

In Vivo Tumor Volume Reduction,
Thio anti-cyno CD79b(ch10D10)-HC(A118C) DM1 or Thio
HuMA79b.v28-HC(A118C) DM1 Conjugate Administration
In BJAB-cynoCD79b Xenografts in CB17 SCID Mice

| Antibody administered | PR | CR | Dose MMAF, MMAE or DM1 (μg/m²) | Dose Ab (mg/kg) | DAR (Drug/Ab) |
|---|---|---|---|---|---|
| Thio Control hu-anti-HER2-HC(A118C)-BMPEO-DM1 | 0/10 | 0/10 | 57 | 2 | 1.86 |
| Thio Control huMA79b.v28-HC(A118C) | 0/10 | 0/10 | NA | 2 | NA |
| Thio Control anti-cynoCD79b(ch10D10)-HC(A118C) | 0/10 | 0/10 | NA | 2 | NA |
| Thio huMA79b.v28-HC(A118C)-BMPEO-DM1 | 1/10 | 0/10 | 27 | 1 | 1.85 |
| Thio huMA79b.v28-HC(A118C)-BMPEO-DM1 | 0/10 | 2/10 | 55 | 2 | 1.85 |
| Thio anti-cynoCD79b(ch10D10)-HC(A118C)-BMPEO-DM1 | 0/10 | 0/10 | 27 | 1 | 1.8 |
| Thio anti-cynoCD79b(ch10D10)-HC(A118C)-BMPEO-DM1 | 0/10 | 1/10 | 53 | 2 | 1.8 |

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An immunoconjugate comprising an anti-CD79b antibody comprising:
    (i) an HVR-L1 sequence of KASQSVDYEGDSFLN (SEQ ID NO: 194)
    (ii) an HVR-L2 sequence of AASNLES (SEQ ID NO: 195)
    (iii) an HVR-L3 sequence of QQSNEDPLT (SEQ ID NO: 196)
    (iv) an HVR-H1 sequence of GYTFSSYWIE (SEQ ID NO: 202)
    (v) an HVR-H2 sequence of GEILPGGGDTNYNEIFKG (SEQ ID NO: 203), and
    (vi) an HVR-H3 sequence of TRRVPIRLDY (SEQ ID NO: 204),
    wherein said antibody is covalently attached to a cytotoxic agent.

2. The immunoconjugate of claim 1, wherein the cytotoxic agent is selected from a toxin, a chemotherapeutic agent, a drug moiety, an antibiotic, a radioactive isotope and a nucleolytic enzyme.

3. The immunoconjugate of claim 2, wherein the immunoconjugate having the formula Ab-(L-D)p, wherein:
    (a) Ab is an anti-CD79b antibody comprising:
        (i) an HVR-L1 sequence of KASQSVDYEGDSFLN (SEQ ID NO: 194)
        (ii) an HVR-L2 sequence of AASNLES (SEQ ID NO: 195)
        (iii) an HVR-L3 sequence of QQSNEDPLT (SEQ ID NO: 196)
        (iv) an HVR-H1 sequence of GYTFSSYWIE (SEQ ID NO: 202)
        (v) an HVR-H2 sequence of GEILPGGGDTNYNEIFKG (SEQ ID NO: 203), and
        (vi) an HVR-H3 sequence of TRRVPIRLDY (SEQ ID NO: 204);
    (b) L is a linker;
    (c) D is a drug moiety; and
    (d) p ranges from about 1 to 8.

4. The immunoconjugate of claim 3, wherein L is selected from 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl)cyclohexane-1 carboxylate (SMCC), and N-Succinimidyl (4-iodo-acetyl)aminobenzoate (SIAB).

5. The immunoconjugate of claim 3, wherein D is selected from an auristatin and dolostatin.

6. The immunoconjugate of claim 3, wherein L has Formula II:

$$-A_a\text{-}W_w\text{—}Y_y\text{—}$$

wherein:
A is a Stretcher unit,
a is 0 or 1,
each W is independently an Amino Acid unit,
w is an integer ranging from 0 to 12,
Y is a Spacer unit, and
y is 0, 1 or 2,
p ranges from 1 to 20, and
D is a drug moiety of Formula $D_E$:

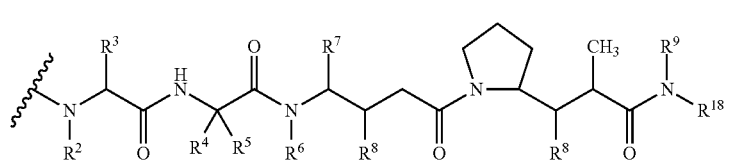

wherein the wavy line of $D_E$ indicates the covalent attachment site to A, W, or Y, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl; and $R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle).

7. The immunoconjugate of claim 6, having the formula:

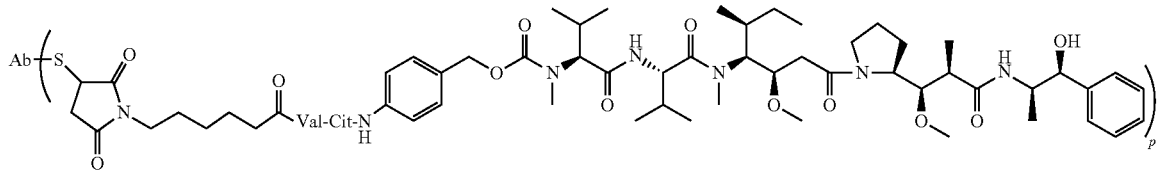

Ab-MC-vc-PAB-MMAE wherein Val is valine, and Cit is citrulline.

8. A pharmaceutical composition comprising the immunoconjugate of claim 3 or 6 and a pharmaceutically acceptable carrier.

* * * * *

```
                        SEQUENCE LISTING

<160> NUMBER OF SEQ ID NOS: 310

<210> SEQ ID NO 1
<211> LENGTH: 1270
<212> TYPE: DNA
<213> ORGANISM: Homo sapiens

<400> SEQUENCE: 1
caggggacag gctgcagccg gtgcagttac acgttttcct ccaaggagcc            50
tcggacgttg tcacgggttt ggggtcgggg acagagcagt gaccatggcc           100
aggctggcgt tgtctcctgt gcccagccac tggatggtgg cgttgctgct           150
gctgctctca gctgagccag taccagcagc cagatcggag gaccggtacc           200
ggaatcccaa aggtagtgct tgttcgcgga tctggcagag cccacgtttc           250
atagccagga aacggggctt cacggtgaaa atgcactgct acatgaacag           300
cgcctccggc aatgtgagct ggctctggaa gcaggagatg gacgagaatc           350
cccagcagct gaagctggaa aagggccgca tggaagagtc ccagaacgaa           400
tctctcgcca ccctcaccat ccaaggcatc cggtttgagg acaatggcat           450
ctacttctgt cagcagaagt gcaacaacac ctcggaggtc taccagggct           500
gcggcacaga gctgcgagtc atgggattca gcaccttggc acagctgaag           550
cagaggaaca cgctgaagga tggtatcatc atgatccaga cgctgctgat           600
catcctcttc atcatcgtgc ctatcttcct gctgctggac aaggatgaca           650
gcaaggctgg catggaggaa gatcacacct acgagggcct ggacattgac           700
cagacagcca cctatgagga catagtgacg ctgcggacag gggaagtgaa           750
gtggtctgta ggtgagcacc caggccagga gtgagagcca ggtcgcccca           800
```

-continued

```
tgacctgggt gcaggctccc tggcctcagt gactgcttcg gagctgcctg        850
gctcatggcc caaccccttt cctggacccc ccagctggcc tctgaagctg        900
gcccaccaga gctgccattt gtctccagcc cctggtcccc agctcttgcc        950
aaagggcctg gagtagaagg acaacagggc agcaacttgg agggagttct       1000
ctggggatgg acgggaccca gccttctggg ggtgctatga ggtgatccgt       1050
ccccacacat gggatggggg aggcagagac tggtccagag cccgcaaatg       1100
gactcggagc cgagggcctc ccagcagagc ttgggaaggg ccatggaccc       1150
aactgggccc cagaagagcc acaggaacat cattcctctc ccgcaaccac       1200
tcccacccca gggaggccct ggcctccagt gccttccccc gtggaataaa       1250
cggtgtgtcc tgagaaacca                                        1270
```

<210> SEQ ID NO 2
<211> LENGTH: 229
<212> TYPE: PRT
<213> ORGANISM: Homo sapiens

<400> SEQUENCE: 2

```
Met Ala Arg Leu Ala Leu Ser Pro Val Pro Ser His Trp Met Val
 1               5                  10                  15

Ala Leu Leu Leu Leu Ser Ala Glu Pro Val Pro Ala Ala Arg
                20                  25                  30

Ser Glu Asp Arg Tyr Arg Asn Pro Lys Gly Ser Ala Cys Ser Arg
                35                  40                  45

Ile Trp Gln Ser Pro Arg Phe Ile Ala Arg Lys Arg Gly Phe Thr
                50                  55                  60

Val Lys Met His Cys Tyr Met Asn Ser Ala Ser Gly Asn Val Ser
                65                  70                  75

Trp Leu Trp Lys Gln Glu Met Asp Glu Asn Pro Gln Gln Leu Lys
                80                  85                  90

Leu Glu Lys Gly Arg Met Glu Glu Ser Gln Asn Glu Ser Leu Ala
                95                 100                 105

Thr Leu Thr Ile Gln Gly Ile Arg Phe Glu Asp Asn Gly Ile Tyr
               110                 115                 120

Phe Cys Gln Gln Lys Cys Asn Asn Thr Ser Glu Val Tyr Gln Gly
               125                 130                 135

Cys Gly Thr Glu Leu Arg Val Met Gly Phe Ser Thr Leu Ala Gln
               140                 145                 150

Leu Lys Gln Arg Asn Thr Leu Lys Asp Gly Ile Ile Met Ile Gln
               155                 160                 165

Thr Leu Leu Ile Ile Leu Phe Ile Ile Val Pro Ile Phe Leu Leu
               170                 175                 180

Leu Asp Lys Asp Asp Ser Lys Ala Gly Met Glu Glu Asp His Thr
               185                 190                 195

Tyr Glu Gly Leu Asp Ile Asp Gln Thr Ala Thr Tyr Glu Asp Ile
               200                 205                 210

Val Thr Leu Arg Thr Gly Glu Val Lys Trp Ser Val Gly Glu His
               215                 220                 225

Pro Gly Gln Glu
```

<210> SEQ ID NO 3
<211> LENGTH: 929
<212> TYPE: DNA

<213> ORGANISM: Artificial sequence
<220> FEATURE:
<223> OTHER INFORMATION: Light Chain of Chimeric Antibody (chMA79b)

<400> SEQUENCE: 3

```
cactcccagc tccaactgca cctcggttct atcgattgaa ttccaccatg        50
ggatggtcat gtatcatcct ttttctagta gcaactgcaa ctggagtaca       100
ttcagatatc gtgctgaccc aatctccagc ttctttggct gtgtctctgg       150
ggcagagggc caccatctcc tgcaaggcca gccaaagtgt tgattatgat       200
ggtgatagtt ttttgaactg gtaccaacag aaaccaggac agccacccaa       250
actcttcatc tatgctgcat ccaatctaga atctgggatc ccagccaggt       300
ttagtggcag tgggtctggg acagacttca ccctcaacat ccatcctgtg       350
gaggaggagg atgctgcaac ctattactgt cagcaaagta atgaggatcc       400
gctcacgttc ggggcaggca ccgagctgga actcaaacgg accgtggctg       450
caccatctgt cttcatcttc cgccatctg atgagcagtt gaaatctgga        500
actgcctctg ttgtgtgcct gctgaataac ttctatccca gagaggccaa       550
agtacagtgg aaggtggata acgccctcca atcgggtaac tcccaggaga       600
gtgtcacaga gcaggacagc aaggacagca cctacagcct cagcagcacc       650
ctgacgctga gcaaagcaga ctacgagaaa cacaaagtct acgcctgcga       700
agtcacccat cagggcctga gctcgcccgt cacaaagagc ttcaacaggg       750
gagagtgtta agcttggccg ccatggccca acttgtttat tgcagcttat       800
aatggttaca ataaagcaa tagcatcaca aatttcacaa ataaagcatt        850
tttttcactg cattctagtt gtggtttgtc caaactcatc aatgtatctt       900
atcatgtctg gatcgggaat taattcggc                              929
```

<210> SEQ ID NO 4
<211> LENGTH: 218
<212> TYPE: PRT
<213> ORGANISM: Artificial sequence
<220> FEATURE:
<223> OTHER INFORMATION: Light Chain of Chimeric Antibody (chMA79b)

<400> SEQUENCE: 4

```
Asp Ile Val Leu Thr Gln Ser Pro Ala Ser Leu Ala Val Ser Leu
  1               5                  10                  15

Gly Gln Arg Ala Thr Ile Ser Cys Lys Ala Ser Gln Ser Val Asp
                 20                  25                  30

Tyr Asp Gly Asp Ser Phe Leu Asn Trp Tyr Gln Gln Lys Pro Gly
                 35                  40                  45

Gln Pro Pro Lys Leu Phe Ile Tyr Ala Ala Ser Asn Leu Glu Ser
                 50                  55                  60

Gly Ile Pro Ala Arg Phe Ser Gly Ser Gly Ser Gly Thr Asp Phe
                 65                  70                  75

Thr Leu Asn Ile His Pro Val Glu Glu Glu Asp Ala Ala Thr Tyr
                 80                  85                  90

Tyr Cys Gln Gln Ser Asn Glu Asp Pro Leu Thr Phe Gly Ala Gly
                 95                 100                 105

Thr Glu Leu Glu Leu Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135
```

```
Val Val Cys Leu Leu Asn Asn Phe Tyr Pro Arg Glu Ala Lys Val
            140                 145                 150

Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
            170                 175                 180

Ser Thr Leu Thr Leu Ser Lys Ala Asp Tyr Glu Lys His Lys Val
            185                 190                 195

Tyr Ala Cys Glu Val Thr His Gln Gly Leu Ser Ser Pro Val Thr
            200                 205                 210

Lys Ser Phe Asn Arg Gly Glu Cys
            215

<210> SEQ ID NO 5
<211> LENGTH: 1469
<212> TYPE: DNA
<213> ORGANISM: Artificial sequence
<220> FEATURE:
<223> OTHER INFORMATION: Heavy Chain of Chimeric Antibody (chMA79b)

<400> SEQUENCE: 5
```

| | | | |
|---|---|---|---|
| tcggttctat cgattgaatt ccaccatggg atggtcatgt atcatccttt | 50 |
| ttctagtagc aactgcaact ggagtacatt cagaagttca gctgcagcag | 100 |
| tctggggctg aactgatgaa gcctggggcc tcagtgaaga tatcctgcaa | 150 |
| ggctactggc tacacattca gtagttactg gatagagtgg gtaaagcaga | 200 |
| ggcctggaca tggccttgag tggattggag agattttacc tggaggtggt | 250 |
| gatactaact acaatgagat tttcaagggc aaggccacat tcactgcaga | 300 |
| tacatcctcc aacacagcct acatgcaact cagcagcctg acatctgagg | 350 |
| actctgccgt ctattactgt acaagacgag taccggttta cttttgactac | 400 |
| tggggccaag gaacctcagt caccgtctcc tcagcctcca ccaagggccc | 450 |
| atcggtcttc cccctggcac cctcctccaa gagcacctct gggggcacag | 500 |
| cggccctggg ctgcctggtc aaggactact tccccgaacc ggtgacggtg | 550 |
| tcgtggaact caggcgccct gaccagcggc gtgcacacct tcccggctgt | 600 |
| cctacagtcc tcaggactct actccctcag cagcgtggtg actgtgccct | 650 |
| ctagcagctt gggcacccag acctacatct gcaacgtgaa tcacaagccc | 700 |
| agcaacacca aggtggacaa gaaagttgag cccaaatctt gtgacaaaac | 750 |
| tcacacatgc ccaccgtgcc cagcacctga actcctgggg ggaccgtcag | 800 |
| tcttcctctt ccccccaaaa cccaaggaca cctcatgat ctcccggacc | 850 |
| cctgaggtca catgcgtggt ggtggacgtg agccacgaag accctgaggt | 900 |
| caagttcaac tggtacgtgg acggcgtgga ggtgcataat gccaagacaa | 950 |
| agccgcggga ggagcagtac aacagcacgt accgtgtggt cagcgtcctc | 1000 |
| accgtcctgc accaggactg gctgaatggc aaggagtaca agtgcaaggt | 1050 |
| ctccaacaaa gccctcccag cccccatcga gaaaaccatc tccaaagcca | 1100 |
| aagggcagcc ccgagaacca caggtgtaca ccctgccccc atcccgggaa | 1150 |
| gagatgacca agaaccaggt cagcctgacc tgcctggtca aaggcttcta | 1200 |
| tcccagcgac atcgccgtgg agtgggagag caatgggcag ccggagaaca | 1250 |
| actacaagac cacgcctccc gtgctggact ccgacggctc cttcttcctc | 1300 |

```
tacagcaagc tcaccgtgga caagagcagg tggcagcagg ggaacgtctt              1350
ctcatgctcc gtgatgcatg aggctctgca caaccactac acgcagaaga              1400
gcctctccct gtctccgggt aaatgagtgc gacggcccta gagtcgacct              1450
gcagaagctt  ggccgccat                                              1469

<210> SEQ ID NO 6
<211> LENGTH: 446
<212> TYPE: PRT
<213> ORGANISM: Artificial sequence
<220> FEATURE:
<223> OTHER INFORMATION: Heavy Chain of Chimeric Antibody (chMA79b)

<400> SEQUENCE: 6
```

Glu Val Gln Leu Gln Gln Ser Gly Ala Glu Leu Met Lys Pro Gly
 1               5                  10                  15

Ala Ser Val Lys Ile Ser Cys Lys Ala Thr Gly Tyr Thr Phe Ser
                20                  25                  30

Ser Tyr Trp Ile Glu Trp Val Lys Gln Arg Pro Gly His Gly Leu
                35                  40                  45

Glu Trp Ile Gly Glu Ile Leu Pro Gly Gly Gly Asp Thr Asn Tyr
                50                  55                  60

Asn Glu Ile Phe Lys Gly Lys Ala Thr Phe Thr Ala Asp Thr Ser
                65                  70                  75

Ser Asn Thr Ala Tyr Met Gln Leu Ser Ser Leu Thr Ser Glu Asp
                80                  85                  90

Ser Ala Val Tyr Tyr Cys Thr Arg Arg Val Pro Val Tyr Phe Asp
                95                 100                 105

Tyr Trp Gly Gln Gly Thr Ser Val Thr Val Ser Ser Ala Ser Thr
               110                 115                 120

Lys Gly Pro Ser Val Phe Pro Leu Ala Pro Ser Ser Lys Ser Thr
               125                 130                 135

Ser Gly Gly Thr Ala Ala Leu Gly Cys Leu Val Lys Asp Tyr Phe
               140                 145                 150

Pro Glu Pro Val Thr Val Ser Trp Asn Ser Gly Ala Leu Thr Ser
               155                 160                 165

Gly Val His Thr Phe Pro Ala Val Leu Gln Ser Ser Gly Leu Tyr
               170                 175                 180

Ser Leu Ser Ser Val Val Thr Val Pro Ser Ser Ser Leu Gly Thr
               185                 190                 195

Gln Thr Tyr Ile Cys Asn Val Asn His Lys Pro Ser Asn Thr Lys
               200                 205                 210

Val Asp Lys Lys Val Glu Pro Lys Ser Cys Asp Lys Thr His Thr
               215                 220                 225

Cys Pro Pro Cys Pro Ala Pro Glu Leu Leu Gly Gly Pro Ser Val
               230                 235                 240

Phe Leu Phe Pro Pro Lys Pro Lys Asp Thr Leu Met Ile Ser Arg
               245                 250                 255

Thr Pro Glu Val Thr Cys Val Val Val Asp Val Ser His Glu Asp
               260                 265                 270

Pro Glu Val Lys Phe Asn Trp Tyr Val Asp Gly Val Glu Val His
               275                 280                 285

Asn Ala Lys Thr Lys Pro Arg Glu Glu Gln Tyr Asn Ser Thr Tyr
               290                 295                 300

Arg Val Val Ser Val Leu Thr Val Leu His Gln Asp Trp Leu Asn

```
                    305                 310                 315
Gly Lys Glu Tyr Lys Cys Lys Val Ser Asn Lys Ala Leu Pro Ala
                320                 325                 330
Pro Ile Glu Lys Thr Ile Ser Lys Ala Lys Gly Gln Pro Arg Glu
                335                 340                 345
Pro Gln Val Tyr Thr Leu Pro Pro Ser Arg Glu Met Thr Lys
                350                 355                 360
Asn Gln Val Ser Leu Thr Cys Leu Val Lys Gly Phe Tyr Pro Ser
                365                 370                 375
Asp Ile Ala Val Glu Trp Glu Ser Asn Gly Gln Pro Glu Asn Asn
                380                 385                 390
Tyr Lys Thr Thr Pro Pro Val Leu Asp Ser Asp Gly Ser Phe Phe
                395                 400                 405
Leu Tyr Ser Lys Leu Thr Val Asp Lys Ser Arg Trp Gln Gln Gly
                410                 415                 420
Asn Val Phe Ser Cys Ser Val Met His Glu Ala Leu His Asn His
                425                 430                 435
Tyr Thr Gln Lys Ser Leu Ser Leu Ser Pro Gly
                440                 445

<210> SEQ ID NO 7
<211> LENGTH: 231
<212> TYPE: PRT
<213> ORGANISM: Macaca fascicularis

<400> SEQUENCE: 7

Met Ala Arg Leu Ala Leu Ser Pro Val Ser His Trp Leu Val
  1               5                  10                  15
Ala Leu Leu Leu Leu Ser Ala Ala Glu Pro Val Pro Ala Ala
                 20                  25                  30
Lys Ser Glu Asp Leu Tyr Pro Asn Pro Lys Gly Ser Ala Cys Ser
                 35                  40                  45
Arg Ile Trp Gln Ser Pro Arg Phe Ile Ala Arg Lys Arg Gly Phe
                 50                  55                  60
Thr Val Lys Met His Cys Tyr Val Thr Asn Ser Thr Phe Ser Ile
                 65                  70                  75
Val Ser Trp Leu Arg Lys Arg Glu Thr Asp Lys Glu Pro Gln Gln
                 80                  85                  90
Val Asn Leu Glu Gln Gly His Met His Gln Thr Gln Asn Ser Ser
                 95                 100                 105
Val Thr Thr Leu Ile Ile Gln Asp Ile Arg Phe Glu Asp Asn Gly
                110                 115                 120
Ile Tyr Phe Cys Gln Gln Glu Cys Ser Lys Thr Ser Glu Val Tyr
                125                 130                 135
Arg Gly Cys Gly Thr Glu Leu Arg Val Met Gly Phe Ser Thr Leu
                140                 145                 150
Ala Gln Leu Lys Gln Arg Asn Thr Leu Lys Asp Gly Ile Ile Met
                155                 160                 165
Ile Gln Thr Leu Leu Ile Ile Leu Phe Ile Ile Val Pro Ile Phe
                170                 175                 180
Leu Leu Leu Asp Lys Asp Asp Ser Lys Ala Gly Met Glu Ala Asp
                185                 190                 195
His Thr Tyr Glu Gly Leu Asp Ile Asp Gln Thr Ala Thr Tyr Glu
                200                 205                 210
Asp Ile Val Thr Leu Arg Thr Gly Glu Val Lys Trp Ser Val Gly
```

-continued

```
                215                 220                 225

Glu His Pro Gly Gln Glu
                230

<210> SEQ ID NO 8
<211> LENGTH: 228
<212> TYPE: PRT
<213> ORGANISM: Mus musculus

<400> SEQUENCE: 8

Met Ala Thr Leu Val Leu Ser Ser Met Pro Cys His Trp Leu Leu
  1               5                  10                  15

Phe Leu Leu Leu Leu Phe Ser Gly Glu Pro Val Pro Ala Met Thr
                 20                  25                  30

Ser Ser Asp Leu Pro Leu Asn Phe Gln Gly Ser Pro Cys Ser Gln
                 35                  40                  45

Ile Trp Gln His Pro Arg Phe Ala Ala Lys Lys Arg Ser Ser Met
                 50                  55                  60

Val Lys Phe His Cys Tyr Thr Asn His Ser Gly Ala Leu Thr Trp
                 65                  70                  75

Phe Arg Lys Arg Gly Ser Gln Gln Pro Gln Glu Leu Val Ser Glu
                 80                  85                  90

Glu Gly Arg Ile Val Gln Thr Gln Asn Gly Ser Val Tyr Thr Leu
                 95                 100                 105

Thr Ile Gln Asn Ile Gln Tyr Glu Asp Asn Gly Ile Tyr Phe Cys
                110                 115                 120

Lys Gln Lys Cys Asp Ser Ala Asn His Asn Val Thr Asp Ser Cys
                125                 130                 135

Gly Thr Glu Leu Leu Val Leu Gly Phe Ser Thr Leu Asp Gln Leu
                140                 145                 150

Lys Arg Arg Asn Thr Leu Lys Asp Gly Ile Ile Leu Ile Gln Thr
                155                 160                 165

Leu Leu Ile Ile Leu Phe Ile Ile Val Pro Ile Phe Leu Leu Leu
                170                 175                 180

Asp Lys Asp Asp Gly Lys Ala Gly Met Glu Glu Asp His Thr Tyr
                185                 190                 195

Glu Gly Leu Asn Ile Asp Gln Thr Ala Thr Tyr Glu Asp Ile Val
                200                 205                 210

Thr Leu Arg Thr Gly Glu Val Lys Trp Ser Val Gly Glu His Pro
                215                 220                 225

Gly Gln Glu

<210> SEQ ID NO 9
<211> LENGTH: 108
<212> TYPE: PRT
<213> ORGANISM: Homo sapiens

<400> SEQUENCE: 9

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
                 20                  25                  30

Asn Tyr Leu Ala Trp Tyr Gln Gln Lys Pro Gly Lys Ala Pro Lys
                 35                  40                  45

Leu Leu Ile Tyr Ala Ala Ser Ser Leu Glu Ser Gly Val Pro Ser
                 50                  55                  60
```

```
Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
            80                  85                  90

Tyr Asn Ser Leu Pro Trp Thr Phe Gly Gln Gly Thr Lys Val Glu
        95                 100                 105

Ile Lys Arg

<210> SEQ ID NO 10
<211> LENGTH: 111
<212> TYPE: PRT
<213> ORGANISM: Artificial sequence
<220> FEATURE:
<223> OTHER INFORMATION: Variable domain of Light Chain of Chimeric
      Antibody (chMA79b)

<400> SEQUENCE: 10

Asp Ile Val Leu Thr Gln Ser Pro Ala Ser Leu Ala Val Ser Leu
 1               5                  10                  15

Gly Gln Arg Ala Thr Ile Ser Cys Lys Ala Ser Gln Ser Val Asp
                20                  25                  30

Tyr Asp Gly Asp Ser Phe Leu Asn Trp Tyr Gln Lys Pro Gly Gln
            35                  40                  45

Pro Pro Lys Leu Phe Ile Tyr Ala Ala Ser Asn Leu Glu Ser Gly
        50                  55                  60

Ile Pro Ala Arg Phe Ser Gly Ser Gly Ser Gly Thr Asp Phe Thr
                65                  70                  75

Leu Asn Ile His Pro Val Glu Glu Glu Asp Ala Ala Thr Tyr Tyr
            80                  85                  90

Cys Gln Gln Ser Asn Glu Asp Pro Leu Thr Phe Gly Ala Gly Thr
        95                 100                 105

Glu Leu Glu Leu Lys Arg
            110

<210> SEQ ID NO 11
<211> LENGTH: 112
<212> TYPE: PRT
<213> ORGANISM: Artificial sequence
<220> FEATURE:
<223> OTHER INFORMATION: Variable Domain of LIght Chain of Humanized
      Antibody Graft (huMA79b graft)

<400> SEQUENCE: 11

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Ser Val Asp
                20                  25                  30

Tyr Asp Gly Asp Ser Phe Leu Asn Trp Tyr Gln Gln Lys Pro Gly
            35                  40                  45

Lys Ala Pro Lys Leu Leu Ile Tyr Ala Ala Ser Asn Leu Glu Ser
        50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
            80                  85                  90

Tyr Cys Gln Gln Ser Asn Glu Asp Pro Leu Thr Phe Gly Gln Gly
        95                 100                 105

Thr Lys Val Glu Ile Lys Arg
            110
```

<210> SEQ ID NO 12
<211> LENGTH: 11
<212> TYPE: PRT
<213> ORGANISM: Homo sapiens

<400> SEQUENCE: 12

Ala Arg Ser Glu Asp Arg Tyr Arg Asn Pro Lys
 1               5                  10

<210> SEQ ID NO 13
<211> LENGTH: 113
<212> TYPE: PRT
<213> ORGANISM: Homo sapiens

<400> SEQUENCE: 13

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Ser Val Ile Ser Gly Asp Gly Gly Ser Thr Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Phe Asp Tyr Trp Gly Gln
                95                  100                 105

Gly Thr Leu Val Thr Val Ser Ser
                110

<210> SEQ ID NO 14
<211> LENGTH: 117
<212> TYPE: PRT
<213> ORGANISM: Artificial Sequence
<220> FEATURE:
<223> OTHER INFORMATION: Variable domain of Heavy Chain of Chimeric
      Antibody (chMA79b)

<400> SEQUENCE: 14

Glu Val Gln Leu Gln Gln Ser Gly Ala Glu Leu Met Lys Pro Gly
 1               5                  10                  15

Ala Ser Val Lys Ile Ser Cys Lys Ala Thr Gly Tyr Thr Phe Ser
                20                  25                  30

Ser Tyr Trp Ile Glu Trp Val Lys Gln Arg Pro Gly His Gly Leu
                35                  40                  45

Glu Trp Ile Gly Glu Ile Leu Pro Gly Gly Gly Asp Thr Asn Tyr
                50                  55                  60

Asn Glu Ile Phe Lys Gly Lys Ala Thr Phe Thr Ala Asp Thr Ser
                65                  70                  75

Ser Asn Thr Ala Tyr Met Gln Leu Ser Ser Leu Thr Ser Glu Asp
                80                  85                  90

Ser Ala Val Tyr Tyr Cys Thr Arg Arg Val Pro Val Tyr Phe Asp
                95                  100                 105

Tyr Trp Gly Gln Gly Thr Ser Val Thr Val Ser Ser
                110                 115

```
<210> SEQ ID NO 15
<211> LENGTH: 117
<212> TYPE: PRT
<213> ORGANISM: Artificial sequence
<220> FEATURE:
<223> OTHER INFORMATION: Variable Domain of Heavy Chain of Humanized
      Antibody Graft (huMA79b graft)

<400> SEQUENCE: 15

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Ser
                20                  25                  30

Ser Tyr Trp Ile Glu Trp Val Arg Gln Ala Pro Gly Lys Gly Leu
                35                  40                  45

Glu Trp Val Gly Glu Ile Leu Pro Gly Gly Gly Asp Thr Asn Tyr
                50                  55                  60

Asn Glu Ile Phe Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Thr Arg Arg Val Pro Val Tyr Phe Asp
                95                  100                 105

Tyr Trp Gly Gln Gly Thr Leu Val Thr Val Ser Ser
                110                 115

<210> SEQ ID NO 16
<211> LENGTH: 16
<212> TYPE: PRT
<213> ORGANISM: Homo sapiens

<400> SEQUENCE: 16

Ala Arg Ser Glu Asp Arg Tyr Arg Asn Pro Lys Gly Ser Ala Cys
 1               5                  10                  15

Lys

<210> SEQ ID NO 17
<211> LENGTH: 15
<212> TYPE: PRT
<213> ORGANISM: Artificial sequence
<220> FEATURE:
<223> OTHER INFORMATION: Humanized Antibody Variant

<400> SEQUENCE: 17

Lys Ala Ser Lys Ser Val Asp Tyr Asp Gly Asp Ser Phe Leu Asn
 1               5                  10                  15

<210> SEQ ID NO 18
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 18

Ala Ala Ser Asn Arg Glu Ser
 5

<210> SEQ ID NO 19
<211> LENGTH: 7
<212> TYPE: PRT
<213> ORGANISM: Artificial sequence
<220> FEATURE:
<223> OTHER INFORMATION: Humanized Antibody Variant
```

```
<400> SEQUENCE: 19

Ala Ala Ser Asn Leu Lys Ser
  5

<210> SEQ ID NO 20
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 20

Gln Gln Ser Asn Ser Asp Pro Leu Thr
  5

<210> SEQ ID NO 21
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 21

Gln Gln Ser Asn Lys Asp Pro Leu Thr
  5

<210> SEQ ID NO 22
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 22

Ala Ala Arg Lys Leu Gly Arg
  5

<210> SEQ ID NO 23
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 23

Ala Ala Ser Arg Leu Glu Ser
  5

<210> SEQ ID NO 24
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 24

Ala Ala Arg Lys Leu Gly Asn
  5

<210> SEQ ID NO 25
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 25
```

Ala Ala Arg Lys Leu Lys Arg
5

<210> SEQ ID NO 26
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 26

Ala Ala Arg Tyr Leu Lys Arg
5

<210> SEQ ID NO 27
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 27

Ala Ala Arg Lys Leu Lys Ser
5

<210> SEQ ID NO 28
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 28

Ala Ala Arg Lys Leu Ala Ser
5

<210> SEQ ID NO 29
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 29

Ala Ala Gly Ile Leu Ala Arg
5

<210> SEQ ID NO 30
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 30

Ala Ala Arg Lys Leu Arg Ser
5

<210> SEQ ID NO 31
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 31

Ala Ala Arg Lys Leu Gly Ser

<210> SEQ ID NO 32
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 32

Ala Ala Arg His Leu Lys Arg
 5

<210> SEQ ID NO 33
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 33

Ala Ser Arg Tyr Leu Ser Arg
 5

<210> SEQ ID NO 34
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 34

Ala Gly Ser Lys Leu Leu Arg
 5

<210> SEQ ID NO 35
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 35

Ala Ala Ser Asn Arg Lys Ser
 5

<210> SEQ ID NO 36
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 36

Ala Ala Ser Lys Leu Gly Ser
 5

<210> SEQ ID NO 37
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 37

Ala Ala Arg Tyr Leu Arg Arg
 5

```
<210> SEQ ID NO 38
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 38

Ala Ala Arg Arg Leu Arg Thr
                5

<210> SEQ ID NO 39
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 39

Ala Ala Arg Arg Leu Gly Arg
                5

<210> SEQ ID NO 40
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 40

Ala Ala Arg Gln Arg Lys Arg
                5

<210> SEQ ID NO 41
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 41

Ala Ala Arg Lys Leu Leu Arg
                5

<210> SEQ ID NO 42
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 42

Ala Ala Arg Lys Leu Lys Asn
                5

<210> SEQ ID NO 43
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 43

Ala Ala Arg Lys Leu Gly Thr
                5

<210> SEQ ID NO 44
```

```
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 44

Ala Ala Arg Lys Leu Gly Gly
  5

<210> SEQ ID NO 45
<211> LENGTH: 7
<212> TYPE: PRT
<213> ORGANISM: Artificial sequence
<220> FEATURE:
<223> OTHER INFORMATION: Humanized Antibody Variant

<400> SEQUENCE: 45

Ala Ala Arg Lys Leu Ala Arg
  5

<210> SEQ ID NO 46
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 46

Gln Gln Ser Asn Ala Asp Pro Leu Thr
  5

<210> SEQ ID NO 47
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 47

Gln Gln Ser Asn Gln Asp Pro Leu Thr
  5

<210> SEQ ID NO 48
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 48

Gln Gln Ser Asn Glu Asp Pro Leu Thr
  5

<210> SEQ ID NO 49
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 49

Gln Gln Ser Asn Asp Asp Pro Leu Thr
  5

<210> SEQ ID NO 50
<211> LENGTH: 9
<212> TYPE: PRT
```

```
<213> ORGANISM: Artificial sequence
<220> FEATURE:
<223> OTHER INFORMATION: Humanized Antibody Variant

<400> SEQUENCE: 50

Gln Gln Ser Asn Leu Asp Pro Leu Thr
                5

<210> SEQ ID NO 51
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 51

Asn Asn Ser Asn Gly Asp Pro Leu Asn
                5

<210> SEQ ID NO 52
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 52

Gln Pro Asp Asn Glu Ala Pro Arg Thr
                5

<210> SEQ ID NO 53
<211> LENGTH: 9
<212> TYPE: PRT
<213> ORGANISM: Artificial sequence
<220> FEATURE:
<223> OTHER INFORMATION: Humanized Antibody Variant

<400> SEQUENCE: 53

Asp Gln Arg Asn Ala Asp Pro Leu Thr
                5

<210> SEQ ID NO 54
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 54

Gly Tyr Pro Phe Thr Arg Tyr Trp Ile Ser
                5                   10

<210> SEQ ID NO 55
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 55

Gly Tyr Pro Phe Arg Ser Tyr Trp Ile Gln
                5                   10

<210> SEQ ID NO 56
<211> LENGTH: 10
<212> TYPE: PRT
<213> ORGANISM: Artificial sequence
<220> FEATURE:
```

<223> OTHER INFORMATION: Humanized Antibody Variant

<400> SEQUENCE: 56

Gly Tyr Pro Phe Thr Ser Tyr Trp Ile Asn
 5                  10

<210> SEQ ID NO 57
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 57

Gly Tyr Pro Phe Thr Arg Tyr Trp Ile Asn
 5                  10

<210> SEQ ID NO 58
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 58

Gly Tyr Thr Phe Asn Arg Tyr Trp Ile Asn
 5                  10

<210> SEQ ID NO 59
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 59

Gly Tyr Ser Phe Lys Ser Tyr Trp Ile Glu
 5                  10

<210> SEQ ID NO 60
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 60

Pro Tyr Ser Leu Cys Thr Tyr Phe Ile Asp
 5                  10

<210> SEQ ID NO 61
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 61

Gly Tyr Tyr Phe Thr Ser Tyr Trp Ile Glu
 5                  10

<210> SEQ ID NO 62
<211> LENGTH: 10
<212> TYPE: PRT
<213> ORGANISM: Artificial sequence
<220> FEATURE:
<223> OTHER INFORMATION: Humanized Antibody Variant

```
<400> SEQUENCE: 62

Gly Tyr Pro Phe Gly Arg Tyr Trp Val Asn
              5                   10

<210> SEQ ID NO 63
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 63

Gly Tyr Thr Phe Lys Lys Tyr Trp Ile Glu
              5                   10

<210> SEQ ID NO 64
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 64

Gly Tyr Pro Phe Thr Ser Tyr Trp Ile Gln
              5                   10

<210> SEQ ID NO 65
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 65

Gly Tyr Pro Phe Arg Arg Tyr Trp Ile Glu
              5                   10

<210> SEQ ID NO 66
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 66

Gly Tyr Pro Val Gly Arg Tyr Trp Ile Ser
              5                   10

<210> SEQ ID NO 67
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 67

Gly Tyr Pro Phe Asn Arg Tyr Trp Ile Asn
              5                   10

<210> SEQ ID NO 68
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 68
```

```
Gly Tyr Gly Phe Thr Ser Tyr Trp Ile Ser
 5                  10

<210> SEQ ID NO 69
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 69

Gly Tyr Thr Phe Thr Ser Tyr Trp Leu Ser
 5                  10

<210> SEQ ID NO 70
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 70

Gly Tyr Thr Phe Thr Ser Tyr Trp Ile Glu
 5                  10

<210> SEQ ID NO 71
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 71

Gly Tyr Thr Phe Ser Gly Tyr Trp Ile Asn
 5                  10

<210> SEQ ID NO 72
<211> LENGTH: 10
<212> TYPE: PRT
<213> ORGANISM: Artificial sequence
<220> FEATURE:
<223> OTHER INFORMATION: sequence is synthesized

<400> SEQUENCE: 72

Gly Tyr Thr Phe Arg Arg Tyr Trp Ile Asn
 5                  10

<210> SEQ ID NO 73
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 73

Gly Tyr Ser Phe Arg Ser Tyr Trp Ile Asn
 5                  10

<210> SEQ ID NO 74
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 74

Gly Tyr Ser Phe Arg Arg Tyr Trp Ile Asn
 5                  10
```

<210> SEQ ID NO 75
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 75

Gly Tyr Ser Phe Arg Arg Tyr Trp Ile Glu
 5                  10

<210> SEQ ID NO 76
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 76

Gly Tyr Ser Phe Pro Ser Tyr Trp Leu Gln
 5                  10

<210> SEQ ID NO 77
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 77

Gly Tyr Pro Phe Thr Arg Tyr Trp Ile Glu
 5                  10

<210> SEQ ID NO 78
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 78

Gly Tyr Pro Phe Ser Gly Tyr Trp Ile Glu
 5                  10

<210> SEQ ID NO 79
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 79

Gly Tyr Pro Phe Arg Ser Tyr Trp Ile Ser
 5                  10

<210> SEQ ID NO 80
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 80

Gly Tyr Pro Phe Arg Ser Tyr Trp Ile Asn
 5                  10

```
<210> SEQ ID NO 81
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 81

Gly Tyr Pro Phe Arg Gly Tyr Trp Ile Glu
  5                  10

<210> SEQ ID NO 82
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 82

Gly Tyr Pro Phe Asn Arg Tyr Trp Ile Glu
  5                  10

<210> SEQ ID NO 83
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 83

Gly Tyr Pro Phe Asn Gly Tyr Trp Ile Asn
  5                  10

<210> SEQ ID NO 84
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 84

Gly Tyr Asn Val Ser Ser Tyr Trp Leu Ser
  5                  10

<210> SEQ ID NO 85
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 85

Gly Phe Pro Phe Thr Ser Tyr Trp Ile Ser
  5                  10

<210> SEQ ID NO 86
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 86

Gly Phe Pro Phe Asn Arg Tyr Trp Ile Asn
  5                  10

<210> SEQ ID NO 87
<211> LENGTH: 10
```

```
<212> TYPE: PRT
<213> ORGANISM: Artificial sequence
<220> FEATURE:
<223> OTHER INFORMATION: Humanized Antibody Variant

<400> SEQUENCE: 87

Cys Thr Arg Arg Val Pro Ile Tyr Leu Asp
  5                  10

<210> SEQ ID NO 88
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 88

Cys Thr Arg Arg Val Pro Val Tyr Phe Asp
  5                  10

<210> SEQ ID NO 89
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 89

Cys Thr Arg Arg Val Pro Val Lys Leu Asp
  5                  10

<210> SEQ ID NO 90
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 90

Cys Thr Arg Arg Val Pro Val Tyr Leu Asp
  5                  10

<210> SEQ ID NO 91
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 91

Cys Thr Arg Arg Val Pro Ile Tyr Phe Asp
  5                  10

<210> SEQ ID NO 92
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 92

Cys Thr Arg Arg Val Pro Phe Cys Leu Asp
  5                  10

<210> SEQ ID NO 93
<211> LENGTH: 10
<212> TYPE: PRT
<213> ORGANISM: Artificial sequence
```

```
<220> FEATURE:
<223> OTHER INFORMATION: Humanized Antibody Variant

<400> SEQUENCE: 93

Cys Thr Arg Arg Val Pro Val Tyr Leu Asp
  5                   10

<210> SEQ ID NO 94
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 94

Cys Thr Arg Arg Val Pro Ile Arg Leu Asp
  5                   10

<210> SEQ ID NO 95
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 95

Cys Thr Arg Arg Val Pro Ile Lys Leu Asp
  5                   10

<210> SEQ ID NO 96
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 96

Cys Thr Arg Arg Val Pro Ile Arg Phe Asp
  5                   10

<210> SEQ ID NO 97
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 97

Cys Thr Arg Arg Val Pro Ile Tyr Phe Asp
  5                   10

<210> SEQ ID NO 98
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 98

Cys Thr Arg Arg Val Pro Val Tyr Phe Ser
  5                   10

<210> SEQ ID NO 99
<211> LENGTH: 10
<212> TYPE: PRT
<213> ORGANISM: Artificial sequence
<220> FEATURE:
<223> OTHER INFORMATION: Humanized Antibody Variant
```

```
<400> SEQUENCE: 99

Cys Thr Arg Arg Val Pro Val Val Leu Asp
  5                  10

<210> SEQ ID NO 100
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 100

Cys Thr Arg Arg Val Pro Val Arg Leu Asp
  5                  10

<210> SEQ ID NO 101
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 101

Cys Thr Arg Arg Val Pro Val Arg Phe Asp
  5                  10

<210> SEQ ID NO 102
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 102

Cys Thr Arg Arg Val Pro Val Phe Leu Asp
  5                  10

<210> SEQ ID NO 103
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 103

Cys Thr Arg Arg Val Pro Ile Tyr Leu Asp
  5                  10

<210> SEQ ID NO 104
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 104

Cys Thr Arg Arg Val Pro Ile Tyr Phe Asp
  5                  10

<210> SEQ ID NO 105
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 105
```

Cys Thr Arg Arg Pro Val Cys Leu Asp
 5              10

<210> SEQ ID NO 106
<211> LENGTH: 10
<212> TYPE: PRT
<213> ORGANISM: Artificial sequence
<220> FEATURE:
<223> OTHER INFORMATION: Humanized Antibody Variant

<400> SEQUENCE: 106

Cys Thr Arg Arg Ile Pro Val Tyr Phe Asp
 5              10

<210> SEQ ID NO 107
<211> LENGTH: 10
<212> TYPE: PRT
<213> ORGANISM: Mus musculus

<400> SEQUENCE: 107

Cys Thr Arg Arg Val Pro Val Tyr Phe Asp
 5              10

<210> SEQ ID NO 108
<211> LENGTH: 87
<212> TYPE: PRT
<213> ORGANISM: Homo sapiens

<400> SEQUENCE: 108

Gln Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Thr
                20                  25                  30

Trp Val Arg Gln Ala Pro Gly Gln Gly Leu Glu Trp Met Gly Arg
                35                  40                  45

Val Thr Ile Thr Ala Asp Thr Ser Thr Ser Thr Ala Tyr Met Glu
                50                  55                  60

Leu Ser Ser Leu Arg Ser Glu Asp Thr Ala Val Tyr Tyr Cys Ala
                65                  70                  75

Arg Trp Gly Gln Gly Thr Leu Val Thr Val Ser Ser
                80                  85

<210> SEQ ID NO 109
<211> LENGTH: 81
<212> TYPE: PRT
<213> ORGANISM: Homo sapiens

<400> SEQUENCE: 109

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
                20                  25                  30

Pro Gly Gln Gly Leu Glu Trp Met Arg Val Thr Ile Thr Ala Asp
                35                  40                  45

Thr Ser Thr Ser Thr Ala Tyr Met Glu Leu Ser Ser Leu Arg Ser
                50                  55                  60

Glu Asp Thr Ala Val Tyr Tyr Cys Ala Arg Trp Gly Gln Gly Thr
                65                  70                  75

Leu Val Thr Val Ser Ser
                80

<210> SEQ ID NO 110
<211> LENGTH: 80
<212> TYPE: PRT
<213> ORGANISM: Homo sapiens

<400> SEQUENCE: 110

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
            20                  25                  30

Pro Gly Gln Gly Leu Glu Trp Met Arg Val Thr Ile Thr Ala Asp
        35                  40                  45

Thr Ser Thr Ser Thr Ala Tyr Met Glu Leu Ser Ser Leu Arg Ser
    50                  55                  60

Glu Asp Thr Ala Val Tyr Tyr Cys Ala Trp Gly Gln Gly Thr Leu
65                  70                  75

Val Thr Val Ser Ser
            80

<210> SEQ ID NO 111
<211> LENGTH: 79
<212> TYPE: PRT
<213> ORGANISM: Homo sapiens

<400> SEQUENCE: 111

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
            20                  25                  30

Pro Gly Gln Gly Leu Glu Trp Met Arg Val Thr Ile Thr Ala Asp
        35                  40                  45

Thr Ser Thr Ser Thr Ala Tyr Met Glu Leu Ser Ser Leu Arg Ser
    50                  55                  60

Glu Asp Thr Ala Val Tyr Tyr Cys Trp Gly Gln Gly Thr Leu Val
65                  70                  75

Thr Val Ser Ser

<210> SEQ ID NO 112
<211> LENGTH: 86
<212> TYPE: PRT
<213> ORGANISM: Homo sapiens

<400> SEQUENCE: 112

Gln Val Gln Leu Gln Glu Ser Gly Pro Gly Leu Val Lys Pro Ser
 1               5                  10                  15

Gln Thr Leu Ser Leu Thr Cys Thr Val Ser Gly Gly Ser Val Ser
            20                  25                  30

Trp Ile Arg Gln Pro Pro Gly Lys Gly Leu Glu Trp Ile Arg Val
        35                  40                  45

Thr Ile Ser Val Asp Thr Ser Lys Asn Gln Phe Ser Leu Lys Leu
    50                  55                  60

Ser Ser Val Thr Ala Ala Asp Thr Ala Val Tyr Tyr Cys Ala Arg
65                  70                  75

Trp Gly Gln Gly Thr Leu Val Thr Val Ser Ser
        80                  85

<210> SEQ ID NO 113
<211> LENGTH: 81

<212> TYPE: PRT
<213> ORGANISM: Homo sapiens

<400> SEQUENCE: 113

```
Gln Val Gln Leu Gln Glu Ser Gly Pro Gly Leu Val Lys Pro Ser
  1               5                  10                  15

Gln Thr Leu Ser Leu Thr Cys Thr Val Ser Trp Ile Arg Gln Pro
             20                  25                  30

Pro Gly Lys Gly Leu Glu Trp Ile Arg Val Thr Ile Ser Val Asp
         35                  40                  45

Thr Ser Lys Asn Gln Phe Ser Leu Lys Leu Ser Ser Val Thr Ala
     50                  55                  60

Ala Asp Thr Ala Val Tyr Tyr Cys Ala Arg Trp Gly Gln Gly Thr
 65                  70                  75

Leu Val Thr Val Ser Ser
             80
```

<210> SEQ ID NO 114
<211> LENGTH: 80
<212> TYPE: PRT
<213> ORGANISM: Homo sapiens

<400> SEQUENCE: 114

```
Gln Val Gln Leu Gln Glu Ser Gly Pro Gly Leu Val Lys Pro Ser
  1               5                  10                  15

Gln Thr Leu Ser Leu Thr Cys Thr Val Ser Trp Ile Arg Gln Pro
             20                  25                  30

Pro Gly Lys Gly Leu Glu Trp Ile Arg Val Thr Ile Ser Val Asp
         35                  40                  45

Thr Ser Lys Asn Gln Phe Ser Leu Lys Leu Ser Ser Val Thr Ala
     50                  55                  60

Ala Asp Thr Ala Val Tyr Tyr Cys Ala Trp Gly Gln Gly Thr Leu
 65                  70                  75

Val Thr Val Ser Ser
             80
```

<210> SEQ ID NO 115
<211> LENGTH: 79
<212> TYPE: PRT
<213> ORGANISM: Homo sapiens

<400> SEQUENCE: 115

```
Gln Val Gln Leu Gln Glu Ser Gly Pro Gly Leu Val Lys Pro Ser
  1               5                  10                  15

Gln Thr Leu Ser Leu Thr Cys Thr Val Ser Trp Ile Arg Gln Pro
             20                  25                  30

Pro Gly Lys Gly Leu Glu Trp Ile Arg Val Thr Ile Ser Val Asp
         35                  40                  45

Thr Ser Lys Asn Gln Phe Ser Leu Lys Leu Ser Ser Val Thr Ala
     50                  55                  60

Ala Asp Thr Ala Val Tyr Tyr Cys Trp Gly Gln Gly Thr Leu Val
 65                  70                  75

Thr Val Ser Ser
```

<210> SEQ ID NO 116
<211> LENGTH: 87
<212> TYPE: PRT
<213> ORGANISM: Homo sapiens

<400> SEQUENCE: 116

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Trp Val Arg Gln Ala Pro Gly Lys Gly Leu Glu Trp Val Ser Arg
                35                  40                  45

Phe Thr Ile Ser Arg Asp Asn Ser Lys Asn Thr Leu Tyr Leu Gln
                50                  55                  60

Met Asn Ser Leu Arg Ala Glu Asp Thr Ala Val Tyr Tyr Cys Ala
                65                  70                  75

Arg Trp Gly Gln Gly Thr Leu Val Thr Val Ser Ser
                80                  85

<210> SEQ ID NO 117
<211> LENGTH: 81
<212> TYPE: PRT
<213> ORGANISM: Homo sapiens

<400> SEQUENCE: 117

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Arg Asp
                35                  40                  45

Asn Ser Lys Asn Thr Leu Tyr Leu Gln Met Asn Ser Leu Arg Ala
                50                  55                  60

Glu Asp Thr Ala Val Tyr Tyr Cys Ala Arg Trp Gly Gln Gly Thr
                65                  70                  75

Leu Val Thr Val Ser Ser
                80

<210> SEQ ID NO 118
<211> LENGTH: 80
<212> TYPE: PRT
<213> ORGANISM: Homo sapiens

<400> SEQUENCE: 118

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Arg Asp
                35                  40                  45

Asn Ser Lys Asn Thr Leu Tyr Leu Gln Met Asn Ser Leu Arg Ala
                50                  55                  60

Glu Asp Thr Ala Val Tyr Tyr Cys Ala Trp Gly Gln Gly Thr Leu
                65                  70                  75

Val Thr Val Ser Ser
                80

<210> SEQ ID NO 119
<211> LENGTH: 79
<212> TYPE: PRT
<213> ORGANISM: Homo sapiens

<400> SEQUENCE: 119

-continued

Glu Val Gln Leu Val Glu Ser Gly Gly Gly Leu Val Gln Pro Gly
1               5                   10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Arg Asp
        35                  40                  45

Asn Ser Lys Asn Thr Leu Tyr Leu Gln Met Asn Ser Leu Arg Ala
    50                  55                  60

Glu Asp Thr Ala Val Tyr Tyr Cys Trp Gly Gln Gly Thr Leu Val
65                  70                  75

Thr Val Ser Ser

<210> SEQ ID NO 120
<211> LENGTH: 87
<212> TYPE: PRT
<213> ORGANISM: Homo sapiens

<400> SEQUENCE: 120

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys
            20                  25                  30

Trp Val Arg Gln Ala Pro Gly Lys Gly Leu Glu Trp Val Ser Arg
        35                  40                  45

Phe Thr Ile Ser Ala Asp Thr Ser Lys Asn Thr Ala Tyr Leu Gln
    50                  55                  60

Met Asn Ser Leu Arg Ala Glu Asp Thr Ala Val Tyr Tyr Cys Ser
65                  70                  75

Arg Trp Gly Gln Gly Thr Leu Val Thr Val Ser Ser
        80                  85

<210> SEQ ID NO 121
<211> LENGTH: 81
<212> TYPE: PRT
<213> ORGANISM: Homo sapiens

<400> SEQUENCE: 121

Glu Val Gln Leu Val Glu Ser Gly Gly Gly Leu Val Gln Pro Gly
                1               5                   10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
        35                  40                  45

Thr Ser Lys Asn Thr Ala Tyr Leu Gln Met Asn Ser Leu Arg Ala
    50                  55                  60

Glu Asp Thr Ala Val Tyr Tyr Cys Ser Arg Trp Gly Gln Gly Thr
65                  70                  75

Leu Val Thr Val Ser Ser
            80

<210> SEQ ID NO 122
<211> LENGTH: 80
<212> TYPE: PRT
<213> ORGANISM: Homo sapiens

<400> SEQUENCE: 122

Glu Val Gln Leu Val Glu Ser Gly Gly Gly Leu Val Gln Pro Gly
1               5                   10                  15

-continued

```
Gly Ser Leu Arg Leu Ser Cys Ala Ala Ser Trp Val Arg Gln Ala
         20                  25                  30

Pro Gly Lys Gly Leu Glu Trp Val Arg Phe Thr Ile Ser Ala Asp
         35                  40                  45

Thr Ser Lys Asn Thr Ala Tyr Leu Gln Met Asn Ser Leu Arg Ala
         50                  55                  60

Glu Asp Thr Ala Val Tyr Tyr Cys Ser Trp Gly Gln Gly Thr Leu
         65                  70                  75

Val Thr Val Ser Ser
         80

<210> SEQ ID NO 123
<211> LENGTH: 86
<212> TYPE: PRT
<213> ORGANISM: Homo sapiens

<400> SEQUENCE: 123

Glu Val Gln Leu Val Glu Ser Gly Gly Gly Leu Val Gln Pro Gly
  1              5                  10                  15

Gly Ser Leu Arg Leu Ser Cys Ala Ala Ser Gly Phe Asn Ile Lys
         20                  25                  30

Trp Val Arg Gln Ala Pro Gly Lys Gly Leu Glu Trp Val Ser Arg
         35                  40                  45

Phe Thr Ile Ser Ala Asp Thr Ser Lys Asn Thr Ala Tyr Leu Gln
         50                  55                  60

Met Asn Ser Leu Arg Ala Glu Asp Thr Ala Val Tyr Cys Ala Arg
         65                  70                  75

Trp Gly Gln Gly Thr Leu Val Thr Val Ser Ser
         80                  85

<210> SEQ ID NO 124
<211> LENGTH: 81
<212> TYPE: PRT
<213> ORGANISM: Homo sapiens

<400> SEQUENCE: 124

Glu Val Gln Leu Val Glu Ser Gly Gly Gly Leu Val Gln Pro Gly
  1              5                  10                  15

Gly Ser Leu Arg Leu Ser Cys Ala Ala Ser Trp Val Arg Gln Ala
         20                  25                  30

Pro Gly Lys Gly Leu Glu Trp Val Arg Phe Thr Ile Ser Ala Asp
         35                  40                  45

Thr Ser Lys Asn Thr Ala Tyr Leu Gln Met Asn Ser Leu Arg Ala
         50                  55                  60

Glu Asp Thr Ala Val Tyr Tyr Cys Ala Arg Trp Gly Gln Gly Thr
         65                  70                  75

Leu Val Thr Val Ser Ser
         80

<210> SEQ ID NO 125
<211> LENGTH: 80
<212> TYPE: PRT
<213> ORGANISM: Homo sapiens

<400> SEQUENCE: 125

Glu Val Gln Leu Val Glu Ser Gly Gly Gly Leu Val Gln Pro Gly
  1              5                  10                  15

Gly Ser Leu Arg Leu Ser Cys Ala Ala Ser Trp Val Arg Gln Ala
         20                  25                  30
```

```
Pro Gly Lys Gly Leu Glu Trp Val Arg Phe Thr Ile Ser Ala Asp
             35                  40                  45

Thr Ser Lys Asn Thr Ala Tyr Leu Gln Met Asn Ser Leu Arg Ala
         50                  55                  60

Glu Asp Thr Ala Val Tyr Tyr Cys Ala Trp Gly Gln Gly Thr Leu
 65                  70                  75

Val Thr Val Ser Ser
             80

<210> SEQ ID NO 126
<211> LENGTH: 79
<212> TYPE: PRT
<213> ORGANISM: Homo sapiens

<400> SEQUENCE: 126

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
             20                  25                  30

Pro Gly Lys Gly Leu Glu Trp Val Arg Phe Thr Ile Ser Ala Asp
             35                  40                  45

Thr Ser Lys Asn Thr Ala Tyr Leu Gln Met Asn Ser Leu Arg Ala
         50                  55                  60

Glu Asp Thr Ala Val Tyr Tyr Cys Trp Gly Gln Gly Thr Leu Val
 65                  70                  75

Thr Val Ser Ser

<210> SEQ ID NO 127
<211> LENGTH: 80
<212> TYPE: PRT
<213> ORGANISM: Homo sapiens

<400> SEQUENCE: 127

Asp Ile Gln Met Thr Gln Ser Pro Ser Ser Leu Ser Ala Ser Val
 1               5                  10                  15

Gly Asp Arg Val Thr Ile Thr Cys Trp Tyr Gln Gln Lys Pro Gly
             20                  25                  30

Lys Ala Pro Lys Leu Leu Ile Tyr Gly Val Pro Ser Arg Phe Ser
             35                  40                  45

Gly Ser Gly Ser Gly Thr Asp Phe Thr Leu Thr Ile Ser Ser Leu
         50                  55                  60

Gln Pro Glu Asp Phe Ala Thr Tyr Tyr Cys Phe Gly Gln Gly Thr
 65                  70                  75

Lys Val Glu Ile Lys
             80

<210> SEQ ID NO 128
<211> LENGTH: 80
<212> TYPE: PRT
<213> ORGANISM: Homo sapiens

<400> SEQUENCE: 128

Asp Ile Val Met Thr Gln Ser Pro Leu Ser Leu Pro Val Thr Pro
 1               5                  10                  15

Gly Glu Pro Ala Ser Ile Ser Cys Trp Tyr Leu Gln Lys Pro Gly
             20                  25                  30

Gln Ser Pro Gln Leu Leu Ile Tyr Gly Val Pro Asp Arg Phe Ser
             35                  40                  45
```

```
Gly Ser Gly Ser Gly Thr Asp Phe Thr Leu Lys Ile Ser Arg Val
            50                  55                  60

Glu Ala Glu Asp Val Gly Val Tyr Tyr Cys Phe Gln Gly Thr
            65                  70                  75

Lys Val Glu Ile Lys
            80
```

<210> SEQ ID NO 129
<211> LENGTH: 80
<212> TYPE: PRT
<213> ORGANISM: Homo sapiens

<400> SEQUENCE: 129

```
Glu Ile Val Leu Thr Gln Ser Pro Gly Thr Leu Ser Leu Ser Pro
 1               5                  10                  15

Gly Glu Arg Ala Thr Leu Ser Cys Trp Tyr Gln Gln Lys Pro Gly
            20                  25                  30

Gln Ala Pro Arg Leu Leu Ile Tyr Gly Ile Pro Asp Arg Phe Ser
            35                  40                  45

Gly Ser Gly Ser Gly Thr Asp Phe Thr Leu Thr Ile Ser Arg Leu
            50                  55                  60

Glu Pro Glu Asp Phe Ala Val Tyr Tyr Cys Phe Gly Gln Gly Thr
            65                  70                  75

Lys Val Glu Ile Lys
            80
```

<210> SEQ ID NO 130
<211> LENGTH: 80
<212> TYPE: PRT
<213> ORGANISM: Homo sapiens

<400> SEQUENCE: 130

```
Asp Ile Val Met Thr Gln Ser Pro Asp Ser Leu Ala Val Ser Leu
 1               5                  10                  15

Gly Glu Arg Ala Thr Ile Asn Cys Trp Tyr Gln Gln Lys Pro Gly
            20                  25                  30

Gln Pro Pro Lys Leu Leu Ile Tyr Gly Val Pro Asp Arg Phe Ser
            35                  40                  45

Gly Ser Gly Ser Gly Thr Asp Phe Thr Leu Thr Ile Ser Ser Leu
            50                  55                  60

Gln Ala Glu Asp Val Ala Val Tyr Tyr Cys Phe Gly Gln Gly Thr
            65                  70                  75

Lys Val Glu Ile Lys
            80
```

<210> SEQ ID NO 131
<211> LENGTH: 15
<212> TYPE: PRT
<213> ORGANISM: Artificial Sequence
<220> FEATURE:
<223> OTHER INFORMATION: HVR1-LC of huMA79b graft

<400> SEQUENCE: 131

```
Lys Ala Ser Gln Ser Val Asp Tyr Asp Gly Asp Ser Phe Leu Asn
 1               5                  10                  15
```

<210> SEQ ID NO 132
<211> LENGTH: 7
<212> TYPE: PRT
<213> ORGANISM: Artificial Sequence

```
<220> FEATURE:
<223> OTHER INFORMATION: HVR2-LC of huMA79b graft

<400> SEQUENCE: 132

Ala Ala Ser Asn Leu Glu Ser
                5

<210> SEQ ID NO 133
<211> LENGTH: 9
<212> TYPE: PRT
<213> ORGANISM: Artificial Sequence
<220> FEATURE:
<223> OTHER INFORMATION: HVR3-LC of huMA79b graft

<400> SEQUENCE: 133

Gln Gln Ser Asn Glu Asp Pro Leu Thr
                5

<210> SEQ ID NO 134
<211> LENGTH: 10
<212> TYPE: PRT
<213> ORGANISM: Artificial Sequence
<220> FEATURE:
<223> OTHER INFORMATION: HVR1-HC of huMA79b graft

<400> SEQUENCE: 134

Gly Tyr Thr Phe Ser Ser Tyr Trp Ile Glu
                5                  10

<210> SEQ ID NO 135
<211> LENGTH: 18
<212> TYPE: PRT
<213> ORGANISM: Artificial Sequence
<220> FEATURE:
<223> OTHER INFORMATION: HVR2-HC of huMA79b graft

<400> SEQUENCE: 135

Gly Glu Ile Leu Pro Gly Gly Gly Asp Thr Asn Tyr Asn Glu Ile
  1               5                  10                  15

Phe Lys Gly

<210> SEQ ID NO 136
<211> LENGTH: 10
<212> TYPE: PRT
<213> ORGANISM: Artificial Sequence
<220> FEATURE:
<223> OTHER INFORMATION: HVR3-HC of huMA79b graft

<400> SEQUENCE: 136

Thr Arg Arg Val Pro Val Tyr Phe Asp Tyr
                5                  10

<210> SEQ ID NO 137
<211> LENGTH: 15
<212> TYPE: PRT
<213> ORGANISM: Artificial sequence
<220> FEATURE:
<223> OTHER INFORMATION: HVR1-LC of Humanized Antibody Variant (huMA79b.
      V28)

<400> SEQUENCE: 137

Lys Ala Ser Gln Ser Val Asp Tyr Glu Gly Asp Ser Phe Leu Asn
  1               5                  10                  15

<210> SEQ ID NO 138
<211> LENGTH: 10
<212> TYPE: PRT
```

<213> ORGANISM: Artificial sequence
<220> FEATURE:
<223> OTHER INFORMATION: HVR3-HC of Humanized Antibody Variant (huMA79b.
      V28)

<400> SEQUENCE: 138

Thr Arg Arg Val Pro Ile Arg Leu Asp Tyr
            5                   10

<210> SEQ ID NO 139
<211> LENGTH: 23
<212> TYPE: PRT
<213> ORGANISM: Homo sapiens

<400> SEQUENCE: 139

Asp Ile Gln Met Thr Gln Ser Pro Ser Ser Leu Ser Ala Ser Val
1               5                   10                  15

Gly Asp Arg Val Thr Ile Thr Cys
                20

<210> SEQ ID NO 140
<211> LENGTH: 15
<212> TYPE: PRT
<213> ORGANISM: Homo sapiens

<400> SEQUENCE: 140

Trp Tyr Gln Gln Lys Pro Gly Lys Ala Pro Lys Leu Leu Ile Tyr
1               5                   10                  15

<210> SEQ ID NO 141
<211> LENGTH: 32
<212> TYPE: PRT
<213> ORGANISM: Homo sapiens

<400> SEQUENCE: 141

Gly Val Pro Ser Arg Phe Ser Gly Ser Gly Ser Gly Thr Asp Phe
1               5                   10                  15

Thr Leu Thr Ile Ser Ser Leu Gln Pro Glu Asp Phe Ala Thr Tyr
                20                  25                  30

Tyr Cys

<210> SEQ ID NO 142
<211> LENGTH: 11
<212> TYPE: PRT
<213> ORGANISM: Homo sapiens

<400> SEQUENCE: 142

Phe Gly Gln Gly Thr Lys Val Glu Ile Lys Arg
            5                   10

<210> SEQ ID NO 143
<211> LENGTH: 25
<212> TYPE: PRT
<213> ORGANISM: Homo sapiens

<400> SEQUENCE: 143

Glu Val Gln Leu Val Glu Ser Gly Gly Gly Leu Val Gln Pro Gly
1               5                   10                  15

Gly Ser Leu Arg Leu Ser Cys Ala Ala Ser
                20                  25

<210> SEQ ID NO 144
<211> LENGTH: 13
<212> TYPE: PRT

<213> ORGANISM: Homo sapiens

<400> SEQUENCE: 144

Trp Val Arg Gln Ala Pro Gly Lys Gly Leu Glu Trp Val
 1               5                  10

<210> SEQ ID NO 145
<211> LENGTH: 30
<212> TYPE: PRT
<213> ORGANISM: Homo sapiens

<400> SEQUENCE: 145

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
                20                  25                  30

<210> SEQ ID NO 146
<211> LENGTH: 11
<212> TYPE: PRT
<213> ORGANISM: Homo sapiens

<400> SEQUENCE: 146

Trp Gly Gln Gly Thr Leu Val Thr Val Ser Ser
 1               5                  10

<210> SEQ ID NO 147
<211> LENGTH: 30
<212> TYPE: PRT
<213> ORGANISM: Artificial Sequence
<220> FEATURE:
<223> OTHER INFORMATION: FR3-HC Composite of Humanized Antibody Varients
<220> FEATURE:
<221> NAME/KEY: Xaa
<222> LOCATION: 6
<223> OTHER INFORMATION: Xaa is A or R
<220> FEATURE:
<221> NAME/KEY: Xaa
<222> LOCATION: 8
<223> OTHER INFORMATION: Xaa is T or N
<220> FEATURE:
<221> NAME/KEY: Xaa
<222> LOCATION: 13
<223> OTHER INFORMATION: Xaa is A or L

<400> SEQUENCE: 147

Arg Phe Thr Ile Ser Xaa Asp Xaa Ser Lys Asn Thr Xaa Tyr Leu
 1               5                  10                  15

Gln Met Asn Ser Leu Arg Ala Glu Asp Thr Ala Val Tyr Tyr Cys
                20                  25                  30

<210> SEQ ID NO 148
<211> LENGTH: 31
<212> TYPE: PRT
<213> ORGANISM: Homo sapiens

<400> SEQUENCE: 148

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala

<210> SEQ ID NO 149
<211> LENGTH: 32
<212> TYPE: PRT

<213> ORGANISM: Homo sapiens

<400> SEQUENCE: 149

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

Ala Arg

<210> SEQ ID NO 150
<211> LENGTH: 31
<212> TYPE: PRT
<213> ORGANISM: Homo sapiens

<400> SEQUENCE: 150

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

Ser

<210> SEQ ID NO 151
<211> LENGTH: 32
<212> TYPE: PRT
<213> ORGANISM: Homo sapiens

<400> SEQUENCE: 151

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

Ser Arg

<210> SEQ ID NO 152
<211> LENGTH: 23
<212> TYPE: PRT
<213> ORGANISM: Artificial sequence
<220> FEATURE:
<223> OTHER INFORMATION: FR1-LC of Humanized Antibody Variant (huMA79b.
      v17)

<400> SEQUENCE: 152

Asp Ile Gln Leu Thr Gln Ser Pro Ser Ser Leu Ser Ala Ser Val
1               5                   10                  15

Gly Asp Arg Val Thr Ile Thr Cys
            20

<210> SEQ ID NO 153
<211> LENGTH: 15
<212> TYPE: PRT
<213> ORGANISM: Artificial sequence
<220> FEATURE:
<223> OTHER INFORMATION: FR2-LC Humanized Antibody variant huMA79b.v17)

<400> SEQUENCE: 153

Trp Tyr Gln Gln Lys Pro Gly Lys Ala Pro Lys Leu Leu Ile Tyr
1               5                   10                  15

<210> SEQ ID NO 154
<211> LENGTH: 32
<212> TYPE: PRT
<213> ORGANISM: Artificial sequence
<220> FEATURE:

-continued

<223> OTHER INFORMATION: FR3-LC of Humanized Antibody variant (huMA79b.
      v17)

<400> SEQUENCE: 154

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys

<210> SEQ ID NO 155
<211> LENGTH: 11
<212> TYPE: PRT
<213> ORGANISM: Artificial sequence
<220> FEATURE:
<223> OTHER INFORMATION: FR4-LC of Humanized Antibody Variant (huMA79b.
      v17)

<400> SEQUENCE: 155

Phe Gly Gln Gly Thr Lys Val Glu Ile Lys Arg
 5                  10

<210> SEQ ID NO 156
<211> LENGTH: 15
<212> TYPE: PRT
<213> ORGANISM: Artificial sequence
<220> FEATURE:
<223> OTHER INFORMATION: HVR1-LC of Humanized Antibody Variant (huMA79b.
      v17)

<400> SEQUENCE: 156

Lys Ala Ser Gln Ser Val Asp Tyr Asp Gly Asp Ser Phe Leu Asn
 1               5                  10                  15

<210> SEQ ID NO 157
<211> LENGTH: 7
<212> TYPE: PRT
<213> ORGANISM: Artificial sequence
<220> FEATURE:
<223> OTHER INFORMATION: HVR2-LC of Humanized Antibody Variant (huMA79b.
      v17)

<400> SEQUENCE: 157

Ala Ala Ser Asn Leu Glu Ser
                 5

<210> SEQ ID NO 158
<211> LENGTH: 9
<212> TYPE: PRT
<213> ORGANISM: Artificial sequence
<220> FEATURE:
<223> OTHER INFORMATION: HVR3-LC of Humanized Antibody Variant (huMA79b.
      v17)

<400> SEQUENCE: 158

Gln Gln Ser Asn Glu Asp Pro Leu Thr
                 5

<210> SEQ ID NO 159
<211> LENGTH: 106
<212> TYPE: PRT
<213> ORGANISM: Artificial sequence
<220> FEATURE:
<223> OTHER INFORMATION: CL1-LC ofHumanized Antibody Variant (huMA79b.
      v17)

<400> SEQUENCE: 159

```
Thr Val Ala Ala Pro Ser Val Phe Ile Phe Pro Pro Ser Asp Glu
  1               5                  10                 15

Gln Leu Lys Ser Gly Thr Ala Ser Val Val Cys Leu Leu Asn Asn
             20                  25                  30

Phe Tyr Pro Arg Glu Ala Lys Val Gln Trp Lys Val Asp Asn Ala
             35                  40                  45

Leu Gln Ser Gly Asn Ser Gln Glu Ser Val Thr Glu Gln Asp Ser
             50                  55                  60

Lys Asp Ser Thr Tyr Ser Leu Ser Ser Thr Leu Thr Leu Ser Lys
             65                  70                  75

Ala Asp Tyr Glu Lys His Lys Val Tyr Ala Cys Glu Val Thr His
             80                  85                  90

Gln Gly Leu Ser Ser Pro Val Thr Lys Ser Phe Asn Arg Gly Glu
             95                 100                 105

Cys

<210> SEQ ID NO 160
<211> LENGTH: 25
<212> TYPE: PRT
<213> ORGANISM: Artificial sequence
<220> FEATURE:
<223> OTHER INFORMATION: FR1-HC of Humanized Antibody Variant (huMA79b.
      v17)

<400> SEQUENCE: 160

Glu Val Gln Leu Val Glu Ser Gly Gly Gly Leu Val Gln Pro Gly
  1               5                  10                 15

Gly Ser Leu Arg Leu Ser Cys Ala Ala Ser
             20                  25

<210> SEQ ID NO 161
<211> LENGTH: 13
<212> TYPE: PRT
<213> ORGANISM: Artificial sequence
<220> FEATURE:
<223> OTHER INFORMATION: FR2-HC of Humanized Antibody Variant (huMA79b.
      v17)

<400> SEQUENCE: 161

Trp Val Arg Gln Ala Pro Gly Lys Gly Leu Glu Trp Ile
               5                  10

<210> SEQ ID NO 162
<211> LENGTH: 30
<212> TYPE: PRT
<213> ORGANISM: Artificial sequence
<220> FEATURE:
<223> OTHER INFORMATION: FR3-HC of Humanized Antibody Variant (huMA79b.
      v17)

<400> SEQUENCE: 162

Arg Ala Thr Phe Ser Ala Asp Thr Ser Lys Asn Thr Ala Tyr Leu
  1               5                  10                 15

Gln Met Asn Ser Leu Arg Ala Glu Asp Thr Ala Val Tyr Tyr Cys
             20                  25                  30

<210> SEQ ID NO 163
<211> LENGTH: 11
<212> TYPE: PRT
<213> ORGANISM: Artificial sequence
<220> FEATURE:
<223> OTHER INFORMATION: FR4-HC of Humanized Antibody Variant (huMA79b.
      v17)
```

```
<400> SEQUENCE: 163

Trp Gly Gln Gly Thr Leu Val Thr Val Ser Ser
              5                   10

<210> SEQ ID NO 164
<211> LENGTH: 10
<212> TYPE: PRT
<213> ORGANISM: Artificial sequence
<220> FEATURE:
<223> OTHER INFORMATION: HVR1-HC of Humanized Antibody Variant (huMA79b.
      v17)

<400> SEQUENCE: 164

Gly Tyr Thr Phe Ser Ser Tyr Trp Ile Glu
              5                   10

<210> SEQ ID NO 165
<211> LENGTH: 18
<212> TYPE: PRT
<213> ORGANISM: Artificial sequence
<220> FEATURE:
<223> OTHER INFORMATION: HVR2-HC of Humanized Antibody Variant (huMA79b.
      v17)

<400> SEQUENCE: 165

Gly Glu Ile Leu Pro Gly Gly Gly Asp Thr Asn Tyr Asn Glu Ile
 1              5                   10                  15

Phe Lys Gly

<210> SEQ ID NO 166
<211> LENGTH: 10
<212> TYPE: PRT
<213> ORGANISM: Artificial sequence
<220> FEATURE:
<223> OTHER INFORMATION: HVR-H3 of Humanized Antibody Variant (huMA79b.
      v17)

<400> SEQUENCE: 166

Thr Arg Arg Val Pro Val Tyr Phe Asp Tyr
              5                   10

<210> SEQ ID NO 167
<211> LENGTH: 108
<212> TYPE: PRT
<213> ORGANISM: Artificial Sequence
<220> FEATURE:
<223> OTHER INFORMATION: CH1-HC of Humanized Antibody Varient (huMA79b.
      v17)

<400> SEQUENCE: 167

Ala Ser Thr Lys Gly Pro Ser Val Phe Pro Leu Ala Pro Ser Ser
 1              5                   10                  15

Lys Ser Thr Ser Gly Gly Thr Ala Ala Leu Gly Cys Leu Val Lys
                20                  25                  30

Asp Tyr Phe Pro Glu Pro Val Thr Val Ser Trp Asn Ser Gly Ala
                35                  40                  45

Leu Thr Ser Gly Val His Thr Phe Pro Ala Val Leu Gln Ser Ser
                50                  55                  60

Gly Leu Tyr Ser Leu Ser Ser Val Val Thr Val Pro Ser Ser Ser
                65                  70                  75

Leu Gly Thr Gln Thr Tyr Ile Cys Asn Val Asn His Lys Pro Ser
                80                  85                  90

Asn Thr Lys Val Asp Lys Lys Val Glu Pro Lys Ser Cys Asp Lys
                95                  100                 105
```

Thr His Thr

<210> SEQ ID NO 168
<211> LENGTH: 221
<212> TYPE: PRT
<213> ORGANISM: Artificial Sequence
<220> FEATURE:
<223> OTHER INFORMATION: Fc-HC of Humanized Antibody Variant (huMA79b.
      v17)

<400> SEQUENCE: 168

```
Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp
                35                  40                  45

Pro Glu Val Lys Phe Asn Trp Tyr Val Asp Gly Val Glu Val His
                50                  55                  60

Asn Ala Lys Thr Lys Pro Arg Glu Glu Gln Tyr Asn Ser Thr Tyr
                65                  70                  75

Arg Val Val Ser Val Leu Thr Val Leu His Gln Asp Trp Leu Asn
                80                  85                  90

Gly Lys Glu Tyr Lys Cys Lys Val Ser Asn Lys Ala Leu Pro Ala
                95                 100                 105

Pro Ile Glu Lys Thr Ile Ser Lys Ala Lys Gly Gln Pro Arg Glu
               110                 115                 120

Pro Gln Val Tyr Thr Leu Pro Pro Ser Arg Glu Glu Met Thr Lys
               125                 130                 135

Asn Gln Val Ser Leu Thr Cys Leu Val Lys Gly Phe Tyr Pro Ser
               140                 145                 150

Asp Ile Ala Val Glu Trp Glu Ser Asn Gly Gln Pro Glu Asn Asn
               155                 160                 165

Tyr Lys Thr Thr Pro Pro Val Leu Asp Ser Asp Gly Ser Phe Phe
               170                 175                 180

Leu Tyr Ser Lys Leu Thr Val Asp Lys Ser Arg Trp Gln Gln Gly
               185                 190                 195

Asn Val Phe Ser Cys Ser Val Met His Glu Ala Leu His Asn His
               200                 205                 210

Tyr Thr Gln Lys Ser Leu Ser Leu Ser Pro Gly
               215                 220
```

<210> SEQ ID NO 169
<211> LENGTH: 112
<212> TYPE: PRT
<213> ORGANISM: Artificial sequence
<220> FEATURE:
<223> OTHER INFORMATION: LC-HC Variety Domain of Humanized Antibody
      Varient(huMA79b.v17)

<400> SEQUENCE: 169

```
Asp Ile Gln Leu Thr Gln Ser Pro Ser Ser Leu Ser Ala Ser Val
 1               5                  10                  15

Gly Asp Arg Val Thr Ile Thr Cys Lys Ala Ser Gln Ser Val Asp
                20                  25                  30

Tyr Asp Gly Asp Ser Phe Leu Asn Trp Tyr Gln Gln Lys Pro Gly
                35                  40                  45

Lys Ala Pro Lys Leu Leu Ile Tyr Ala Ala Ser Asn Leu Glu Ser
```

```
                              50                  55                  60
Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser Asn Glu Asp Pro Leu Thr Phe Gly Gln Gly
                95                 100                 105

Thr Lys Val Glu Ile Lys Arg
                110

<210> SEQ ID NO 170
<211> LENGTH: 117
<212> TYPE: PRT
<213> ORGANISM: Artificial sequence
<220> FEATURE:
<223> OTHER INFORMATION: HC-Variable Domain of Humanized Antibody
      Variant (huMA79b.v17)

<400> SEQUENCE: 170

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Ser
                 20                  25                  30

Ser Tyr Trp Ile Glu Trp Val Arg Gln Ala Pro Gly Lys Gly Leu
                 35                  40                  45

Glu Trp Ile Gly Glu Ile Leu Pro Gly Gly Gly Asp Thr Asn Tyr
                 50                  55                  60

Asn Glu Ile Phe Lys Gly Arg Ala Thr Phe Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Thr Arg Arg Val Pro Val Tyr Phe Asp
                 95                 100                 105

Tyr Trp Gly Gln Gly Thr Leu Val Thr Val Ser Ser
                110                 115

<210> SEQ ID NO 171
<211> LENGTH: 23
<212> TYPE: PRT
<213> ORGANISM: Artificial sequence
<220> FEATURE:
<223> OTHER INFORMATION: FR1-LC of Humanized Antibody Variant (huMA79b.
      v18)

<400> SEQUENCE: 171

Asp Ile Gln Leu Thr Gln Ser Pro Ser Ser Leu Ser Ala Ser Val
  1               5                  10                  15

Gly Asp Arg Val Thr Ile Thr Cys
                 20

<210> SEQ ID NO 172
<211> LENGTH: 15
<212> TYPE: PRT
<213> ORGANISM: Artificial sequence
<220> FEATURE:
<223> OTHER INFORMATION: FR2-LC of Humanized Antibody Variant (huMA79b.
      v18)

<400> SEQUENCE: 172

Trp Tyr Gln Gln Lys Pro Gly Lys Ala Pro Lys Leu Leu Ile Tyr
  1               5                  10                  15
```

<210> SEQ ID NO 173
<211> LENGTH: 32
<212> TYPE: PRT
<213> ORGANISM: Artificial sequence
<220> FEATURE:
<223> OTHER INFORMATION: FR3-LC of Humanized Antibody Variant (huMA79b.v18)

<400> SEQUENCE: 173

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys

<210> SEQ ID NO 174
<211> LENGTH: 11
<212> TYPE: PRT
<213> ORGANISM: Artificial sequence
<220> FEATURE:
<223> OTHER INFORMATION: FR4-LC of Humanized Antibody Variant (huMA79b.v18)

<400> SEQUENCE: 174

Phe Gly Gln Gly Thr Lys Val Glu Ile Lys Arg
                 5                  10

<210> SEQ ID NO 175
<211> LENGTH: 15
<212> TYPE: PRT
<213> ORGANISM: Artificial sequence
<220> FEATURE:
<223> OTHER INFORMATION: HVR1-LC of Humanized Antibody Variant (huMA79b.v18)

<400> SEQUENCE: 175

Lys Ala Ser Gln Ser Val Asp Tyr Asp Gly Asp Ser Phe Leu Asn
 1               5                  10                  15

<210> SEQ ID NO 176
<211> LENGTH: 7
<212> TYPE: PRT
<213> ORGANISM: Artificial sequence
<220> FEATURE:
<223> OTHER INFORMATION: HVR2-LC of Humanized Antibody Variant (huMA79b.v18)

<400> SEQUENCE: 176

Ala Ala Ser Asn Leu Glu Ser
                 5

<210> SEQ ID NO 177
<211> LENGTH: 9
<212> TYPE: PRT
<213> ORGANISM: Artificial sequence
<220> FEATURE:
<223> OTHER INFORMATION: HVR3-LC of Humanized Antibody Variant (huMA79b.v18)

<400> SEQUENCE: 177

Gln Gln Ser Asn Glu Asp Pro Leu Thr
                 5

<210> SEQ ID NO 178
<211> LENGTH: 106
<212> TYPE: PRT
<213> ORGANISM: Artificial Sequence

```
<220> FEATURE:
<223> OTHER INFORMATION: CL1-LC of Humanized Antibody Variant (huMA79b.
      v18)

<400> SEQUENCE: 178

Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn
             20                  25                  30

Phe Tyr Pro Arg Glu Ala Lys Val Gln Trp Lys Val Asp Asn Ala
         35                  40                  45

Leu Gln Ser Gly Asn Ser Gln Glu Ser Val Thr Glu Gln Asp Ser
     50                  55                  60

Lys Asp Ser Thr Tyr Ser Leu Ser Ser Thr Leu Thr Leu Ser Lys
 65                  70                  75

Ala Asp Tyr Glu Lys His Lys Val Tyr Ala Cys Glu Val Thr His
                 80                  85                  90

Gln Gly Leu Ser Ser Pro Val Thr Lys Ser Phe Asn Arg Gly Glu
             95                 100                 105

Cys

<210> SEQ ID NO 179
<211> LENGTH: 25
<212> TYPE: PRT
<213> ORGANISM: Artificial sequence
<220> FEATURE:
<223> OTHER INFORMATION: FR1-HC of Humanized Antibody Variant (huMA79b.
      v18)

<400> SEQUENCE: 179

Glu Val Gln Leu Val Glu Ser Gly Gly Gly Leu Val Gln Pro Gly
 1               5                  10                  15

Gly Ser Leu Arg Leu Ser Cys Ala Ala Ser
             20                  25

<210> SEQ ID NO 180
<211> LENGTH: 13
<212> TYPE: PRT
<213> ORGANISM: Artificial sequence
<220> FEATURE:
<223> OTHER INFORMATION: FR2-HC of Humanized Antibody Variant (huMA79b.
      v18)

<400> SEQUENCE: 180

Trp Val Arg Gln Ala Pro Gly Lys Gly Leu Glu Trp Ile
                 5                  10

<210> SEQ ID NO 181
<211> LENGTH: 30
<212> TYPE: PRT
<213> ORGANISM: Artificial sequence
<220> FEATURE:
<223> OTHER INFORMATION: FR3-HC of Humanized Antibody Variant (huMA79b.
      v18)

<400> SEQUENCE: 181

Arg Ala Thr Phe Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
             20                  25                  30

<210> SEQ ID NO 182
<211> LENGTH: 11
```

```
<212> TYPE: PRT
<213> ORGANISM: Artificial sequence
<220> FEATURE:
<223> OTHER INFORMATION: FR4-HC of Humanized Antibody Variant (huMA79b.
      v18)

<400> SEQUENCE: 182

Trp Gly Gln Gly Thr Leu Val Thr Val Ser Ser
 1               5                   10

<210> SEQ ID NO 183
<211> LENGTH: 10
<212> TYPE: PRT
<213> ORGANISM: Artificial sequence
<220> FEATURE:
<223> OTHER INFORMATION: HVR1-HC of Humanized Antibody Variant (huMA79b.
      v18)

<400> SEQUENCE: 183

Gly Tyr Thr Phe Ser Ser Tyr Trp Ile Glu
 1               5                   10

<210> SEQ ID NO 184
<211> LENGTH: 18
<212> TYPE: PRT
<213> ORGANISM: Artificial sequence
<220> FEATURE:
<223> OTHER INFORMATION: HVR2-HC of Humanized Antibody Variant (huMA79b.
      v18)

<400> SEQUENCE: 184

Gly Glu Ile Leu Pro Gly Gly Gly Asp Thr Asn Tyr Asn Glu Ile
 1               5                   10                  15

Phe Lys Gly

<210> SEQ ID NO 185
<211> LENGTH: 10
<212> TYPE: PRT
<213> ORGANISM: Artificial sequence
<220> FEATURE:
<223> OTHER INFORMATION: HVR3-HC of Humanized Antibody Variant (huMA79b.
      v18)

<400> SEQUENCE: 185

Thr Arg Arg Val Pro Ile Arg Leu Asp Tyr
 1               5                   10

<210> SEQ ID NO 186
<211> LENGTH: 108
<212> TYPE: PRT
<213> ORGANISM: Artificial Sequence
<220> FEATURE:
<223> OTHER INFORMATION: CH1-HC of Humanized Antibody Variant (huMA79b.
      v18)

<400> SEQUENCE: 186

Ala Ser Thr Lys Gly Pro Ser Val Phe Pro Leu Ala Pro Ser Ser
 1               5                   10                  15

Lys Ser Thr Ser Gly Gly Thr Ala Ala Leu Gly Cys Leu Val Lys
                 20                  25                  30

Asp Tyr Phe Pro Glu Pro Val Thr Val Ser Trp Asn Ser Gly Ala
                 35                  40                  45

Leu Thr Ser Gly Val His Thr Phe Pro Ala Val Leu Gln Ser Ser
                 50                  55                  60

Gly Leu Tyr Ser Leu Ser Ser Val Val Thr Val Pro Ser Ser Ser
                 65                  70                  75
```

Leu Gly Thr Gln Thr Tyr Ile Cys Asn Val Asn His Lys Pro Ser
            80                  85                  90

Asn Thr Lys Val Asp Lys Lys Val Glu Pro Lys Ser Cys Asp Lys
            95                 100                 105

Thr His Thr

<210> SEQ ID NO 187
<211> LENGTH: 221
<212> TYPE: PRT
<213> ORGANISM: Artificial Sequence
<220> FEATURE:
<223> OTHER INFORMATION: Fc-HC of Humanized Antibody Variant (huMA79b.
      v18)

<400> SEQUENCE: 187

Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg
             20                  25                  30

Thr Pro Glu Val Thr Cys Val Val Val Asp Val Ser His Glu Asp
             35                  40                  45

Pro Glu Val Lys Phe Asn Trp Tyr Val Asp Gly Val Glu Val His
             50                  55                  60

Asn Ala Lys Thr Lys Pro Arg Glu Glu Gln Tyr Asn Ser Thr Tyr
             65                  70                  75

Arg Val Val Ser Val Leu Thr Val Leu His Gln Asp Trp Leu Asn
             80                  85                  90

Gly Lys Glu Tyr Lys Cys Lys Val Ser Asn Lys Ala Leu Pro Ala
             95                 100                 105

Pro Ile Glu Lys Thr Ile Ser Lys Ala Lys Gly Gln Pro Arg Glu
            110                 115                 120

Pro Gln Val Tyr Thr Leu Pro Pro Ser Arg Glu Glu Met Thr Lys
            125                 130                 135

Asn Gln Val Ser Leu Thr Cys Leu Val Lys Gly Phe Tyr Pro Ser
            140                 145                 150

Asp Ile Ala Val Glu Trp Glu Ser Asn Gly Gln Pro Glu Asn Asn
            155                 160                 165

Tyr Lys Thr Thr Pro Pro Val Leu Asp Ser Asp Gly Ser Phe Phe
            170                 175                 180

Leu Tyr Ser Lys Leu Thr Val Asp Lys Ser Arg Trp Gln Gln Gly
            185                 190                 195

Asn Val Phe Ser Cys Ser Val Met His Glu Ala Leu His Asn His
            200                 205                 210

Tyr Thr Gln Lys Ser Leu Ser Leu Ser Pro Gly
            215                 220

<210> SEQ ID NO 188
<211> LENGTH: 112
<212> TYPE: PRT
<213> ORGANISM: Artificial sequence
<220> FEATURE:
<223> OTHER INFORMATION: LC-Variable Domain of Humanized Antibody
      Variant (huMA79b.v18)

<400> SEQUENCE: 188

Asp Ile Gln Leu Thr Gln Ser Pro Ser Ser Leu Ser Ala Ser Val
  1               5                  10                  15

Gly Asp Arg Val Thr Ile Thr Cys Lys Ala Ser Gln Ser Val Asp

```
                    20                  25                  30

Tyr Asp Gly Asp Ser Phe Leu Asn Trp Tyr Gln Gln Lys Pro Gly
                35                  40                  45

Lys Ala Pro Lys Leu Leu Ile Tyr Ala Ala Ser Asn Leu Glu Ser
            50                  55                  60

Gly Val Pro Ser Arg Phe Ser Gly Ser Gly Ser Gly Thr Asp Phe
        65                  70                  75

Thr Leu Thr Ile Ser Ser Leu Gln Pro Glu Asp Phe Ala Thr Tyr
    80                  85                  90

Tyr Cys Gln Gln Ser Asn Glu Asp Pro Leu Thr Phe Gly Gln Gly
95                  100                 105

Thr Lys Val Glu Ile Lys Arg
                110

<210> SEQ ID NO 189
<211> LENGTH: 117
<212> TYPE: PRT
<213> ORGANISM: Artificial sequence
<220> FEATURE:
<223> OTHER INFORMATION: HC-Variable Domain of Humanized Antibody
      Variant (huMA79b.v18)

<400> SEQUENCE: 189

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Ser
                20                  25                  30

Ser Tyr Trp Ile Glu Trp Val Arg Gln Ala Pro Gly Lys Gly Leu
            35                  40                  45

Glu Trp Ile Gly Glu Ile Leu Pro Gly Gly Gly Asp Thr Asn Tyr
        50                  55                  60

Asn Glu Ile Phe Lys Gly Arg Ala Thr Phe Ser Ala Asp Thr Ser
    65                  70                  75

Lys Asn Thr Ala Tyr Leu Gln Met Asn Ser Leu Arg Ala Glu Asp
80                  85                  90

Thr Ala Val Tyr Tyr Cys Thr Arg Arg Val Pro Ile Arg Leu Asp
                95                  100                 105

Tyr Trp Gly Gln Gly Thr Leu Val Thr Val Ser Ser
            110                 115

<210> SEQ ID NO 190
<211> LENGTH: 23
<212> TYPE: PRT
<213> ORGANISM: Artificial sequence
<220> FEATURE:
<223> OTHER INFORMATION: FR1-LC of Humanized Antibody Variant (huMA79b.
      v28)

<400> SEQUENCE: 190

Asp Ile Gln Leu Thr Gln Ser Pro Ser Ser Leu Ser Ala Ser Val
1               5                   10                  15

Gly Asp Arg Val Thr Ile Thr Cys
                20

<210> SEQ ID NO 191
<211> LENGTH: 15
<212> TYPE: PRT
<213> ORGANISM: Artificial sequence
<220> FEATURE:
<223> OTHER INFORMATION: FR2-LC of Humanized Antibody Variant (huMA79b.
      v28)
```

<400> SEQUENCE: 191

Trp Tyr Gln Gln Lys Pro Gly Lys Ala Pro Lys Leu Leu Ile Tyr
 1               5                  10                  15

<210> SEQ ID NO 192
<211> LENGTH: 32
<212> TYPE: PRT
<213> ORGANISM: Artificial sequence
<220> FEATURE:
<223> OTHER INFORMATION: FR3-LC of Humanized Antibody Variant (huMA79b.
      v28)

<400> SEQUENCE: 192

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys

<210> SEQ ID NO 193
<211> LENGTH: 11
<212> TYPE: PRT
<213> ORGANISM: Artificial sequence
<220> FEATURE:
<223> OTHER INFORMATION: FR4-LC of Humanized Antibody Variant (huMA79b.
      v28)

<400> SEQUENCE: 193

Phe Gly Gln Gly Thr Lys Val Glu Ile Lys Arg
                 5                  10

<210> SEQ ID NO 194
<211> LENGTH: 15
<212> TYPE: PRT
<213> ORGANISM: Artificial sequence
<220> FEATURE:
<223> OTHER INFORMATION: HVR1-LC of Humanized Antibody Variant (huMA79b.
      v28)

<400> SEQUENCE: 194

Lys Ala Ser Gln Ser Val Asp Tyr Glu Gly Asp Ser Phe Leu Asn
 1               5                  10                  15

<210> SEQ ID NO 195
<211> LENGTH: 7
<212> TYPE: PRT
<213> ORGANISM: Artificial sequence
<220> FEATURE:
<223> OTHER INFORMATION: HVR2-LC of Humanized Antibody Variant (huMA79b.
      v28)

<400> SEQUENCE: 195

Ala Ala Ser Asn Leu Glu Ser
                 5

<210> SEQ ID NO 196
<211> LENGTH: 9
<212> TYPE: PRT
<213> ORGANISM: Artificial sequence
<220> FEATURE:
<223> OTHER INFORMATION: HVR3-LC of Humanized Antibody Variant (huMA79b.
      v28)

<400> SEQUENCE: 196

Gln Gln Ser Asn Glu Asp Pro Leu Thr
                 5

<210> SEQ ID NO 197
<211> LENGTH: 106
<212> TYPE: PRT
<213> ORGANISM: Artificial Sequence
<220> FEATURE:
<223> OTHER INFORMATION: CL1-LC of Humanized Antibody Variant (huMA79b.
      v28)

<400> SEQUENCE: 197

Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala
        35                  40                  45

Leu Gln Ser Gly Asn Ser Gln Glu Ser Val Thr Glu Gln Asp Ser
    50                  55                  60

Lys Asp Ser Thr Tyr Ser Leu Ser Ser Thr Leu Thr Leu Ser Lys
65                  70                  75

Ala Asp Tyr Glu Lys His Lys Val Tyr Ala Cys Glu Val Thr His
                80                  85                  90

Gln Gly Leu Ser Ser Pro Val Thr Lys Ser Phe Asn Arg Gly Glu
            95                  100                 105

Cys

<210> SEQ ID NO 198
<211> LENGTH: 25
<212> TYPE: PRT
<213> ORGANISM: Artificial sequence
<220> FEATURE:
<223> OTHER INFORMATION: FR1-HC of Humanized Antibody Variant (huMA79b.
      v28)

<400> SEQUENCE: 198

Glu Val Gln Leu Val Glu Ser Gly Gly Gly Leu Val Gln Pro Gly
 1               5                  10                  15

Gly Ser Leu Arg Leu Ser Cys Ala Ala Ser
            20                  25

<210> SEQ ID NO 199
<211> LENGTH: 13
<212> TYPE: PRT
<213> ORGANISM: Artificial sequence
<220> FEATURE:
<223> OTHER INFORMATION: FR2-HC of Humanized Antibody Variant (huMA79b.
      v28)

<400> SEQUENCE: 199

Trp Val Arg Gln Ala Pro Gly Lys Gly Leu Glu Trp Ile
         5                  10

<210> SEQ ID NO 200
<211> LENGTH: 30
<212> TYPE: PRT
<213> ORGANISM: Artificial sequence
<220> FEATURE:
<223> OTHER INFORMATION: FR3-HC of Humanized Antibody Variant (huMA79b.
      v28)

<400> SEQUENCE: 200

Arg Ala Thr Phe Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

<210> SEQ ID NO 201
<211> LENGTH: 11
<212> TYPE: PRT
<213> ORGANISM: Artificial sequence
<220> FEATURE:
<223> OTHER INFORMATION: FR4-HC of Humanized Antibody Variant (huMA79b.
      v28)

<400> SEQUENCE: 201

Trp Gly Gln Gly Thr Leu Val Thr Val Ser Ser
  5                   10

<210> SEQ ID NO 202
<211> LENGTH: 10
<212> TYPE: PRT
<213> ORGANISM: Artificial sequence
<220> FEATURE:
<223> OTHER INFORMATION: HVR1-HC of Humanized Antibody Variant (huMA79b.
      v28)

<400> SEQUENCE: 202

Gly Tyr Thr Phe Ser Ser Tyr Trp Ile Glu
  5                   10

<210> SEQ ID NO 203
<211> LENGTH: 18
<212> TYPE: PRT
<213> ORGANISM: Artificial sequence
<220> FEATURE:
<223> OTHER INFORMATION: HVR2-HLC of Humanized Antibody Variant
      (huMA79b.v28)

<400> SEQUENCE: 203

Gly Glu Ile Leu Pro Gly Gly Gly Asp Thr Asn Tyr Asn Glu Ile
  1               5                   10                  15

Phe Lys Gly

<210> SEQ ID NO 204
<211> LENGTH: 10
<212> TYPE: PRT
<213> ORGANISM: Artificial sequence
<220> FEATURE:
<223> OTHER INFORMATION: HVR3-HC of Humanized Antibody Variant
      (huMA79b.v28)

<400> SEQUENCE: 204

Thr Arg Arg Val Pro Ile Arg Leu Asp Tyr
  5                   10

<210> SEQ ID NO 205
<211> LENGTH: 108
<212> TYPE: PRT
<213> ORGANISM: Artificial Sequence
<220> FEATURE:
<223> OTHER INFORMATION: CH1-HC of Humanized Antibody Variant
      (huMA79b.v28)

<400> SEQUENCE: 205

Ala Ser Thr Lys Gly Pro Ser Val Phe Pro Leu Ala Pro Ser Ser
  1               5                   10                  15

Lys Ser Thr Ser Gly Gly Thr Ala Ala Leu Gly Cys Leu Val Lys
                20                  25                  30

Asp Tyr Phe Pro Glu Pro Val Thr Val Ser Trp Asn Ser Gly Ala
                35                  40                  45

```
Leu Thr Ser Gly Val His Thr Phe Pro Ala Val Leu Gln Ser Ser
             50                  55                  60

Gly Leu Tyr Ser Leu Ser Ser Val Val Thr Val Pro Ser Ser Ser
         65                  70                  75

Leu Gly Thr Gln Thr Tyr Ile Cys Asn Val Asn His Lys Pro Ser
     80                  85                  90

Asn Thr Lys Val Asp Lys Lys Val Glu Pro Lys Ser Cys Asp Lys
 95                 100                 105

Thr His Thr

<210> SEQ ID NO 206
<211> LENGTH: 221
<212> TYPE: PRT
<213> ORGANISM: Artificial Sequence
<220> FEATURE:
<223> OTHER INFORMATION: Fc-HC of Humanized Antibody Variant
      (huMA79b.V28)

<400> SEQUENCE: 206

Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg
             20                  25                  30

Thr Pro Glu Val Thr Cys Val Val Val Asp Val Ser His Glu Asp
         35                  40                  45

Pro Glu Val Lys Phe Asn Trp Tyr Val Asp Gly Val Glu Val His
     50                  55                  60

Asn Ala Lys Thr Lys Pro Arg Glu Glu Gln Tyr Asn Ser Thr Tyr
 65                  70                  75

Arg Val Val Ser Val Leu Thr Val Leu His Gln Asp Trp Leu Asn
             80                  85                  90

Gly Lys Glu Tyr Lys Cys Lys Val Ser Asn Lys Ala Leu Pro Ala
         95                 100                 105

Pro Ile Glu Lys Thr Ile Ser Lys Ala Lys Gly Gln Pro Arg Glu
    110                 115                 120

Pro Gln Val Tyr Thr Leu Pro Pro Ser Arg Glu Glu Met Thr Lys
125                 130                 135

Asn Gln Val Ser Leu Thr Cys Leu Val Lys Gly Phe Tyr Pro Ser
            140                 145                 150

Asp Ile Ala Val Glu Trp Glu Ser Asn Gly Gln Pro Glu Asn Asn
        155                 160                 165

Tyr Lys Thr Thr Pro Pro Val Leu Asp Ser Asp Gly Ser Phe Phe
    170                 175                 180

Leu Tyr Ser Lys Leu Thr Val Asp Lys Ser Arg Trp Gln Gln Gly
185                 190                 195

Asn Val Phe Ser Cys Ser Val Met His Glu Ala Leu His Asn His
            200                 205                 210

Tyr Thr Gln Lys Ser Leu Ser Leu Ser Pro Gly
        215                 220

<210> SEQ ID NO 207
<211> LENGTH: 112
<212> TYPE: PRT
<213> ORGANISM: Artificial sequence
<220> FEATURE:
<223> OTHER INFORMATION: LC-variable domain of (huMA79b.v28)

<400> SEQUENCE: 207
```

```
Asp Ile Gln Leu Thr Gln Ser Pro Ser Ser Leu Ser Ala Ser Val
  1               5                  10                  15

Gly Asp Arg Val Thr Ile Thr Cys Lys Ala Ser Gln Ser Val Asp
             20                  25                  30

Tyr Glu Gly Asp Ser Phe Leu Asn Trp Tyr Gln Gln Lys Pro Gly
         35                  40                  45

Lys Ala Pro Lys Leu Leu Ile Tyr Ala Ala Ser Asn Leu Glu Ser
     50                  55                  60

Gly Val Pro Ser Arg Phe Ser Gly Ser Gly Ser Gly Thr Asp Phe
 65                  70                  75

Thr Leu Thr Ile Ser Ser Leu Gln Pro Glu Asp Phe Ala Thr Tyr
             80                  85                  90

Tyr Cys Gln Gln Ser Asn Glu Asp Pro Leu Thr Phe Gly Gln Gly
         95                 100                 105

Thr Lys Val Glu Ile Lys Arg
            110
```

<210> SEQ ID NO 208
<211> LENGTH: 117
<212> TYPE: PRT
<213> ORGANISM: Artificial sequence
<220> FEATURE:
<223> OTHER INFORMATION: HC-Variable Domain of Humanized Antibody
      (huMA79b.v28)

<400> SEQUENCE: 208

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Ser
             20                  25                  30

Ser Tyr Trp Ile Glu Trp Val Arg Gln Ala Pro Gly Lys Gly Leu
         35                  40                  45

Glu Trp Ile Gly Glu Ile Leu Pro Gly Gly Gly Asp Thr Asn Tyr
     50                  55                  60

Asn Glu Ile Phe Lys Gly Arg Ala Thr Phe Ser Ala Asp Thr Ser
 65                  70                  75

Lys Asn Thr Ala Tyr Leu Gln Met Asn Ser Leu Arg Ala Glu Asp
             80                  85                  90

Thr Ala Val Tyr Tyr Cys Thr Arg Arg Val Pro Ile Arg Leu Asp
         95                 100                 105

Tyr Trp Gly Gln Gly Thr Leu Val Thr Val Ser Ser
            110                 115
```

<210> SEQ ID NO 209
<211> LENGTH: 23
<212> TYPE: PRT
<213> ORGANISM: Artificial sequence
<220> FEATURE:
<223> OTHER INFORMATION: FR1-LC of Humanized Antibody Variant
      (huMA79b.v32)

<400> SEQUENCE: 209

```
Asp Ile Gln Leu Thr Gln Ser Pro Ser Ser Leu Ser Ala Ser Val
  1               5                  10                  15

Gly Asp Arg Val Thr Ile Thr Cys
             20
```

<210> SEQ ID NO 210
<211> LENGTH: 15

-continued

```
<212> TYPE: PRT
<213> ORGANISM: Artificial sequence
<220> FEATURE:
<223> OTHER INFORMATION: FR2-LC of Humanized Antibody Variant
      (huMA79b.v32)

<400> SEQUENCE: 210

Trp Tyr Gln Gln Lys Pro Gly Lys Ala Pro Lys Leu Phe Ile Tyr
 1               5                  10                  15

<210> SEQ ID NO 211
<211> LENGTH: 32
<212> TYPE: PRT
<213> ORGANISM: Artificial sequence
<220> FEATURE:
<223> OTHER INFORMATION: FR3-LC of Humanized Antibody Variant (huMA79b.
      v32)

<400> SEQUENCE: 211

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys

<210> SEQ ID NO 212
<211> LENGTH: 11
<212> TYPE: PRT
<213> ORGANISM: Artificial sequence
<220> FEATURE:
<223> OTHER INFORMATION: FR4-LC of Humanized Antibody Variant (huMA79b.
      v32)

<400> SEQUENCE: 212

Phe Gly Gln Gly Thr Lys Val Glu Ile Lys Arg
                 5                  10

<210> SEQ ID NO 213
<211> LENGTH: 15
<212> TYPE: PRT
<213> ORGANISM: Artificial sequence
<220> FEATURE:
<223> OTHER INFORMATION: HVR1-LC of Humanized Antibody Variant (huMA79b.
      v32)

<400> SEQUENCE: 213

Lys Ala Ser Gln Ser Val Asp Tyr Ser Gly Asp Ser Phe Leu Asn
 1               5                  10                  15

<210> SEQ ID NO 214
<211> LENGTH: 7
<212> TYPE: PRT
<213> ORGANISM: Artificial sequence
<220> FEATURE:
<223> OTHER INFORMATION: HVR2-LC of Humanized Antibody Variant (huMA79b.
      v32)

<400> SEQUENCE: 214

Ala Ala Ser Asn Leu Glu Ser
                 5

<210> SEQ ID NO 215
<211> LENGTH: 9
<212> TYPE: PRT
<213> ORGANISM: Artificial sequence
<220> FEATURE:
<223> OTHER INFORMATION: HVR3-LC of Humanized Antibody Variant (huMA79b.
      v32)
```

-continued

<400> SEQUENCE: 215

Gln Gln Ser Asn Glu Asp Pro Leu Thr
1               5

<210> SEQ ID NO 216
<211> LENGTH: 106
<212> TYPE: PRT
<213> ORGANISM: Artificial Sequence
<220> FEATURE:
<223> OTHER INFORMATION: CL1-LC of Humanized Antibody Variant (huMA79b.
      v32)

<400> SEQUENCE: 216

Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn
                20                  25                  30

Phe Tyr Pro Arg Glu Ala Lys Val Gln Trp Lys Val Asp Asn Ala
                35                  40                  45

Leu Gln Ser Gly Asn Ser Gln Glu Ser Val Thr Glu Gln Asp Ser
                50                  55                  60

Lys Asp Ser Thr Tyr Ser Leu Ser Ser Thr Leu Thr Leu Ser Lys
                65                  70                  75

Ala Asp Tyr Glu Lys His Lys Val Tyr Ala Cys Glu Val Thr His
                80                  85                  90

Gln Gly Leu Ser Ser Pro Val Thr Lys Ser Phe Asn Arg Gly Glu
                95                  100                 105

Cys

<210> SEQ ID NO 217
<211> LENGTH: 25
<212> TYPE: PRT
<213> ORGANISM: Artificial sequence
<220> FEATURE:
<223> OTHER INFORMATION: FR1-HC of Humanized Antibody Variant (huMA79b.
      v32)

<400> SEQUENCE: 217

Glu Val Gln Leu Val Glu Ser Gly Gly Gly Leu Val Gln Pro Gly
1               5                   10                  15

Gly Ser Leu Arg Leu Ser Cys Ala Ala Ser
                20                  25

<210> SEQ ID NO 218
<211> LENGTH: 13
<212> TYPE: PRT
<213> ORGANISM: Artificial sequence
<220> FEATURE:
<223> OTHER INFORMATION: FR2-HC of Humanized Antibody Variant (huMA79b.
      v32)

<400> SEQUENCE: 218

Trp Val Arg Gln Ala Pro Gly Lys Gly Leu Glu Trp Ile
1               5                   10

<210> SEQ ID NO 219
<211> LENGTH: 30
<212> TYPE: PRT
<213> ORGANISM: Artificial sequence
<220> FEATURE:
<223> OTHER INFORMATION: FR3-HC of Humanized Antibody Variant (huMA79b.
      v32)

```
<400> SEQUENCE: 219

Arg Ala Thr Phe Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

<210> SEQ ID NO 220
<211> LENGTH: 11
<212> TYPE: PRT
<213> ORGANISM: Artificial sequence
<220> FEATURE:
<223> OTHER INFORMATION: FR4-HC of Humanized Antibody Variant (huMA79b.
      v32)

<400> SEQUENCE: 220

Trp Gly Gln Gly Thr Leu Val Thr Val Ser Ser
                 5                  10

<210> SEQ ID NO 221
<211> LENGTH: 10
<212> TYPE: PRT
<213> ORGANISM: Artificial sequence
<220> FEATURE:
<223> OTHER INFORMATION: HVR1-HC of Humanized Antibody Variant (huMA79b.
      v32)

<400> SEQUENCE: 221

Gly Tyr Thr Phe Ser Ser Tyr Trp Ile Glu
                 5                  10

<210> SEQ ID NO 222
<211> LENGTH: 18
<212> TYPE: PRT
<213> ORGANISM: Artificial sequence
<220> FEATURE:
<223> OTHER INFORMATION: HVR2-HC of Humanized Antibody Variant (huMA79b.
      v32)

<400> SEQUENCE: 222

Gly Glu Ile Leu Pro Gly Gly Gly Asp Thr Asn Tyr Asn Glu Ile
 1               5                  10                  15

Phe Lys Gly

<210> SEQ ID NO 223
<211> LENGTH: 10
<212> TYPE: PRT
<213> ORGANISM: Artificial sequence
<220> FEATURE:
<223> OTHER INFORMATION: HVR3-HC of Humanized Antibody Variant (huMA79b.
      v32)

<400> SEQUENCE: 223

Thr Arg Arg Val Pro Ile Arg Leu Asp Tyr
                 5                  10

<210> SEQ ID NO 224
<211> LENGTH: 108
<212> TYPE: PRT
<213> ORGANISM: Artificial Sequence
<220> FEATURE:
<223> OTHER INFORMATION: CH1-HC of Humanized Antibody Variant (huMA79b.
      v32)

<400> SEQUENCE: 224

Ala Ser Thr Lys Gly Pro Ser Val Phe Pro Leu Ala Pro Ser Ser
 1               5                  10                  15
```

```
Lys Ser Thr Ser Gly Gly Thr Ala Ala Leu Gly Cys Leu Val Lys
                 20                  25                  30

Asp Tyr Phe Pro Glu Pro Val Thr Val Ser Trp Asn Ser Gly Ala
                 35                  40                  45

Leu Thr Ser Gly Val His Thr Phe Pro Ala Val Leu Gln Ser Ser
                 50                  55                  60

Gly Leu Tyr Ser Leu Ser Ser Val Val Thr Val Pro Ser Ser Ser
                 65                  70                  75

Leu Gly Thr Gln Thr Tyr Ile Cys Asn Val Asn His Lys Pro Ser
                 80                  85                  90

Asn Thr Lys Val Asp Lys Val Glu Pro Lys Ser Cys Asp Lys
                 95                 100                 105

Thr His Thr

<210> SEQ ID NO 225
<211> LENGTH: 221
<212> TYPE: PRT
<213> ORGANISM: Artificial Sequence
<220> FEATURE:
<223> OTHER INFORMATION: Fc-HC of Humanized Antibody Variant (huMA79b.
      v32)

<400> SEQUENCE: 225

Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg
                 20                  25                  30

Thr Pro Glu Val Thr Cys Val Val Val Asp Val Ser His Glu Asp
                 35                  40                  45

Pro Glu Val Lys Phe Asn Trp Tyr Val Asp Gly Val Glu Val His
                 50                  55                  60

Asn Ala Lys Thr Lys Pro Arg Glu Glu Gln Tyr Asn Ser Thr Tyr
                 65                  70                  75

Arg Val Val Ser Val Leu Thr Val Leu His Gln Asp Trp Leu Asn
                 80                  85                  90

Gly Lys Glu Tyr Lys Cys Lys Val Ser Asn Lys Ala Leu Pro Ala
                 95                 100                 105

Pro Ile Glu Lys Thr Ile Ser Lys Ala Lys Gly Gln Pro Arg Glu
                110                 115                 120

Pro Gln Val Tyr Thr Leu Pro Pro Ser Arg Glu Glu Met Thr Lys
                125                 130                 135

Asn Gln Val Ser Leu Thr Cys Leu Val Lys Gly Phe Tyr Pro Ser
                140                 145                 150

Asp Ile Ala Val Glu Trp Glu Ser Asn Gly Gln Pro Glu Asn Asn
                155                 160                 165

Tyr Lys Thr Thr Pro Pro Val Leu Asp Ser Asp Gly Ser Phe Phe
                170                 175                 180

Leu Tyr Ser Lys Leu Thr Val Asp Lys Ser Arg Trp Gln Gln Gly
                185                 190                 195

Asn Val Phe Ser Cys Ser Val Met His Glu Ala Leu His Asn His
                200                 205                 210

Tyr Thr Gln Lys Ser Leu Ser Leu Ser Pro Gly
                215                 220

<210> SEQ ID NO 226
<211> LENGTH: 112
<212> TYPE: PRT
```

<213> ORGANISM: Artificial sequence
<220> FEATURE:
<223> OTHER INFORMATION: LC -Variable Domain of Humanized Antibody
      Variant (huMA79b.v32)

<400> SEQUENCE: 226

Asp Ile Gln Leu Thr Gln Ser Pro Ser Ser Leu Ser Ala Ser Val
1               5                   10                  15

Gly Asp Arg Val Thr Ile Thr Cys Lys Ala Ser Gln Ser Val Asp
                20                  25                  30

Tyr Ser Gly Asp Ser Phe Leu Asn Trp Tyr Gln Gln Lys Pro Gly
                35                  40                  45

Lys Ala Pro Lys Leu Phe Ile Tyr Ala Ala Ser Asn Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser Asn Glu Asp Pro Leu Thr Phe Gly Gln Gly
                95                  100                 105

Thr Lys Val Glu Ile Lys Arg
                110

<210> SEQ ID NO 227
<211> LENGTH: 117
<212> TYPE: PRT
<213> ORGANISM: Artificial sequence
<220> FEATURE:
<223> OTHER INFORMATION: HC-Variable Domain of Humanized Antibody
      Variant (huMA79b.v32)

<400> SEQUENCE: 227

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Ser
                20                  25                  30

Ser Tyr Trp Ile Glu Trp Val Arg Gln Ala Pro Gly Lys Gly Leu
                35                  40                  45

Glu Trp Ile Gly Glu Ile Leu Pro Gly Gly Gly Asp Thr Asn Tyr
                50                  55                  60

Asn Glu Ile Phe Lys Gly Arg Ala Thr Phe Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Thr Arg Arg Val Pro Ile Arg Leu Asp
                95                  100                 105

Tyr Trp Gly Gln Gly Thr Leu Val Thr Val Ser Ser
                110                 115

<210> SEQ ID NO 228
<211> LENGTH: 446
<212> TYPE: PRT
<213> ORGANISM: Artificial sequence
<220> FEATURE:
<223> OTHER INFORMATION: ThioMAb-huMA79b.v17-HC(A118C) Variant - HC

<400> SEQUENCE: 228

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Ser

```
                    20                  25                  30
Ser Tyr Trp Ile Glu Trp Val Arg Gln Ala Pro Gly Lys Gly Leu
                35                  40                  45

Glu Trp Ile Gly Glu Ile Leu Pro Gly Gly Asp Thr Asn Tyr
                50                  55                  60

Asn Glu Ile Phe Lys Gly Arg Ala Thr Phe Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Thr Arg Arg Val Pro Val Tyr Phe Asp
                95                 100                 105

Tyr Trp Gly Gln Gly Thr Leu Val Thr Val Ser Ser Cys Ser Thr
               110                 115                 120

Lys Gly Pro Ser Val Phe Pro Leu Ala Pro Ser Ser Lys Ser Thr
               125                 130                 135

Ser Gly Gly Thr Ala Ala Leu Gly Cys Leu Val Lys Asp Tyr Phe
               140                 145                 150

Pro Glu Pro Val Thr Val Ser Trp Asn Ser Gly Ala Leu Thr Ser
               155                 160                 165

Gly Val His Thr Phe Pro Ala Val Leu Gln Ser Ser Gly Leu Tyr
               170                 175                 180

Ser Leu Ser Ser Val Val Thr Val Pro Ser Ser Ser Leu Gly Thr
               185                 190                 195

Gln Thr Tyr Ile Cys Asn Val Asn His Lys Pro Ser Asn Thr Lys
               200                 205                 210

Val Asp Lys Lys Val Glu Pro Lys Ser Cys Asp Lys Thr His Thr
               215                 220                 225

Cys Pro Pro Cys Pro Ala Pro Glu Leu Leu Gly Gly Pro Ser Val
               230                 235                 240

Phe Leu Phe Pro Pro Lys Pro Lys Asp Thr Leu Met Ile Ser Arg
               245                 250                 255

Thr Pro Glu Val Thr Cys Val Val Val Asp Val Ser His Glu Asp
               260                 265                 270

Pro Glu Val Lys Phe Asn Trp Tyr Val Asp Gly Val Glu Val His
               275                 280                 285

Asn Ala Lys Thr Lys Pro Arg Glu Glu Gln Tyr Asn Ser Thr Tyr
               290                 295                 300

Arg Val Val Ser Val Leu Thr Val Leu His Gln Asp Trp Leu Asn
               305                 310                 315

Gly Lys Glu Tyr Lys Cys Lys Val Ser Asn Lys Ala Leu Pro Ala
               320                 325                 330

Pro Ile Glu Lys Thr Ile Ser Lys Ala Lys Gly Gln Pro Arg Glu
               335                 340                 345

Pro Gln Val Tyr Thr Leu Pro Pro Ser Arg Glu Glu Met Thr Lys
               350                 355                 360

Asn Gln Val Ser Leu Thr Cys Leu Val Lys Gly Phe Tyr Pro Ser
               365                 370                 375

Asp Ile Ala Val Glu Trp Glu Ser Asn Gly Gln Pro Glu Asn Asn
               380                 385                 390

Tyr Lys Thr Thr Pro Pro Val Leu Asp Ser Asp Gly Ser Phe Phe
               395                 400                 405

Leu Tyr Ser Lys Leu Thr Val Asp Lys Ser Arg Trp Gln Gln Gly
               410                 415                 420
```

```
Asn Val Phe Ser Cys Ser Val Met His Glu Ala Leu His Asn His
                425                 430                 435

Tyr Thr Gln Lys Ser Leu Ser Leu Ser Pro Gly
                440                 445

<210> SEQ ID NO 229
<211> LENGTH: 218
<212> TYPE: PRT
<213> ORGANISM: Artificial sequence
<220> FEATURE:
<223> OTHER INFORMATION: ThioMAb-huMA79b.v17-HC(A118C) Variant - LC

<400> SEQUENCE: 229

Asp Ile Gln Leu Thr Gln Ser Pro Ser Ser Leu Ser Ala Ser Val
  1               5                  10                  15

Gly Asp Arg Val Thr Ile Thr Cys Lys Ala Ser Gln Ser Val Asp
                 20                  25                  30

Tyr Asp Gly Asp Ser Phe Leu Asn Trp Tyr Gln Gln Lys Pro Gly
                 35                  40                  45

Lys Ala Pro Lys Leu Leu Ile Tyr Ala Ala Ser Asn Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Ser Asn Glu Asp Pro Leu Thr Phe Gly Gln Gly
                 95                 100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215

<210> SEQ ID NO 230
<211> LENGTH: 446
<212> TYPE: PRT
<213> ORGANISM: Artificial sequence
<220> FEATURE:
<223> OTHER INFORMATION: ThioMAb-huMA79b.v18-HC(A118C) Variant - HC

<400> SEQUENCE: 230

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Ser
                 20                  25                  30

Ser Tyr Trp Ile Glu Trp Val Arg Gln Ala Pro Gly Lys Gly Leu
                 35                  40                  45
```

```
Glu Trp Ile Gly Glu Ile Leu Pro Gly Gly Asp Thr Asn Tyr
            50                  55                  60
Asn Glu Ile Phe Lys Gly Arg Ala Thr Phe Ser Ala Asp Thr Ser
            65                  70                  75
Lys Asn Thr Ala Tyr Leu Gln Met Asn Ser Leu Arg Ala Glu Asp
            80                  85                  90
Thr Ala Val Tyr Tyr Cys Thr Arg Arg Val Pro Ile Arg Leu Asp
            95                 100                 105
Tyr Trp Gly Gln Gly Thr Leu Val Thr Val Ser Ser Cys Ser Thr
           110                 115                 120
Lys Gly Pro Ser Val Phe Pro Leu Ala Pro Ser Ser Lys Ser Thr
           125                 130                 135
Ser Gly Gly Thr Ala Ala Leu Gly Cys Leu Val Lys Asp Tyr Phe
           140                 145                 150
Pro Glu Pro Val Thr Val Ser Trp Asn Ser Gly Ala Leu Thr Ser
           155                 160                 165
Gly Val His Thr Phe Pro Ala Val Leu Gln Ser Ser Gly Leu Tyr
           170                 175                 180
Ser Leu Ser Ser Val Val Thr Val Pro Ser Ser Ser Leu Gly Thr
           185                 190                 195
Gln Thr Tyr Ile Cys Asn Val Asn His Lys Pro Ser Asn Thr Lys
           200                 205                 210
Val Asp Lys Lys Val Glu Pro Lys Ser Cys Asp Lys Thr His Thr
           215                 220                 225
Cys Pro Pro Cys Pro Ala Pro Glu Leu Leu Gly Gly Pro Ser Val
           230                 235                 240
Phe Leu Phe Pro Pro Lys Pro Lys Asp Thr Leu Met Ile Ser Arg
           245                 250                 255
Thr Pro Glu Val Thr Cys Val Val Val Asp Val Ser His Glu Asp
           260                 265                 270
Pro Glu Val Lys Phe Asn Trp Tyr Val Asp Gly Val Glu Val His
           275                 280                 285
Asn Ala Lys Thr Lys Pro Arg Glu Glu Gln Tyr Asn Ser Thr Tyr
           290                 295                 300
Arg Val Val Ser Val Leu Thr Val Leu His Gln Asp Trp Leu Asn
           305                 310                 315
Gly Lys Glu Tyr Lys Cys Lys Val Ser Asn Lys Ala Leu Pro Ala
           320                 325                 330
Pro Ile Glu Lys Thr Ile Ser Lys Ala Lys Gly Gln Pro Arg Glu
           335                 340                 345
Pro Gln Val Tyr Thr Leu Pro Pro Ser Arg Glu Glu Met Thr Lys
           350                 355                 360
Asn Gln Val Ser Leu Thr Cys Leu Val Lys Gly Phe Tyr Pro Ser
           365                 370                 375
Asp Ile Ala Val Glu Trp Glu Ser Asn Gly Gln Pro Glu Asn Asn
           380                 385                 390
Tyr Lys Thr Thr Pro Pro Val Leu Asp Ser Asp Gly Ser Phe Phe
           395                 400                 405
Leu Tyr Ser Lys Leu Thr Val Asp Lys Ser Arg Trp Gln Gln Gly
           410                 415                 420
Asn Val Phe Ser Cys Ser Val Met His Glu Ala Leu His Asn His
           425                 430                 435
Tyr Thr Gln Lys Ser Leu Ser Leu Ser Pro Gly
           440                 445
```

<210> SEQ ID NO 231
<211> LENGTH: 218
<212> TYPE: PRT
<213> ORGANISM: Artificial sequence
<220> FEATURE:
<223> OTHER INFORMATION: ThioMAb-huMA79b.v18-HC(A118C) Variant - LC

<400> SEQUENCE: 231

```
Asp Ile Gln Leu Thr Gln Ser Pro Ser Ser Leu Ser Ala Ser Val
 1               5                  10                  15

Gly Asp Arg Val Thr Ile Thr Cys Lys Ala Ser Gln Ser Val Asp
            20                  25                  30

Tyr Asp Gly Asp Ser Phe Leu Asn Trp Tyr Gln Gln Lys Pro Gly
        35                  40                  45

Lys Ala Pro Lys Leu Leu Ile Tyr Ala Ala Ser Asn Leu Glu Ser
    50                  55                  60

Gly Val Pro Ser Arg Phe Ser Gly Ser Gly Ser Gly Thr Asp Phe
65                  70                  75

Thr Leu Thr Ile Ser Ser Leu Gln Pro Glu Asp Phe Ala Thr Tyr
                80                  85                  90

Tyr Cys Gln Gln Ser Asn Glu Asp Pro Leu Thr Phe Gly Gln Gly
            95                 100                 105

Thr Lys Val Glu Ile Lys Arg Thr Val Ala Ala Pro Ser Val Phe
       110                 115                 120

Ile Phe Pro Pro Ser Asp Glu Gln Leu Lys Ser Gly Thr Ala Ser
   125                 130                 135

Val Val Cys Leu Leu Asn Asn Phe Tyr Pro Arg Glu Ala Lys Val
            140                 145                 150

Gln Trp Lys Val Asp Asn Ala Leu Gln Ser Gly Asn Ser Gln Glu
       155                 160                 165

Ser Val Thr Glu Gln Asp Ser Lys Asp Ser Thr Tyr Ser Leu Ser
   170                 175                 180

Ser Thr Leu Thr Leu Ser Lys Ala Asp Tyr Glu Lys His Lys Val
            185                 190                 195

Tyr Ala Cys Glu Val Thr His Gln Gly Leu Ser Ser Pro Val Thr
       200                 205                 210

Lys Ser Phe Asn Arg Gly Glu Cys
   215
```

<210> SEQ ID NO 232
<211> LENGTH: 446
<212> TYPE: PRT
<213> ORGANISM: Artificial sequence
<220> FEATURE:
<223> OTHER INFORMATION: ThioMAb-huMA79b.v28-HC(A118C) Variant - HC

<400> SEQUENCE: 232

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Ser
            20                  25                  30

Ser Tyr Trp Ile Glu Trp Val Arg Gln Ala Pro Gly Lys Gly Leu
        35                  40                  45

Glu Trp Ile Gly Glu Ile Leu Pro Gly Gly Gly Asp Thr Asn Tyr
    50                  55                  60

Asn Glu Ile Phe Lys Gly Arg Ala Thr Phe Ser Ala Asp Thr Ser
65                  70                  75
```

```
Lys Asn Thr Ala Tyr Leu Gln Met Asn Ser Leu Arg Ala Glu Asp
                80                  85                  90
Thr Ala Val Tyr Tyr Cys Thr Arg Arg Val Pro Ile Arg Leu Asp
                95                 100                 105
Tyr Trp Gly Gln Gly Thr Leu Val Thr Val Ser Ser Cys Ser Thr
               110                 115                 120
Lys Gly Pro Ser Val Phe Pro Leu Ala Pro Ser Ser Lys Ser Thr
               125                 130                 135
Ser Gly Gly Thr Ala Ala Leu Gly Cys Leu Val Lys Asp Tyr Phe
               140                 145                 150
Pro Glu Pro Val Thr Val Ser Trp Asn Ser Gly Ala Leu Thr Ser
               155                 160                 165
Gly Val His Thr Phe Pro Ala Val Leu Gln Ser Ser Gly Leu Tyr
               170                 175                 180
Ser Leu Ser Ser Val Val Thr Val Pro Ser Ser Ser Leu Gly Thr
               185                 190                 195
Gln Thr Tyr Ile Cys Asn Val Asn His Lys Pro Ser Asn Thr Lys
               200                 205                 210
Val Asp Lys Lys Val Glu Pro Lys Ser Cys Asp Lys Thr His Thr
               215                 220                 225
Cys Pro Pro Cys Pro Ala Pro Glu Leu Leu Gly Gly Pro Ser Val
               230                 235                 240
Phe Leu Phe Pro Pro Lys Pro Lys Asp Thr Leu Met Ile Ser Arg
               245                 250                 255
Thr Pro Glu Val Thr Cys Val Val Val Asp Val Ser His Glu Asp
               260                 265                 270
Pro Glu Val Lys Phe Asn Trp Tyr Val Asp Gly Val Glu Val His
               275                 280                 285
Asn Ala Lys Thr Lys Pro Arg Glu Glu Gln Tyr Asn Ser Thr Tyr
               290                 295                 300
Arg Val Val Ser Val Leu Thr Val Leu His Gln Asp Trp Leu Asn
               305                 310                 315
Gly Lys Glu Tyr Lys Cys Lys Val Ser Asn Lys Ala Leu Pro Ala
               320                 325                 330
Pro Ile Glu Lys Thr Ile Ser Lys Ala Lys Gly Gln Pro Arg Glu
               335                 340                 345
Pro Gln Val Tyr Thr Leu Pro Pro Ser Arg Glu Glu Met Thr Lys
               350                 355                 360
Asn Gln Val Ser Leu Thr Cys Leu Val Lys Gly Phe Tyr Pro Ser
               365                 370                 375
Asp Ile Ala Val Glu Trp Glu Ser Asn Gly Gln Pro Glu Asn Asn
               380                 385                 390
Tyr Lys Thr Thr Pro Pro Val Leu Asp Ser Asp Gly Ser Phe Phe
               395                 400                 405
Leu Tyr Ser Lys Leu Thr Val Asp Lys Ser Arg Trp Gln Gln Gly
               410                 415                 420
Asn Val Phe Ser Cys Ser Val Met His Glu Ala Leu His Asn His
               425                 430                 435
Tyr Thr Gln Lys Ser Leu Ser Leu Ser Pro Gly
               440                 445

<210> SEQ ID NO 233
<211> LENGTH: 218
<212> TYPE: PRT
```

<213> ORGANISM: Artificial sequence
<220> FEATURE:
<223> OTHER INFORMATION: ThioMAb-huMA79b.v28-HC(A118C) Variant - LC

<400> SEQUENCE: 233

```
Asp Ile Gln Leu Thr Gln Ser Pro Ser Ser Leu Ser Ala Ser Val
  1               5                  10                  15

Gly Asp Arg Val Thr Ile Thr Cys Lys Ala Ser Gln Ser Val Asp
             20                  25                  30

Tyr Glu Gly Asp Ser Phe Leu Asn Trp Tyr Gln Gln Lys Pro Gly
             35                  40                  45

Lys Ala Pro Lys Leu Leu Ile Tyr Ala Ala Ser Asn Leu Glu Ser
             50                  55                  60

Gly Val Pro Ser Arg Phe Ser Gly Ser Gly Ser Gly Thr Asp Phe
             65                  70                  75

Thr Leu Thr Ile Ser Ser Leu Gln Pro Glu Asp Phe Ala Thr Tyr
             80                  85                  90

Tyr Cys Gln Gln Ser Asn Glu Asp Pro Leu Thr Phe Gly Gln Gly
             95                 100                 105

Thr Lys Val Glu Ile Lys Arg Thr Val Ala Ala Pro Ser Val Phe
            110                 115                 120

Ile Phe Pro Pro Ser Asp Glu Gln Leu Lys Ser Gly Thr Ala Ser
            125                 130                 135

Val Val Cys Leu Leu Asn Asn Phe Tyr Pro Arg Glu Ala Lys Val
            140                 145                 150

Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
            170                 175                 180

Ser Thr Leu Thr Leu Ser Lys Ala Asp Tyr Glu Lys His Lys Val
            185                 190                 195

Tyr Ala Cys Glu Val Thr His Gln Gly Leu Ser Ser Pro Val Thr
            200                 205                 210

Lys Ser Phe Asn Arg Gly Glu Cys
            215
```

<210> SEQ ID NO 234
<211> LENGTH: 446
<212> TYPE: PRT
<213> ORGANISM: Artificial sequence
<220> FEATURE:
<223> OTHER INFORMATION: ThioMAb-chMA79b- LC(V205C) Variant - HC

<400> SEQUENCE: 234

```
Glu Val Gln Leu Gln Gln Ser Gly Ala Glu Leu Met Lys Pro Gly
  1               5                  10                  15

Ala Ser Val Lys Ile Ser Cys Lys Ala Thr Gly Tyr Thr Phe Ser
             20                  25                  30

Ser Tyr Trp Ile Glu Trp Val Lys Gln Arg Pro Gly His Gly Leu
             35                  40                  45

Glu Trp Ile Gly Glu Ile Leu Pro Gly Gly Gly Asp Thr Asn Tyr
             50                  55                  60

Asn Glu Ile Phe Lys Gly Lys Ala Thr Phe Thr Ala Asp Thr Ser
             65                  70                  75

Ser Asn Thr Ala Tyr Met Gln Leu Ser Ser Leu Thr Ser Glu Asp
             80                  85                  90

Ser Ala Val Tyr Tyr Cys Thr Arg Arg Val Pro Val Tyr Phe Asp
```

```
                         95                  100                 105
Tyr Trp Gly Gln Gly Thr Ser Val Thr Val Ser Ser Ala Ser Thr
                    110                 115                 120
Lys Gly Pro Ser Val Phe Pro Leu Ala Pro Ser Ser Lys Ser Thr
                    125                 130                 135
Ser Gly Gly Thr Ala Ala Leu Gly Cys Leu Val Lys Asp Tyr Phe
                    140                 145                 150
Pro Glu Pro Val Thr Val Ser Trp Asn Ser Gly Ala Leu Thr Ser
                    155                 160                 165
Gly Val His Thr Phe Pro Ala Val Leu Gln Ser Ser Gly Leu Tyr
                    170                 175                 180
Ser Leu Ser Ser Val Val Thr Val Pro Ser Ser Ser Leu Gly Thr
                    185                 190                 195
Gln Thr Tyr Ile Cys Asn Val Asn His Lys Pro Ser Asn Thr Lys
                    200                 205                 210
Val Asp Lys Lys Val Glu Pro Lys Ser Cys Asp Lys Thr His Thr
                    215                 220                 225
Cys Pro Pro Cys Pro Ala Pro Glu Leu Leu Gly Gly Pro Ser Val
                    230                 235                 240
Phe Leu Phe Pro Pro Lys Pro Lys Asp Thr Leu Met Ile Ser Arg
                    245                 250                 255
Thr Pro Glu Val Thr Cys Val Val Val Asp Val Ser His Glu Asp
                    260                 265                 270
Pro Glu Val Lys Phe Asn Trp Tyr Val Asp Gly Val Glu Val His
                    275                 280                 285
Asn Ala Lys Thr Lys Pro Arg Glu Glu Gln Tyr Asn Ser Thr Tyr
                    290                 295                 300
Arg Val Val Ser Val Leu Thr Val Leu His Gln Asp Trp Leu Asn
                    305                 310                 315
Gly Lys Glu Tyr Lys Cys Lys Val Ser Asn Lys Ala Leu Pro Ala
                    320                 325                 330
Pro Ile Glu Lys Thr Ile Ser Lys Ala Lys Gly Gln Pro Arg Glu
                    335                 340                 345
Pro Gln Val Tyr Thr Leu Pro Pro Ser Arg Glu Glu Met Thr Lys
                    350                 355                 360
Asn Gln Val Ser Leu Thr Cys Leu Val Lys Gly Phe Tyr Pro Ser
                    365                 370                 375
Asp Ile Ala Val Glu Trp Glu Ser Asn Gly Gln Pro Glu Asn Asn
                    380                 385                 390
Tyr Lys Thr Thr Pro Pro Val Leu Asp Ser Asp Gly Ser Phe Phe
                    395                 400                 405
Leu Tyr Ser Lys Leu Thr Val Asp Lys Ser Arg Trp Gln Gln Gly
                    410                 415                 420
Asn Val Phe Ser Cys Ser Val Met His Glu Ala Leu His Asn His
                    425                 430                 435
Tyr Thr Gln Lys Ser Leu Ser Leu Ser Pro Gly
                    440                 445

<210> SEQ ID NO 235
<211> LENGTH: 218
<212> TYPE: PRT
<213> ORGANISM: Artificial sequence
<220> FEATURE:
<223> OTHER INFORMATION: ThioMAb-chMA79b- LC(V205C)  Variant - LC

<400> SEQUENCE: 235
```

```
Asp Ile Val Leu Thr Gln Ser Pro Ala Ser Leu Ala Val Ser Leu
  1               5                  10                  15

Gly Gln Arg Ala Thr Ile Ser Cys Lys Ala Ser Gln Ser Val Asp
                 20                  25                  30

Tyr Asp Gly Asp Ser Phe Leu Asn Trp Tyr Gln Gln Lys Pro Gly
                 35                  40                  45

Gln Pro Pro Lys Leu Phe Ile Tyr Ala Ala Ser Asn Leu Glu Ser
                 50                  55                  60

Gly Ile Pro Ala Arg Phe Ser Gly Ser Gly Ser Gly Thr Asp Phe
                 65                  70                  75

Thr Leu Asn Ile His Pro Val Glu Glu Glu Asp Ala Ala Thr Tyr
                 80                  85                  90

Tyr Cys Gln Gln Ser Asn Glu Asp Pro Leu Thr Phe Gly Ala Gly
                 95                 100                 105

Thr Glu Leu Glu Leu Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Cys Thr
                200                 205                 210

Lys Ser Phe Asn Arg Gly Glu Cys
                215

<210> SEQ ID NO 236
<211> LENGTH: 446
<212> TYPE: PRT
<213> ORGANISM: Artificial sequence
<220> FEATURE:
<223> OTHER INFORMATION: ThioMAb-chMA79b- HC(A118C)  Variant - HC

<400> SEQUENCE: 236

Glu Val Gln Leu Gln Gln Ser Gly Ala Glu Leu Met Lys Pro Gly
  1               5                  10                  15

Ala Ser Val Lys Ile Ser Cys Lys Ala Thr Gly Tyr Thr Phe Ser
                 20                  25                  30

Ser Tyr Trp Ile Glu Trp Val Lys Gln Arg Pro Gly His Gly Leu
                 35                  40                  45

Glu Trp Ile Gly Glu Ile Leu Pro Gly Gly Gly Asp Thr Asn Tyr
                 50                  55                  60

Asn Glu Ile Phe Lys Gly Lys Ala Thr Phe Thr Ala Asp Thr Ser
                 65                  70                  75

Ser Asn Thr Ala Tyr Met Gln Leu Ser Ser Leu Thr Ser Glu Asp
                 80                  85                  90

Ser Ala Val Tyr Tyr Cys Thr Arg Arg Val Pro Val Tyr Phe Asp
                 95                 100                 105

Tyr Trp Gly Gln Gly Thr Ser Val Thr Val Ser Ser Cys Ser Thr
                110                 115                 120
```

```
Lys Gly Pro Ser Val Phe Pro Leu Ala Pro Ser Ser Lys Ser Thr
            125                 130                 135

Ser Gly Gly Thr Ala Ala Leu Gly Cys Leu Val Lys Asp Tyr Phe
            140                 145                 150

Pro Glu Pro Val Thr Val Ser Trp Asn Ser Gly Ala Leu Thr Ser
            155                 160                 165

Gly Val His Thr Phe Pro Ala Val Leu Gln Ser Ser Gly Leu Tyr
            170                 175                 180

Ser Leu Ser Ser Val Val Thr Val Pro Ser Ser Ser Leu Gly Thr
            185                 190                 195

Gln Thr Tyr Ile Cys Asn Val Asn His Lys Pro Ser Asn Thr Lys
            200                 205                 210

Val Asp Lys Lys Val Glu Pro Lys Ser Cys Asp Lys Thr His Thr
            215                 220                 225

Cys Pro Pro Cys Pro Ala Pro Glu Leu Leu Gly Gly Pro Ser Val
            230                 235                 240

Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp
            260                 265                 270

Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn
            305                 310                 315

Gly Lys Glu Tyr Lys Cys Lys Val Ser Asn Lys Ala Leu Pro Ala
            320                 325                 330

Pro Ile Glu Lys Thr Ile Ser Lys Ala Lys Gly Gln Pro Arg Glu
            335                 340                 345

Pro Gln Val Tyr Thr Leu Pro Pro Ser Arg Glu Glu Met Thr Lys
            350                 355                 360

Asn Gln Val Ser Leu Thr Cys Leu Val Lys Gly Phe Tyr Pro Ser
            365                 370                 375

Asp Ile Ala Val Glu Trp Glu Ser Asn Gly Gln Pro Glu Asn Asn
            380                 385                 390

Tyr Lys Thr Thr Pro Pro Val Leu Asp Ser Asp Gly Ser Phe Phe
            395                 400                 405

Leu Tyr Ser Lys Leu Thr Val Asp Lys Ser Arg Trp Gln Gln Gly
            410                 415                 420

Asn Val Phe Ser Cys Ser Val Met His Glu Ala Leu His Asn His
            425                 430                 435

Tyr Thr Gln Lys Ser Leu Ser Leu Ser Pro Gly
            440                 445

<210> SEQ ID NO 237
<211> LENGTH: 218
<212> TYPE: PRT
<213> ORGANISM: Artificial sequence
<220> FEATURE:
<223> OTHER INFORMATION: ThioMAb-chMA79b- HC(A118C)  Variant - LC

<400> SEQUENCE: 237

Asp Ile Val Leu Thr Gln Ser Pro Ala Ser Leu Ala Val Ser Leu
 1               5                  10                  15

Gly Gln Arg Ala Thr Ile Ser Cys Lys Ala Ser Gln Ser Val Asp
```

```
                    20                  25                  30
Tyr Asp Gly Asp Ser Phe Leu Asn Trp Tyr Gln Gln Lys Pro Gly
            35                  40                  45

Gln Pro Pro Lys Leu Phe Ile Tyr Ala Ala Ser Asn Leu Glu Ser
        50                  55                  60

Gly Ile Pro Ala Arg Phe Ser Gly Ser Gly Thr Asp Phe
    65                  70                  75

Thr Leu Asn Ile His Pro Val Glu Glu Asp Ala Ala Thr Tyr
80                  85                  90

Tyr Cys Gln Gln Ser Asn Glu Asp Pro Leu Thr Phe Gly Ala Gly
            95                  100                 105

Thr Glu Leu Glu Leu Lys Arg Thr Val Ala Ala Pro Ser Val Phe
        110                 115                 120

Ile Phe Pro Pro Ser Asp Glu Gln Leu Lys Ser Gly Thr Ala Ser
    125                 130                 135

Val Val Cys Leu Leu Asn Asn Phe Tyr Pro Arg Glu Ala Lys Val
140                 145                 150

Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
        170                 175                 180

Ser Thr Leu Thr Leu Ser Lys Ala Asp Tyr Glu Lys His Lys Val
    185                 190                 195

Tyr Ala Cys Glu Val Thr His Gln Gly Leu Ser Ser Pro Val Thr
200                 205                 210

Lys Ser Phe Asn Arg Gly Glu Cys
            215

<210> SEQ ID NO 238
<211> LENGTH: 893
<212> TYPE: DNA
<213> ORGANISM: Macaca fascicularis

<400> SEQUENCE: 238
tcatggtgat ggtgatgatg accggtacgc gtagaatcga gaccgaggag        50
agggttaggg ataggcttac cttcgaaccg cgggccctct agactcgagc       100
ggccgccact gtgctggata tctgcagaat tgcccttggg acagagcag        150 tgaccatggc caggctggcg ttgtctcctg tgtccagcca ctggctggtg       200
gcgttgctgc tgctgctctc agcagctgag ccagtgccag cagccaaatc       250
agaggacctg tacccgaatc ccaaaggtag tgcttgttct cggatctggc       300
agagcccacg tttcatagcc aggaaacggg gcttcacggt gaaaatgcac       350
tgctacgtga ccaacagcac cttcagcatc gtgagctggc tccggaagcg       400
ggagacggac aaggagcccc aacaggtgaa cctggagcag ggccacatgc       450
atcagaccca aaacagctct gtcaccaccc tcatcatcca agacatccgg       500
tttgaggaca acggcatcta cttctgtcag caggagtgca gcaagacctc       550
ggaggtctac cggggctgcg gcacggagct gcgagtcatg gggttcagca       600
ccttggcaca gctgaagcag aggaacacgc tgaaggatgg catcatcatg       650
atccagacgc tgctgatcat cctcttcatc atcgtgccca tcttcctgct       700
gctggacaag gatgacagca aggccggcat ggaggaagat cacacctacg       750
agggcctgga cattgaccag acggccacct acgaggacat agtgacgctg       800
```

```
cggacagggg aagtgaagtg gtctgtgggt gagcacccag gtcaggagtg            850
agagccagga cctccccacg gcctgggtgc aggctcccca gcc                   893
```

<210> SEQ ID NO 239
<211> LENGTH: 231
<212> TYPE: PRT
<213> ORGANISM: Macaca fascicularis

<400> SEQUENCE: 239

```
Met Ala Arg Leu Ala Leu Ser Pro Val Ser His Trp Leu Val
 1               5                  10                  15

Ala Leu Leu Leu Leu Leu Ser Ala Ala Glu Pro Val Pro Ala Ala
                20                  25                  30

Lys Ser Glu Asp Leu Tyr Pro Asn Pro Lys Gly Ser Ala Cys Ser
                35                  40                  45

Arg Ile Trp Gln Ser Pro Arg Phe Ile Ala Arg Lys Arg Gly Phe
                50                  55                  60

Thr Val Lys Met His Cys Tyr Val Thr Asn Ser Thr Phe Ser Ile
                65                  70                  75

Val Ser Trp Leu Arg Lys Arg Glu Thr Asp Lys Glu Pro Gln Gln
                80                  85                  90

Val Asn Leu Glu Gln Gly His Met His Gln Thr Gln Asn Ser Ser
                95                 100                 105

Val Thr Thr Leu Ile Ile Gln Asp Ile Arg Phe Glu Asp Asn Gly
               110                 115                 120

Ile Tyr Phe Cys Gln Gln Glu Cys Ser Lys Thr Ser Glu Val Tyr
               125                 130                 135

Arg Gly Cys Gly Thr Glu Leu Arg Val Met Gly Phe Ser Thr Leu
               140                 145                 150

Ala Gln Leu Lys Gln Arg Asn Thr Leu Lys Asp Gly Ile Ile Met
               155                 160                 165

Ile Gln Thr Leu Leu Ile Ile Leu Phe Ile Ile Val Pro Ile Phe
               170                 175                 180

Leu Leu Leu Asp Lys Asp Asp Ser Lys Ala Gly Met Glu Glu Asp
               185                 190                 195

His Thr Tyr Glu Gly Leu Asp Ile Asp Gln Thr Ala Thr Tyr Glu
               200                 205                 210

Asp Ile Val Thr Leu Arg Thr Gly Glu Val Lys Trp Ser Val Gly
               215                 220                 225

Glu His Pro Gly Gln Glu
               230
```

<210> SEQ ID NO 240
<211> LENGTH: 800
<212> TYPE: DNA
<213> ORGANISM: Artificial sequence
<220> FEATURE:
<223> OTHER INFORMATION: Chimeric anti-cyno CD79b (ch10D10)- LC

<400> SEQUENCE: 240

```
acctcggttc tatcgattga attccaccat gggatggtca tgtatcatcc            50
tttttctagt agcaactgca actggagtac attcagatat cgtgctgacc           100
caatctccac cctctttggc tgtgtctcta gggcagaggg ccaccatatc           150
ctgcagagcc agtgaaagtg ttgatagtta tggcaaaact tttatgcact           200
ggcaccagca gaaaccagga cagccacccc aactcctcat ctatcgtgta           250
```

```
tccaacctag aatctgggat ccctgccagg ttcagtggca gtgggtcaag        300
gacagacttc accctcacca ttaatcctgt ggaggctgat gatgttgcaa        350
cctattactg tcagcaaagt aatgaggatc cgttcacgtt cggtggaggc        400
accaagctgg aaatcaaacg gaccgtggct gcaccatctg tcttcatctt        450
cccgccatct gatgagcagt tgaaatctgg aactgcctct gttgtgtgcc        500
tgctgaataa cttctatccc agagaggcca agtacagtg gaaggtggat         550 aacgccctcc aatcgggtaa ctcccaggag agtgtcacag agcaggacag         600
caaggacagc acctacagcc tcagcagcac cctgacgctg agcaaagcag        650
actacgagaa acacaaagtc tacgcctgcg aagtcaccca tcagggcctg        700
agctcgcccg tcacaaagag cttcaacagg ggagagtgtt aagcttggcc        750
gccatggccc aacttgttta ttgcagctta taatggttac aaataaagca        800
```

<210> SEQ ID NO 241
<211> LENGTH: 218
<212> TYPE: PRT
<213> ORGANISM: Artificial sequence
<220> FEATURE:
<223> OTHER INFORMATION: Chimeric anti-cyno CD79b (ch10D10)- LC

<400> SEQUENCE: 241

```
Asp Ile Val Leu Thr Gln Ser Pro Pro Ser Leu Ala Val Ser Leu
 1               5                  10                  15

Gly Gln Arg Ala Thr Ile Ser Cys Arg Ala Ser Glu Ser Val Asp
                20                  25                  30

Ser Tyr Gly Lys Thr Phe Met His Trp His Gln Gln Lys Pro Gly
                35                  40                  45

Gln Pro Pro Lys Leu Leu Ile Tyr Arg Val Ser Asn Leu Glu Ser
                50                  55                  60

Gly Ile Pro Ala Arg Phe Ser Gly Ser Gly Ser Arg Thr Asp Phe
                65                  70                  75

Thr Leu Thr Ile Asn Pro Val Glu Ala Asp Asp Val Ala Thr Tyr
                80                  85                  90

Tyr Cys Gln Gln Ser Asn Glu Asp Pro Phe Thr Phe Gly Gly Gly
                95                  100                 105

Thr Lys Leu Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215
```

<210> SEQ ID NO 242

<211> LENGTH: 1500
<212> TYPE: DNA
<213> ORGANISM: Artificial sequence
<220> FEATURE:
<223> OTHER INFORMATION: Chimeric anti-cyno CD79b (ch10D10)- LC

<400> SEQUENCE: 242

```
cacctcggtt ctatcgattg aattccacca tgggatggtc atgtatcatc         50
cttttctag tagcaactgc aactggagta cattcagaag ttcagctgca         100
ggagtcggga cctggcctgg tgaaacttc tcagtctctg tccctcacct          150
gcactgtcac tggctactca atcaccagtg attatgcctg gaactggatc        200
cggcagtttc caggaaacaa actggagtgg atgggcaaca tatggtacag         250
tggtagcact acctacaacc catctctcaa aagtcgaatc tctatcactc         300
gagacacatc caagaaccag ttcttcctgc agttgaattc tgtgacttct         350
gaggacacag ccacatatta ctgttcaaga atggacttct ggggtcaagg         400
caccactctc acagtctcct cagcctccac caagggccca tcggtcttcc         450
ccctggcacc ctcctccaag agcacctctg gggcacagc ggccctgggc          500
tgcctggtca aggactactt ccccgaaccg gtgacggtgt cgtggaactc         550
aggcgccctg accagcggcg tgcacacctt cccggctgtc ctacagtcct         600
caggactcta ctccctcagc agcgtggtga ctgtgccctc tagcagcttg         650
ggcacccaga cctacatctg caacgtgaat cacaagccca gcaacaccaa         700
ggtggacaag aaagttgagc ccaaatcttg tgacaaaact cacacatgcc         750
caccgtgccc agcacctgaa ctcctggggg gaccgtcagt cttcctcttc         800
cccccaaaac ccaaggacac cctcatgatc tcccggaccc ctgaggtcac         850
atgcgtggtg gtggacgtga gccacgaaga ccctgaggtc aagttcaact         900
ggtacgtgga cggcgtggag gtgcataatg ccaagacaaa gccgcgggag         950
gagcagtaca acagcacgta ccgtgtggtc agcgtcctca ccgtcctgca        1000
ccaggactgg ctgaatggca aggagtacaa gtgcaaggtc tccaacaaag        1050
ccctcccagc ccccatcgag aaaaccatct ccaaagccaa agggcagccc        1100
cgagaaccac aggtgtacac cctgccccca tcccgggaag atgaccaa         1150
gaaccaggtc agcctgacct gcctggtcaa aggcttctat cccagcgaca        1200
tcgccgtgga gtgggagagc aatgggcagc cggagaacaa ctacaagacc        1250
acgcctcccg tgctggactc cgacggctcc ttcttcctct acagcaagct        1300
caccgtggac aagagcaggt ggcagcaggg gaacgtcttc tcatgctccg        1350
tgatgcatga ggctctgcac aaccactaca cgcagaagag cctctccctg        1400
tctccgggta aatgagtgcg acggccctag agtcgacctg cagaagcttg        1450
gccgccatgg cccaacttgt ttattgcagc ttataatggt tacaaataaa        1500
```

<210> SEQ ID NO 243
<211> LENGTH: 441
<212> TYPE: PRT
<213> ORGANISM: Artificial sequence
<220> FEATURE:
<223> OTHER INFORMATION: Chimeric anti-cyno CD79b (ch10D10)- LC

<400> SEQUENCE: 243

```
Glu Val Gln Leu Gln Glu Ser Gly Pro Gly Leu Val Lys Pro Ser
 1               5                  10                  15
```

```
Gln Ser Leu Ser Leu Thr Cys Thr Val Thr Gly Tyr Ser Ile Thr
                 20                  25                  30

Ser Asp Tyr Ala Trp Asn Trp Ile Arg Gln Phe Pro Gly Asn Lys
                 35                  40                  45

Leu Glu Trp Met Gly Asn Ile Trp Tyr Ser Gly Ser Thr Thr Tyr
                 50                  55                  60

Asn Pro Ser Leu Lys Ser Arg Ile Ser Ile Thr Arg Asp Thr Ser
                 65                  70                  75

Lys Asn Gln Phe Phe Leu Gln Leu Asn Ser Val Thr Ser Glu Asp
                 80                  85                  90

Thr Ala Thr Tyr Tyr Cys Ser Arg Met Asp Phe Trp Gly Gln Gly
                 95                 100                 105

Thr Thr Leu Thr Val Ser Ser Ala Ser Thr Lys Gly Pro Ser Val
                110                 115                 120

Phe Pro Leu Ala Pro Ser Ser Lys Ser Thr Ser Gly Gly Thr Ala
                125                 130                 135

Ala Leu Gly Cys Leu Val Lys Asp Tyr Phe Pro Glu Pro Val Thr
                140                 145                 150

Val Ser Trp Asn Ser Gly Ala Leu Thr Ser Gly Val His Thr Phe
                155                 160                 165

Pro Ala Val Leu Gln Ser Ser Gly Leu Tyr Ser Leu Ser Ser Val
                170                 175                 180

Val Thr Val Pro Ser Ser Ser Leu Gly Thr Gln Thr Tyr Ile Cys
                185                 190                 195

Asn Val Asn His Lys Pro Ser Asn Thr Lys Val Asp Lys Lys Val
                200                 205                 210

Glu Pro Lys Ser Cys Asp Lys Thr His Thr Cys Pro Pro Cys Pro
                215                 220                 225

Ala Pro Glu Leu Leu Gly Gly Pro Ser Val Phe Leu Phe Pro Pro
                230                 235                 240

Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe
                260                 265                 270

Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys
                305                 310                 315

Cys Lys Val Ser Asn Lys Ala Leu Pro Ala Pro Ile Glu Lys Thr
                320                 325                 330

Ile Ser Lys Ala Lys Gly Gln Pro Arg Glu Pro Gln Val Tyr Thr
                335                 340                 345

Leu Pro Pro Ser Arg Glu Glu Met Thr Lys Asn Gln Val Ser Leu
                350                 355                 360

Thr Cys Leu Val Lys Gly Phe Tyr Pro Ser Asp Ile Ala Val Glu
                365                 370                 375

Trp Glu Ser Asn Gly Gln Pro Glu Asn Asn Tyr Lys Thr Thr Pro
                380                 385                 390

Pro Val Leu Asp Ser Asp Gly Ser Phe Phe Leu Tyr Ser Lys Leu
                395                 400                 405

Thr Val Asp Lys Ser Arg Trp Gln Gln Gly Asn Val Phe Ser Cys
```

```
                        410                 415                 420
Ser Val Met His Glu Ala Leu His Asn His Tyr Thr Gln Lys Ser
                425                 430                 435

Leu Ser Leu Ser Pro Gly
                440

<210> SEQ ID NO 244
<211> LENGTH: 441
<212> TYPE: PRT
<213> ORGANISM: Artificial sequence
<220> FEATURE:
<223> OTHER INFORMATION: Thio-MAb-anti-cynoCD79b(ch10D10)-HC(A118C)
      Variant - HC

<400> SEQUENCE: 244

Asp Val Gln Leu Gln Glu Ser Gly Pro Gly Leu Val Lys Pro Ser
  1               5                  10                  15

Gln Ser Leu Ser Leu Thr Cys Thr Val Thr Gly Tyr Ser Ile Thr
                 20                  25                  30

Ser Asp Tyr Ala Trp Asn Trp Ile Arg Gln Phe Pro Gly Asn Lys
                 35                  40                  45

Leu Glu Trp Met Gly Asn Ile Trp Tyr Ser Gly Ser Thr Thr Tyr
                 50                  55                  60

Asn Pro Ser Leu Lys Ser Arg Ile Ser Ile Thr Arg Asp Thr Ser
                 65                  70                  75

Lys Asn Gln Phe Phe Leu Gln Leu Asn Ser Val Thr Ser Glu Asp
                 80                  85                  90

Thr Ala Thr Tyr Tyr Cys Ser Arg Met Asp Phe Trp Gly Gln Gly
                 95                 100                 105

Thr Thr Leu Thr Val Ser Ser Cys Ser Thr Lys Gly Pro Ser Val
                110                 115                 120

Phe Pro Leu Ala Pro Ser Ser Lys Ser Thr Ser Gly Gly Thr Ala
                125                 130                 135

Ala Leu Gly Cys Leu Val Lys Asp Tyr Phe Pro Glu Pro Val Thr
                140                 145                 150

Val Ser Trp Asn Ser Gly Ala Leu Thr Ser Gly Val His Thr Phe
                155                 160                 165

Pro Ala Val Leu Gln Ser Ser Gly Leu Tyr Ser Leu Ser Ser Val
                170                 175                 180

Val Thr Val Pro Ser Ser Ser Leu Gly Thr Gln Thr Tyr Ile Cys
                185                 190                 195

Asn Val Asn His Lys Pro Ser Asn Thr Lys Val Asp Lys Lys Val
                200                 205                 210

Glu Pro Lys Ser Cys Asp Lys Thr His Thr Cys Pro Pro Cys Pro
                215                 220                 225

Ala Pro Glu Leu Leu Gly Gly Pro Ser Val Phe Leu Phe Pro Pro
                230                 235                 240

Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe
                260                 265                 270

Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys
```

```
            305                 310                 315
Cys Lys Val Ser Asn Lys Ala Leu Pro Ala Pro Ile Glu Lys Thr
        320                 325                 330
Ile Ser Lys Ala Lys Gly Gln Pro Arg Glu Pro Gln Val Tyr Thr
        335                 340                 345
Leu Pro Pro Ser Arg Glu Glu Met Thr Lys Asn Gln Val Ser Leu
        350                 355                 360
Thr Cys Leu Val Lys Gly Phe Tyr Pro Ser Asp Ile Ala Val Glu
        365                 370                 375
Trp Glu Ser Asn Gly Gln Pro Glu Asn Asn Tyr Lys Thr Thr Pro
        380                 385                 390
Pro Val Leu Asp Ser Asp Gly Ser Phe Phe Leu Tyr Ser Lys Leu
        395                 400                 405
Thr Val Asp Lys Ser Arg Trp Gln Gln Gly Asn Val Phe Ser Cys
        410                 415                 420
Ser Val Met His Glu Ala Leu His Asn His Tyr Thr Gln Lys Ser
        425                 430                 435
Leu Ser Leu Ser Pro Gly
        440

<210> SEQ ID NO 245
<211> LENGTH: 218
<212> TYPE: PRT
<213> ORGANISM: Artificial sequence
<220> FEATURE:
<223> OTHER INFORMATION: Thio-MAb-anti-cynoCD79b(ch10D10)-HC(A118C)
      Variant - LC

<400> SEQUENCE: 245

Asp Ile Val Leu Thr Gln Ser Pro Pro Ser Leu Ala Val Ser Leu
  1               5                  10                  15
Gly Gln Arg Ala Thr Ile Ser Cys Arg Ala Ser Glu Ser Val Asp
                 20                  25                  30
Ser Tyr Gly Lys Thr Phe Met His Trp His Gln Gln Lys Pro Gly
                 35                  40                  45
Gln Pro Pro Lys Leu Leu Ile Tyr Arg Val Ser Asn Leu Glu Ser
                 50                  55                  60
Gly Ile Pro Ala Arg Phe Ser Gly Ser Gly Ser Arg Thr Asp Phe
                 65                  70                  75
Thr Leu Thr Ile Asn Pro Val Glu Ala Asp Val Ala Thr Tyr
                 80                  85                  90
Tyr Cys Gln Gln Ser Asn Glu Asp Pro Phe Thr Phe Gly Gly Gly
                 95                 100                 105
Thr Lys Leu Glu Ile Lys Arg Thr Val Ala Ala Pro Ser Val Phe
                110                 115                 120
Ile Phe Pro Pro Ser Asp Glu Gln Leu Lys Ser Gly Thr Ala Ser
                125                 130                 135
Val Val Cys Leu Leu Asn Asn Phe Tyr Pro Arg Glu Ala Lys Val
                140                 145                 150
Gln Trp Lys Val Asp Asn Ala Leu Gln Ser Gly Asn Ser Gln Glu
                155                 160                 165
Ser Val Thr Glu Gln Asp Ser Lys Asp Ser Thr Tyr Ser Leu Ser
                170                 175                 180
Ser Thr Leu Thr Leu Ser Lys Ala Asp Tyr Glu Lys His Lys Val
                185                 190                 195
Tyr Ala Cys Glu Val Thr His Gln Gly Leu Ser Ser Pro Val Thr
```

Lys Ser Phe Asn Arg Gly Glu Cys
            215

<210> SEQ ID NO 246
<211> LENGTH: 30
<212> TYPE: PRT
<213> ORGANISM: Artificial sequence
<220> FEATURE:
<223> OTHER INFORMATION: Albumin binding peptide

<400> SEQUENCE: 246

Cys Asp Lys Thr His Thr Gly Gly Gly Ser Gln Arg Leu Met Glu
1               5                   10                  15

Asp Ile Cys Leu Pro Arg Trp Gly Cys Leu Trp Glu Asp Asp Phe
            20                  25                  30

<210> SEQ ID NO 247
<211> LENGTH: 20
<212> TYPE: PRT
<213> ORGANISM: Artificial sequence
<220> FEATURE:
<223> OTHER INFORMATION: Albumin binding peptide

<400> SEQUENCE: 247

Gln Arg Leu Met Glu Asp Ile Cys Leu Pro Arg Trp Gly Cys Leu
1               5                   10                  15

Trp Glu Asp Asp Phe
            20

<210> SEQ ID NO 248
<211> LENGTH: 20
<212> TYPE: PRT
<213> ORGANISM: Artificial sequence
<220> FEATURE:
<223> OTHER INFORMATION: Albumin binding peptide

<400> SEQUENCE: 248

Gln Arg Leu Ile Glu Asp Ile Cys Leu Pro Arg Trp Gly Cys Leu
1               5                   10                  15

Trp Glu Asp Asp Phe
            20

<210> SEQ ID NO 249
<211> LENGTH: 18
<212> TYPE: PRT
<213> ORGANISM: Artificial sequence
<220> FEATURE:
<223> OTHER INFORMATION: Albumin binding peptide

<400> SEQUENCE: 249

Arg Leu Ile Glu Asp Ile Cys Leu Pro Arg Trp Gly Cys Leu Trp
1               5                   10                  15

Glu Asp Asp

<210> SEQ ID NO 250
<211> LENGTH: 11
<212> TYPE: PRT
<213> ORGANISM: Artificial sequence
<220> FEATURE:
<223> OTHER INFORMATION: Albumin binding peptide

<400> SEQUENCE: 250

Asp Ile Cys Leu Pro Arg Trp Gly Cys Leu Trp
 5                  10

-continued

```
<210> SEQ ID NO 251
<211> LENGTH: 10
<212> TYPE: PRT
<213> ORGANISM: Artificial sequence
<220> FEATURE:
<223> OTHER INFORMATION: Thio-huMA79b HC-variant

<400> SEQUENCE: 251

Glu Val Gln Leu Cys Glu Ser Gly Gly Gly
                5                   10

<210> SEQ ID NO 252
<211> LENGTH: 11
<212> TYPE: PRT
<213> ORGANISM: Artificial sequence
<220> FEATURE:
<223> OTHER INFORMATION: Thio-huMA79b HC-variant

<400> SEQUENCE: 252

Leu Arg Leu Ser Cys Cys Ala Ser Gly Tyr Thr
                5                   10

<210> SEQ ID NO 253
<211> LENGTH: 11
<212> TYPE: PRT
<213> ORGANISM: Artificial sequence
<220> FEATURE:
<223> OTHER INFORMATION: Thio-huMA79b HC-variant

<400> SEQUENCE: 253

Met Asn Ser Leu Arg Cys Glu Asp Thr Ala Val
                5                   10

<210> SEQ ID NO 254
<211> LENGTH: 11
<212> TYPE: PRT
<213> ORGANISM: Artificial sequence
<220> FEATURE:
<223> OTHER INFORMATION: Thio-huMA79b HC-variant

<400> SEQUENCE: 254

Thr Leu Val Thr Val Cys Ser Ala Ser Thr Lys
                5                   10

<210> SEQ ID NO 255
<211> LENGTH: 11
<212> TYPE: PRT
<213> ORGANISM: Artificial sequence
<220> FEATURE:
<223> OTHER INFORMATION: Thio-huMA79b HC-variant

<400> SEQUENCE: 255

Val Thr Val Ser Ser Cys Ser Thr Lys Gly Pro
                5                   10

<210> SEQ ID NO 256
<211> LENGTH: 11
<212> TYPE: PRT
<213> ORGANISM: Artificial sequence
<220> FEATURE:
<223> OTHER INFORMATION: Thio-huMA79b HC-variant

<400> SEQUENCE: 256

Val Ser Ser Ala Ser Cys Lys Gly Pro Ser Val
                5                   10
```

```
<210> SEQ ID NO 257
<211> LENGTH: 11
<212> TYPE: PRT
<213> ORGANISM: Artificial sequence
<220> FEATURE:
<223> OTHER INFORMATION: Thio-huMA79b HC-variant

<400> SEQUENCE: 257

Trp Tyr Val Asp Gly Cys Glu Val His Asn Ala
  5                  10

<210> SEQ ID NO 258
<211> LENGTH: 11
<212> TYPE: PRT
<213> ORGANISM: Artificial sequence
<220> FEATURE:
<223> OTHER INFORMATION: Thio-huMA79b HC-variant

<400> SEQUENCE: 258

Lys Gly Phe Tyr Pro Cys Asp Ile Ala Val Glu
  5                  10

<210> SEQ ID NO 259
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 259

Pro Pro Val Leu Asp Cys Asp Gly Ser Phe Phe
  5                  10

<210> SEQ ID NO 260
<211> LENGTH: 10
<212> TYPE: PRT
<213> ORGANISM: Artificial sequence
<220> FEATURE:
<223> OTHER INFORMATION: Thio-chMA79b HC-variant

<400> SEQUENCE: 260

Glu Val Gln Leu Cys Gln Ser Gly Ala Glu
  5                  10

<210> SEQ ID NO 261
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 261

Val Lys Ile Ser Cys Cys Ala Thr Gly Tyr Thr
  5                  10

<210> SEQ ID NO 262
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 262

Leu Ser Ser Leu Thr Cys Glu Asp Ser Ala Val
  5                  10

<210> SEQ ID NO 263
<211> LENGTH: 11
```

```
<212> TYPE: PRT
<213> ORGANISM: Artificial sequence
<220> FEATURE:
<223> OTHER INFORMATION: Thio-chMA79b HC-variant

<400> SEQUENCE: 263

Thr Ser Val Thr Val Cys Ser Ala Ser Thr Lys
 5                   10

<210> SEQ ID NO 264
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 264

Val Thr Val Ser Ser Cys Ser Thr Lys Gly Pro
 5                   10

<210> SEQ ID NO 265
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 265

Val Ser Ser Ala Ser Cys Lys Gly Pro Ser Val
 5                   10

<210> SEQ ID NO 266
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 266

Trp Tyr Val Asp Gly Cys Glu Val His Asn Ala
 5                   10

<210> SEQ ID NO 267
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 267

Lys Gly Phe Tyr Pro Cys Asp Ile Ala Val Glu
 5                   10

<210> SEQ ID NO 268
<211> LENGTH: 11
<212> TYPE: PRT
<213> ORGANISM: Artificial sequence
<220> FEATURE:
<223> OTHER INFORMATION: Thio-chMA79b HC-variant

<400> SEQUENCE: 268

Pro Pro Val Leu Asp Cys Asp Gly Ser Phe Phe
 5                   10

<210> SEQ ID NO 269
<211> LENGTH: 10
<212> TYPE: PRT
<213> ORGANISM: Artificial sequence
```

```
<220> FEATURE:
<223> OTHER INFORMATION: Thio anti-cynoCD79b(ch10D10)-HC-variant

<400> SEQUENCE: 269

Glu Val Gln Leu Cys Glu Ser Gly Pro Gly
  5                   10

<210> SEQ ID NO 270
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 270

Leu Ser Leu Thr Cys Cys Val Thr Gly Tyr Ser
  5                   10

<210> SEQ ID NO 271
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 271

Leu Asn Ser Val Thr Cys Glu Asp Thr Ala Thr
  5                   10

<210> SEQ ID NO 272
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 272

Thr Thr Leu Thr Val Cys Ser Ala Ser Thr Lys
  5                   10

<210> SEQ ID NO 273
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 273

Leu Thr Val Ser Ser Cys Ser Thr Lys Gly Pro
  5                   10

<210> SEQ ID NO 274
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 274

Val Ser Ser Ala Ser Cys Lys Gly Pro Ser Val
  5                   10

<210> SEQ ID NO 275
<211> LENGTH: 11
<212> TYPE: PRT
<213> ORGANISM: Artificial sequence
<220> FEATURE:
<223> OTHER INFORMATION: Thio-anti-cynoCD79b (ch10D10)-HC-variant
```

```
<400> SEQUENCE: 275

Trp Tyr Val Asp Gly Cys Glu Val His Asn Ala
  5                  10

<210> SEQ ID NO 276
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 276

Lys Gly Phe Tyr Pro Cys Asp Ile Ala Val Glu
  5                  10

<210> SEQ ID NO 277
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 277

Pro Pro Val Leu Asp Cys Asp Gly Ser Phe Phe
  5                  10

<210> SEQ ID NO 278
<211> LENGTH: 11
<212> TYPE: PRT
<213> ORGANISM: Artificial sequence
<220> FEATURE:
<223> OTHER INFORMATION: Thio-huMA79b LC-variant

<400> SEQUENCE: 278

Ser Leu Ser Ala Ser Cys Gly Asp Arg Val Thr
  5                  10

<210> SEQ ID NO 279
<211> LENGTH: 11
<212> TYPE: PRT
<213> ORGANISM: Artificial sequence
<220> FEATURE:
<223> OTHER INFORMATION: Thio-huMA79b LC-variant

<400> SEQUENCE: 279

Glu Ile Lys Arg Thr Cys Ala Ala Pro Ser Val
  5                  10

<210> SEQ ID NO 280
<211> LENGTH: 11
<212> TYPE: PRT
<213> ORGANISM: Artificial sequence
<220> FEATURE:
<223> OTHER INFORMATION: Thio-huMA79b LC-variant

<400> SEQUENCE: 280

Thr Val Ala Ala Pro Cys Val Phe Ile Phe Pro
  5                  10

<210> SEQ ID NO 281
<211> LENGTH: 11
<212> TYPE: PRT
<213> ORGANISM: Artificial sequence
<220> FEATURE:
<223> OTHER INFORMATION: Thio-huMA79b LC-variant

<400> SEQUENCE: 281
```

```
Phe Ile Phe Pro Pro Cys Asp Glu Gln Leu Lys
 5                  10

<210> SEQ ID NO 282
<211> LENGTH: 11
<212> TYPE: PRT
<213> ORGANISM: Artificial sequence
<220> FEATURE:
<223> OTHER INFORMATION: Thio-huMA79b LC-variant

<400> SEQUENCE: 282

Asp Glu Gln Leu Lys Cys Gly Thr Ala Ser Val
 5                  10

<210> SEQ ID NO 283
<211> LENGTH: 11
<212> TYPE: PRT
<213> ORGANISM: Artificial sequence
<220> FEATURE:
<223> OTHER INFORMATION: Thio-huMA79b LC-variant

<400> SEQUENCE: 283

Val Thr Glu Gln Asp Cys Lys Asp Ser Thr Tyr
 5                  10

<210> SEQ ID NO 284
<211> LENGTH: 11
<212> TYPE: PRT
<213> ORGANISM: Artificial sequence
<220> FEATURE:
<223> OTHER INFORMATION: Thio-huMA79b LC-variant

<400> SEQUENCE: 284

Gly Leu Ser Ser Pro Cys Thr Lys Ser Phe Asn
 5                  10

<210> SEQ ID NO 285
<211> LENGTH: 11
<212> TYPE: PRT
<213> ORGANISM: Artificial sequence
<220> FEATURE:
<223> OTHER INFORMATION: Thio-chMA79b LC-variant

<400> SEQUENCE: 285

Ser Leu Ala Val Ser Cys Gly Gln Arg Ala Thr
 5                  10

<210> SEQ ID NO 286
<211> LENGTH: 11
<212> TYPE: PRT
<213> ORGANISM: Artificial sequence
<220> FEATURE:
<223> OTHER INFORMATION: Thio-chMA79b LC-variant

<400> SEQUENCE: 286

Glu Leu Lys Arg Thr Cys Ala Ala Pro Ser Val
 5                  10

<210> SEQ ID NO 287
<211> LENGTH: 11
<212> TYPE: PRT
<213> ORGANISM: Artificial sequence
<220> FEATURE:
<223> OTHER INFORMATION: Thio-chMA79b LC-variant

<400> SEQUENCE: 287

Thr Val Ala Ala Pro Cys Val Phe Ile Phe Pro
```

<210> SEQ ID NO 288
<211> LENGTH: 11
<212> TYPE: PRT
<213> ORGANISM: Artificial sequence
<220> FEATURE:
<223> OTHER INFORMATION: Thio-chMA79b LC-variant

<400> SEQUENCE: 288

Phe Ile Phe Pro Pro Cys Asp Glu Gln Leu Lys
 5                  10

<210> SEQ ID NO 289
<211> LENGTH: 11
<212> TYPE: PRT
<213> ORGANISM: Artificial sequence
<220> FEATURE:
<223> OTHER INFORMATION: Thio-chMA79b LC-variant

<400> SEQUENCE: 289

Asp Glu Gln Leu Lys Cys Gly Thr Ala Ser Val
 5                  10

<210> SEQ ID NO 290
<211> LENGTH: 11
<212> TYPE: PRT
<213> ORGANISM: Artificial sequence
<220> FEATURE:
<223> OTHER INFORMATION: Thio-chMA79b LC-variant

<400> SEQUENCE: 290

Val Thr Glu Gln Asp Cys Lys Asp Ser Thr Tyr
 5                  10

<210> SEQ ID NO 291
<211> LENGTH: 11
<212> TYPE: PRT
<213> ORGANISM: Artificial sequence
<220> FEATURE:
<223> OTHER INFORMATION: Thio-chMA79b LC-variant

<400> SEQUENCE: 291

Gly Leu Ser Ser Pro Cys Thr Lys Ser Phe Asn
 5                  10

<210> SEQ ID NO 292
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 292

Ser Leu Ala Val Ser Cys Gly Gln Arg Ala Thr
 5                  10

<210> SEQ ID NO 293
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 293

Glu Ile Lys Arg Thr Cys Ala Ala Pro Ser Val
 5                  10

```
<210> SEQ ID NO 294
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 294

Thr Val Ala Ala Pro Cys Val Phe Ile Phe Pro
                 5                  10

<210> SEQ ID NO 295
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 295

Phe Ile Phe Pro Pro Cys Asp Glu Gln Leu Lys
                 5                  10

<210> SEQ ID NO 296
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 296

Asp Glu Gln Leu Lys Cys Gly Thr Ala Ser Val
                 5                  10

<210> SEQ ID NO 297
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 297

Val Thr Glu Gln Asp Cys Lys Asp Ser Thr Tyr
                 5                  10

<210> SEQ ID NO 298
<211> LENGTH: 11
<212> TYPE: PRT
<213> ORGANISM: Artificial sequence
<220> FEATURE:
<223> OTHER INFORMATION: Thio anti-cynoCD79b(ch10D10)-HC-variant

<400> SEQUENCE: 298

Gly Leu Ser Ser Pro Cys Thr Lys Ser Phe Asn
                 5                  10

<210> SEQ ID NO 299
<211> LENGTH: 441
<212> TYPE: PRT
<213> ORGANISM: Artificial sequence
<220> FEATURE:
<223> OTHER INFORMATION: Thio anti-cynoCD79b-LC(V205C) Variant - HC

<400> SEQUENCE: 299

Asp Val Gln Leu Gln Glu Ser Gly Pro Gly Leu Val Lys Pro Ser
 1               5                  10                  15

Gln Ser Leu Ser Leu Thr Cys Thr Val Thr Gly Tyr Ser Ile Thr
                20                  25                  30
```

Ser Asp Tyr Ala Trp Asn Trp Ile Arg Gln Phe Pro Gly Asn Lys
                35                  40                  45

Leu Glu Trp Met Gly Asn Ile Trp Tyr Ser Gly Ser Thr Thr Tyr
    50                  55                  60

Asn Pro Ser Leu Lys Ser Arg Ile Ser Ile Thr Arg Asp Thr Ser
                65                  70                  75

Lys Asn Gln Phe Phe Leu Gln Leu Asn Ser Val Thr Ser Glu Asp
                80                  85                  90

Thr Ala Thr Tyr Tyr Cys Ser Arg Met Asp Phe Trp Gly Gln Gly
                95                  100                 105

Thr Thr Leu Thr Val Ser Ser Ala Ser Thr Lys Gly Pro Ser Val
                110                 115                 120

Phe Pro Leu Ala Pro Ser Ser Lys Ser Thr Ser Gly Gly Thr Ala
                125                 130                 135

Ala Leu Gly Cys Leu Val Lys Asp Tyr Phe Pro Glu Pro Val Thr
                140                 145                 150

Val Ser Trp Asn Ser Gly Ala Leu Thr Ser Gly Val His Thr Phe
                155                 160                 165

Pro Ala Val Leu Gln Ser Ser Gly Leu Tyr Ser Leu Ser Ser Val
                170                 175                 180

Val Thr Val Pro Ser Ser Ser Leu Gly Thr Gln Thr Tyr Ile Cys
                185                 190                 195

Asn Val Asn His Lys Pro Ser Asn Thr Lys Val Asp Lys Lys Val
                200                 205                 210

Glu Pro Lys Ser Cys Asp Lys Thr His Thr Cys Pro Pro Cys Pro
                215                 220                 225

Ala Pro Glu Leu Leu Gly Gly Pro Ser Val Phe Leu Phe Pro Pro
                230                 235                 240

Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe
                260                 265                 270

Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys
                305                 310                 315

Cys Lys Val Ser Asn Lys Ala Leu Pro Ala Pro Ile Glu Lys Thr
                320                 325                 330

Ile Ser Lys Ala Lys Gly Gln Pro Arg Glu Pro Gln Val Tyr Thr
                335                 340                 345

Leu Pro Pro Ser Arg Glu Glu Met Thr Lys Asn Gln Val Ser Leu
                350                 355                 360

Thr Cys Leu Val Lys Gly Phe Tyr Pro Ser Asp Ile Ala Val Glu
                365                 370                 375

Trp Glu Ser Asn Gly Gln Pro Glu Asn Asn Tyr Lys Thr Thr Pro
                380                 385                 390

Pro Val Leu Asp Ser Asp Gly Ser Phe Phe Leu Tyr Ser Lys Leu
                395                 400                 405

Thr Val Asp Lys Ser Arg Trp Gln Gln Gly Asn Val Phe Ser Cys
                410                 415                 420

Ser Val Met His Glu Ala Leu His Asn His Tyr Thr Gln Lys Ser

Leu Ser Leu Ser Pro Gly
                440

<210> SEQ ID NO 300
<211> LENGTH: 218
<212> TYPE: PRT
<213> ORGANISM: Artificial sequence
<220> FEATURE:
<223> OTHER INFORMATION: Thio anti-cynoCD79b(ch10D10)-LC(V205C) Variant
      - LC

<400> SEQUENCE: 300

Asp Ile Val Leu Thr Gln Ser Pro Pro Ser Leu Ala Val Ser Leu
  1               5                  10                  15

Gly Gln Arg Ala Thr Ile Ser Cys Arg Ala Ser Glu Ser Val Asp
                 20                  25                  30

Ser Tyr Gly Lys Thr Phe Met His Trp His Gln Gln Lys Pro Gly
                 35                  40                  45

Gln Pro Pro Lys Leu Leu Ile Tyr Arg Val Ser Asn Leu Glu Ser
                 50                  55                  60

Gly Ile Pro Ala Arg Phe Ser Gly Ser Gly Ser Arg Thr Asp Phe
                 65                  70                  75

Thr Leu Thr Ile Asn Pro Val Glu Ala Asp Asp Val Ala Thr Tyr
                 80                  85                  90

Tyr Cys Gln Gln Ser Asn Glu Asp Pro Phe Thr Phe Gly Gly Gly
                 95                 100                 105

Thr Lys Leu Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Cys Thr
                200                 205                 210

Lys Ser Phe Asn Arg Gly Glu Cys
                215

<210> SEQ ID NO 301
<211> LENGTH: 112
<212> TYPE: PRT
<213> ORGANISM: Artificial sequence
<220> FEATURE:
<223> OTHER INFORMATION: anti-cynoCD79b (ch10D10) - variable of HC

<400> SEQUENCE: 301

Glu Val Gln Leu Gln Glu Ser Gly Pro Gly Leu Val Lys Pro Ser
  1               5                  10                  15

Gln Ser Leu Ser Leu Thr Cys Thr Val Thr Gly Tyr Ser Ile Thr
                 20                  25                  30

Ser Asp Tyr Ala Trp Asn Trp Ile Arg Gln Phe Pro Gly Asn Lys
                 35                  40                  45

```
Leu Glu Trp Met Gly Asn Ile Trp Tyr Ser Gly Ser Thr Thr Tyr
             50                  55                  60

Asn Pro Ser Leu Lys Ser Arg Ile Ser Ile Thr Arg Asp Thr Ser
             65                  70                  75

Lys Asn Gln Phe Phe Leu Gln Leu Asn Ser Val Thr Ser Glu Asp
             80                  85                  90

Thr Ala Thr Tyr Tyr Cys Ser Arg Met Asp Phe Trp Gly Gln Gly
             95                 100                 105

Thr Thr Leu Thr Val Ser Ser
            110

<210> SEQ ID NO 302
<211> LENGTH: 112
<212> TYPE: PRT
<213> ORGANISM: Artificial sequence
<220> FEATURE:
<223> OTHER INFORMATION: anti-cynoCD79b (ch10D10) - variable  domain of
      LC

<400> SEQUENCE: 302

Asp Ile Val Leu Thr Gln Ser Pro Pro Ser Leu Ala Val Ser Leu
  1               5                  10                  15

Gly Gln Arg Ala Thr Ile Ser Cys Arg Ala Ser Glu Ser Val Asp
             20                  25                  30

Ser Tyr Gly Lys Thr Phe Met His Trp His Gln Gln Lys Pro Gly
             35                  40                  45

Gln Pro Pro Lys Leu Leu Ile Tyr Arg Val Ser Asn Leu Glu Ser
             50                  55                  60

Gly Ile Pro Ala Arg Phe Ser Gly Ser Gly Ser Arg Thr Asp Phe
             65                  70                  75

Thr Leu Thr Ile Asn Pro Val Glu Ala Asp Val Ala Thr Tyr
             80                  85                  90

Tyr Cys Gln Gln Ser Asn Glu Asp Pro Phe Thr Phe Gly Gly Gly
             95                 100                 105

Thr Lys Leu Glu Ile Lys Arg
            110

<210> SEQ ID NO 303
<211> LENGTH: 218
<212> TYPE: PRT
<213> ORGANISM: Artificial sequence
<220> FEATURE:
<223> OTHER INFORMATION: Light chain of huMA79bv.17

<400> SEQUENCE: 303

Asp Ile Gln Leu Thr Gln Ser Pro Ser Ser Leu Ser Ala Ser Val
  1               5                  10                  15

Gly Asp Arg Val Thr Ile Thr Cys Lys Ala Ser Gln Ser Val Asp
             20                  25                  30

Tyr Asp Gly Asp Ser Phe Leu Asn Trp Tyr Gln Gln Lys Pro Gly
             35                  40                  45

Lys Ala Pro Lys Leu Leu Ile Tyr Ala Ala Ser Asn Leu Glu Ser
             50                  55                  60

Gly Val Pro Ser Arg Phe Ser Gly Ser Gly Ser Gly Thr Asp Phe
             65                  70                  75

Thr Leu Thr Ile Ser Ser Leu Gln Pro Glu Asp Phe Ala Thr Tyr
             80                  85                  90

Tyr Cys Gln Gln Ser Asn Glu Asp Pro Leu Thr Phe Gly Gln Gly
             95                 100                 105
```

```
Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215

<210> SEQ ID NO 304
<211> LENGTH: 446
<212> TYPE: PRT
<213> ORGANISM: Artificial sequence
<220> FEATURE:
<223> OTHER INFORMATION: Heavy chain of huMA79bv.17

<400> SEQUENCE: 304

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Ser
                 20                  25                  30

Ser Tyr Trp Ile Glu Trp Val Arg Gln Ala Pro Gly Lys Gly Leu
                 35                  40                  45

Glu Trp Ile Gly Glu Ile Leu Pro Gly Gly Gly Asp Thr Asn Tyr
                 50                  55                  60

Asn Glu Ile Phe Lys Gly Arg Ala Thr Phe Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Thr Arg Arg Val Pro Val Tyr Phe Asp
                 95                 100                 105

Tyr Trp Gly Gln Gly Thr Leu Val Thr Val Ser Ser Ala Ser Thr
                110                 115                 120

Lys Gly Pro Ser Val Phe Pro Leu Ala Pro Ser Ser Lys Ser Thr
                125                 130                 135

Ser Gly Gly Thr Ala Ala Leu Gly Cys Leu Val Lys Asp Tyr Phe
                140                 145                 150

Pro Glu Pro Val Thr Val Ser Trp Asn Ser Gly Ala Leu Thr Ser
                155                 160                 165

Gly Val His Thr Phe Pro Ala Val Leu Gln Ser Ser Gly Leu Tyr
                170                 175                 180

Ser Leu Ser Ser Val Val Thr Val Pro Ser Ser Ser Leu Gly Thr
                185                 190                 195

Gln Thr Tyr Ile Cys Asn Val Asn His Lys Pro Ser Asn Thr Lys
                200                 205                 210

Val Asp Lys Lys Val Glu Pro Lys Ser Cys Asp Lys Thr His Thr
                215                 220                 225
```

```
Cys Pro Pro Cys Pro Ala Pro Glu Leu Leu Gly Gly Pro Ser Val
                230                 235                 240

Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp
                260                 265                 270

Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn
                305                 310                 315

Gly Lys Glu Tyr Lys Cys Lys Val Ser Asn Lys Ala Leu Pro Ala
                320                 325                 330

Pro Ile Glu Lys Thr Ile Ser Lys Ala Lys Gly Gln Pro Arg Glu
                335                 340                 345

Pro Gln Val Tyr Thr Leu Pro Pro Ser Arg Glu Glu Met Thr Lys
                350                 355                 360

Asn Gln Val Ser Leu Thr Cys Leu Val Lys Gly Phe Tyr Pro Ser
                365                 370                 375

Asp Ile Ala Val Glu Trp Glu Ser Asn Gly Gln Pro Glu Asn Asn
                380                 385                 390

Tyr Lys Thr Thr Pro Pro Val Leu Asp Ser Asp Gly Ser Phe Phe
                395                 400                 405

Leu Tyr Ser Lys Leu Thr Val Asp Lys Ser Arg Trp Gln Gln Gly
                410                 415                 420

Asn Val Phe Ser Cys Ser Val Met His Glu Ala Leu His Asn His
                425                 430                 435

Tyr Thr Gln Lys Ser Leu Ser Leu Ser Pro Gly
                440                 445

<210> SEQ ID NO 305
<211> LENGTH: 218
<212> TYPE: PRT
<213> ORGANISM: Artificial sequence
<220> FEATURE:
<223> OTHER INFORMATION: Light chain of huMA79bv.18

<400> SEQUENCE: 305

Asp Ile Gln Leu Thr Gln Ser Pro Ser Ser Leu Ser Ala Ser Val
  1               5                  10                  15

Gly Asp Arg Val Thr Ile Thr Cys Lys Ala Ser Gln Ser Val Asp
                 20                  25                  30

Tyr Asp Gly Asp Ser Phe Leu Asn Trp Tyr Gln Gln Lys Pro Gly
                 35                  40                  45

Lys Ala Pro Lys Leu Leu Ile Tyr Ala Ala Ser Asn Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Ser Asn Glu Asp Pro Leu Thr Phe Gly Gln Gly
                 95                 100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
```

```
                        125                 130                 135
Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215

<210> SEQ ID NO 306
<211> LENGTH: 446
<212> TYPE: PRT
<213> ORGANISM: Artificial sequence
<220> FEATURE:
<223> OTHER INFORMATION: Heavy chain of huMA79bv.18

<400> SEQUENCE: 306

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Ser
                20                  25                  30

Ser Tyr Trp Ile Glu Trp Val Arg Gln Ala Pro Gly Lys Gly Leu
                35                  40                  45

Glu Trp Ile Gly Glu Ile Leu Pro Gly Gly Gly Asp Thr Asn Tyr
                50                  55                  60

Asn Glu Ile Phe Lys Gly Arg Ala Thr Phe Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Thr Arg Arg Val Pro Ile Arg Leu Asp
                95                  100                 105

Tyr Trp Gly Gln Gly Thr Leu Val Thr Val Ser Ser Ala Ser Thr
                110                 115                 120

Lys Gly Pro Ser Val Phe Pro Leu Ala Pro Ser Ser Lys Ser Thr
                125                 130                 135

Ser Gly Gly Thr Ala Ala Leu Gly Cys Leu Val Lys Asp Tyr Phe
                140                 145                 150

Pro Glu Pro Val Thr Val Ser Trp Asn Ser Gly Ala Leu Thr Ser
                155                 160                 165

Gly Val His Thr Phe Pro Ala Val Leu Gln Ser Ser Gly Leu Tyr
                170                 175                 180

Ser Leu Ser Ser Val Val Thr Val Pro Ser Ser Ser Leu Gly Thr
                185                 190                 195

Gln Thr Tyr Ile Cys Asn Val Asn His Lys Pro Ser Asn Thr Lys
                200                 205                 210

Val Asp Lys Lys Val Glu Pro Lys Ser Cys Asp Lys Thr His Thr
                215                 220                 225

Cys Pro Pro Cys Pro Ala Pro Glu Leu Leu Gly Gly Pro Ser Val
                230                 235                 240

Phe Leu Phe Pro Pro Lys Pro Lys Asp Thr Leu Met Ile Ser Arg
                245                 250                 255
```

```
Thr Pro Glu Val Thr Cys Val Val Val Asp Val Ser His Glu Asp
            260                 265                 270

Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn
            305                 310                 315

Gly Lys Glu Tyr Lys Cys Lys Val Ser Asn Lys Ala Leu Pro Ala
            320                 325                 330

Pro Ile Glu Lys Thr Ile Ser Lys Ala Lys Gly Gln Pro Arg Glu
            335                 340                 345

Pro Gln Val Tyr Thr Leu Pro Pro Ser Arg Glu Glu Met Thr Lys
            350                 355                 360

Asn Gln Val Ser Leu Thr Cys Leu Val Lys Gly Phe Tyr Pro Ser
            365                 370                 375

Asp Ile Ala Val Glu Trp Glu Ser Asn Gly Gln Pro Glu Asn Asn
            380                 385                 390

Tyr Lys Thr Thr Pro Pro Val Leu Asp Ser Asp Gly Ser Phe Phe
            395                 400                 405

Leu Tyr Ser Lys Leu Thr Val Asp Lys Ser Arg Trp Gln Gln Gly
            410                 415                 420

Asn Val Phe Ser Cys Ser Val Met His Glu Ala Leu His Asn His
            425                 430                 435

Tyr Thr Gln Lys Ser Leu Ser Leu Ser Pro Gly
            440                 445

<210> SEQ ID NO 307
<211> LENGTH: 218
<212> TYPE: PRT
<213> ORGANISM: Artificial sequence
<220> FEATURE:
<223> OTHER INFORMATION: Light chain of huMA79bv.28

<400> SEQUENCE: 307

Asp Ile Gln Leu Thr Gln Ser Pro Ser Ser Leu Ser Ala Ser Val
 1               5                  10                  15

Gly Asp Arg Val Thr Ile Thr Cys Lys Ala Ser Gln Ser Val Asp
                20                  25                  30

Tyr Glu Gly Asp Ser Phe Leu Asn Trp Tyr Gln Gln Lys Pro Gly
                35                  40                  45

Lys Ala Pro Lys Leu Leu Ile Tyr Ala Ala Ser Asn Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser Asn Glu Asp Pro Leu Thr Phe Gly Gln Gly
                95                  100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150
```

-continued

```
Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
        170                 175                 180

Ser Thr Leu Thr Leu Ser Lys Ala Asp Tyr Glu Lys His Lys Val
        185                 190                 195

Tyr Ala Cys Glu Val Thr His Gln Gly Leu Ser Ser Pro Val Thr
        200                 205                 210

Lys Ser Phe Asn Arg Gly Glu Cys
        215

<210> SEQ ID NO 308
<211> LENGTH: 446
<212> TYPE: PRT
<213> ORGANISM: Artificial sequence
<220> FEATURE:
<223> OTHER INFORMATION: Heavy chain of huMA79bv.28

<400> SEQUENCE: 308

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Ser
                 20                  25                  30

Ser Tyr Trp Ile Glu Trp Val Arg Gln Ala Pro Gly Lys Gly Leu
                 35                  40                  45

Glu Trp Ile Gly Glu Ile Leu Pro Gly Gly Gly Asp Thr Asn Tyr
             50                  55                  60

Asn Glu Ile Phe Lys Gly Arg Ala Thr Phe Ser Ala Asp Thr Ser
 65                  70                  75

Lys Asn Thr Ala Tyr Leu Gln Met Asn Ser Leu Arg Ala Glu Asp
         80                  85                  90

Thr Ala Val Tyr Tyr Cys Thr Arg Arg Val Pro Ile Arg Leu Asp
         95                 100                 105

Tyr Trp Gly Gln Gly Thr Leu Val Thr Val Ser Ser Ala Ser Thr
        110                 115                 120

Lys Gly Pro Ser Val Phe Pro Leu Ala Pro Ser Ser Lys Ser Thr
        125                 130                 135

Ser Gly Gly Thr Ala Ala Leu Gly Cys Leu Val Lys Asp Tyr Phe
        140                 145                 150

Pro Glu Pro Val Thr Val Ser Trp Asn Ser Gly Ala Leu Thr Ser
        155                 160                 165

Gly Val His Thr Phe Pro Ala Val Leu Gln Ser Ser Gly Leu Tyr
        170                 175                 180

Ser Leu Ser Ser Val Val Thr Val Pro Ser Ser Ser Leu Gly Thr
        185                 190                 195

Gln Thr Tyr Ile Cys Asn Val Asn His Lys Pro Ser Asn Thr Lys
        200                 205                 210

Val Asp Lys Lys Val Glu Pro Lys Ser Cys Asp Lys Thr His Thr
        215                 220                 225

Cys Pro Pro Cys Pro Ala Pro Glu Leu Leu Gly Gly Pro Ser Val
        230                 235                 240

Phe Leu Phe Pro Pro Lys Pro Lys Asp Thr Leu Met Ile Ser Arg
        245                 250                 255

Thr Pro Glu Val Thr Cys Val Val Val Asp Val Ser His Glu Asp
        260                 265                 270

Pro Glu Val Lys Phe Asn Trp Tyr Val Asp Gly Val Glu Val His
```

```
                        275                 280                 285

Asn Ala Lys Thr Lys Pro Arg Glu Glu Gln Tyr Asn Ser Thr Tyr
                    290                 295                 300

Arg Val Val Ser Val Leu Thr Val Leu His Gln Asp Trp Leu Asn
                    305                 310                 315

Gly Lys Glu Tyr Lys Cys Lys Val Ser Asn Lys Ala Leu Pro Ala
                    320                 325                 330

Pro Ile Glu Lys Thr Ile Ser Lys Ala Lys Gly Gln Pro Arg Glu
                    335                 340                 345

Pro Gln Val Tyr Thr Leu Pro Pro Ser Arg Glu Glu Met Thr Lys
                    350                 355                 360

Asn Gln Val Ser Leu Thr Cys Leu Val Lys Gly Phe Tyr Pro Ser
                    365                 370                 375

Asp Ile Ala Val Glu Trp Glu Ser Asn Gly Gln Pro Glu Asn Asn
                    380                 385                 390

Tyr Lys Thr Thr Pro Pro Val Leu Asp Ser Asp Gly Ser Phe Phe
                    395                 400                 405

Leu Tyr Ser Lys Leu Thr Val Asp Lys Ser Arg Trp Gln Gln Gly
                    410                 415                 420

Asn Val Phe Ser Cys Ser Val Met His Glu Ala Leu His Asn His
                    425                 430                 435

Tyr Thr Gln Lys Ser Leu Ser Leu Ser Pro Gly
                    440                 445

<210> SEQ ID NO 309
<211> LENGTH: 218
<212> TYPE: PRT
<213> ORGANISM: Artificial sequence
<220> FEATURE:
<223> OTHER INFORMATION: Light chain of huMA79bv.32

<400> SEQUENCE: 309

Asp Ile Gln Leu Thr Gln Ser Pro Ser Ser Leu Ser Ala Ser Val
  1               5                  10                  15

Gly Asp Arg Val Thr Ile Thr Cys Lys Ala Ser Gln Ser Val Asp
                 20                  25                  30

Tyr Ser Gly Asp Ser Phe Leu Asn Trp Tyr Gln Gln Lys Pro Gly
                 35                  40                  45

Lys Ala Pro Lys Leu Phe Ile Tyr Ala Ala Ser Asn Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Ser Asn Glu Asp Pro Leu Thr Phe Gly Gln Gly
                 95                 100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180
```

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
            200                 205                 210

Lys Ser Phe Asn Arg Gly Glu Cys
            215

<210> SEQ ID NO 310
<211> LENGTH: 446
<212> TYPE: PRT
<213> ORGANISM: Artificial sequence
<220> FEATURE:
<223> OTHER INFORMATION: Heavy chain of huMA79bv.32

<400> SEQUENCE: 310

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Ser
             20                  25                  30

Ser Tyr Trp Ile Glu Trp Val Arg Gln Ala Pro Gly Lys Gly Leu
             35                  40                  45

Glu Trp Ile Gly Glu Ile Leu Pro Gly Gly Gly Asp Thr Asn Tyr
             50                  55                  60

Asn Glu Ile Phe Lys Gly Arg Ala Thr Phe Ser Ala Asp Thr Ser
             65                  70                  75

Lys Asn Thr Ala Tyr Leu Gln Met Asn Ser Leu Arg Ala Glu Asp
             80                  85                  90

Thr Ala Val Tyr Tyr Cys Thr Arg Arg Val Pro Ile Arg Leu Asp
             95                 100                 105

Tyr Trp Gly Gln Gly Thr Leu Val Thr Val Ser Ser Ala Ser Thr
            110                 115                 120

Lys Gly Pro Ser Val Phe Pro Leu Ala Pro Ser Ser Lys Ser Thr
            125                 130                 135

Ser Gly Gly Thr Ala Ala Leu Gly Cys Leu Val Lys Asp Tyr Phe
            140                 145                 150

Pro Glu Pro Val Thr Val Ser Trp Asn Ser Gly Ala Leu Thr Ser
            155                 160                 165

Gly Val His Thr Phe Pro Ala Val Leu Gln Ser Ser Gly Leu Tyr
            170                 175                 180

Ser Leu Ser Ser Val Val Thr Val Pro Ser Ser Ser Leu Gly Thr
            185                 190                 195

Gln Thr Tyr Ile Cys Asn Val Asn His Lys Pro Ser Asn Thr Lys
            200                 205                 210

Val Asp Lys Lys Val Glu Pro Lys Ser Cys Asp Lys Thr His Thr
            215                 220                 225

Cys Pro Pro Cys Pro Ala Pro Glu Leu Leu Gly Gly Pro Ser Val
            230                 235                 240

Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp
            260                 265                 270

Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr
            290                 295                 300

```
Arg Val Val Ser Val Leu Thr Val Leu His Gln Asp Trp Leu Asn
            305                 310                 315
Gly Lys Glu Tyr Lys Cys Lys Val Ser Asn Lys Ala Leu Pro Ala
            320                 325                 330
Pro Ile Glu Lys Thr Ile Ser Lys Ala Lys Gly Gln Pro Arg Glu
            335                 340                 345
Pro Gln Val Tyr Thr Leu Pro Pro Ser Arg Glu Glu Met Thr Lys
            350                 355                 360
Asn Gln Val Ser Leu Thr Cys Leu Val Lys Gly Phe Tyr Pro Ser
            365                 370                 375
Asp Ile Ala Val Glu Trp Glu Ser Asn Gly Gln Pro Glu Asn Asn
            380                 385                 390
Tyr Lys Thr Thr Pro Pro Val Leu Asp Ser Asp Gly Ser Phe Phe
            395                 400                 405
Leu Tyr Ser Lys Leu Thr Val Asp Lys Ser Arg Trp Gln Gln Gly
            410                 415                 420
Asn Val Phe Ser Cys Ser Val Met His Glu Ala Leu His Asn His
            425                 430                 435
Tyr Thr Gln Lys Ser Leu Ser Leu Ser Pro Gly
            440                 445
```